United States Patent
Shumer et al.

(10) Patent No.: US 10,639,181 B2
(45) Date of Patent: *May 5, 2020

(54) METHODS AND SYSTEMS FOR DELIVERING AN IMPLANT

(71) Applicant: ABBOTT CARDIOVASCULAR SYSTEMS INC., Santa Clara, CA (US)

(72) Inventors: Daniel H. Shumer, San Jose, CA (US); Ronald G. Earles, Houston, TX (US); Nianjiong J. Bei, Palo Alto, CA (US); Barbara Stamberg, San Jose, CA (US); Daniel Simon, Murrieta, CA (US); Maria Del Rosario Nava, Baldwin Park, CA (US); Michael L. Green, Pleasanton, CA (US); Matthew J. Gillick, Murrieta, CA (US)

(73) Assignee: ABBOTT CARDIOVASCULAR SYSTEMS INC., Santa Clara, CA (US)

(*) Notice: Subject to any disclaimer, the term of this patent is extended or adjusted under 35 U.S.C. 154(b) by 240 days.

This patent is subject to a terminal disclaimer.

(21) Appl. No.: 15/835,418

(22) Filed: Dec. 7, 2017

(65) Prior Publication Data

US 2018/0221182 A1 Aug. 9, 2018

Related U.S. Application Data

(63) Continuation-in-part of application No. 14/932,884, filed on Nov. 4, 2015, now Pat. No. 10,195,065, and
(Continued)

(51) Int. Cl.
*A61F 2/95* (2013.01)
*A61F 2/966* (2013.01)
(Continued)

(52) U.S. Cl.
CPC ............. *A61F 2/966* (2013.01); *F16H 19/04* (2013.01); *F16H 31/007* (2013.01);
(Continued)

(58) Field of Classification Search
CPC ...... A61F 2002/9665; A61F 2002/9517; A61F 2002/9522; A61F 2002/9528;
(Continued)

(56) References Cited

U.S. PATENT DOCUMENTS

| 3,148,595 A | 9/1964 | Looney |
| 5,344,061 A | 9/1994 | Crainich |

(Continued)

FOREIGN PATENT DOCUMENTS

| EP | 2190388 B1 | 3/2014 |
| WO | WO 2012/068389 A1 | 5/2012 |
| WO | WO 2016/073637 A1 | 5/2016 |

OTHER PUBLICATIONS

U.S. Appl. No. 15/836,649, Jul. 12, 2019 Non-Final Office Action.
(Continued)

*Primary Examiner* — Erich G Herbermann
(74) *Attorney, Agent, or Firm* — Baker Botts L.L.P.

(57) ABSTRACT

A system for delivering an implant including a handle, a trigger, an actuation assembly, and a catheter assembly. The actuation assembly is configured to displace the outer tubular member in the proximal direction and to separately move the inner shaft member distally upon deployment of the trigger from the first position to the second position, and move the inner shaft member proximally with no displacement of the outer tubular member upon return of the trigger from the second position to the first position. The catheter assembly includes an outer tubular member, an inner shaft member, and a pusher assembly.

62 Claims, 109 Drawing Sheets

Related U.S. Application Data a continuation-in-part of application No. 14/932,862, filed on Nov. 4, 2015, now Pat. No. 10,271,980, and a continuation-in-part of application No. 14/932,900, filed on Nov. 4, 2015, now Pat. No. 10,154,920, and a continuation-in-part of application No. 14/932,848, filed on Nov. 4, 2015, now Pat. No. 10,149,778, and a continuation-in-part of application No. 14/932,805, filed on Nov. 4, 2015, now abandoned, and a continuation-in-part of application No. 14/932,830, filed on Nov. 4, 2015, now Pat. No. 10,433,994, and a continuation-in-part of application No. 14/932,795, filed on Nov. 4, 2015, now abandoned.

(60) Provisional application No. 62/457,677, filed on Feb. 10, 2017, provisional application No. 62/497,929, filed on Dec. 8, 2016, provisional application No. 62/075,059, filed on Nov. 4, 2014.

(51) Int. Cl.
*F16H 19/04* (2006.01)
*F16H 31/00* (2006.01)
*F16H 19/02* (2006.01)

(52) U.S. Cl.
CPC ............... *A61F 2002/9517* (2013.01); *A61F 2210/0076* (2013.01); *A61F 2250/0098* (2013.01); *F16H 19/025* (2013.01)

(58) Field of Classification Search
CPC .... A61F 2002/9534; A61F 2/966; A61F 2/97; A61F 2/95; A61F 2/962; A61F 2/954; A61F 2/958; A61F 2/93; F16H 19/04; F16H 5/02

See application file for complete search history.

(56) References Cited

U.S. PATENT DOCUMENTS

| | | | |
|---|---|---|---|
| 5,364,351 A | 11/1994 | Heinzelman et al. | |
| 5,443,477 A | 8/1995 | Marin et al. | |
| 5,507,769 A | 4/1996 | Marin et al. | |
| 5,607,466 A | 3/1997 | Imbert et al. | |
| 5,643,319 A | 7/1997 | Green et al. | |
| 5,707,376 A | 1/1998 | Kavteladze et al. | |
| 5,797,927 A | 8/1998 | Yoon | |
| 6,241,758 B1 | 6/2001 | Cox | |
| 6,514,261 B1 | 2/2003 | Randall et al. | |
| 6,676,693 B1 | 1/2004 | Belding et al. | |
| 6,945,989 B1 | 9/2005 | Betelia et al. | |
| 7,052,511 B2 | 5/2006 | Weldon et al. | |
| 7,326,203 B2 | 2/2008 | Papineau et al. | |
| 7,611,497 B2 | 11/2009 | Wollschlager | |
| 7,758,624 B2 | 7/2010 | Dorn et al. | |
| 7,854,746 B2 | 12/2010 | Dorn et al. | |
| 7,985,250 B2 | 7/2011 | Kaufmann et al. | |
| 8,025,692 B2 | 9/2011 | Feeser | |
| 8,292,939 B2 | 10/2012 | Yachia et al. | |
| 8,382,813 B2 | 2/2013 | Shumer | |
| 8,500,789 B2 | 8/2013 | Wuebbeling et al. | |
| 8,568,467 B2 | 10/2013 | Dorn et al. | |
| 8,603,045 B2 | 12/2013 | Weber | |
| 8,652,193 B2 | 2/2014 | Dorn | |
| 9,039,750 B2 | 5/2015 | Ryan | |
| 9,078,779 B2 | 7/2015 | Dorn et al. | |
| 9,095,465 B2 | 8/2015 | Kelly | |
| 9,149,379 B2 | 10/2015 | Keady et al. | |
| 9,192,500 B1 | 11/2015 | Longo et al. | |
| 2002/0068947 A1 | 6/2002 | Kuhns et al. | |
| 2003/0028236 A1 | 2/2003 | Gillick et al. | |
| 2003/0191516 A1 | 10/2003 | Weldon et al. | |
| 2005/0080476 A1 | 4/2005 | Gunderson et al. | |
| 2005/0149159 A1 | 7/2005 | Andreas et al. | |
| 2006/0095050 A1 | 5/2006 | Hartley et al. | |
| 2006/0190069 A1 | 8/2006 | Baker-Janis et al. | |
| 2007/0156225 A1 | 7/2007 | George et al. | |
| 2007/0250150 A1 | 10/2007 | Pal et al. | |
| 2008/0161902 A1 | 7/2008 | Poulson | |
| 2008/0281336 A1 | 11/2008 | Zergiebel | |
| 2008/0319524 A1 | 12/2008 | Yachia et al. | |
| 2009/0024133 A1 | 1/2009 | Keady et al. | |
| 2010/0174290 A1 | 7/2010 | Wüebbeling | |
| 2011/0295354 A1 | 12/2011 | Bueche et al. | |
| 2012/0029607 A1 | 2/2012 | McHugo et al. | |
| 2012/0053671 A1 | 3/2012 | McHugo et al. | |
| 2012/0158117 A1 | 6/2012 | Ryan | |
| 2012/0172963 A1* | 7/2012 | Ryan ..................... A61F 2/966 |
| | | | 623/1.11 |
| 2012/0221093 A1 | 8/2012 | McHugo | |
| 2012/0290066 A1 | 11/2012 | Nabulsi et al. | |
| 2014/0046428 A1 | 2/2014 | Cragg et al. | |
| 2014/0135909 A1 | 5/2014 | Carr et al. | |
| 2014/0180380 A1 | 6/2014 | Kelly | |
| 2014/0214006 A1 | 7/2014 | Hiroshige et al. | |
| 2014/0324151 A1 | 10/2014 | Yamashita | |
| 2015/0320971 A1 | 11/2015 | Leeflang et al. | |
| 2016/0120678 A1 | 5/2016 | Green et al. | |

OTHER PUBLICATIONS

U.S. Appl. No. 14/932,830, May 16, 2018 Response to Restriction Requirement.
U.S. Appl. No. 14/932,830, Jun. 11, 2018 Non-Final Office Action.
U.S. Appl. No. 14/932,795, May 29, 2018 Response to Non-Final Office Action.
U.S. Appl. No. 14/932,795, Jul. 31, 2018 Final Office Action.
U.S. Appl. No. 14/932,805, May 29, 2018 Response to Non-Final Office Action.
U.S. Appl. No. 14/932,805, Aug. 1, 2018 Final Office Action.
U.S. Appl. No. 14/932,862, May 22, 2018 Response to Restriction Requirement.
U.S. Appl. No. 14/932,862, Jul. 19, 2018 Non-Final Office Action.
U.S. Appl. No. 14/932,884, Jul. 20, 2018 Response to Non-Final Office Action.
U.S. Appl. No. 14/932,884, Apr. 20, 2018 Non-Final Office Action.
U.S. Appl. No. 14/932,900, May 7, 2018 Response to Restriction Requirement.
U.S. Appl. No. 14/932,900, Aug. 10, 2018 Notice of Allowance.
U.S. Appl. No. 14/932,848, May 22, 2018 Response to Restriction Requirement.
U.S. Appl. No. 14/932,848, Aug. 9, 2018 Notice of Allowance.
U.S. Appl. No. 15/670,719 (US 2017/0333238), filed Aug. 7, 2017 (Nov. 23, 2017).
U.S. Appl. No. 15/836,649, filed Dec. 8, 2017.
U.S. Appl. No. 29/628,958, filed Dec. 8, 2017.
International Search Report dated Apr. 4, 2018 in International Application No. PCT/US2017/065399.
U.S. Appl. No. 14/560,832 (U.S. Pat. No. 9,724,223), filed Dec. 4, 2014 (Aug. 8, 2017).
U.S. Appl. No. 14/932,795 (US 2016/0120678), filed Nov. 4, 2015 (May 5, 2016).
U.S. Appl. No. 14/932,805 (US 2016/0120679), filed Nov. 4, 2015 (May 5, 2015).
U.S. Appl. No. 14/932,830 (US 2016/0120680), filed Nov. 4, 2015 (May 5, 2016).
U.S. Appl. No. 14/932,848 (US 2016/0128856), filed Nov. 4, 2015 (May 12, 2016).
U.S. Appl. No. 14/932,862 (US 2016/0123440), filed Nov. 4, 2015 (May 5, 2016).
U.S. Appl. No. 14/932,875 (U.S. Pat. No. 9,724,224), filed Nov. 4, 2015 (Aug. 8, 2017).
U.S. Appl. No. 14/932,884 (US 2016/0123442), filed Nov. 4, 2015 (May 5, 2016).
U.S. Appl. No. 14/932,900 (US 2016/0123443), filed Nov. 4, 2015 (May 5, 2016).
U.S. Appl. No. 14/932,830, Jan. 17, 2018 Restriction Requirement.
U.S. Appl. No. 14/932,795, Dec. 26, 2017 Non-Final Office Action.

(56) References Cited

OTHER PUBLICATIONS

U.S. Appl. No. 14/932,805, Dec. 26, 2017 Non-Final Office Action.
U.S. Appl. No. 14/932,900, Jan. 5, 2018 Restriction Requirement.
U.S. Appl. No. 14/932,848, Jan. 22, 2018 Restriction Requirement.
U.S. Appl. No. 14/932,862, Jan. 22, 2018 Restriction Requirement.
U.S. Appl. No. 14/932,875, Jul. 3, 2017 Issue Fee Payment.
U.S. Appl. No. 14/932,875, Apr. 5, 2017 Notice of Allowance.
U.S. Appl. No. 14/932,875, Mar. 29, 2017 Response after Final Action.
U.S. Appl. No. 14/932,875, Mar. 9, 2017 Applicant Initiated Interview Summary.
U.S. Appl. No. 14/932,875, Nov. 29, 2016 Final Office Action.
U.S. Appl. No. 14/932,875, Aug. 19, 2016 Response to Non-Final Office Action.
U.S. Appl. No. 14/932,875, May 19, 2016 Non-Final Office Action.
U.S. Appl. No. 14/560,832, Jun. 30, 2017 Issue Fee Payment.
U.S. Appl. No. 14/560,832, Mar. 31, 2017 Notice of Allowance.
U.S. Appl. No. 14/560,832, Mar. 21, 2017 Response after Final Action.
U.S. Appl. No. 14/560,832, Nov. 21, 2016 Final Office Action.
U.S. Appl. No. 14/560,832, Aug. 22, 2016 Response to Non-Final Office Action.
U.S. Appl. No. 14/560,832, Apr. 22, 2016 Non-Final Office Action.
International Search report and Written Opinion dated Jan. 29, 2016 in International Application No. PCT/US2015/059070.
International Search report and Written Opinion dated Jan. 29, 2016 in International Application No. PCT/US2015/059074.
International Search report and Written Opinion dated Jan. 29, 2016 in International Application No. PCT/US2015/059084.
U.S. Appl. No. 15/836,649, Jan. 27, 2020, Final Office Action.

* cited by examiner

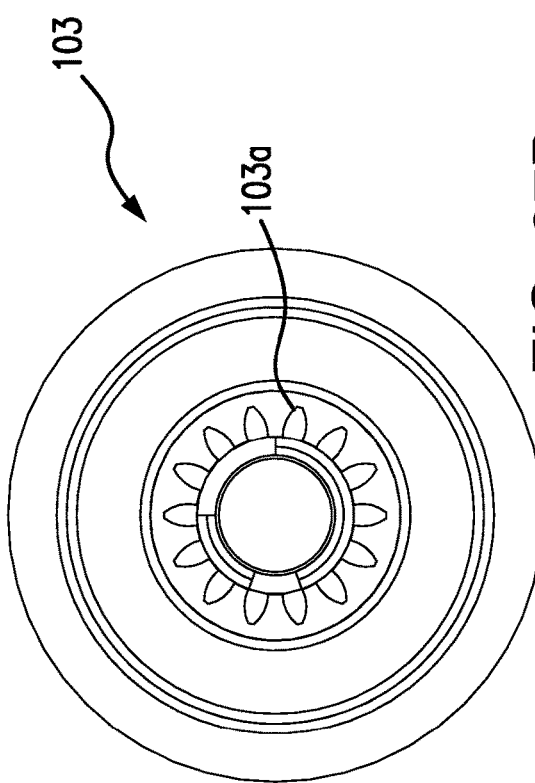
FIG. 27A
FIG. 27B
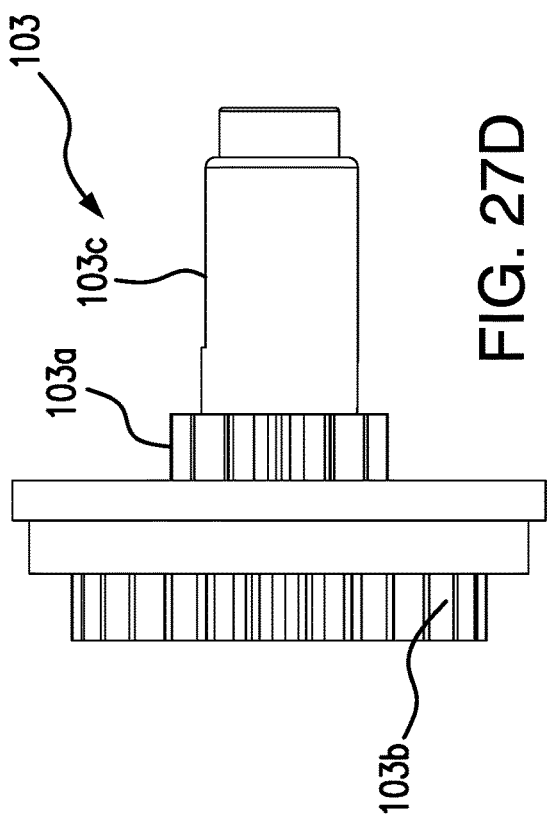
FIG. 27D
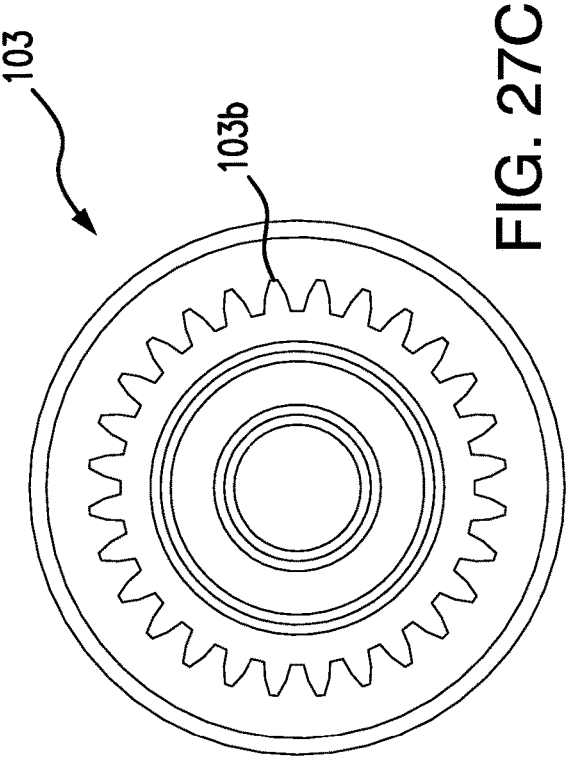
FIG. 27C

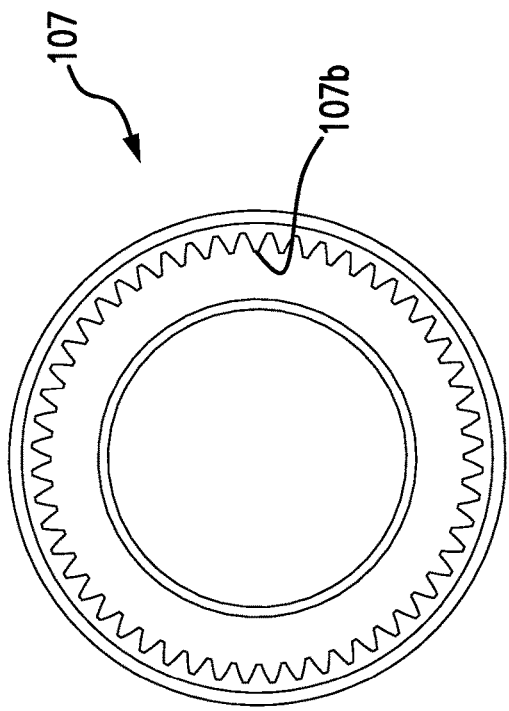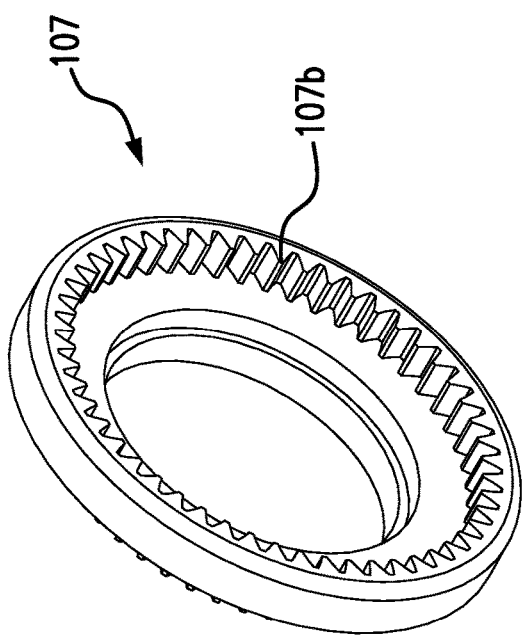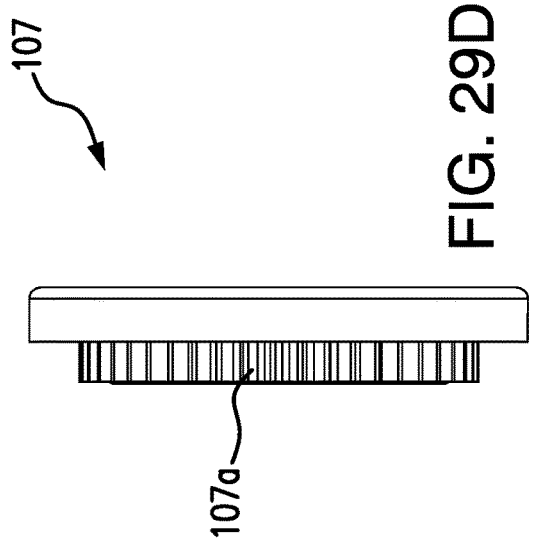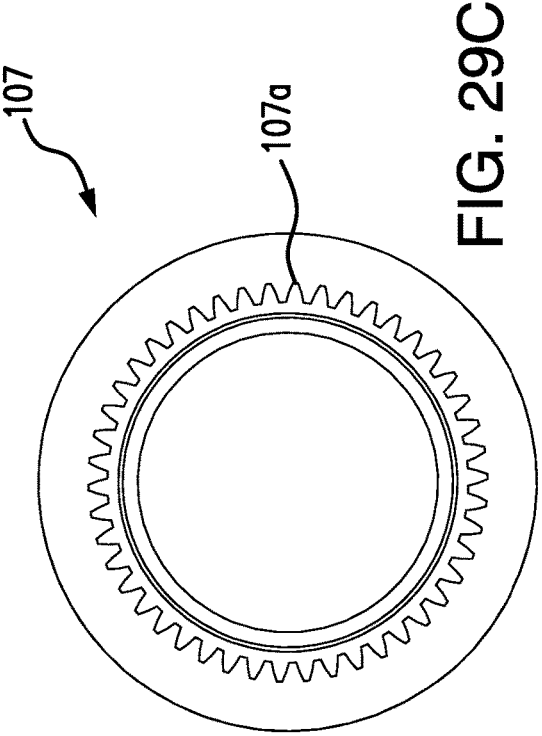
FIG. 29A
FIG. 29B
FIG. 29C
FIG. 29D

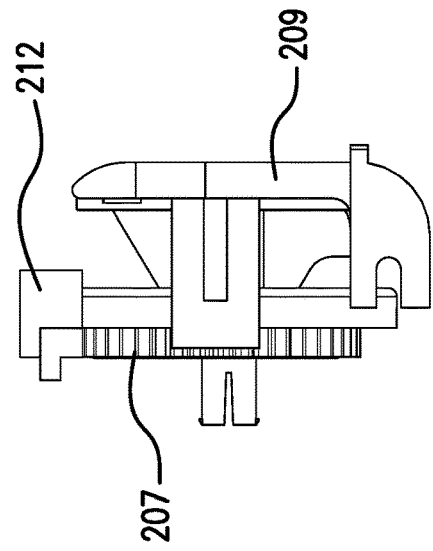
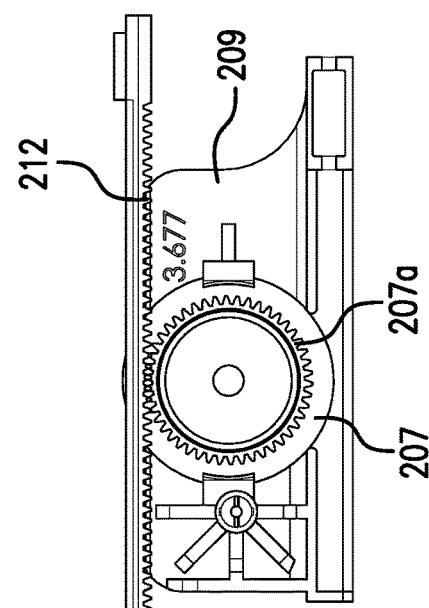
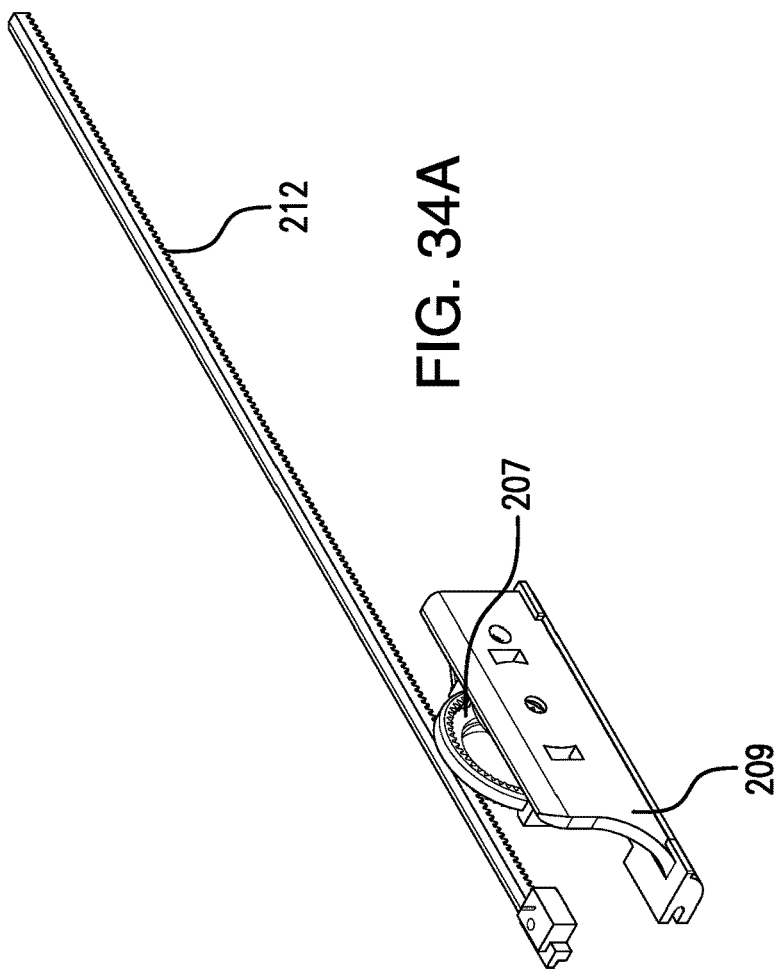
FIG. 34C
FIG. 34B
FIG. 34A

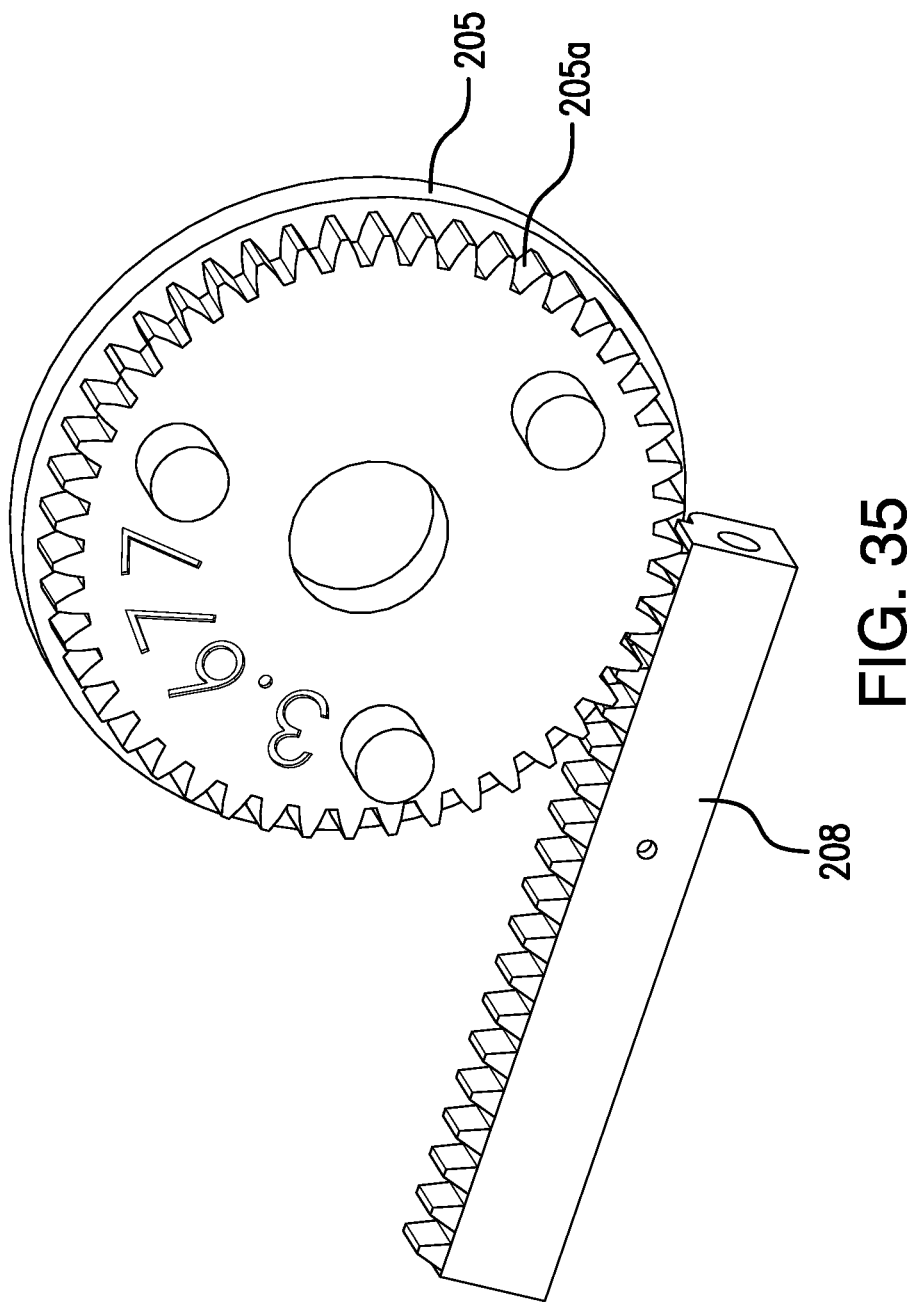

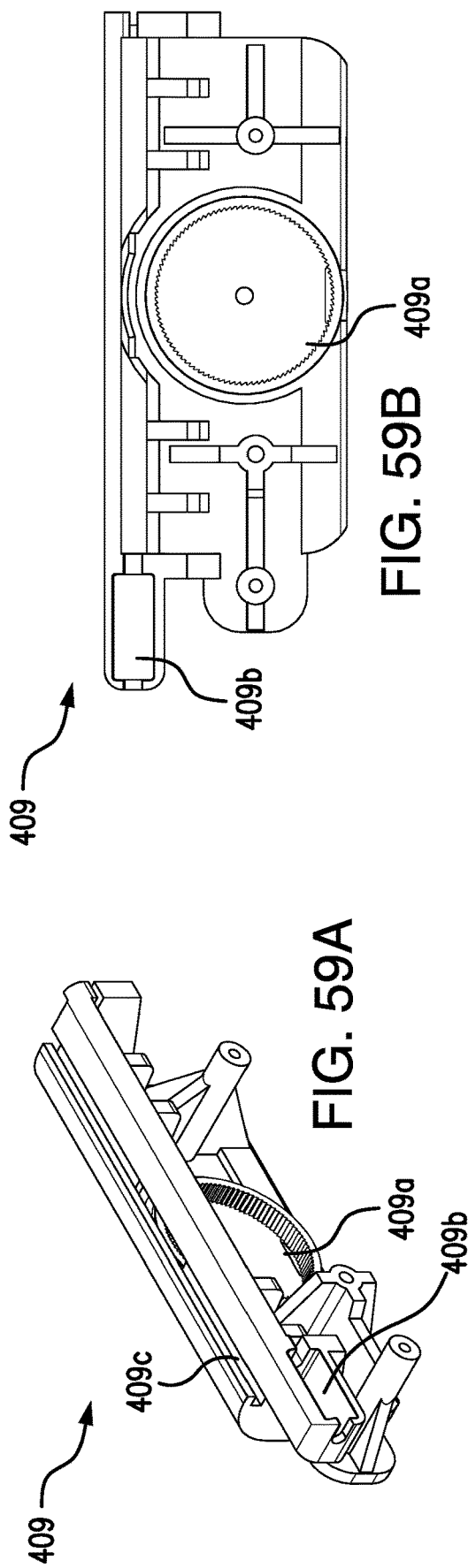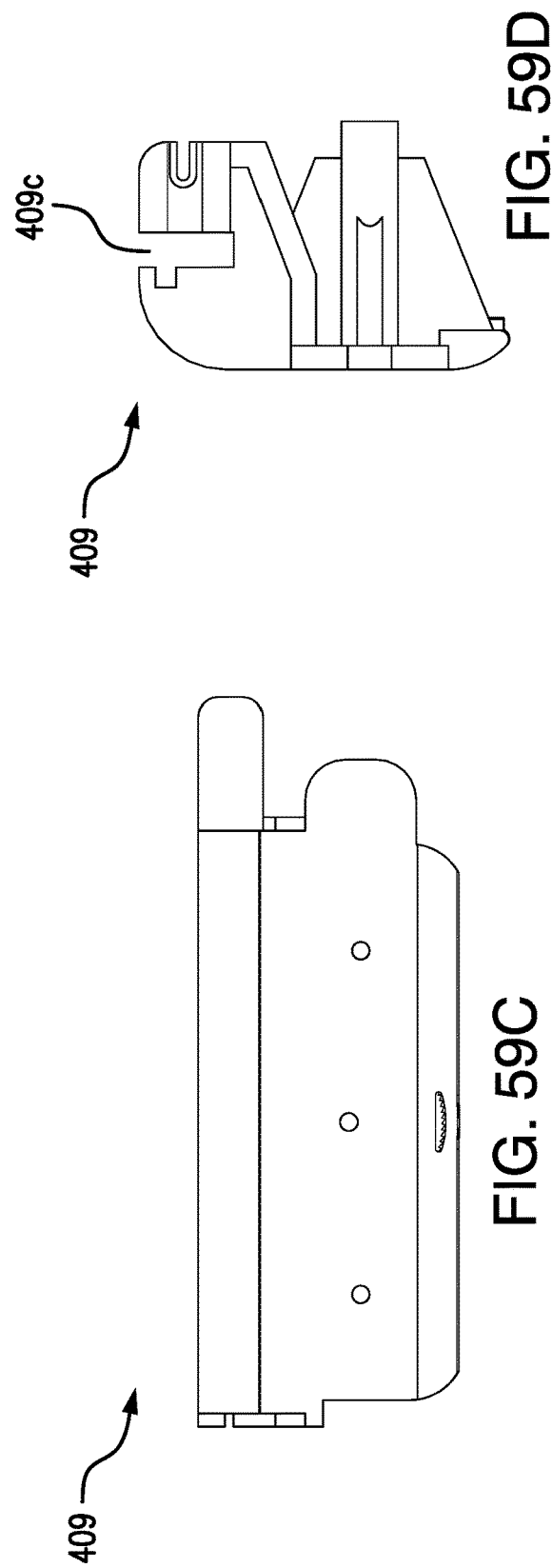

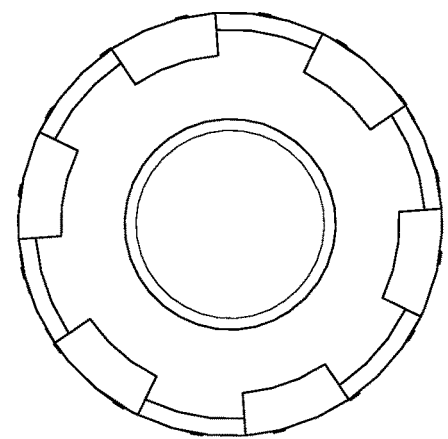
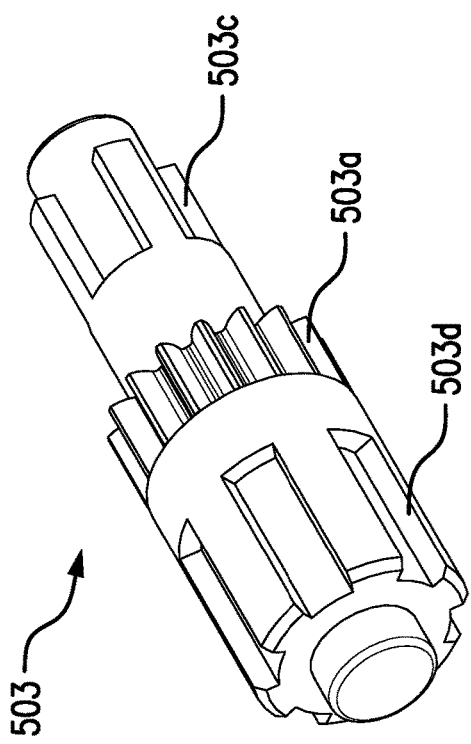
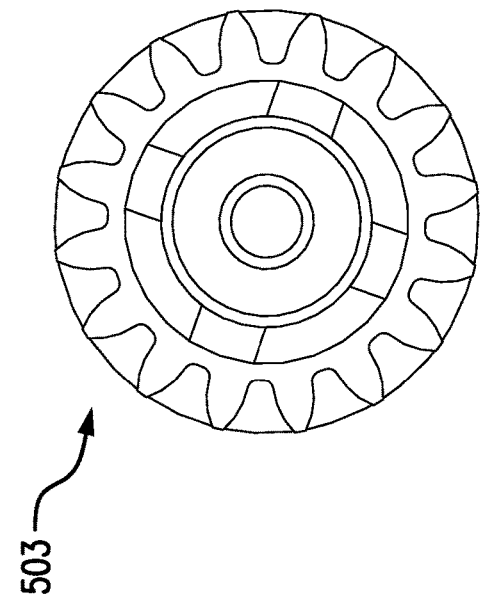
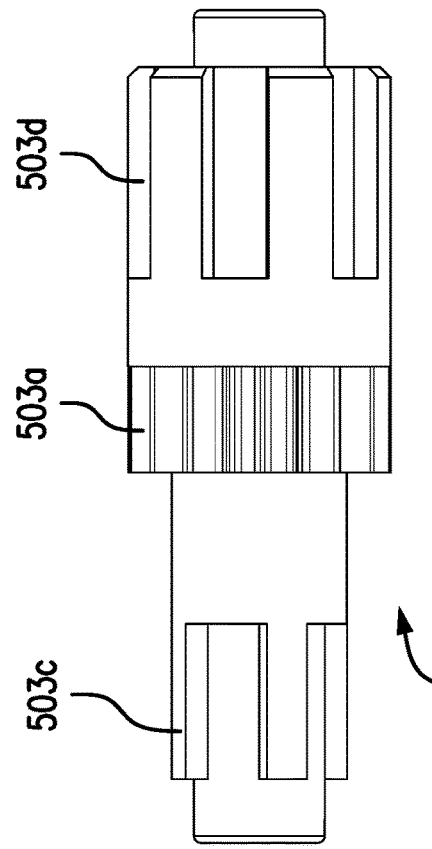
FIG. 65A
FIG. 65B
FIG. 65C
FIG. 65D

528

528

528

528

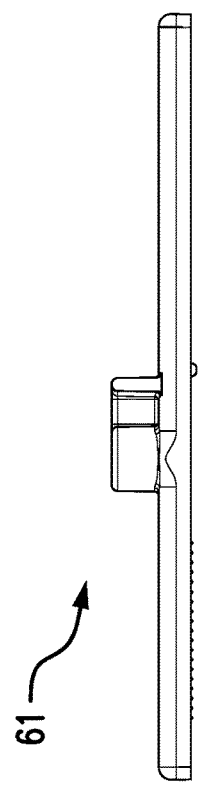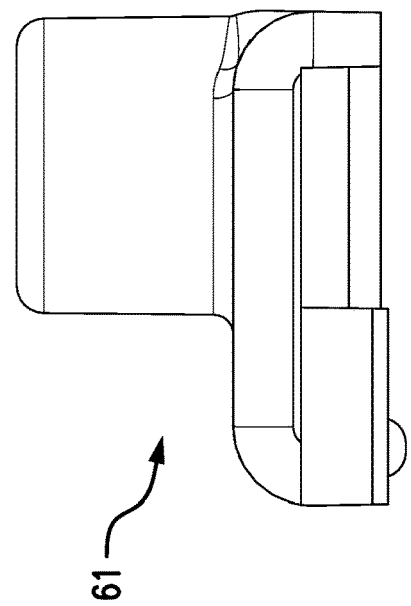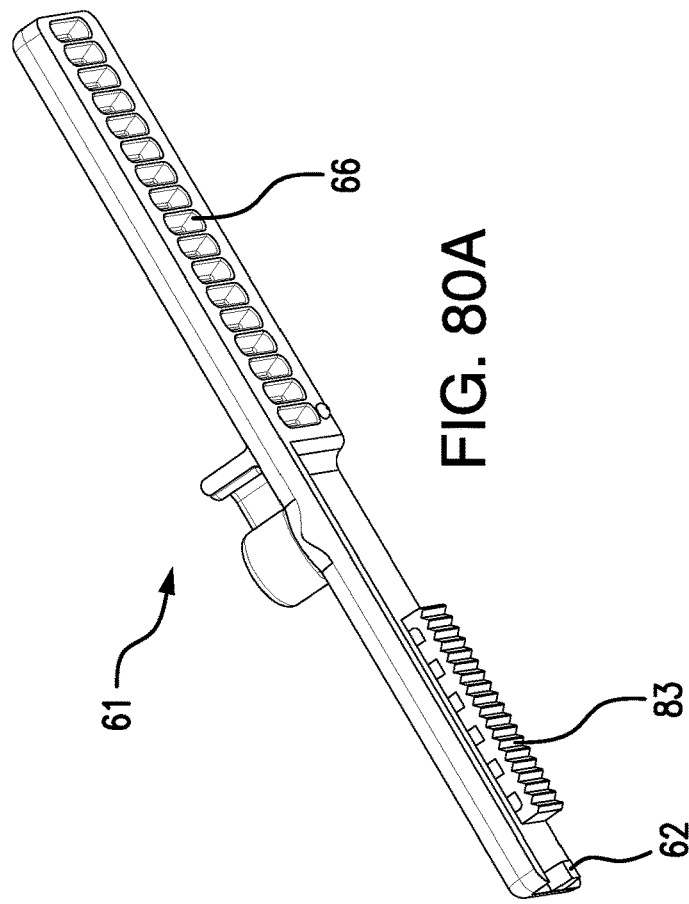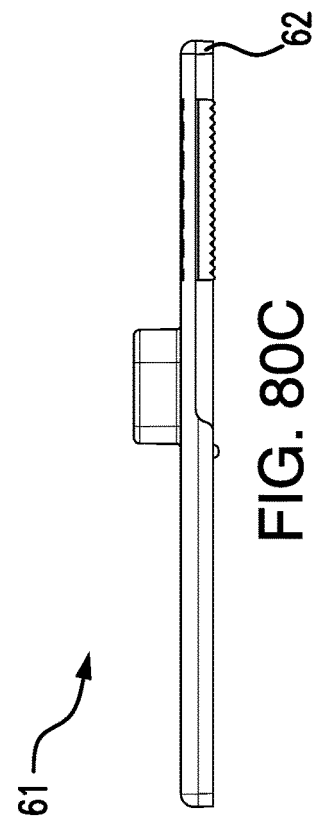

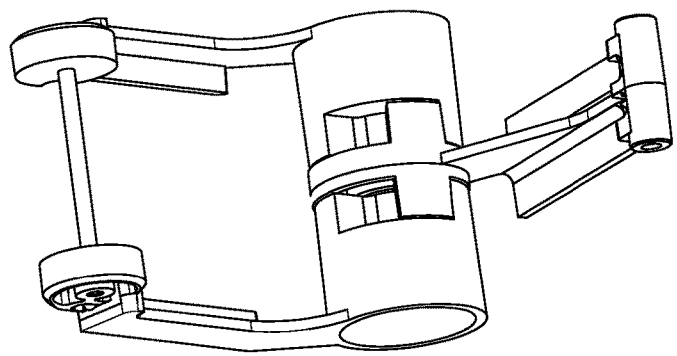
FIG. 84B
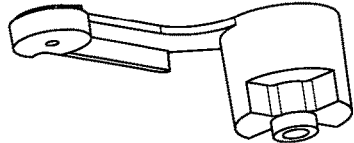
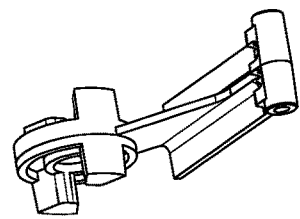
FIG. 84C
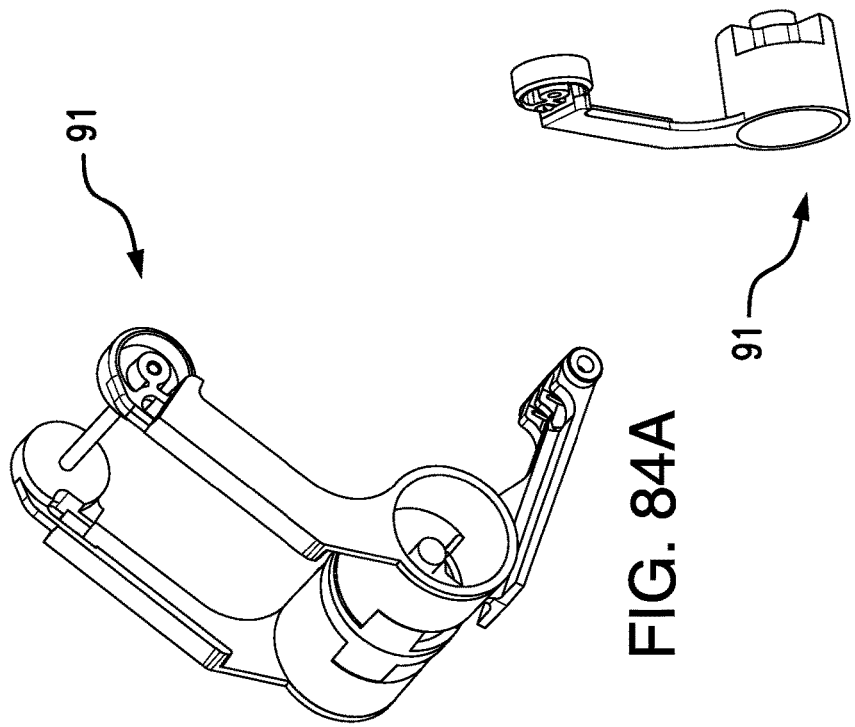
FIG. 84A

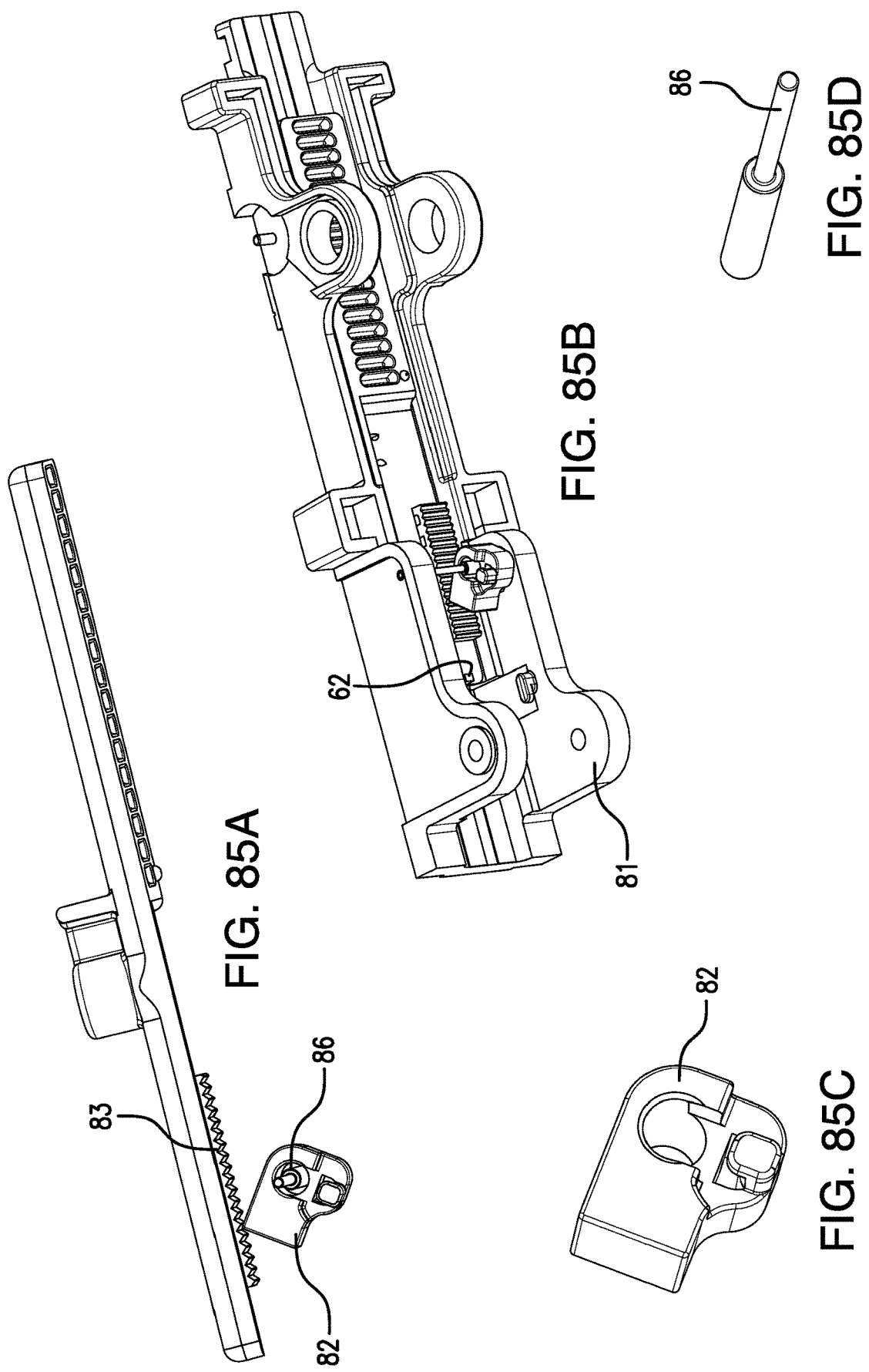

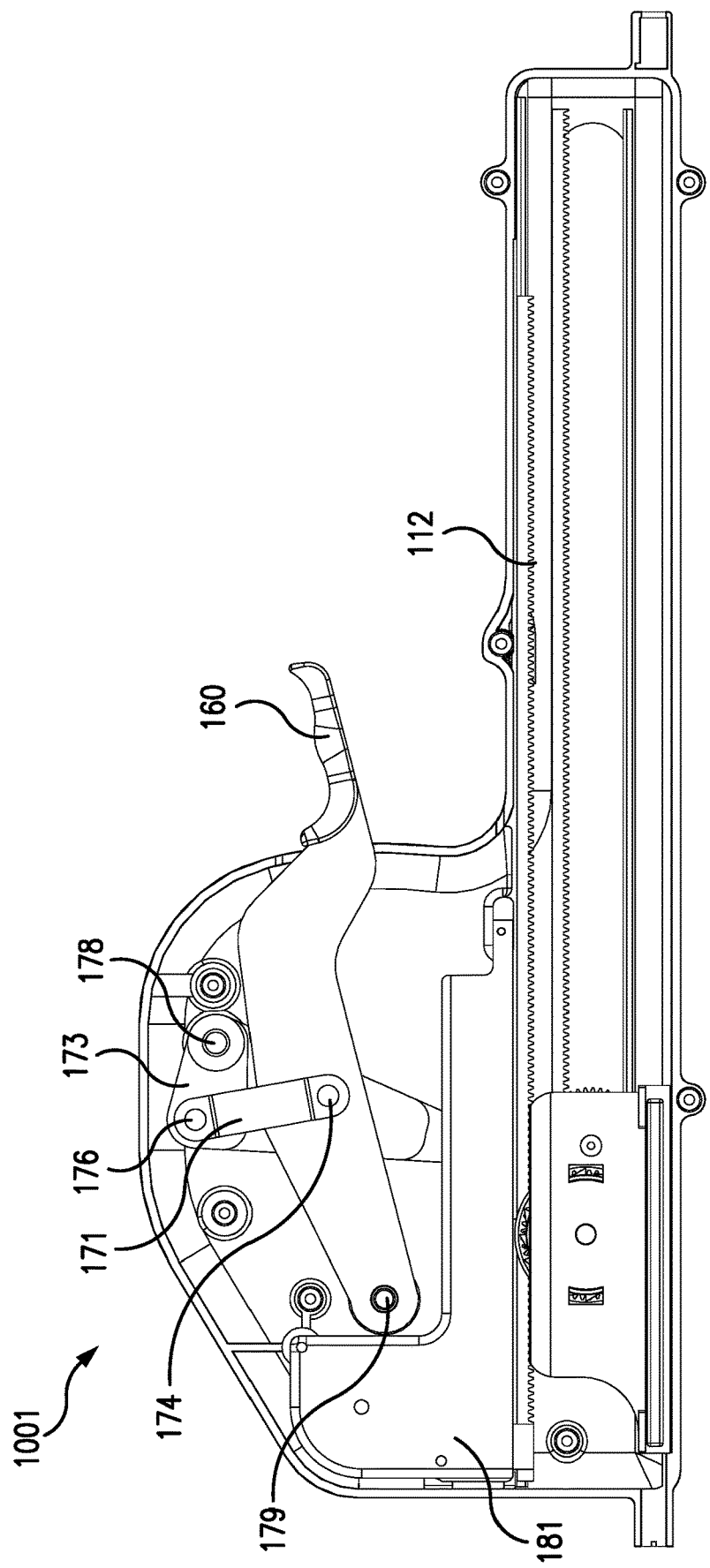

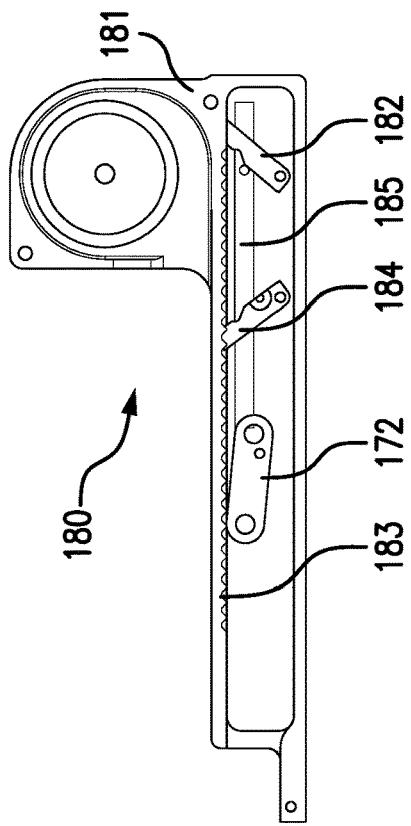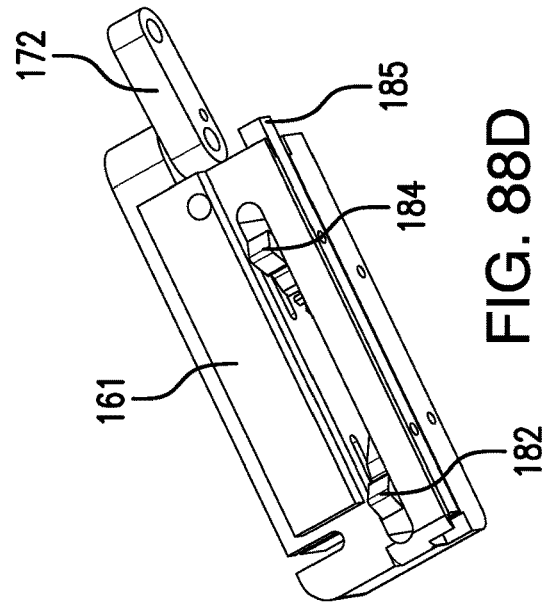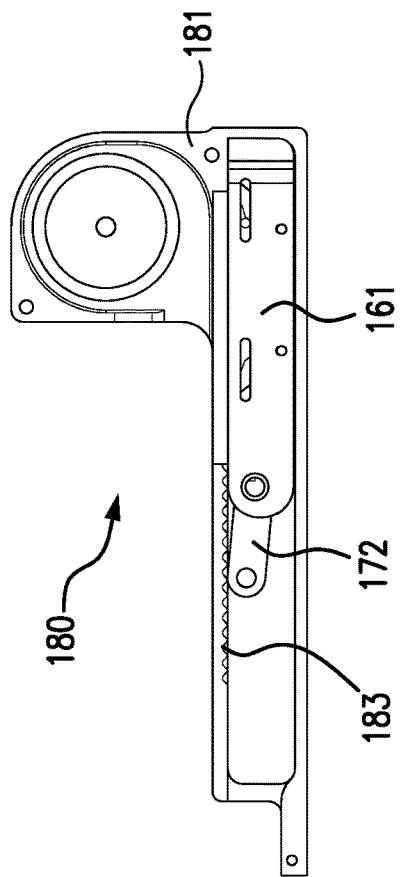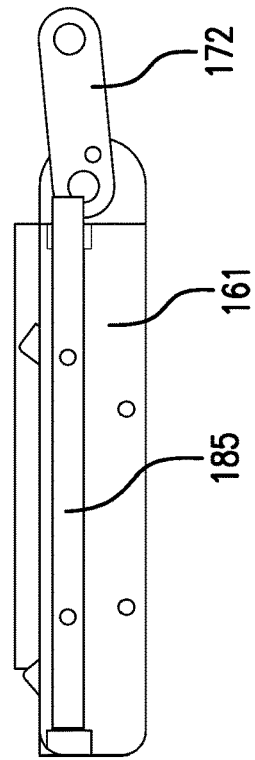

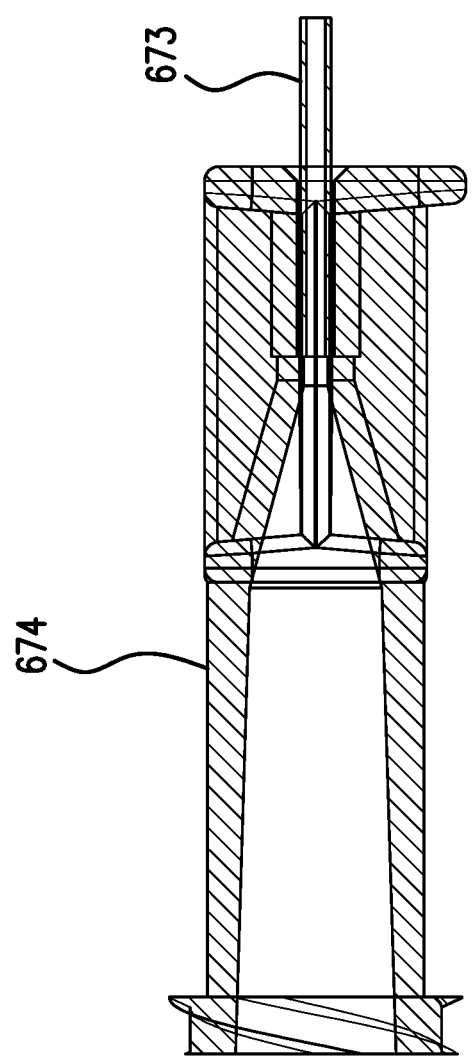

METHODS AND SYSTEMS FOR DELIVERING AN IMPLANT

CROSS-REFERENCE TO RELATED APPLICATIONS

This application claims priority to U.S. patent application Ser. No. 15/835,418, filed Dec. 7, 2017, which claims the benefit of U.S. Provisional Patent Application No. 62/497,929, filed Dec. 8, 2016, and the benefit of U.S. Provisional Patent Application No. 62/457,677, filed Feb. 10, 2017, each of which is incorporated herein by reference in its entirety.

BACKGROUND

Field of Disclosed Subject Matter

The disclosed subject matter is directed to systems and methods for delivering one or more medical devices, for example an implant, and more specifically, a braided implant. The braided implant, for example a stent or scaffold, can be disposed within a delivery system having an actuation assembly and catheter assembly configured to deliver the braided implant using a reciprocating motion.

Description of Related Art

Conventional self-expanding stent delivery systems can include a handle housing portion and an elongated shaft (e.g., a catheter assembly), wherein the stent is disposed within a delivery portion at the distal end of the shaft. To deploy the stent, an outer sheath typically is retracted relative to the stent, whereby the stent is exposed and released from its delivery configuration. In certain systems, an inner member having a pushing mechanism can be used push the stent from the outer sheath, while the outer sheath is retracted.

However, certain self-expanding implants, such as braided stents, experience excessive elongations when compressed to a delivery condition. Such configurations introduce unique challenges for delivery and deployment. As such, there remains a need for a catheter assembly, and related system and method, for delivering an implant, such as a braided stent, using a relatively simple motion and ease of use. Furthermore, there is a need for such a delivery system capable of being secured in a fixed position during activation, and having an outer profile less than or equal to 6 French.

SUMMARY

The purpose and advantages of the disclosed subject matter will be set forth in and apparent from the description that follows, as well as will be learned by practice of the disclosed subject matter. Additional advantages of the disclosed subject matter will be realized and attained by the methods and systems particularly pointed out in the written description and claims hereof, as well as from the appended drawings.

To achieve these and other advantages and in accordance with the purpose of the disclosed subject matter, as embodied and broadly described, the disclosed subject matter is directed to systems and methods for delivering an implant. For example, the system for delivering an implant can include a handle, a trigger operatively coupled to the handle, an actuation assembly operatively coupled to the trigger, and a catheter assembly operatively coupled to the actuation assembly. The catheter assembly can include an outer tubular member, an inner shaft member, and a pusher assembly. The outer tubular member can define an outer tubular member lumen and include an inner layer, a reinforcement layer, a middle layer, and an outer layer. The inner shaft member can be disposed at least partially within the outer tubular member lumen and include a proximal inner shaft portion and a distal inner shaft portion. The distal inner shaft portion can include a distal end portion. The pusher assembly can be coupled to the distal end portion of the distal inner shaft portion.

The actuation assembly as disclosed herein is a planetary gear type assembly. Particularly, the actuation assembly can include a planet carrier, at least one planet gear operatively coupled to the planet carrier, a sun gear shaft operatively engaged with the planet gear, a ring gear operatively engaged with the planet gear, a first clutch driver configured to limit the sun gear shaft to uni-directional rotational motion, and a second clutch driver configured to uni-directionally lock the sun gear shaft and the planet carrier.

The actuation assembly disclosed herein is configured to displace the outer tubular member in the proximal direction a distance (d) relative to the handle and to separately move the inner shaft member distally a distance (x) relative to the handle upon deployment of the trigger from a first position to a second position, and further the actuation assembly is configured to move the inner shaft member proximally a distance (y) relative to the handle with no displacement of the outer tubular member relative to the handle upon return of the trigger from the second position to the first position.

The second clutch driver can be configured to uni-directionally lock the sun gear shaft and the planet carrier such that the sun gear shaft, planet carrier and the ring gear have a 1:1 ratio of rotation during deployment of the trigger from the first position to the second position. The actuation assembly can also include a clutch release operatively coupled to the second clutch driver and configured to prevent the second clutch driver from uni-directionally locking the sun gear shaft and the planet carrier when the clutch release is engaged by a stop. The stop can be disposed on the handle, and the stop can engage the clutch release when the actuation assembly has moved proximally a distance (z) along the handle. For example, the clutch release can include a saw-tooth portion and the stop can include a resilient abutment portion, the resilient abutment portion of the stop can engage the saw-tooth portion of the clutch release when the actuation assembly has moved proximally a distance (z) along the handle.

The first clutch driver can be configured to limit the sun gear shaft to uni-directional motion such that the sun gear shaft does not rotate during return of the trigger from the second position to the first position and the planetary gear rotates about the sun gear shaft. The sun gear shaft can be functionally coupled to the outer tubular member such that upon deployment of the trigger from the first position to the second position the sun gear shaft rotates and thereby causes the outer tubular member to move proximally relative to the handle.

As embodied herein, the actuation assembly can include a shuttle frame having the planet carrier, planet gear, sun gear shaft, ring gear, first clutch driver and second clutch driver disposed thereon. The shuttle frame can be fixedly coupled to the outer tubular member. The sun gear shaft can be functionally coupled to the handle such that upon deployment of the trigger from the first position to the second position the sun gear shaft rotates and the shuttle frame moves proximally a distance relative to the handle. Additionally, the actuation assembly can include an intermediate gear functionally disposed on the shuttle frame between the sun gear shaft and the handle, and operatively engaged with the sun gear shaft.

Furthermore, the actuation assembly can include a ratchet rack fixedly coupled to the inner shaft member and disposed on the shuttle frame. The ratchet rack can be operatively engaged with the planet carrier. The ratchet rack can be operatively engaged with the ring gear.

The actuation assembly can be functionally coupled to the trigger by a driving rack. The driving rack can be operatively engaged with the ring gear and the driving rack can be supported by the handle. The driving rack can be operatively engaged with the planet carrier and the driving rack can be supported by the shuttle frame.

As further embodied herein, the actuation assembly can include at least one boss configured to engage at least one boss track disposed within the handle to thereby guide the shuttle frame along the handle. The at least one boss can include a first boss disposed through an axis of an intermediate gear functionally disposed on the shuttle frame between the sun gear shaft and the handle. The at least one boss can include a second and third boss, each of the second and third boss disposed through the shuttle frame. The at least one boss can include a fourth boss disposed through an axis of the sun gear shaft. The actuation assembly further can include a plate disposed on the shuttle frame.

A sheath gondola can also be provided, disposed between the outer tubular member and the sun gear shaft, wherein the sheath gondola is functionally coupled to the sun gear shaft by a first tension element. The actuation assembly can include a ratchet gondola disposed between the inner tubular member and the ring gear, wherein the ratchet gondola is functionally coupled to the ring gear by a second tension element.

The sun gear shaft can include a sun gear portion, a sheath pinion, and a clutch engagement portion. The planet carrier can include a circumferential pinion, a clutch component, and at least one pin. The ring gear can include a circumferential pinion and a ring gear portion. The first clutch driver and the second clutch driver can each include a sun gear shaft engagement portion and a clutch portion.

As embodied herein, the actuation assembly can be functionally coupled to the trigger by a driving rack. The trigger can include a slide having an engagement surface to be engaged by the user.

The trigger of the disclosed subject matter can be functionally connected to the driving rack by a gear train. The gear train can include a trigger gear sector, a trigger pinion operatively meshed with the trigger gear sector, a slide pinion operatively coupled to the trigger pinion, and a slide rack disposed on a slide coupled to the driving rack and operatively meshed with the trigger pinion. The driving rack can be fixedly coupled to the slide. The driving rack can be detachably coupled to the slide.

The inner layer of the outer tubular member can be fluorinated ethylene propylene. The reinforcement layer of the outer tubular member can be a stainless steel braid. The reinforcement layer of the outer tubular member can be Teflon fibers. The middle layer of the outer tubular member can be polyimide. The outer layer of the outer tubular member can be Grilamid.

The outer tubular member further can include an atraumatic distal tip having a distally tapered end. The atraumatic distal tip can be heat bonded to the outer tubular member. The atraumatic distal tip can be mounted to an outer diameter of the outer tubular member. The atraumatic distal tip can be polyether block amide. The implant can be disposed within the outer tubular member lumen proximate the pusher assembly.

The catheter assembly can include a stabilizer member having a stabilizer lumen defined therethrough. The stabilizer lumen can have an inner diameter sized to receive the outer tubular member therein. The outer tubular member can be configured to rotate about a central longitudinal axis relative to the stabilizer member. The stabilizer member can include an inner layer, a reinforcement layer, a middle layer, and an outer layer. The stabilizer member can have a distal end portion having an atraumatic tip.

The catheter assembly can include a strain relief coupled to a proximal end portion of the stabilizer member. The stabilizer member can be configured to rotate about a central longitudinal axis relative the strain relief. The catheter assembly can have an outer profile less than or equal to 6 French.

At least one of the proximal inner shaft portion and the distal inner shaft portion can include an inner layer, a reinforcement layer, and an outer layer. The distal inner shaft portion can be a distal inner shaft member and the proximal inner shaft portion can be a proximal inner shaft member coupled to the distal inner shaft member. A proximal end portion of the distal inner shaft member can be heat bonded to a distal end portion of the proximal inner shaft member. A proximal end portion of the distal inner shaft portion can be an inner taper. An outer diameter at a proximal end portion of the distal inner shaft member can be sized to be received within an inner diameter at a distal end portion of the proximal inner shaft member.

A support tube can be disposed within the outer tubular member lumen. A support coil can be disposed within the outer tubular member lumen distal of the support tube. The pusher assembly can include a stem coupled to the distal end portion of the distal inner shaft portion and an implant-engaging member extending from the stem. A guidewire lumen can be coupled to a distal end portion of the stem and can extend distally of the outer tubular member. The guidewire lumen can include at least one radiopaque marker. A hypotube can be disposed at least partially within an inner shaft member lumen defined by the inner shaft member. A polymer sleeve can be secured to a distal end portion of the hypotube. A luer coupled to a proximal end portion of the hypotube. A ratchet rack can be coupled to a proximal end portion of the proximal inner shaft portion. The inner shaft member can be configured to rotate about a central axis relative to the actuation assembly.

In accordance with the disclosed subject matter, a catheter assembly is provided. The catheter assembly includes an outer tubular member, an inner shaft member, and a pusher assembly. The outer tubular member defines an outer tubular member lumen and includes an inner layer, a reinforcement layer, a middle layer, and an outer layer. The inner shaft member is disposed at least partially within the outer tubular member lumen and includes a proximal inner shaft portion and a distal inner shaft portion. The distal inner shaft portion includes a distal end portion. The pusher assembly is coupled to the distal end portion of the distal inner shaft portion. The inner shaft member is configured to move distally and proximally relative the outer tubular member between an initial position and a deployed position.

The inner layer of the outer tubular member can be fluorinated ethylene propylene. The reinforcement layer of the outer tubular member can be a stainless steel braid. The reinforcement layer of the outer tubular member can be Teflon fibers. The middle layer of the outer tubular member can be polyimide. The outer layer of the outer tubular member can be Grilamid.

The outer tubular member further can include an atraumatic distal tip having a distally tapered end. The atraumatic distal tip can be heat bonded to the outer tubular member. The atraumatic distal tip can be mounted to an outer diameter of the outer tubular member. The atraumatic distal tip can be polyether block amide. The implant can be disposed within the outer tubular member lumen proximate the pusher assembly.

The catheter assembly can include a stabilizer member having a stabilizer lumen defined therethrough. The stabilizer lumen can have an inner diameter sized to receive the outer tubular member therein. The outer tubular member can be configured to rotate about a central longitudinal axis relative to the stabilizer member. The stabilizer member can include an inner layer, a reinforcement layer, a middle layer, and an outer layer. The stabilizer member can have a distal end portion having an atraumatic tip.

The catheter assembly can include a strain relief coupled to a proximal end portion of the stabilizer member. The stabilizer member can be configured to rotate about a central longitudinal axis relative the strain relief. The catheter assembly can have an outer profile less than or equal to 6 French.

At least one of the proximal inner shaft portion and the distal inner shaft portion can include an inner layer, a reinforcement layer, and an outer layer. The distal inner shaft portion can be a distal inner shaft member and the proximal inner shaft portion can be a proximal inner shaft member coupled to the distal inner shaft member. A proximal end portion of the distal inner shaft member can be heat bonded to a distal end portion of the proximal inner shaft member. A proximal end portion of the distal inner shaft portion can be an inner taper. An outer diameter at a proximal end portion of the distal inner shaft member can be sized to be received within an inner diameter at a distal end portion of the proximal inner shaft member.

A support tube can be disposed within the outer tubular member lumen. A support coil can be disposed within the outer tubular member lumen distal of the support tube. The pusher assembly can include a stem coupled to the distal end portion of the distal inner shaft portion and an implant-engaging member extending from the stem. A guide wire lumen can be coupled to a distal end portion of the stem and can extend distally of the outer tubular member. The guidewire lumen can include at least one radiopaque marker. A ratchet rack can be coupled to a proximal end portion of the proximal inner shaft portion.

A hypotube can be disposed at least partially within an inner shaft member lumen defined by the inner shaft member. A polymer sleeve can be secured to a distal end portion of the hypotube. A luer can be coupled to a proximal end portion of the hypotube. The inner shaft member can be configured to rotate about a central axis relative to the actuation assembly.

In accordance with the disclosed subject matter a deliver system for delivering an implant can include a handle, a trigger operatively coupled to the handle, an actuation assembly operatively coupled to the trigger, and a catheter assembly operatively coupled to the actuation assembly. The catheter assembly can include an outer tubular member, an inner shaft member, and a pusher assembly. The outer tubular member defines an outer tubular member lumen and includes an inner layer, a reinforcement layer, a middle layer, and an outer layer. The inner shaft member is disposed at least partially within the outer tubular member lumen and includes a proximal inner shaft portion and a distal inner shaft portion. The distal inner shaft portion includes a distal end portion. The pusher assembly is coupled to the distal end portion of the distal inner shaft portion. The inner shaft member is configured to move distally and proximally relative the outer tubular member between an initial position and a deployed position. The actuation assembly can be configured to displace the outer tubular member in the proximal direction a first distance (d) relative to the handle and to separately move the inner shaft member distally a second distance (x) relative to the handle upon deployment of the trigger from a first position to a second position, and further wherein the actuation assembly can be configured to move the inner shaft member proximally a third distance (y) relative to the handle with no displacement of the outer tubular member relative to the handle upon return of the trigger from the second position to the first position. The delivery system can include a stabilizer member and the catheter assembly can have an outer profile less than or equal to 6 French.

In accordance with the disclosed subject matter, a method of forming a catheter assembly for delivering a medical device can include forming an outer tubular member having an inner layer, a reinforcement layer, a middle layer, and an outer layer, providing, and inserting into the outer tubular member, an inner shaft member comprising a proximal inner shaft portion and a distal inner shaft portion, each of the proximal inner shaft portion and distal inner shaft portion comprising an inner layer, a reinforcement layer, and an outer layer, and providing, and positioning about the outer tubular member, a stabilizer member having an inner layer, a reinforcement layer, a middle layer, and an outer layer.

Forming the outer tubular member can include forming the outer tubular member by a coating process. Providing the stabilizer member can include forming the stabilizer member by a coating process. Providing the inner shaft member can include forming the stabilizer member by a coating process.

As further disclosed herein, a system for delivering an implant is provided. The system can include a handle, as well as a trigger, an outer tubular member, and an inner shaft member, each operatively coupled to the handle. An implant can be provided with the system as a kit or separately. The trigger can be movable between a first position and a second position. The handle can further have an actuation assembly operatively coupled to the trigger. The outer tubular member can include a proximal end portion and a distal end portion, wherein the outer member is operatively coupled to the actuation assembly and movable in a proximal direction relative to the handle. The inner shaft member can include a proximal end portion and a distal end portion. The inner shaft member is disposed within the outer tubular member and operatively coupled to the actuation assembly. The inner shaft member can be movable distally and proximally relative to the outer tubular member. The implant can be disposed within the distal end portion of the outer tubular member and positioned to be engaged by the distal end portion of the inner shaft member when the inner shaft member is moved distally relative to the outer tubular member. The actuation assembly disclosed herein is configured to displace the outer tubular member in the proximal direction a distance (d) relative to the handle and to separately move the inner shaft member distally a distance (x) relative to the handle upon deployment of the trigger from the first position to the second position, and further wherein the actuation assembly is configured to move the inner shaft member proximally a distance (y) relative to the handle with no displacement of the outer tubular member relative to the handle upon return of the trigger from the second position to the first position.

The distance (y) minus the distance (x) can substantially equal the distance (d). Upon deployment of the trigger from the first position to the second position and return of the trigger from the second position to the first position, a net displacement of the inner shaft member relative to the outer tubular member can be zero. The braided implant can have a length, the length of the braided implant can be less than the distance (x). Repeatedly deploying the trigger from the first position to the second position and returning the trigger from the second position to the first position can cause the inner shaft member to urge the braided implant from the outer tubular member. The actuation assembly can be configured to displace the outer tubular member a distance (d) in the proximal direction relative to the handle upon deployment of the trigger from the first position to the second position. The handle can be configured to fit within a hand of a user and upon repeated deployment of the trigger from the first position to the second position and return of the trigger from the second position to the first position the actuation assembly can be configured to move from a position within the handle distal of the user's hand to a position within the handle proximal of the user's hand. The actuation assembly can include a planetary gear system.

According to another embodiment of the disclosed subject matter, a system for delivering an implant is provided. The system can include a handle, a trigger operatively coupled to the handle, and an actuation means configured to displace the outer tubular member in the proximal direction a distance (d) relative to the handle and to separately move the inner shaft member distally a distance (x) relative to the handle upon deployment of the trigger from a first position to a second position, and further wherein the actuation assembly is configured to move the inner shaft member proximally a distance (y) relative to the handle with no displacement of the outer tubular member relative to the handle upon return of the trigger from the second position to the first position.

Alternatively, or additionally, the trigger can be functionally connected to the driving rack by one or more link elements. For example, a plurality of link elements can be provided. The plurality of link elements can include a first linear link coupled to the trigger at a first joint, a second linear link coupled to the slide at a second joint, and a triangle link coupled to the first linear link at a third joint and the second linear link at a fourth joint. The triangle link can be coupled to the handle at a fifth joint, and the trigger can be coupled to the handle at a sixth joint. Each of the first, second, third, fourth, fifth, and sixth joints can be pivot joints. The third joint, fourth joint, and fifth joint thus can define a triangle. Upon deployment of the trigger from the first position to the second position and return of the trigger from the second position to the first position, the third joint can trace a non-linear path. Alternatively, the trigger can be functionally connected to the driving rack by a trigger pulley system.

Furthermore, the system can include a ratchet mechanism functionally coupled to the trigger. The ratchet mechanism can include a first state configured to allow the trigger to move toward the second position and prohibit motion toward the first position. The ratchet mechanism can include a second state configured to allow the trigger to move toward the first position and prohibit motion toward the second position. As embodied herein, the ratchet mechanism can include a first pawl and a trigger ratchet rack configured to engage the pawl to permit unidirectional motion of the slide. The pawl can include a first state wherein the pawl engages the trigger ratchet rack to permit unidirectional motion of the slide in a first direction. The pawl can include a second state wherein the pawl engages the trigger ratchet rack to permit unidirectional motion of the slide in a second direction. The pawl can be configured to switch from the first state to the second state as the trigger approaches the second position from the first position. The pawl can be configured to switch from the second state to the first state as the trigger approaches the first position from the second position. The pawl can be configured to be disengaged with the trigger ratchet rack by urging the pawl away from the trigger ratchet rack. The pawl can be biased toward engagement with the trigger ratchet rack.

Additionally, the ratchet mechanism can include a second pawl having a first state wherein the second pawl engages the ratchet rack to permit unidirectional motion of the slide in a second direction. The first and second pawl can each have a second state wherein the first and second pawl do not engage the trigger ratchet rack, particularly when the other pawl is in engagement. In this manner when the first pawl is in the first state the second pawl can be in the second state and when the second pawl is in the first state the first pawl can be in the second state. The ratchet mechanism can also include a ratchet trip coupled to the first and second pawls. As the trigger approaches the second position from the first position the ratchet trip can cause the first pawl to switch from the first state to the second state and the ratchet trip can cause the second pawl to switch from the second state to the first state. As the trigger approaches the first position from the second position the ratchet trip can cause the first pawl to switch from the second state to the first state and the ratchet trip can cause the second pawl to switch from the first state to the second state.

As disclosed herein, the trigger can be coupled to a spring such that energy is stored in the spring upon deployment of the trigger from the first position to the second position, and the energy stored in the spring causes the trigger to return from the second position to the first position. The system can include a spring support coupled to the trigger and a base and configured to engage the spring such that energy is stored in the spring when the trigger is in the first position.

It is to be understood that both the foregoing general description and the following detailed description are exemplary and are intended to provide further explanation of the disclosed subject matter claimed.

The accompanying drawings, which are incorporated in and constitute part of this specification, are included to illustrate and provide a further understanding of the disclosed subject matter. Together with the description, the drawings serve to explain the principles of the disclosed subject matter.

BRIEF DESCRIPTION OF THE FIGURES

FIGS. 27A-27D provide perspective FIG. 27A, right FIG. 27B, left FIG. 27C, and front FIG. 27D views of the sun gear shaft of the delivery system of FIG. 24.

FIGS. 29A-29D provide perspective FIG. 29A, right FIG. 29B, left FIG. 29C, and front FIG. 29D views of the ring gear of the delivery system of FIG. 24.

FIGS. 34A-34C are various views showing the relationship between the shuttle frame, driving rack, and ring gear of the delivery system of FIG. 24.

FIG. 35 is a perspective view showing the relationship between the planet carrier and the ratchet member of the delivery system of FIG. 24.

FIGS. 59A-59D provide perspective FIG. 59A, right FIG. 59B, left FIG. 59C, and front FIG. 59D views of the shuttle frame of the delivery system of FIG. 52.

FIGS. 65A-65D provide perspective FIG. 65A, right FIG. 65B, left FIG. 65C, and front FIG. 65D views of the sun gear shaft of the delivery system of FIG. 62.

FIGS. 80A-80D provide perspective FIG. 80A, right FIG. 80B, left FIG. 80C, and front FIG. 80D views of the slide of the delivery system of FIG. 1A.

FIGS. 84A-84C are various views depicting the spring support of the delivery system of FIG. 1A.

FIGS. 85A-85D are various views depicting selected elements and the relationship between selected elements of the ratchet mechanism of the delivery system of FIG. 1A.

FIG. 86 is a right side view, with a portion of the handle housing removed, of the delivery system of FIG. 24.

FIGS. 88A-88D provides various views of selected elements and the relationship between selected elements of the ratchet mechanism of the delivery system of FIG. 24.

FIG. 104 is an enlarged detail view of section 104.

DETAILED DESCRIPTION

Figure 1A:
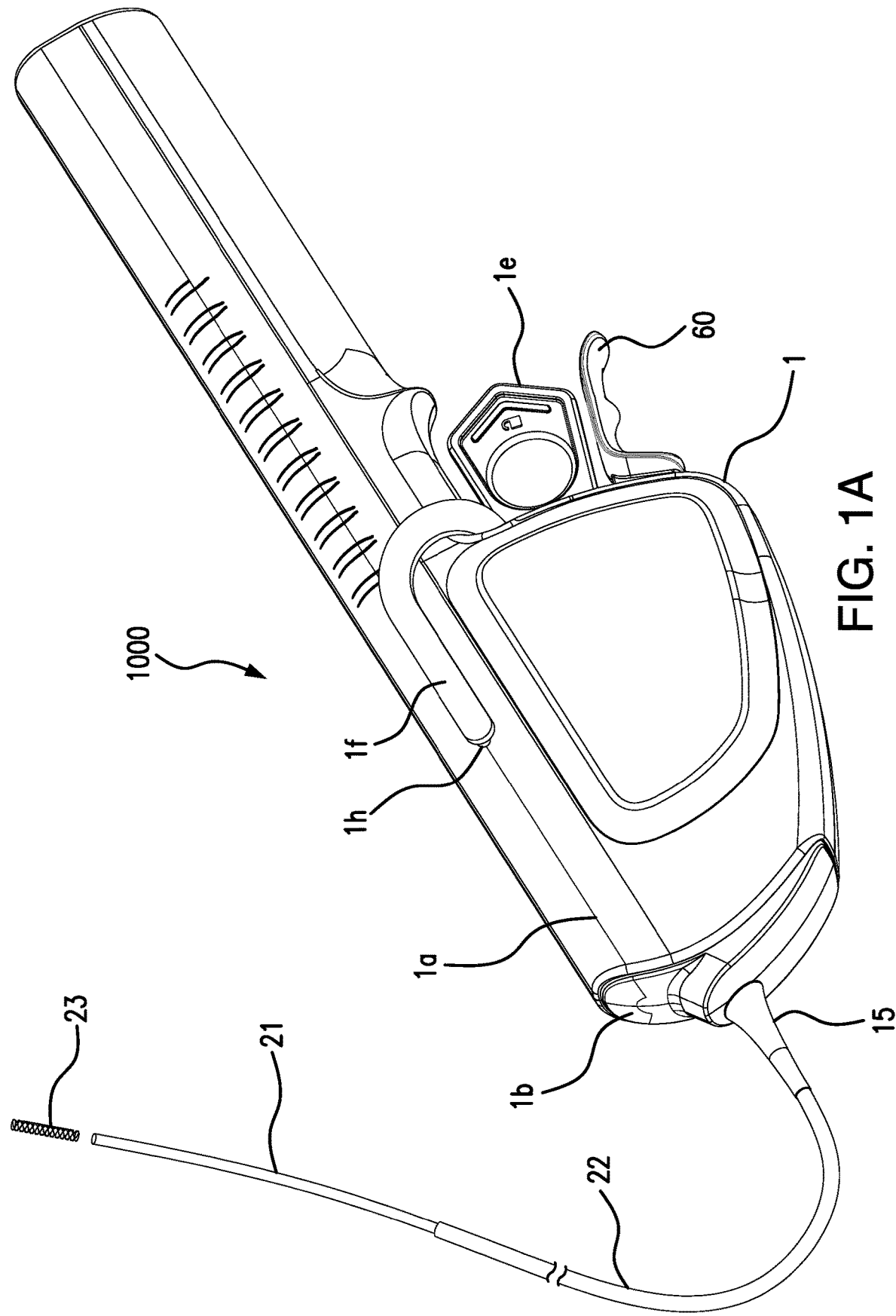
FIG. 1A is a right perspective view as viewed from a front of an exemplary embodiment of a delivery system in accordance with the disclosed subject matter.
Figure 1B:
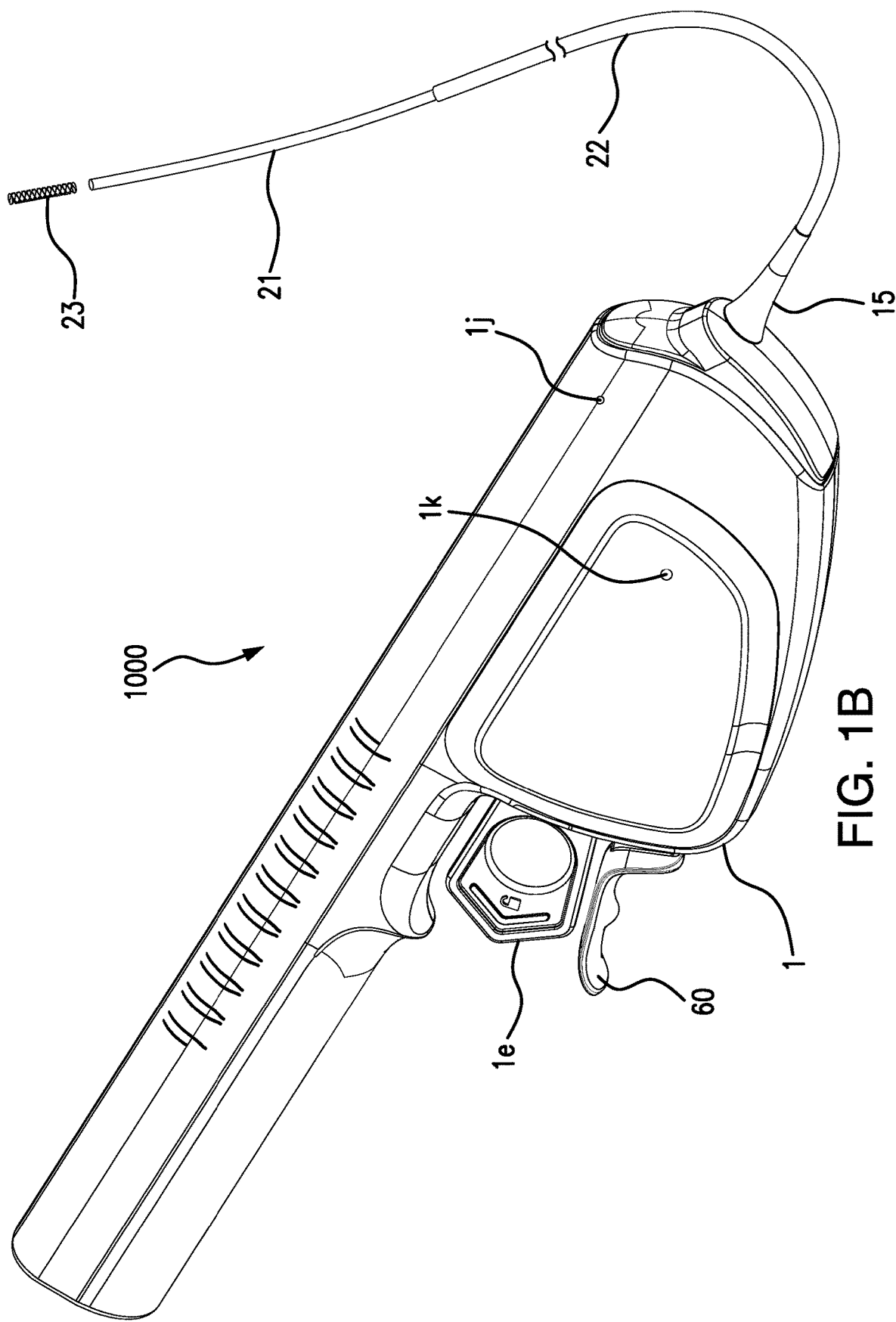
FIG. 1B is left perspective view of the delivery system of FIG. 1A.
Figure 1C:
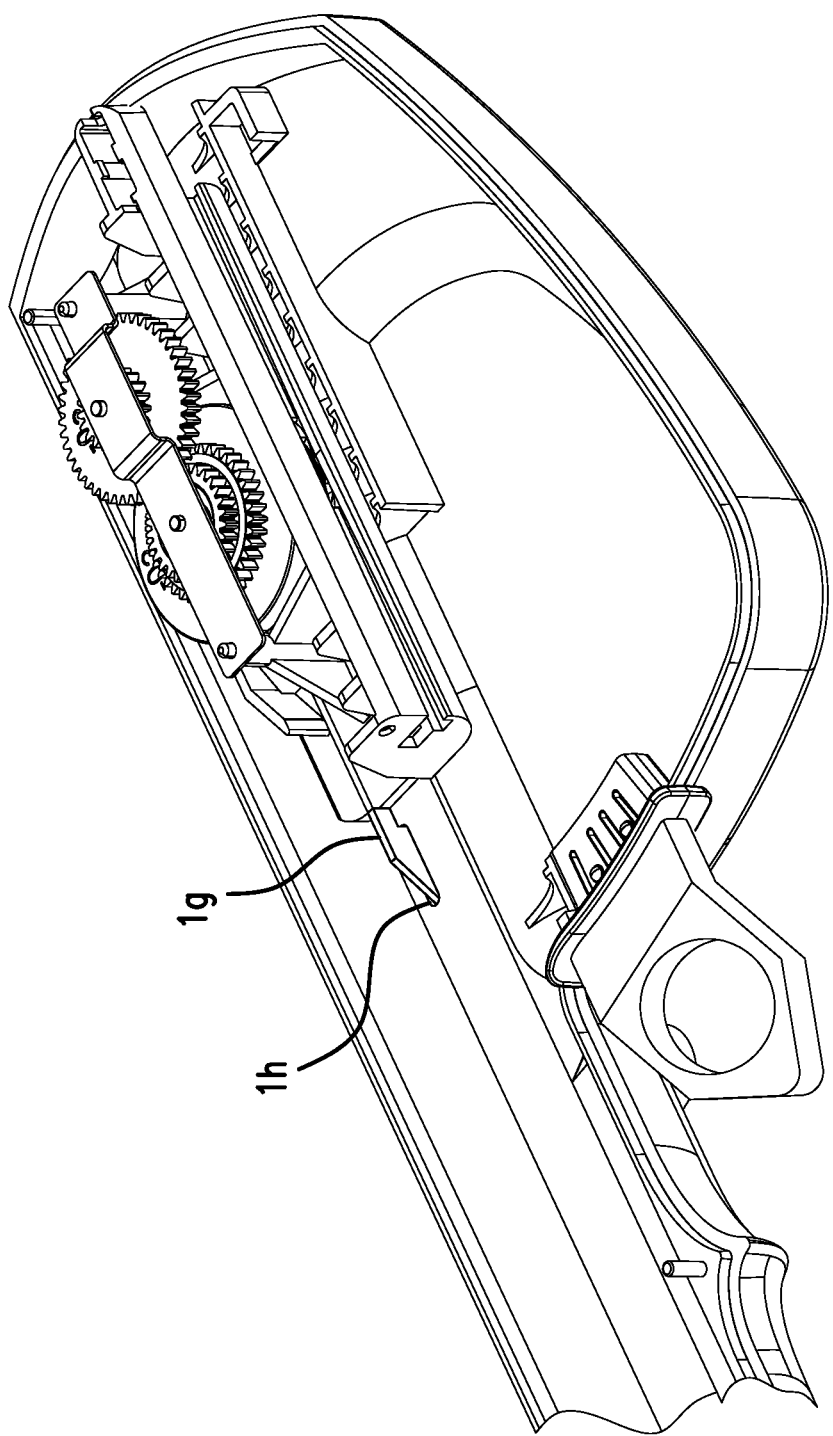
FIG. 1C is a left perspective view of a right half of the housing with a portion of the handle housing removed, of the delivery system of FIG. 1A.

Reference will now be made in detail to the various exemplary embodiments of the disclosed subject matter, exemplary embodiments of which are illustrated in the accompanying drawings. The structure and corresponding method of making and using the disclosed subject matter will be described in conjunction with the detailed description of the delivery system. The methods and systems described herein can be used for delivering a medical device, such as a stent, scaffold stent graft, valve, filter, or other suitable implant to a desired location in a patient.

Generally, and as set forth in greater detail, the disclosed subject matter provided herein includes a delivery system having a handle, a trigger, an actuation assembly, and a catheter assembly. The trigger is operatively coupled to the handle. The actuation assembly is operatively coupled to the trigger, the inner shaft member, and the outer tubular member. As used herein the terms "functionally" and "operatively" as used with "coupled," "engaged," or "connected," are interchangeable and understood by one of skill in the art. The actuation assembly includes a planet carrier, at least one planet gear operatively coupled to the planet carrier, a sun gear shaft operatively engaged with the planet gear, a ring gear operatively engaged with the planet gear, a first clutch driver configured to limit the sun gear shaft to uni-directional rotational motion, and a second clutch driver configured to uni-directionally lock the sun gear shaft and the planet carrier. The actuation assembly is configured to displace the outer tubular member in the proximal direction a distance (d) relative to the handle and to separately move the inner shaft member distally a distance (x) relative to the handle upon deployment of the trigger from a first position to a second position, and further wherein the actuation assembly is configured to move the inner shaft member proximally a distance (y) relative to the handle with no displacement of the outer tubular member relative to the handle upon return of the trigger from the second position to the first position. The catheter assembly as disclosed herein includes the outer tubular member, the inner shaft member, and a pusher assembly. The outer tubular member defines an outer tubular member lumen and includes an inner layer, a reinforcement layer, a middle layer, and an outer layer. The inner shaft member is disposed at least partially within the outer tubular member lumen and includes a proximal inner shaft portion and a distal inner shaft portion. The distal inner shaft portion includes a distal end portion. The pusher assembly is coupled to the distal end portion of the distal inner shaft portion. The inner shaft member is configured to move distally and proximally relative the outer tubular member between an initial position and a deployed position.

In accordance with the described subject matter, a trigger assembly for a delivery system is also provided. The trigger assembly includes a trigger functionally connected to the actuation assembly by a driving rack, a gear train functionally disposed between the trigger and the driving rack. The gear train includes a trigger gear sector, a trigger pinion operatively meshed with the trigger gear sector, a slide pinion operatively coupled to the trigger pinion, and a slide rack disposed on a slide coupled to the driving rack and operatively meshed with the trigger pinion.

A variety of types of medical devices are suitable for delivery by the delivery system of the present invention. For purpose of illustration and not limitation, the delivery system is described herein with a medical device depicted as a self-expanding stent. Particularly, although not by limitation, reference is made herein to the implant being a braided stent or scaffold for purpose of illustration only. However, the delivery system presently disclosed is not limited to the delivery of self-expanding stents. Other devices can also be used. For example, scaffolds, coils, filters, stent grafts, embolic protection devices, and artificial valves can be delivered within a patient's vasculature, heart, or other organs and body lumens using the disclosed delivery system. Other devices such as a prosthesis retrieval mechanism can also be delivered with the delivery system to a predetermined location in a patient's luminal system. Moreover, a combination of medical devices and/or beneficial agents can also be delivered using the disclosed subject matter. For example, multiple stents and/or a combination of stents and embolic protection devices and/or beneficial agents can be delivered by the disclosed subject matter, as described below. Additional information related to delivery of implants can be found in U.S. application Ser. No. 11/876,764, filed on Oct. 22, 2007, and U.S. application Ser. No. 13/118,325, filed on May 27, 2011, U.S. application Ser. No. 14/932,848, filed Nov. 4, 2015, U.S. application Ser. No. 14/932,795, filed Nov. 4, 2015, U.S. application Ser. No. 14/932,875, filed Nov. 4, 2015, U.S. application Ser. No. 14/932,862, filed Nov. 4, 2015, U.S. application Ser. No. 14/932,884, filed Nov. 4, 2015, U.S. application Ser. No. 14/932,805, filed Nov. 4, 2015, U.S. application Ser. No. 14/932,830, filed Nov. 4, 2015, and U.S. application Ser. No. 14/932,900, filed Nov. 4, 2015, each of which is incorporated by reference in its entirety herein.

Referring to FIG. 1A for the purpose of illustration and not limitation, various embodiments of the delivery systems disclosed herein generally can include a handle 1, and a catheter assembly 100 (for purpose of clarity all features of catheter assembly 100 as embodied herein are not shown in FIG. 1A). An implant 23, for example a braided implant, can be provided with the system or independently. The handle can include a trigger assembly including a trigger 60 movable between and first position and a second position, and an actuation assembly 2 (see e.g., FIG. 3) operatively coupled to the trigger 60. The outer tubular member 22 can include a proximal end portion and a distal end portion. The outer tubular member 22 can be operatively coupled to the actuation assembly 2 and can be movable in a proximal direction relative to the handle 1. A stabilizer tube (not shown) can be disposed over at least the proximal end portion of the outer tubular member 22, and a strain relief 15 can be used to couple the stabilizer tube and the handle 1. The inner shaft member 21 can include a proximal end portion and a distal end portion. The inner shaft member 21 can be disposed within the outer tubular member 22 and can be operatively coupled to the actuation assembly 2. The inner shaft member 21 of the disclosed delivery system is movable distally and proximally relative to the outer tubular member 22. The implant 23 can be disposed within the distal end portion of the outer tubular member 22 and can be positioned to be engaged by the distal end portion of the inner shaft member 21 when the inner shaft member is moved distally relative to the outer tubular member 22. To engage the implant, the distal end portion of the inner shaft member 21 can have a pusher assembly 660 disposed thereon. For example, U.S. application Ser. No. 13/118,325, filed on May 27, 2011, which is incorporated by reference in its entirety herein, discloses suitable pusher elements for the delivery system. The outer tubular member 22 is depicted with a break in FIG. 1A to indicate that the length shown is only exemplary and the outer tubular member 22 and inner shaft member 21 can be longer than shown. Indeed, any suitable length can be used. As an example and not by way of limitation, the outer tubular member 22 and inner shaft member 21 can be long enough to extend from outside the body of a patient through a tortuous path to a treatment location within the body of a patient. For example, and not by way of limitation, the outer tubular member 22 can be between 20 and 70 inches long, for example, the outer tubular member 22 can be about 33 or 55 inches long. For example, and not by way of limitation, the inner shaft member 21 can be between 25 and 65 inches long, for example, the inner shaft member 21 can be about 34 or 56 inches long. The handle 1 can further include a luer lock at the proximal end of the handle to receive a guidewire therethrough which can extend through the inner shaft member and/or a flushing device as desired.

The actuation assembly 2 of the disclosed subject matter is configured to displace the outer tubular member 22 in the proximal direction a distance (d) relative to the handle 1 and to separately move the inner shaft member 21 distally a distance (x) relative to the handle 1 upon deployment of the trigger 60 from the first position to the second position. Furthermore, the actuation assembly 2 is configured to move the inner shaft member 21 proximally a distance (y) relative to the handle 1 with no displacement of the outer tubular member 22 relative to the handle 1 upon return of the trigger 60 from the second position to the first position. Put another way, the actuation assembly 2 can be configured to move the outer tubular member 22 in a proximal direction relative to the handle 1 and to separately move the inner shaft member 21 distally relative to the outer tubular member 22 upon deployment of the trigger 60 from the first position to the second position. The actuation assembly 2 can further be configured to move the inner shaft member 21 proximally relative to the outer tubular member 22 with no displacement of the outer tubular member 22 relative to the handle 1 upon return of the trigger 60 from the second position to the first position. Repeatedly deploying the trigger 60 from the first position to the second position and returning the trigger from the second position to the first position can cause the inner shaft member 21 to urge the implant 23 from the outer tubular member 22. The distance (y) minus the distance (x) can be substantially equal to the distance (d).

Upon deployment of the trigger 60 from the first position to the second position and return of the trigger 60 from the second position to the first position a net displacement of the inner shaft member 21 relative to the outer tubular member 22 thus can be zero. The implant 23 can have a length, and the length of the implant 23 can be less than the distance (x). Example lengths of the implant 23, for purpose of illustration and not limitation, can be 20 mm, 30 mm, 40 mm, 60 mm, 80 mm, 100 mm, 120 mm, and 150 mm.

The distances (d), (x) and (y) can be selected based at least in part on the diameter of the implant to be delivered, the desired compression of the implant to be delivered, the path between the insertion point and the location of implant delivery, and/or other variables. As an example, and not by way of limitation, for a stent having a diameter of 4.5 mm when delivered to the vasculature, (d) can be about 12 mm, (x) can be about 28 mm, and (y) can be about 40 mm. As another example and not by way of limitation, the ratio (referred to herein as the "gear ratio") between the net distal motion of the inner shaft member 21 relative to the outer shaft member 22 (i.e., the distance (d) plus the distance (x)) to the distance (d) can be greater than 3. As an example, the gear ratio of (12+28): (12) is about 3.3. The actuation assembly disclosed herein having such a gear ratio can be used to properly deploy a braided stent from an extended delivery configuration to an expanded deployed configuration and address a 3:1 change in length of the stent from the delivery length to the deployment length. Exemplary diameters for stents when delivered to the vasculature can range from 4 mm to 12 mm or greater, such as, exemplary diameters can be 4.5 mm, 5.0 mm, 5.5 mm, 6.0 mm, 6.5 mm, 7.5 mm, or 8 mm, or suitable increments therebetween.

For the purpose of illustration, and not limitation, an exemplary embodiment of a system for delivering an implant is shown in FIGS. 1A and 1s designated generally by reference character 1000. Portions of this exemplary embodiment are depicted in FIGS. 2-23. The handle 1 can include a first handle housing portion and a second handle housing portion. The system can also include a trigger 60. The trigger 60 can be operatively coupled to the handle, such that the trigger 60 can be moveable between a first position and a second position. As embodied herein, the trigger can be biased towards the first or second position, for example, by a spring. A ratchet mechanism 80 can be provided to prevent moving the trigger between the first and second positions, such as to require a full stroke in one or both directions as desired. Additionally, a trigger stop 67 (FIG. 2) can be provided. The trigger stop 67 can be disposed between the trigger 60 and the handle 1, and can limit how far the trigger 60 can be actuated. The size of trigger stop 67 can be selected based at least in part on the diameter of the stent to be delivered, the desired compression of the stent to be delivered, the path between the insertion point and the location of stent delivery, and/or other variables.

The system can include a trigger lock 1e to prevent inadvertent movement of the trigger 60 and/or actuation assembly 2, such as during shipment or the like. For example, the trigger lock 1e can be can be engaged prior to use (e.g., during shipment) and can be disengaged in anticipation of use of the system. The trigger lock 1e can include a tab member to prevent movement of the trigger 60. The tab member can be disposed between the trigger 60 and at least a portion of the housing 1 to prevent movement of the trigger 60. Furthermore, the trigger lock 1e can include an arm member if and a distal portion 1g. The arm member if can be configured to extend along a first side of the handle housing 1a and into a housing slot 1h. The distal portion 1g can protrude into the housing 1 and engage at least a portion of the actuation assembly 2 to prevent inadvertent movement of the actuation assembly 2 prior to use (e.g., during shipment).

The system 1000 also includes an actuation assembly 2. The actuation assembly 2 is operatively coupled to the trigger 60, the inner shaft member 21 and the outer tubular member 22 to provide the desired relative movement as set for in detail above.

Figure 4:
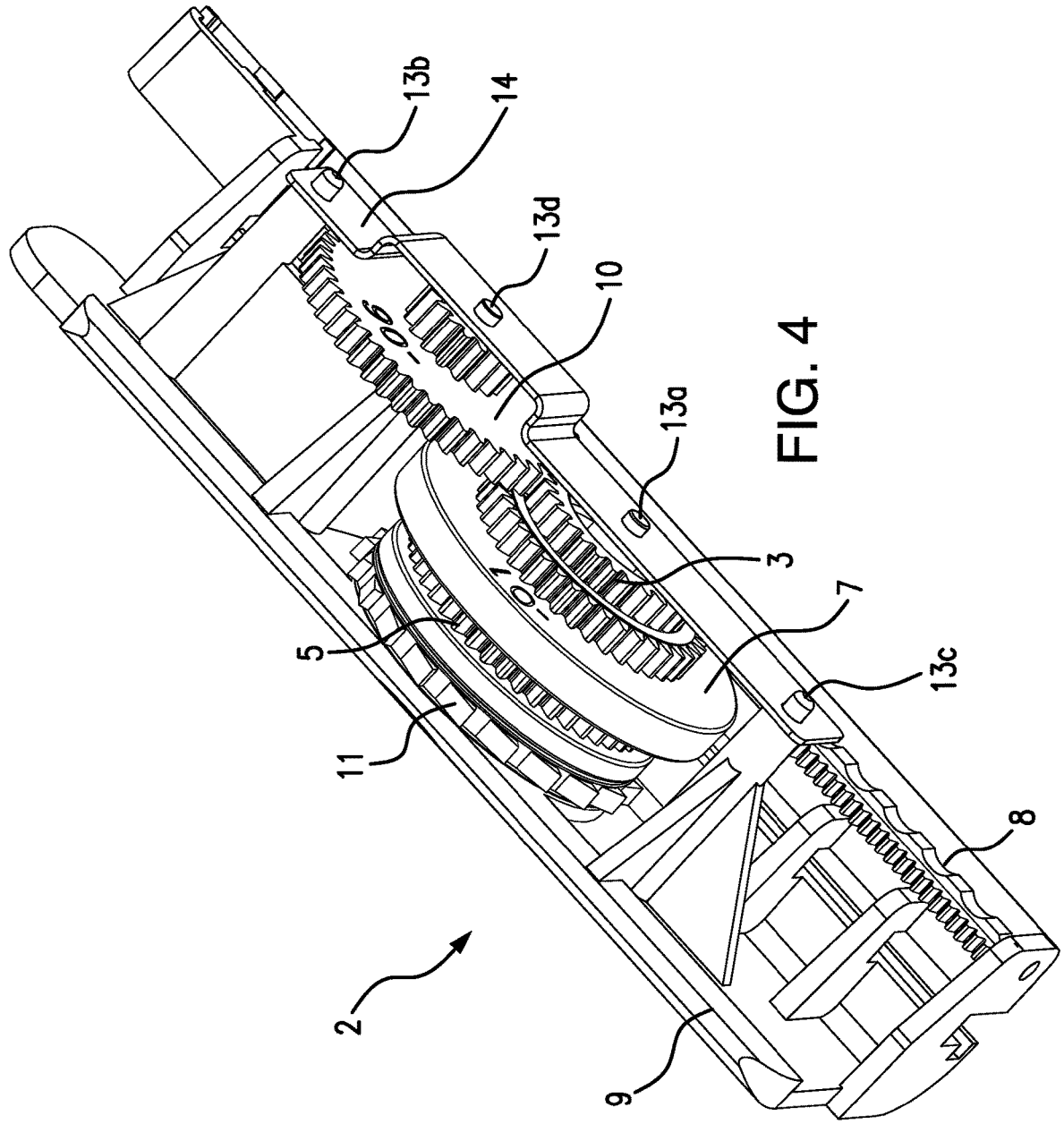
FIG. 4 provides a top perspective view of selected elements of the actuation assembly of the delivery system of FIG. 1A.
Figure 5B:
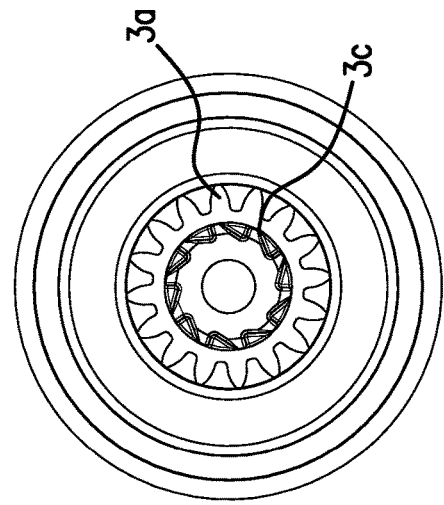
FIGS. 5A-5D provide perspective FIG. 5A, right FIG. 5B, left FIG. 5C, and front FIG. 5D views of the sun gear shaft of the delivery system of FIG. 1A.
Figure 5D:
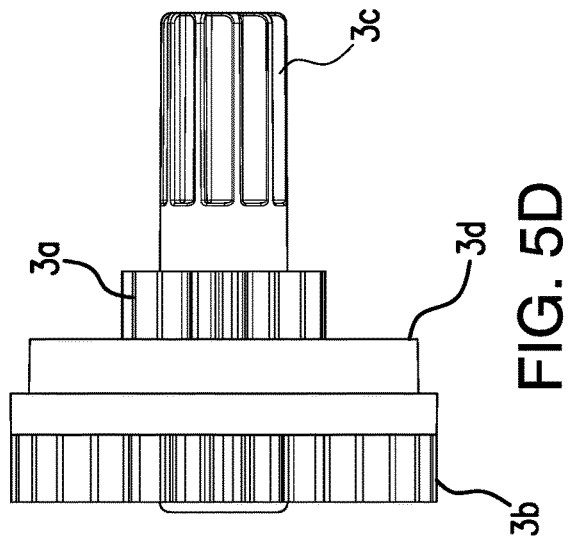
Figure 5A:
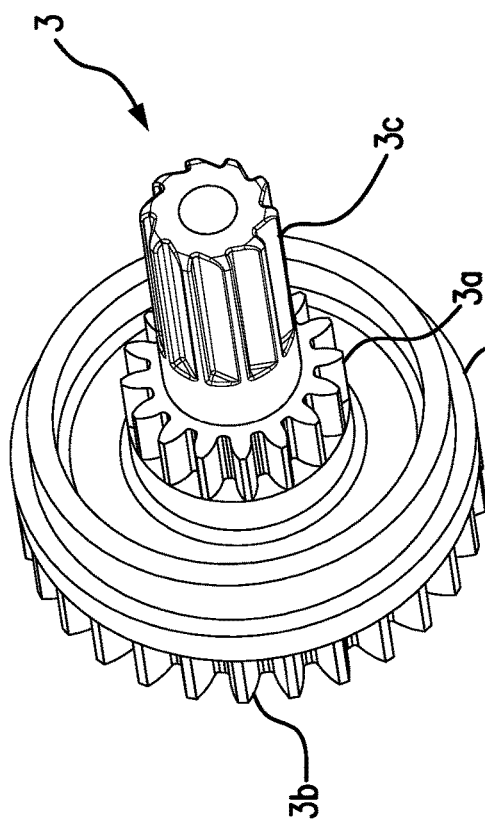
Figure 5C:
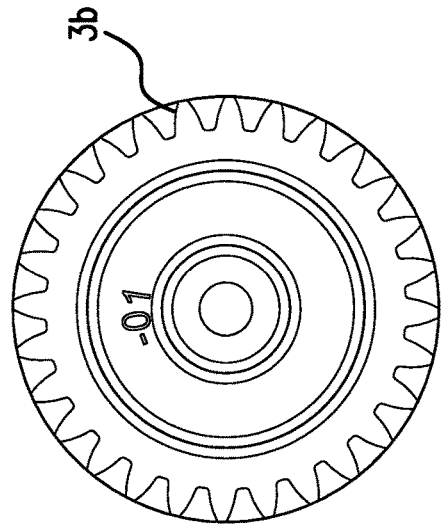
Figure 6B:
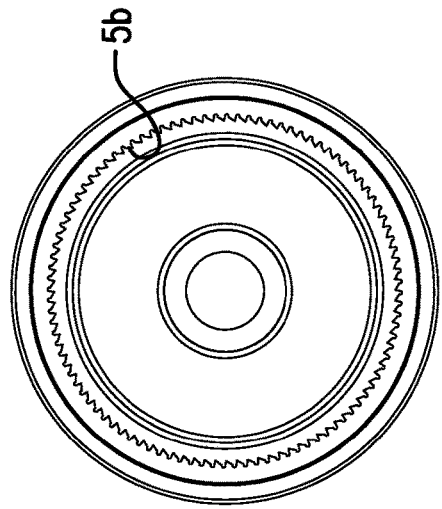
FIGS. 6A-6D provide perspective FIG. 6A, right FIG. 6B, left FIG. 6C, and front FIG. 6D views of the planet carrier of the delivery system of FIG. 1A.
Figure 6D:
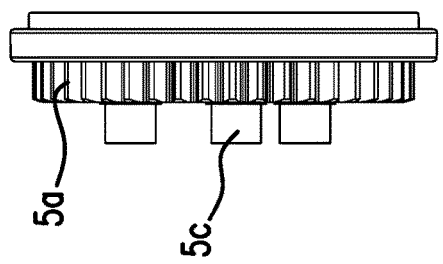
Figure 6A:
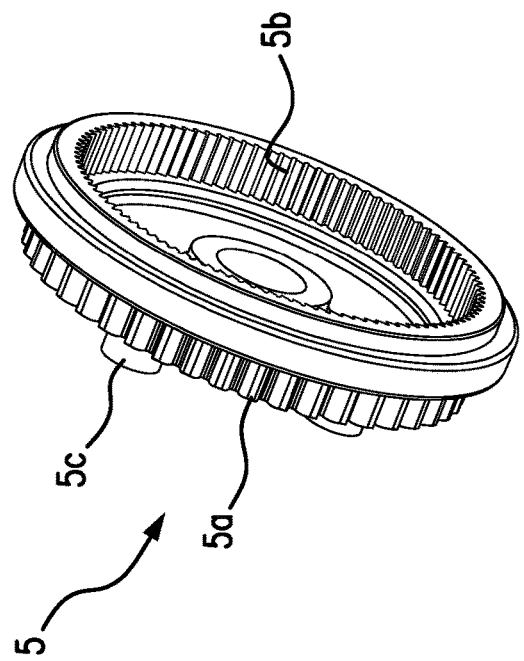
Figure 6C:
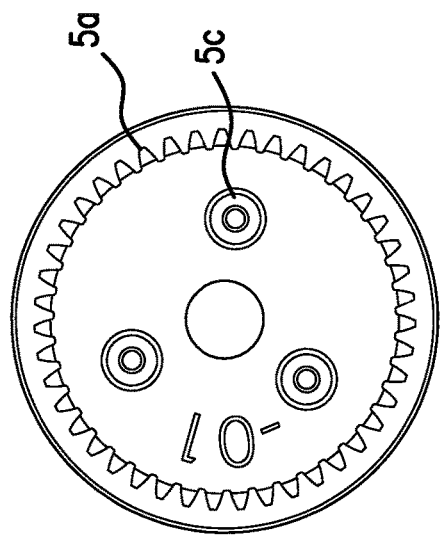
Figure 7A:
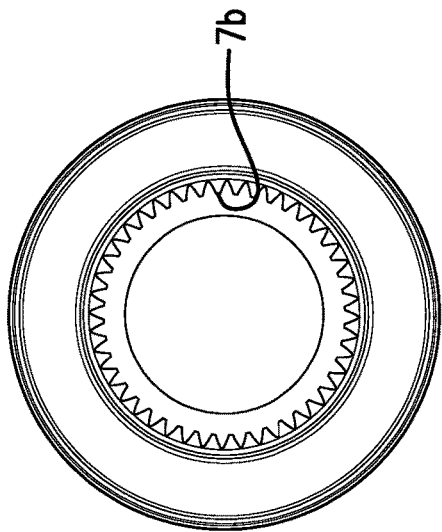
FIGS. 7A-7D provide perspective FIG. 7A, right FIG. 7B, left FIG. 7C, and front FIG. 7D views of the ring gear of the delivery system of FIG. 1A.
Figure 7D:
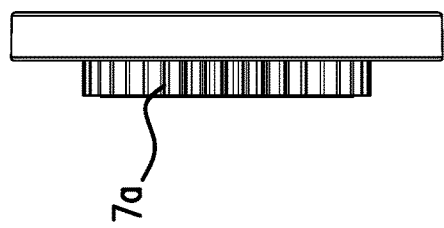
Figure 7B:
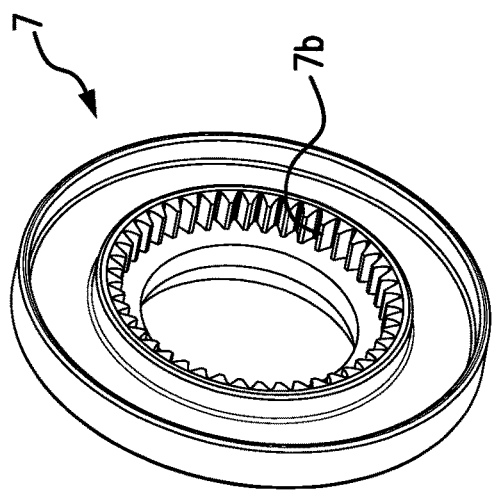
Figure 7C:
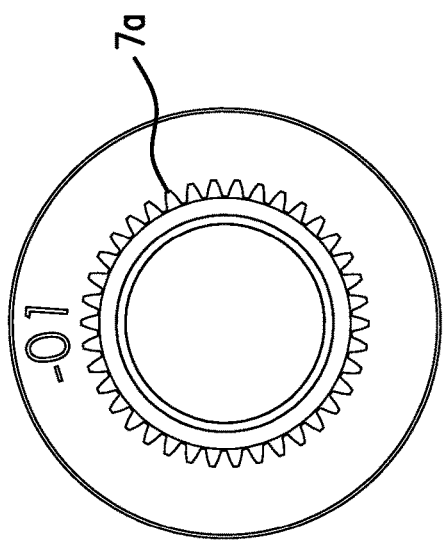
Figure 8B:
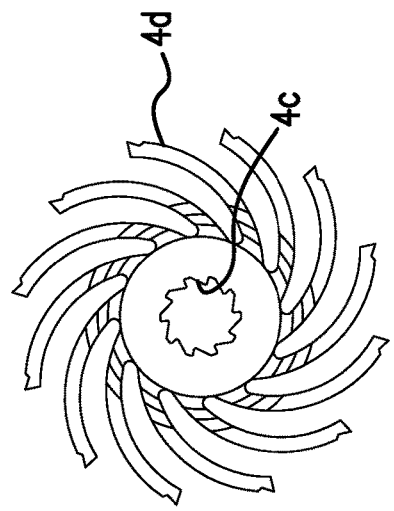
FIGS. 8A-8D provide perspective FIG. 8A, right FIG. 8B, left FIG. 8C, and front FIG. 8D views of the first clutch driver of the delivery system of FIG. 1A.
Figure 8D:
Figure 8A:
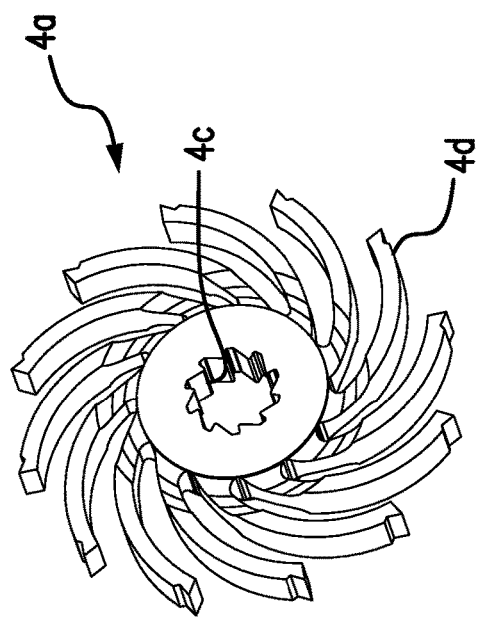
Figure 8C:
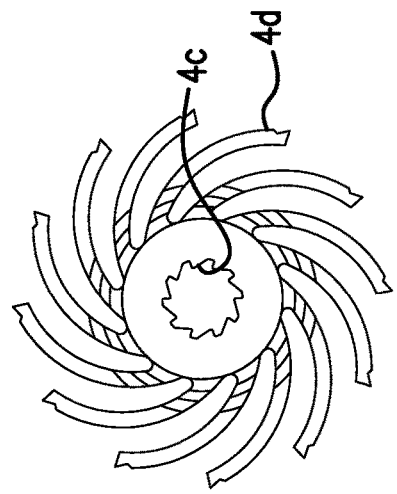
Figure 9B:
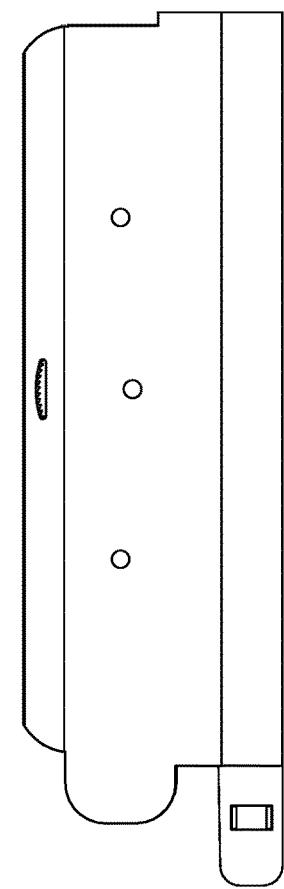
FIGS. 9A-9D provide perspective FIG. 9A, right FIG. 9B, left FIG. 9C, and front FIG. 9D views of the shuttle frame of the delivery system of FIG. 1A.
Figure 9D:
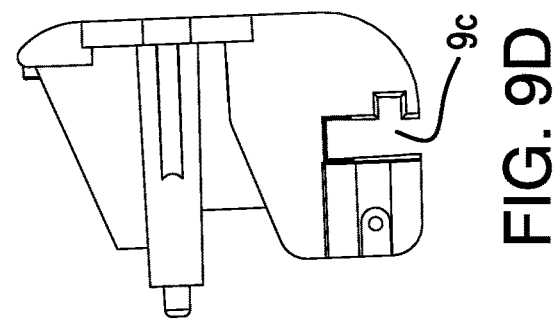
Figure 9A:
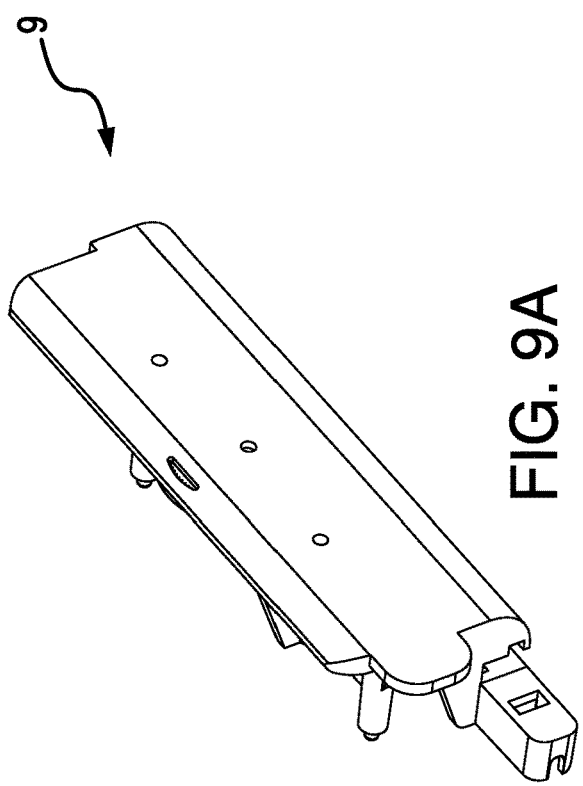
Figure 9C:
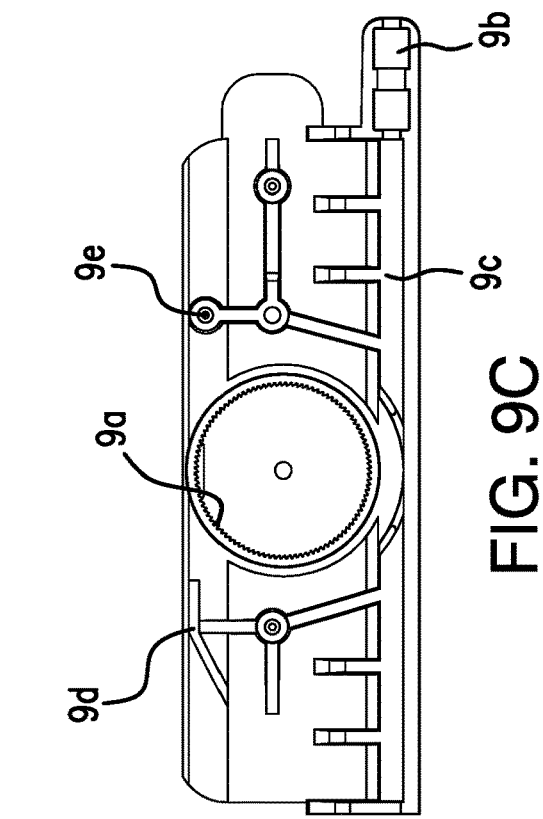
Figure 10B:
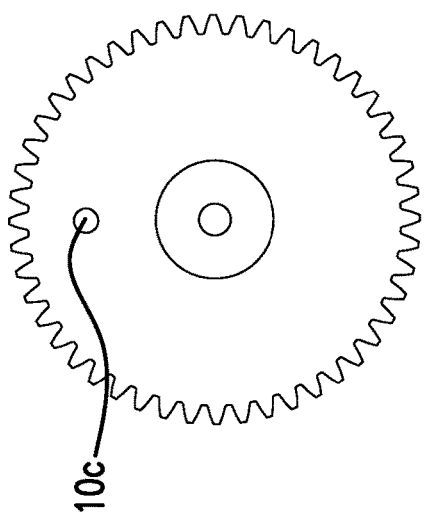
FIGS. 10A-10D provide perspective FIG. 10A, right FIG. 10B, left FIG. 10C, and front FIG. 10D views of the intermediate gear of the delivery system of FIG. 1A.
Figure 10D:
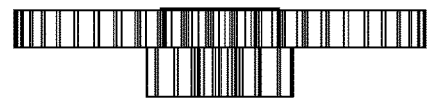
Figure 10A:
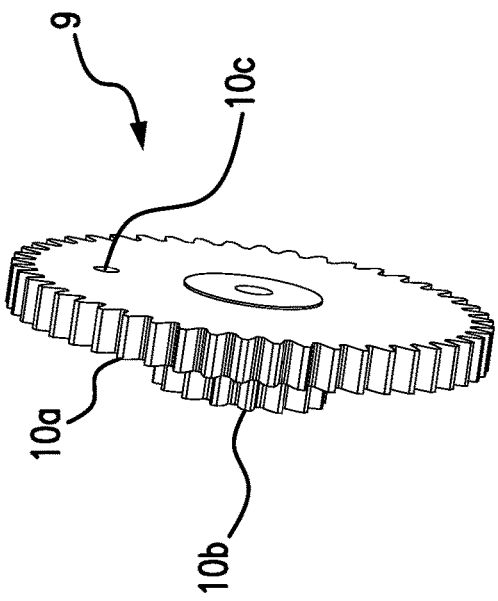
Figure 10C:
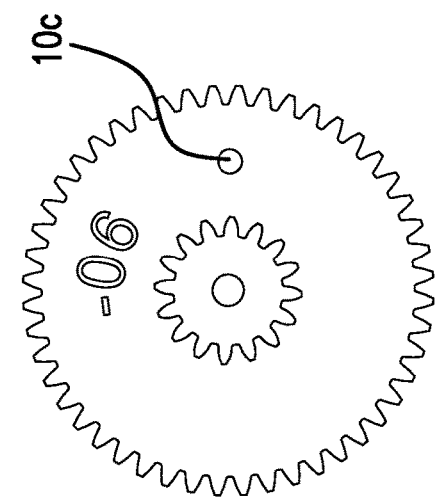
Figure 11B:
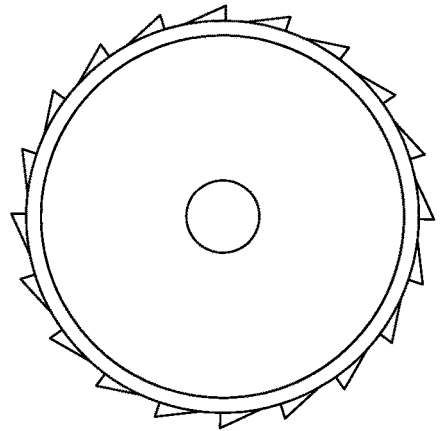
FIGS. 11A-11D provide perspective FIG. 11A, right FIG. 11B, left FIG. 11C, and front FIG. 11D views of the clutch release of the delivery system of FIG. 1A.
Figure 11D:
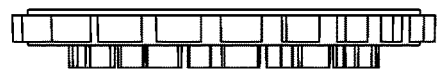
Figure 11A:
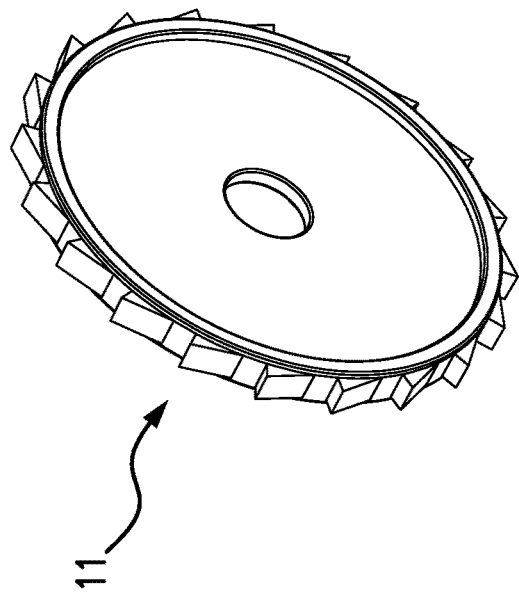
Figure 11C:
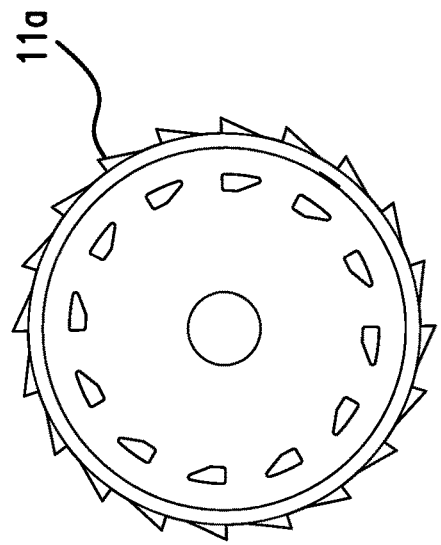

FIG. 4 shows for the purpose of illustration and not limitation, selected elements or components of the actuation assembly of the delivery system 1000. That is, FIGS. 5-11 show for the purpose of illustration and not limitation, selected components of an actuation assembly 2. FIGS. 12-23 show for the purpose of illustration and not limitation, the relationship between selected components of an actuation assembly 2. As noted above, the actuation assembly 2 can be configured to displace the outer tubular member 22 in the proximal direction a distance (d) relative to the handle 1 and to separately move the inner shaft member 21 distally a distance (x) relative to the handle 1 upon deployment of the trigger 60 from the first position to the second position. The actuation assembly 2 can be configured to move the inner shaft member 21 proximally a distance (y) relative to the handle 1 with no displacement of the outer tubular member 22 relative to the handle 1 upon return of the trigger 60 from the second position to the first position.

As depicted herein, the actuation assembly 2 can include a planetary gear system. For example, the actuation assembly can include a planet carrier 5, at least one planet gear 6, a sun gear shaft 3, a ring gear 7, a first clutch driver 4a and a second clutch driver 4b. The actuation assembly can include a shuttle frame 9. The shuttle frame 9 can have the planet carrier 5, the planet gears 6, the sun gear shaft 3, the ring gear 7, and the first and second clutch drivers 4a, 4b disposed thereon. Shuttle frame 9 can be disposed within the handle 1 and can be moveable relative to the handle 1 along the length of the handle 1. The distal portion 1g of the trigger lock 1e, as described above, can engage at least a portion of the shuttle frame 9 to prevent inadvertent movement of the shuttle frame along the length of the handle prior to use (e.g., during shipment).

The sun gear shaft 3 (FIG. 5) can include a sun gear portion 3a, a sheath pinion 3b, a clutch engagement portion 3c, and a step portion 3d. As depicted herein, the clutch engagement portion 3c can be saw-toothed, although other suitable configurations can be used. The planet carrier 5 (FIG. 6) can include a circumferential pinion 5a, a clutch component 5b, and at least one pin 5c. The planet carrier 5 will include one pin 5c for each planet gear 6. For example, as shown at least in FIG. 6, the planet carrier 5 includes three pins 5c. The ring gear 7 (FIG. 7) can include a circumferential pinion 7a and a ring gear portion 7b. Each clutch driver 4a, 4b (FIG. 8) can be identical in shape, and can include a sun gear shaft engagement portion 4c and a clutch portion 4d. The sun gear shaft engagement portion 4c can be saw-toothed, although other suitable configurations can be used.

Figure 12:
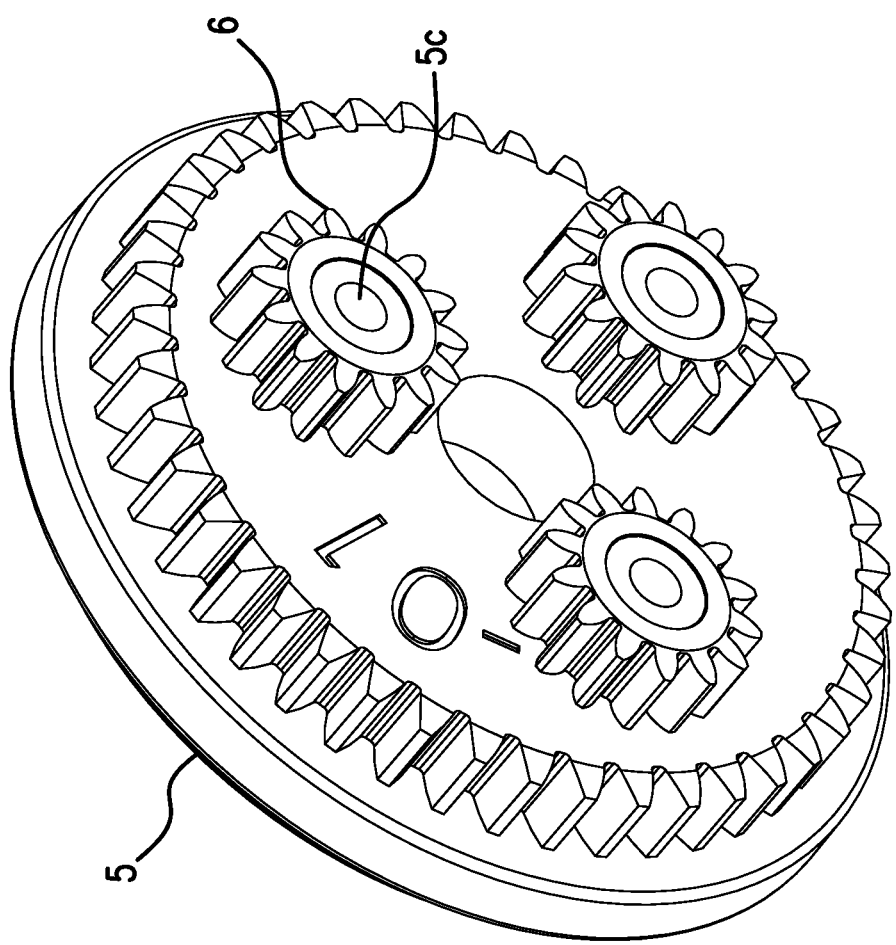
FIG. 12 is a perspective view illustrating the relationship between the planet carrier and the planet gears of the delivery system of FIG. 1A.
Figure 13B:
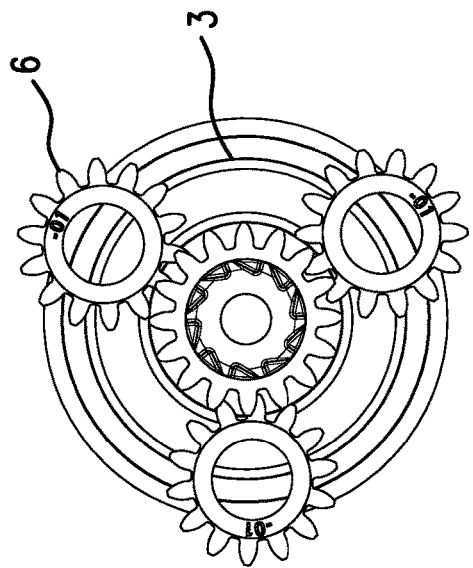
FIGS. 13A-13D are various views depicting the relationship between the sun gear shaft and the planet gears of the delivery system of FIG. 1A.
Figure 13D:
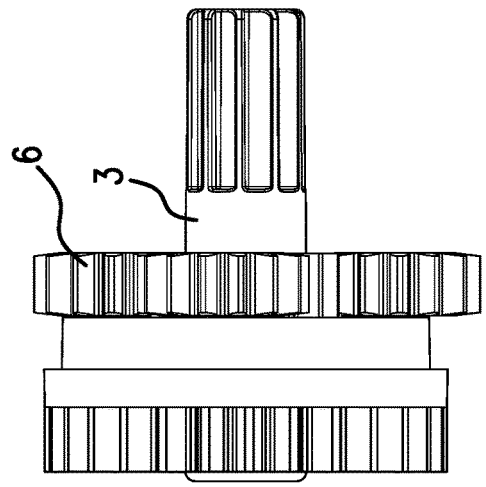
Figure 13A:
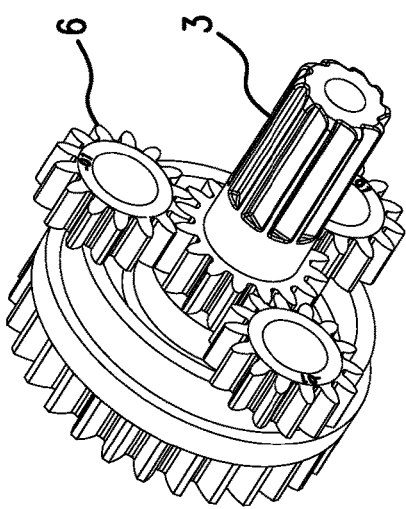
Figure 13C:
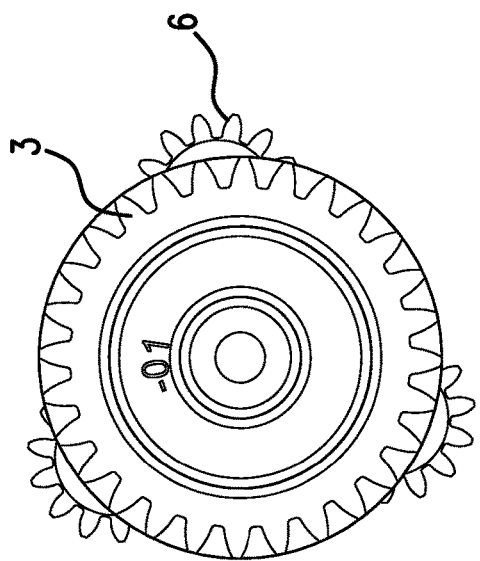
Figure 14A:
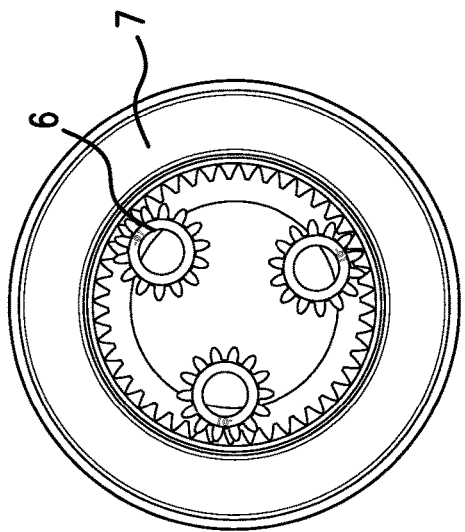
FIGS. 14A-14D are various views depicting the relationship between the ring gear and the planet gears of the delivery system of FIG. 1A.
Figure 14B:
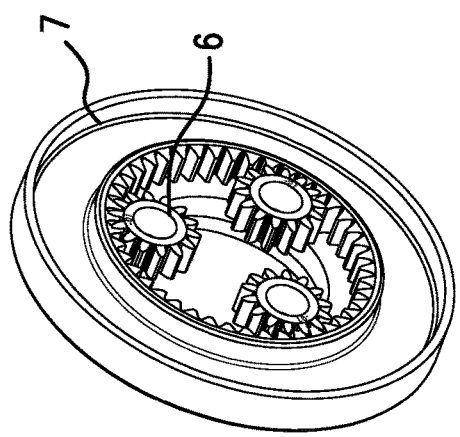
Figure 14D:
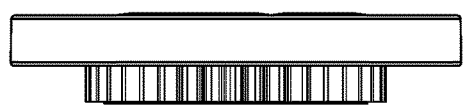
Figure 14C:
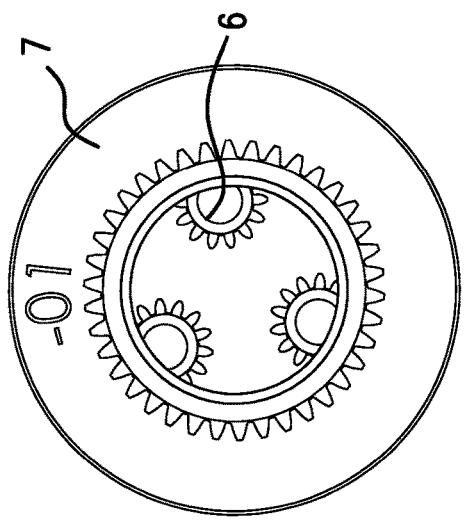
Figure 15B:
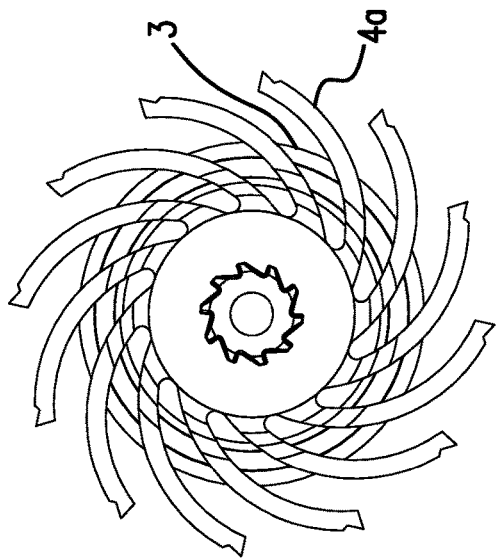
FIGS. 15A-15D are various views depicting relationship between the sun gear shaft and the first and second clutch drivers of the delivery system of FIG. 1A.
Figure 15A:
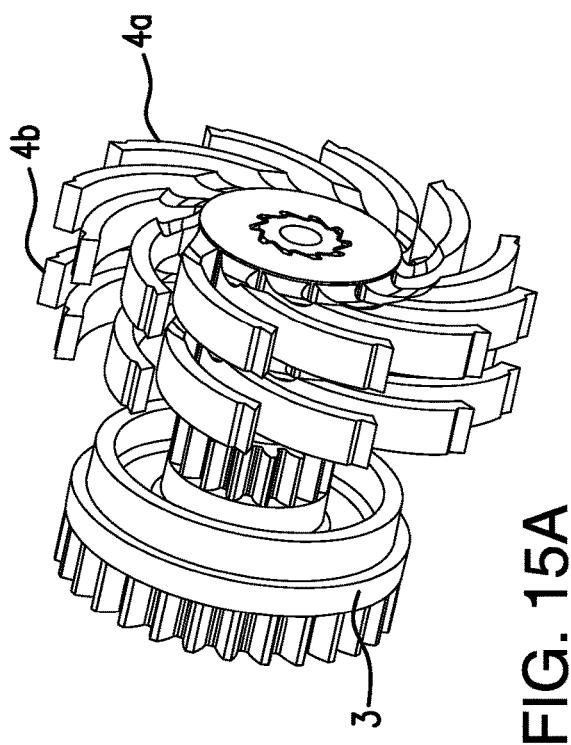
Figure 15D:
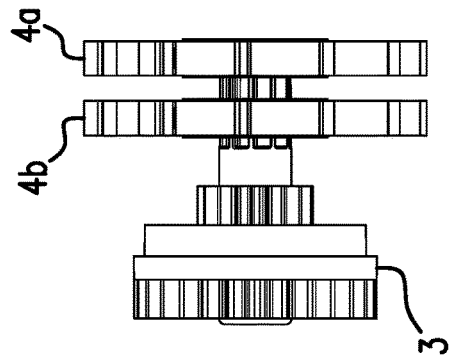
Figure 15C:
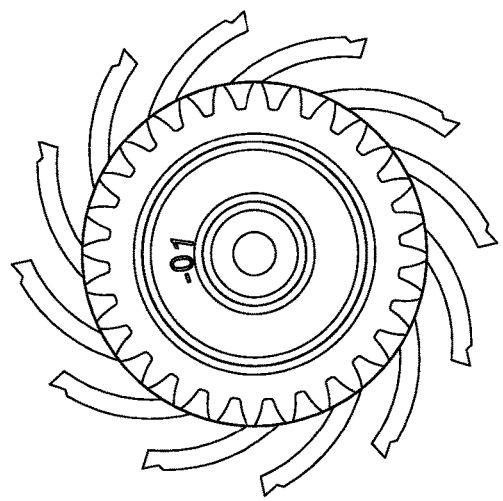

The planet carrier 5 thus operates as the "planet carrier" of the planetary gear system. As such, the at least one planet gear 6 can be operatively coupled to the planet carrier 5. Each planet gear 6 can be operatively coupled to a pin 5c of the planet carrier 5, as shown in FIG. 12 for the purpose of illustration and not limitation. In the exemplary embodiment, the system includes three planet gears 6 operating as the "planet gears" of the planetary gear system; however, one, two, four or more planet gears 6 can be provided. The sun gear shaft 3 can operate as the "sun gear" of the planetary system. The sun gear portion 3a of the sun gear 3 can be operatively engaged with the planet gears 6 such that the planet gears 6 are operatively meshed with the sun gear portion 3a, as shown in FIG. 13 for the purpose of illustration and not limitation. The ring gear 7 can operate as the "ring gear" of the planetary system. The ring gear portion 7b can be operatively engaged with the planet gears 6 such that the planet gears 6 are operatively meshed with the ring gear portion 7b of the ring gear 7, as shown in FIG. 14 for the purpose of illustration and not limitation. The step portion 3d of the sun gear shaft 3 can be configured to maintain the position of the remaining portion the planetary gear system. For example, the step portion 3d can engage the ring gear 7 and reduce undesired movement of the ring gear 7, which can reduce undesired movement of the planet gears 6.

As further depicted, the shuttle frame 9 (FIG. 9) can include a clutch engagement portion 9a, a cavity 9b which can be configured to receive a ferrule coupled to the proximal end of the outer tubular member 22, and a guide 9c.

Figure 16:
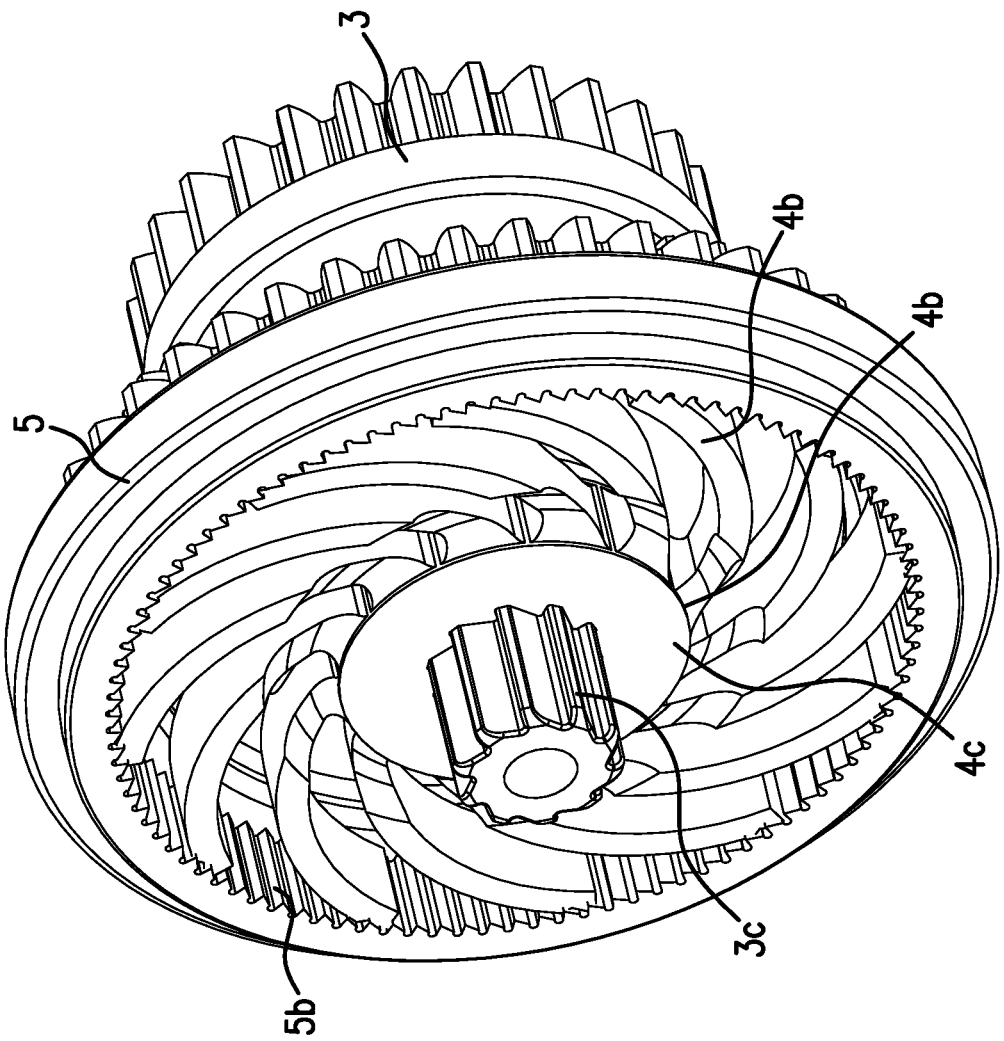
FIG. 16 is a perspective view illustrating the relationship between the sun gear shaft, the planet carrier, and the second clutch driver of the delivery system of FIG. 1A.

The second clutch driver 4b can be configured to uni-directionally lock the sun gear shaft 3 and the planet carrier 5. As such, the sun gear shaft 3, planet carrier 5, and ring gear 7 have a 1:1 ratio of rotation during deployment of the trigger 60 from the first position to the second position. For example, the sun gear engagement portion 4c of the second clutch driver 4b can engage the clutch engagement portion 3c of the sun gear shaft 3, such that the sun gear shaft 3 and the second clutch driver 4b rotate together, as shown in FIG. 15, for the purpose of illustration and not limitation. Additionally, the clutch portion 4d of the second clutch driver 4b can have a ratchet-like engagement with the clutch component 5b of the planet carrier 5, as shown in FIG. 16, for the purpose of illustration and not limitation. Such a configuration can allow the sun gear shaft 3 and planet carrier 5 to rotate independently of one another in a first direction (e.g., when the planet carrier 5 rotates in the counter clockwise direction in FIG. 16), and locked together in a second direction (e.g., when the planet carrier 5 rotates in the clockwise direction in FIG. 16).

Figure 17:
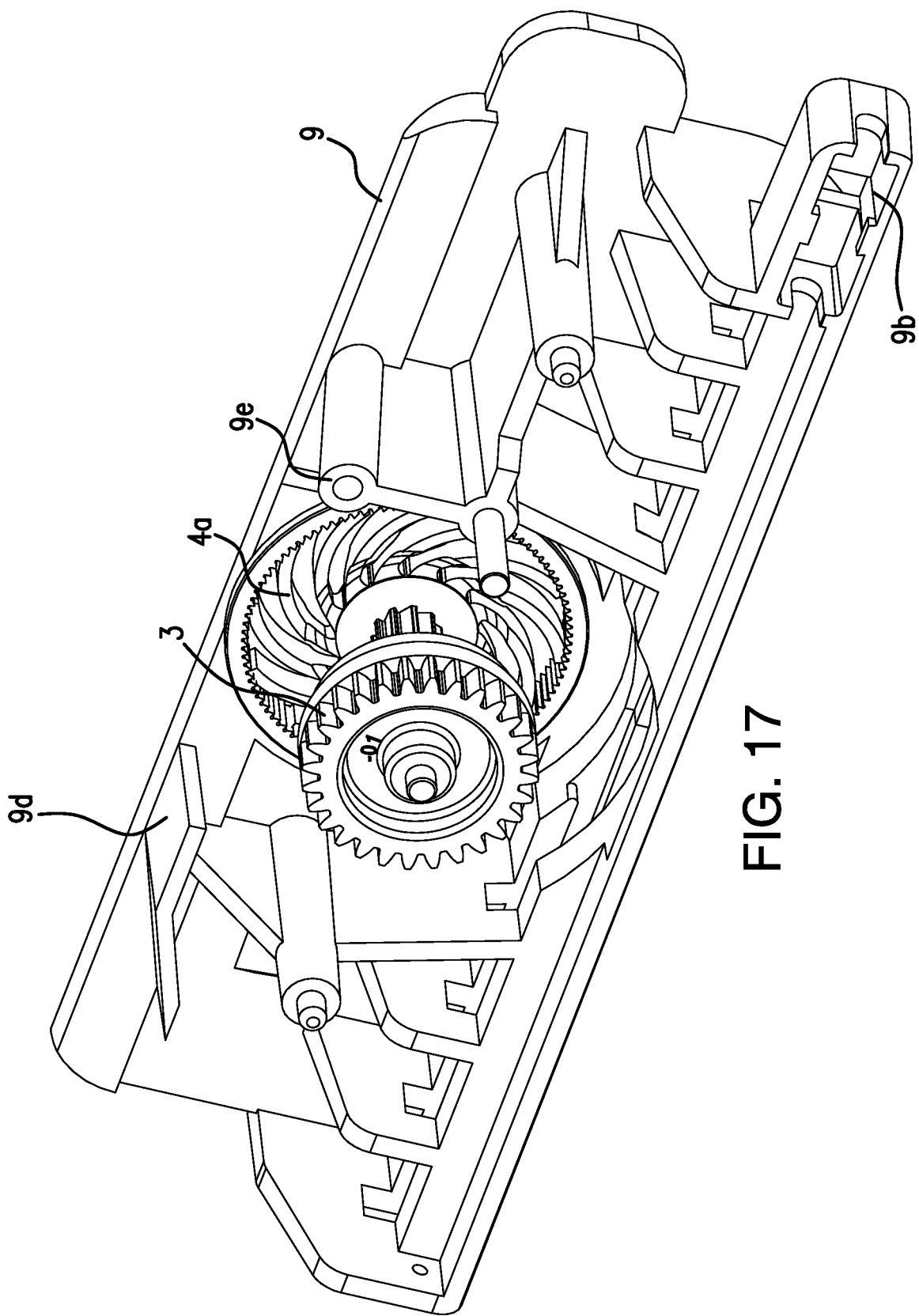
FIG. 17 is a perspective view illustrating the relationship between the sun gear shaft, the first clutch driver, and the shuttle frame of the delivery system of FIG. 1A.

The first clutch driver 4a can be configured to limit the sun gear shaft 3 to uni-direction rotational motion. The first clutch driver 4a and sun gear shaft 3 can be configured such that the sun gear shaft 3 does not rotate during return of the trigger from the second position to the first position. For example, the sun gear engagement portion 4c of the first clutch driver 4a can be fixedly engaged with the clutch engagement portion 3c of the sun gear shaft 3, such that the sun gear shaft 3 and the first clutch driver 4a rotate together, as shown in FIG. 15, for the purpose of illustration and not limitation. Additionally, the first clutch driver 4a can have a ratchet-type engagement with a separate element, for example and as shown in FIG. 17 for the purpose of illustration and not limitation, a clutch engagement portion 9a on the shuttle frame 9. As such, the first clutch driver 4a can be limited to uni-direction motion by the clutch engagement portion 9a, and thereby limit the sun gear shaft 3 to uni-directional motion (e.g., the sun gear shaft 3 can only rotate in the counterclockwise direct in FIG. 17).

Figure 18:
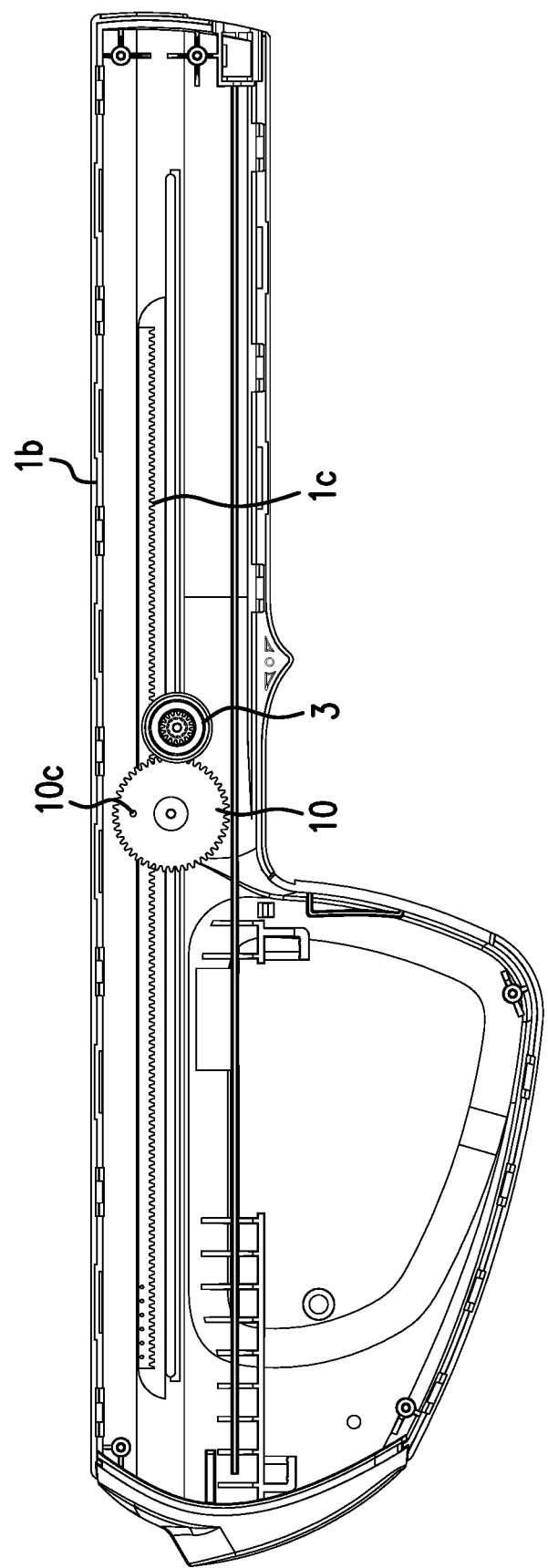
FIG. 18 is a side view illustrating the relationship between the sun gear shaft, intermediate gear, and handle of the delivery system of FIG. 1A.

The sun gear shaft 3 can be functionally coupled to the outer tubular member 22 such that upon deployment of the trigger from the first position to the second position, the sun gear shaft 3 rotates and thereby causes the outer tubular member 22 to move proximally. For example, the shuttle frame 9 can be fixedly coupled to the outer tubular member 22 at the cavity 9b. As depicted herein for illustration, the shuttle frame 9 and outer tubular member 22 can be coupled by a ferrule. The sheath pinion portion 3b of the sun gear shaft 3 can be functionally coupled to the handle 1 such that upon deployment of the trigger 60 from the first position to the second position the sun gear shaft 3 rotates, engages the handle 1, and moves the shuttle frame 9 proximally a distance relative to the handle 1. As such and as embodied herein the outer tubular member 22 also moves proximally relative to the handle 1 because it is fixedly coupled to the shuttle frame 9. Additionally, intermediate gear 10 can be functionally meshed between the sheath pinion portion 3b and a sheath rack 1c disposed on the handle 1, as shown in FIG. 18, for the purpose of illustration and not limitation. Additionally or alternatively, the sheath pinion portion 3b can directly mesh the sheath rack 1c. As noted herein above, the first clutch driver 4b can prevent the sun gear shaft 3 from rotating during return of the trigger 60 from the second position to the first position. Accordingly, the shuttle frame 9, the outer tubular member 22 fixedly coupled thereto, and all other components carried by the shuttle frame 9, will move proximally when the trigger 60 is deployed from the first position to the second position, but remain stationary when the trigger 60 is returned from the second position to the first position as embodied herein. The gears of the small spur gear 10b of the intermediate gear 10 (or the gears of the sheath pinion portion 3b) and the gears of the sheath rack 1c can utilize a non-standard pitch as desired or needed. As an example and not by way of limitation, a standard 48 pitch can be slightly enlarged. Such a change can allow the actuation assembly to achieve the desired value of (d) when the trigger 60 is deployed from the first position to the second position. The intermediate gear 10 can include an alignment hole 10c defined therein. During assembly of the second handle portion on the first handle portion 1a, an alignment member (e.g., a pin) can be inserted through a corresponding alignment hole 1j provided in the second handle portion 1b, the intermediate gear 10, and the shuttle frame 9. Once the first and second handle portions are secured and assembled, the alignment member can be removed. The alignment hole 10c can be aligned relative to either a valley or a crest in the teeth of the small spur gear 10b to thus ensure an operative engagement between the spur gear 10b and the sheath rack 1c. For example, the alignment hole can be aligned with a valley in the teeth of the small spur gear 10b to align with a crest in the teeth of the sheath rack 1c, or vice versa.

Figure 19:
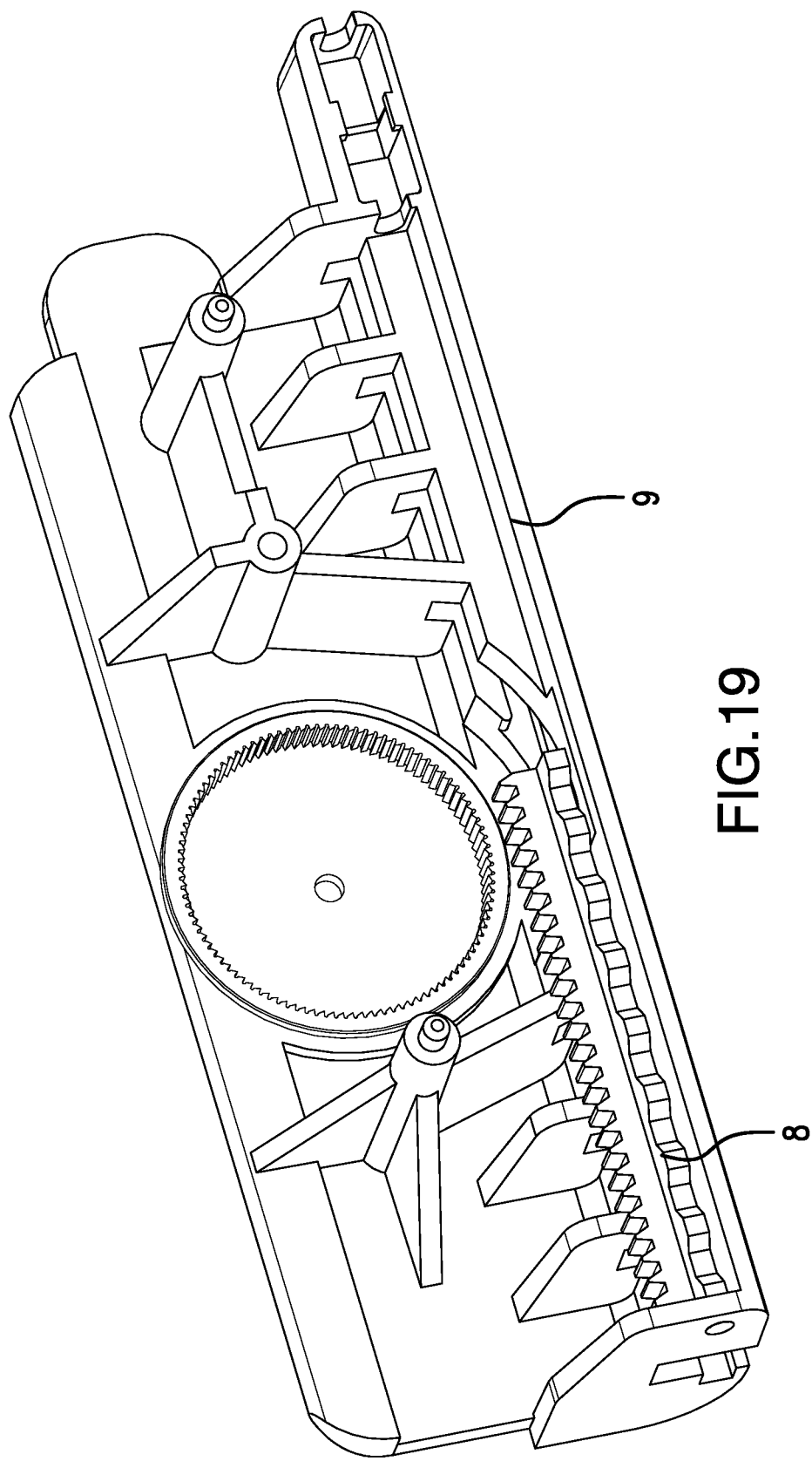
FIG. 19 is a perspective view illustrating the relationship between the shuttle frame and the ratchet member of the delivery system of FIG. 1A.
Figure 20:
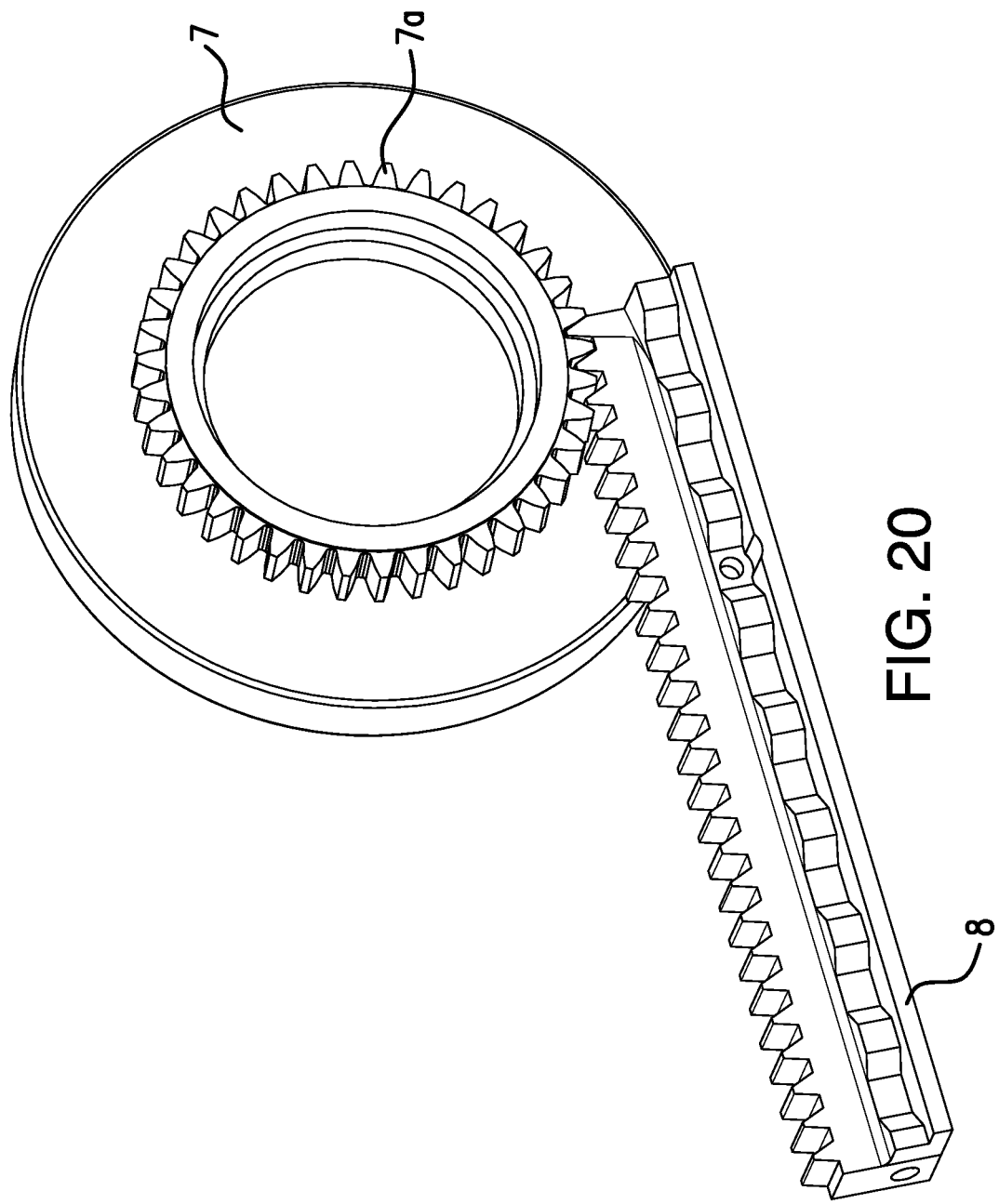
FIG. 20 is a perspective view illustrating the relationship between the ring gear and the ratchet member of the delivery system of FIG. 1A.

The actuation assembly 2 can also include a ratchet rack 8. The ratchet rack 8 can be fixedly coupled to the inner shaft member 21 and can be disposed on the shuttle frame 9, as shown in FIG. 19 for the purpose of illustration and not limitation. The ratchet rack 8 can be operatively engaged with the ring gear 7. For example, the ratchet rack 8 can be operatively meshed with the circumferential pinion 7a of the ring gear 7, as shown in FIG. 20, for the purpose of illustration and not limitation. Upon deployment of the trigger 60 from the first position to the second position, the ring gear 7 can rotate and cause the ratchet rack 8, and therefore the inner shaft member 21, to move distally relative to the handle. Upon return of the trigger 60 from the second position to the first position, the ring gear 7 can rotate in the opposite direction and cause the ratchet rack 8, and therefore the inner shaft member 21, to move proximally relative to the handle.

Figure 21:
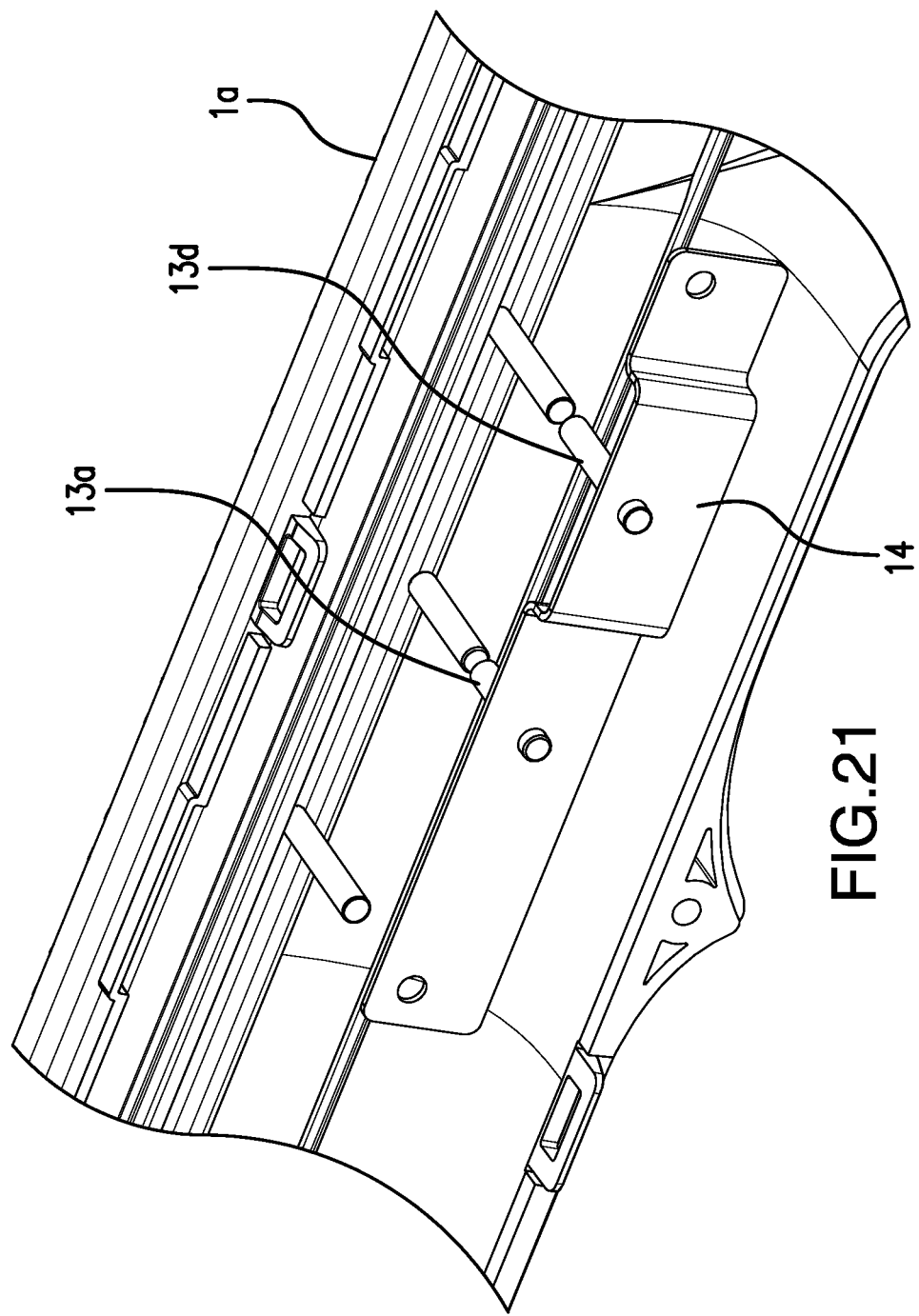
FIG. 21 is an enlarged view showing the relationship between the handle, bosses, and plate of the delivery system of FIG. 1A.

The actuation assembly 2 can further include a plate 14 disposed on the shuttle assembly 9. The plate 14 can hold portions of the actuation assembly 2 in place and can protect the actuation assembly 2. The actuation assembly 2 can also include at least one boss 13 configured to engage at least one boss track disposed within the handle 1 to thereby guide the shuttle frame 9 along the handle, as shown in FIG. 21 for the purpose of illustration and not limitation. A boss track can be on the first side of the handle housing 1a, the second side of the handle housing 1b, or on both sides of handle 1. The at least one boss can include a first boss 13a disposed through an axis of the sun gear shaft 3. The actuation assembly can include additional bosses, such as a second boss 13b and a third boss 13c (FIG. 2), each disposed through the plate 14 and the shuttle frame 9. The second boss 13b and third boss 13c can hold the plate 14 in place on the shuttle frame 9. The actuation assembly 2 can include a fourth boss 13d disposed through an axis of the intermediate gear 10. The fourth boss 13d can engage the handle and act as a guide as the shuttle frame 9 moves relative to the handle 1. The bosses can be any shape, for example cylindrical or rectangular.

Figure 22:
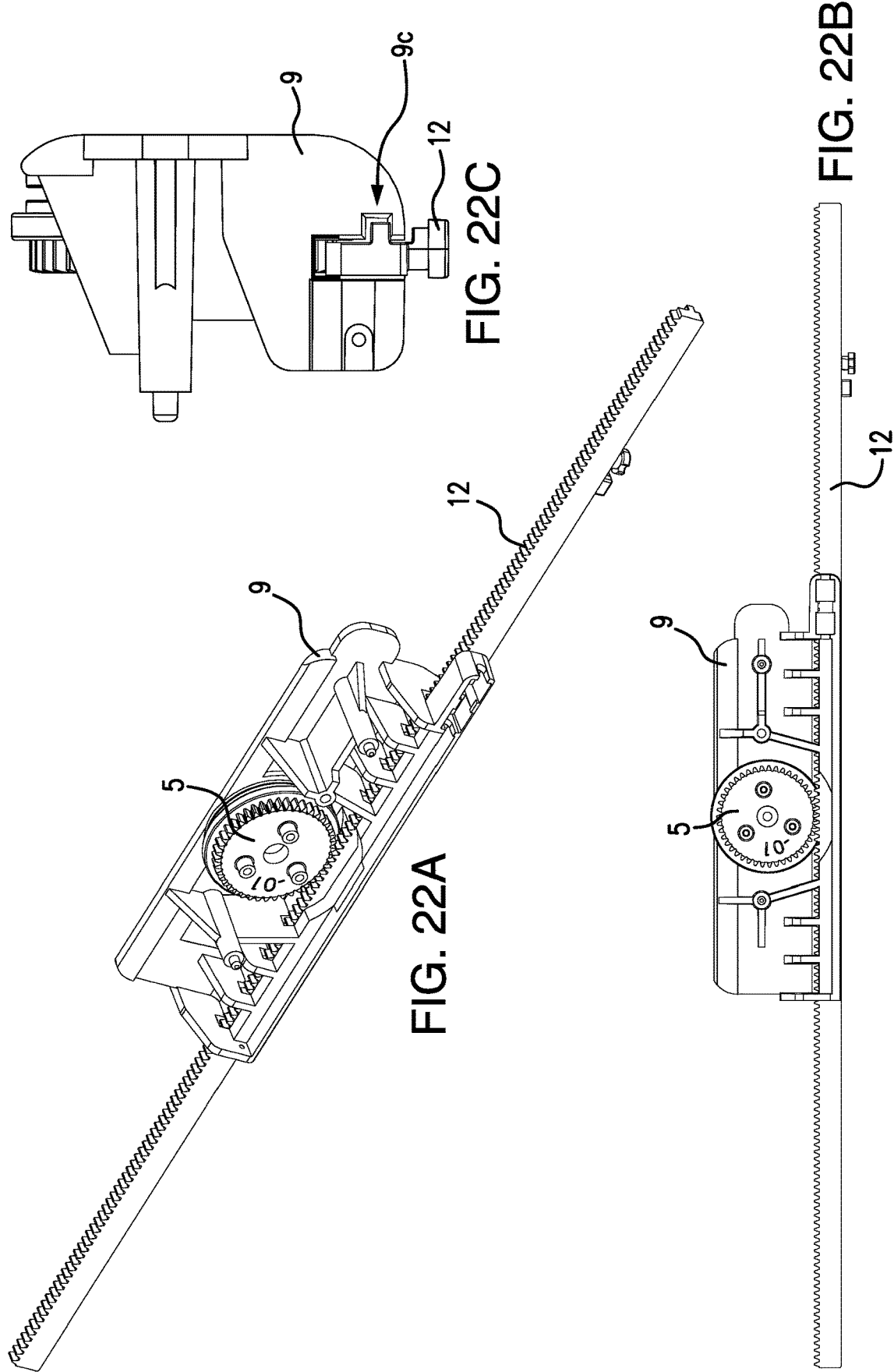
FIGS. 22A-22C are various views showing the relationship between the shuttle frame, driving rack, and planet carrier of the delivery system of FIG. 1A.

In accordance with another aspect of the disclosed subject matter, the actuation assembly 2 can be functionally coupled to the trigger 60 by a driving rack 12. For example, the driving rack 12 can be fixedly coupled or releasably coupled to an intermediate element functionally disposed between the driving rack 12 and the trigger 60. As an example and not by way of limitation, the driving rack 12 can have a bayonet-type engagement with the intermediate element. The driving rack 12 can be operatively engaged with the planet carrier 5. For example, the driving rack 12 can be operatively meshed with the circumferential pinion 5a of the planet carrier 5, as shown in FIG. 22 for the purpose of illustration and not limitation. The driving rack 12 can be supported in a guide 9c disposed on the shuttle 9, as shown in FIG. 22 for the purpose of illustration and not limitation. Such a configuration can allow a limited region of contact between the driving rack 12 and the corresponding support surface, thereby reducing friction. Additionally, such a configuration can provide support proximal to the point of contact between the driving rack 12 and the planet carrier 5, even as that point moves along the length of the driving rack 12. In operation, upon deployment of the trigger 60 from the first position to the second position, the driving rack 12 can move distally, relative to the handle 1, and cause the planet carrier 5 to rotate in a first direction. Upon return of the trigger 60 from the second position to the first position, the driving rack 12 can move proximally relative to the handle, and cause the planet carrier 5 to rotate in an opposite direction.

In view of the disclosed subject matter, the dimensions and features of the trigger stop 67, shuttle 9 and elements disposed thereon, sheath rack 1c, and the handle guide can be designed based on the specifics of the implant 23, for example, the diameter of the implant 23. As an example and not by way of limitation, for a given radius of the intermediate gear 10, the sheath rack 1c and the handle guide, can be a specific distance apart to properly engage the small spur gear 10b of the intermediate gear 10 and the boss 13d disposed through the axis of the intermediate gear 10. If the radius of the intermediate gear is changed, the distance between the sheath rack 1c and the handle guide can also be adjusted accordingly.

For purpose of illustration, reference is now made to the operation of the system with the actuation assembly disclosed herein. During operation, the user can deploy the trigger 60 from the first position to the second position (referred to herein as the "first action"). The trigger 60 thus can cause the driving rack 12 to move in the distal direction. The driving rack 12, functionally meshed with the circumferential pinion 5a of the planet carrier 5, can impart rotational motion on the planet carrier 5. The planet carrier 5 can impart rotational motion on the three planet gears 6. The planet gears 6 can be constrained from rotating freely because they are meshed with the sun gear portion 3a of the sun gear shaft 3. The three planet gears 6 can be meshed with the ring gear portion 7b of the ring gear 7, and can impart rotational motion on the ring gear 7. The ring gear 7, can be operatively meshed with the ratchet rack 8, and can drive the ratchet rack 8 distally. The inner shaft member 21, which can be fixedly coupled to the ratchet rack 8, moves distally. The planet carrier 5 can be rotationally coupled to the sun gear shaft 3 by the second clutch driver 4*b* when rotating in the first action; thus, rotation can be transmitted to the sun gear shaft 3 in a 1:1 ratio. The first clutch driver 4*a* allows the sun gear shaft 3 to rotate freely relative to the shuttle frame 9 during the first action. The sheath pinion 3*b* of the sun gear shaft 3 can be meshed with the large spur gear 10*a* of the intermediate gear 10, and can impart rotational motion on the intermediate gear 10. The small spur gear 10*b* of the intermediate gear 10 can be operatively meshed with a rack 1*c* disposed on the second handle housing portion 1*b*; thus, the rotational motion of the intermediate gear 10 can impart linear motion on the shuttle frame 9 in the proximal direction. The outer tubular member 22, which can be fixedly coupled to the shuttle frame 9 can move proximally relative to the handle. Thus, during the first action, the inner shaft member 21 can move distally relative to the handle 1 and the outer tubular member 22 can move proximally relative to the handle 1.

Upon return of the trigger 60 from the second position to the first position (herein referred to as the "second action"), the driving rack 12 can move proximally relative to the handle 1. The driving rack 12 can impart rotational motion to the planet carrier 5. The planet carrier 5 can transmit rotational motion to the three planet gears 6. The planet gears 6 can rotate about the sun gear shaft 3, which can be held stationary relative the shuttle frame 9 via the first clutch driver 4*a*. The planet gears 6 can impart rotary motion to the ring gear 7. The ratio of motion between the planet carrier 5 and the ring gear 7 can be determined by the ratio of ring gear portion 7*b* teeth to sun gear portion 3*a* teeth (ratio=R/(R+S)). Linear motion can be transmitted to the ratchet rack 8 in the proximal direction by the ring gear 7. The inner shaft member 21 can move proximally relative to the handle 1. Thus, during the second action, the inner shaft member moves proximally relative to the handle 1 and the outer tubular member 22 is stationary relative to the handle.

Figure 2:
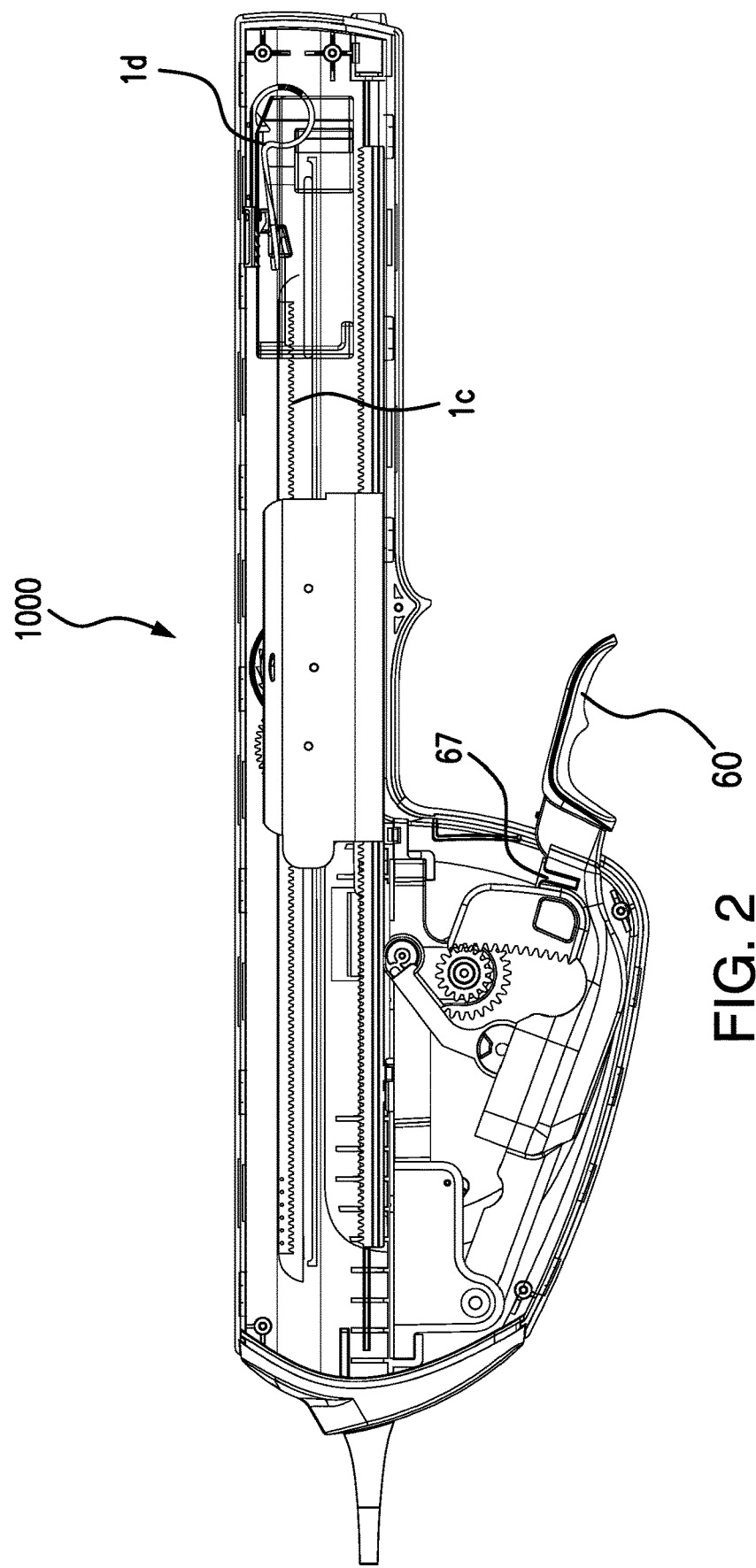
FIG. 2 is a right side view, with a portion of the handle housing removed, of the delivery system of FIG. 1A.
Figure 3:
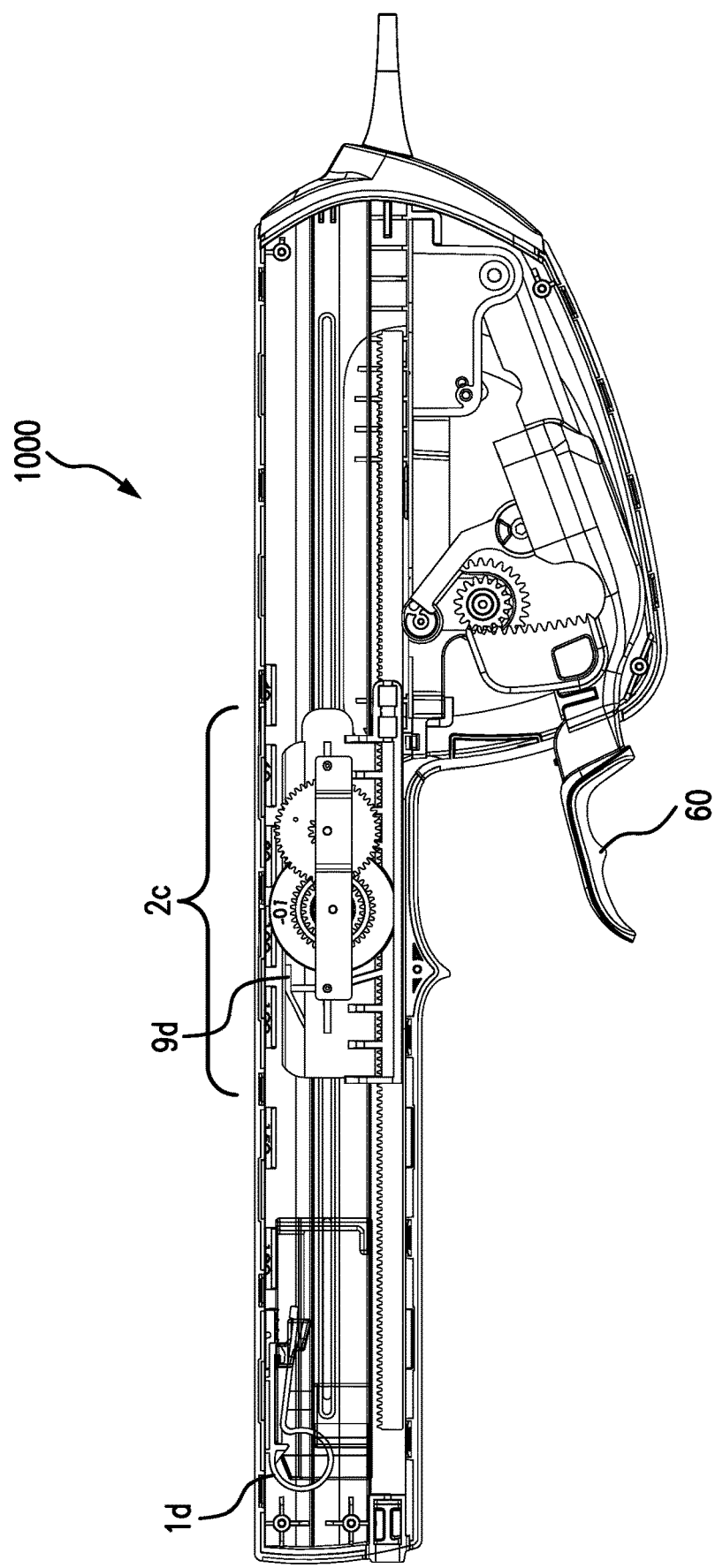
FIG. 3 is a left side view, with a portion of the handle housing removed, of the delivery system of FIG. 1A.
Figure 23:
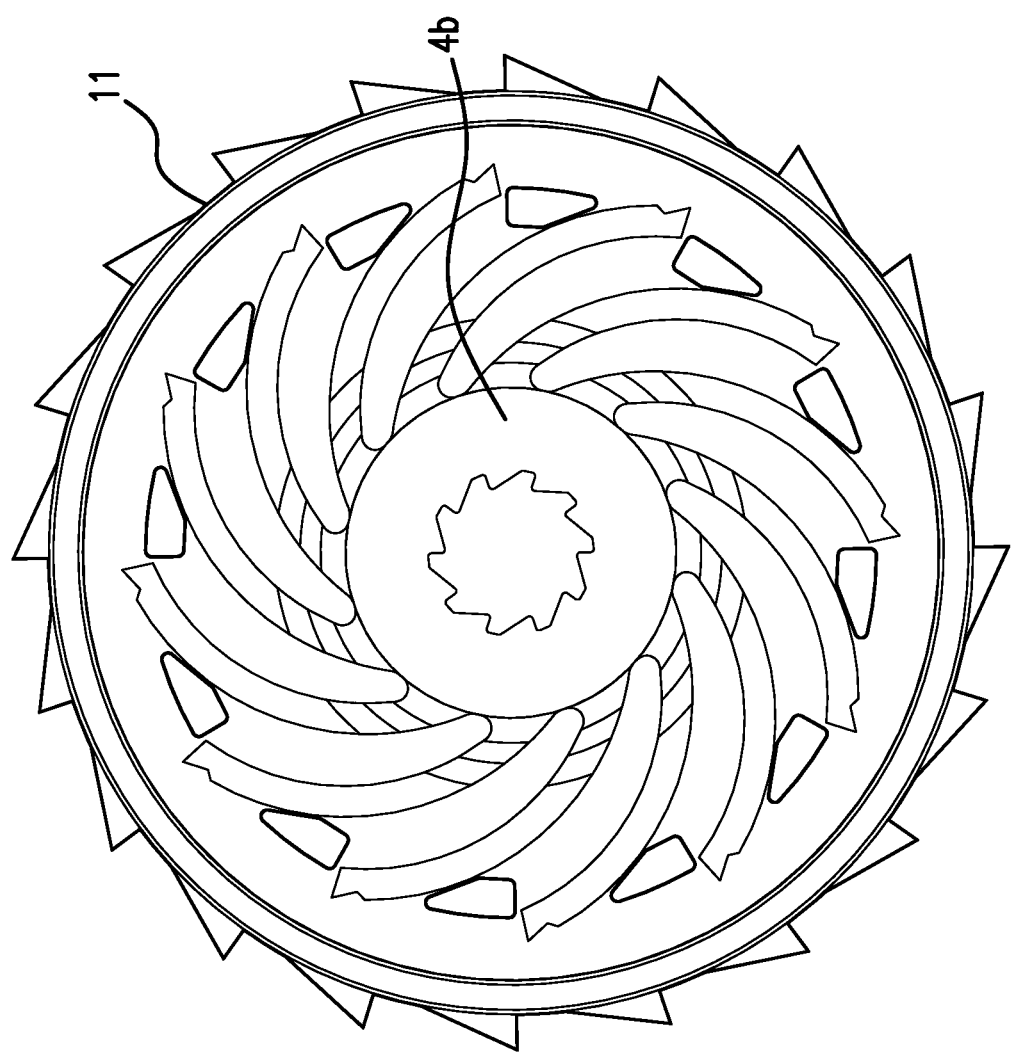
FIG. 23 is a side view showing the relationship between the clutch release and the second clutch driver of the delivery system of FIG. 1A.

As further embodied herein, the actuation assembly 2 can include a clutch release 11. The clutch release 11 can be operatively coupled to the second clutch driver 4*b* and can be configured to prevent the second clutch driver 4*b* from uni-directionally locking the sun gear shaft 3 and the planet carrier 5 when the clutch release 11 is engaged by a stop 1*d*, as shown in FIGS. 2 and 3. For example, the clutch release 11 can prevent the clutch portion of the second clutch driver 4*b* from engaging with the clutch component 5*b* of the planet carrier 5 by urging elements of the clutch portion away from the clutch component 5*b*, as shown in FIG. 23, for the purpose of illustration and not limitation. Thus, the clutch release 11 can prevent the sun gear shaft 3, planet carrier 5 and ring gear 7 rotating with a 1:1 ratio during the first motion. Rather, when the clutch release 11 is engaged by the stop 1*d*, the ratio of motion between planet carrier 5 and the ring gear 7 is the same for the first motion and the second motion. The stop 1*d* can be disposed on the handle 1, for example on the second handle housing portion 1*b*. The stop 1*d* can be configured to engage the clutch release 11 when the actuation assembly 2 has moved proximally a distance (z) along the handle 1. Any suitable distances for (z) can be used. The stop 1*d* can be inserted into a receiving pocket disposed on the handle or otherwise secured with known techniques. The clutch release 11 can include a saw-tooth portion 11*a* or other suitable configuration, and the stop 1*d* can include a resilient abutment portion. The saw-tooth portion of the clutch 11 thus can be configured to engage the resilient abutment portion of the stop 1*d*. As an example, the stop can be a P-shaped stop that can provide compliance and opposing bias when the resilient abutment portion of the stop 1*d* engages the saw-tooth portion of the clutch 11. Such a configuration can prevent or inhibit disengagement of the clutch release 11 and the clutch component 5*b* of the planet carrier 5. Shuttle frame 9 can further include a ramp 9*d*, as shown in FIG. 3, which is configured to guide and assist the P-shaped stop 1*d* into proper operation as designed. For example, if the P-shaped stop 1*d* is in an open position, as shown in FIG. 3, the ramp 9*d* can guide a portion of the stop 1*d* upwardly towards a closed position.

Figure 24:
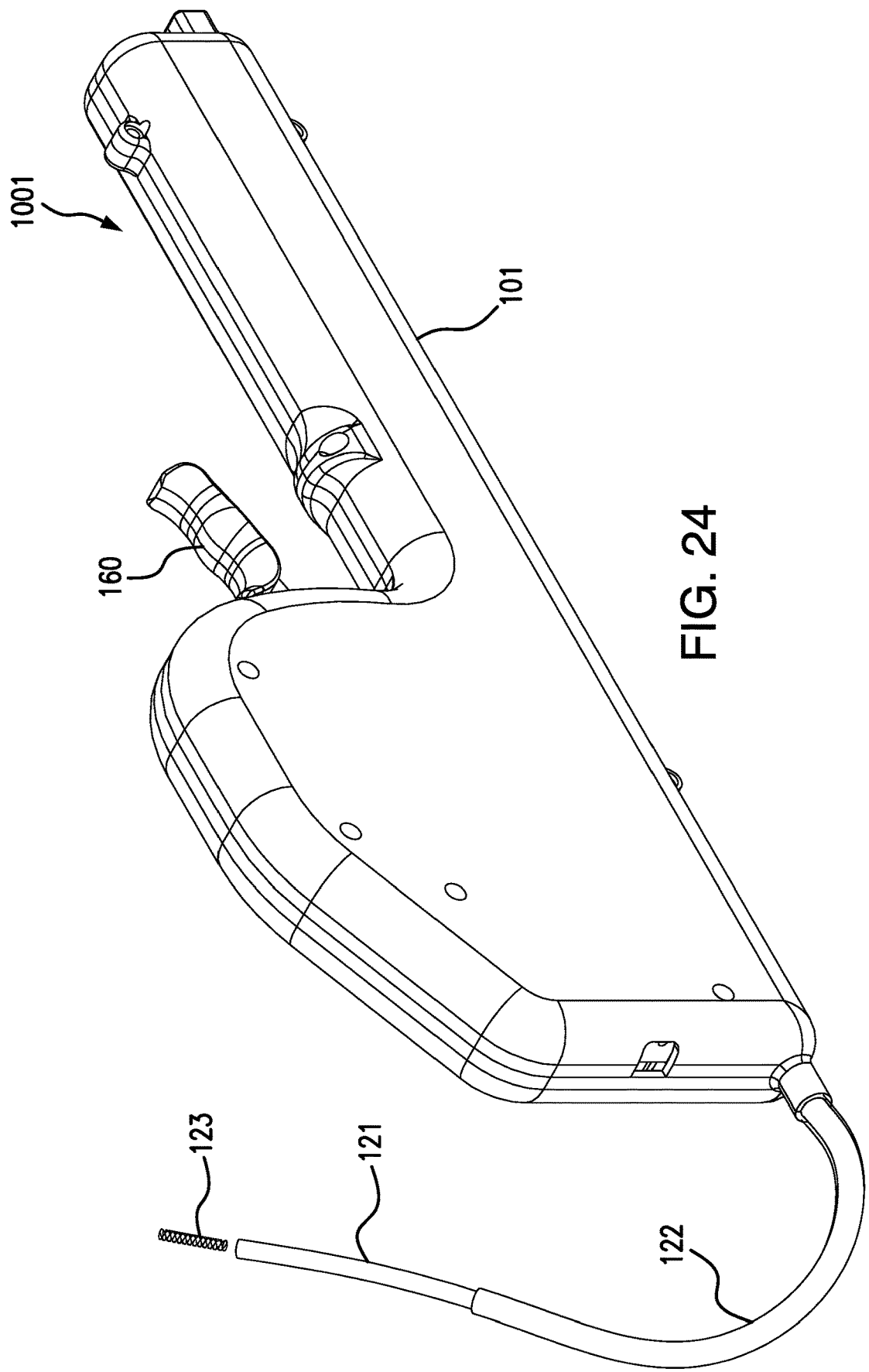
FIG. 24 is a perspective view of another exemplary embodiment of a delivery system in accordance with the disclosed subject matter.
Figure 25:
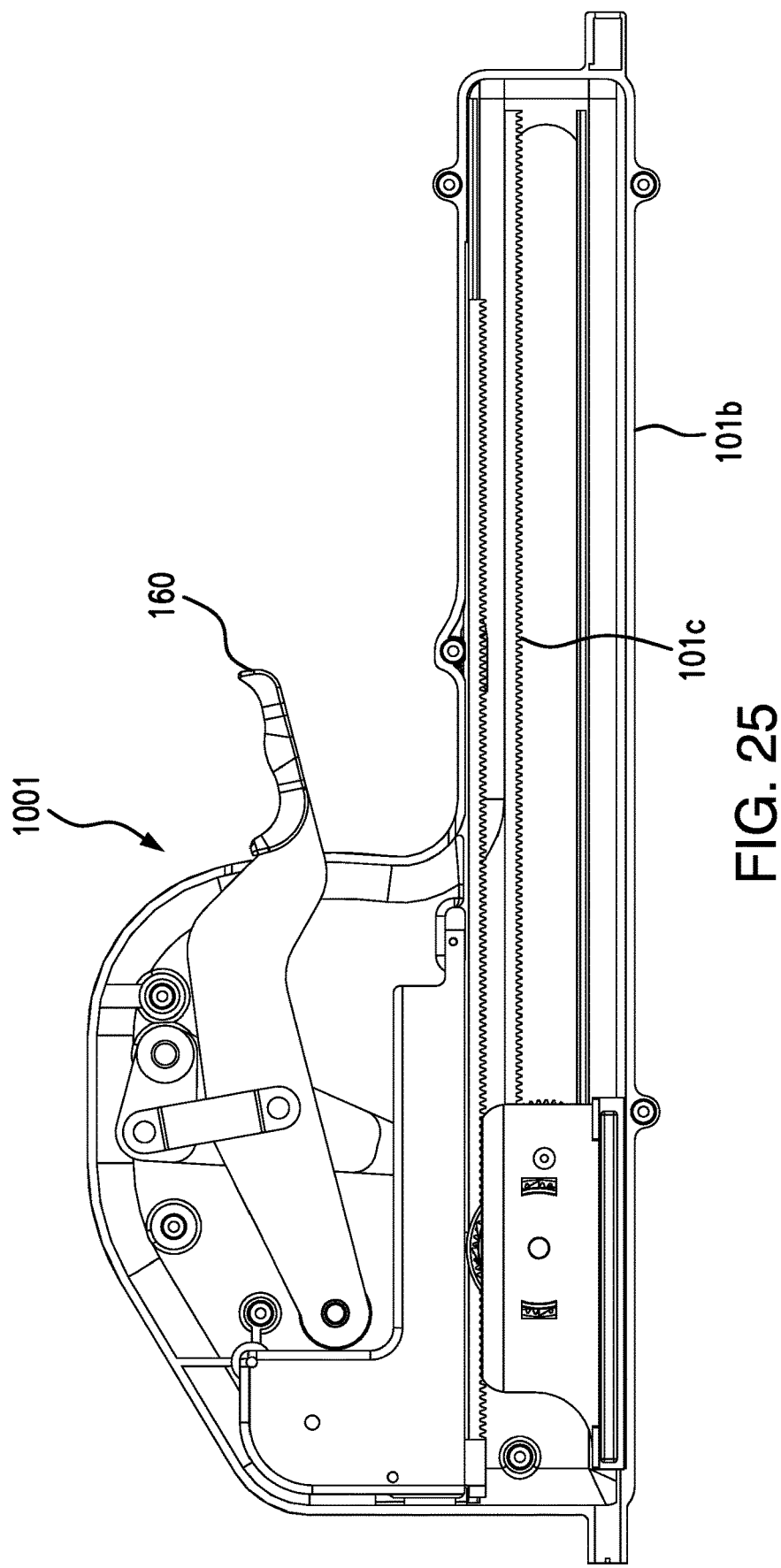
FIG. 25 is a right side view, with a portion of the handle housing removed, of the delivery system of FIG. 24.
Figure 26:
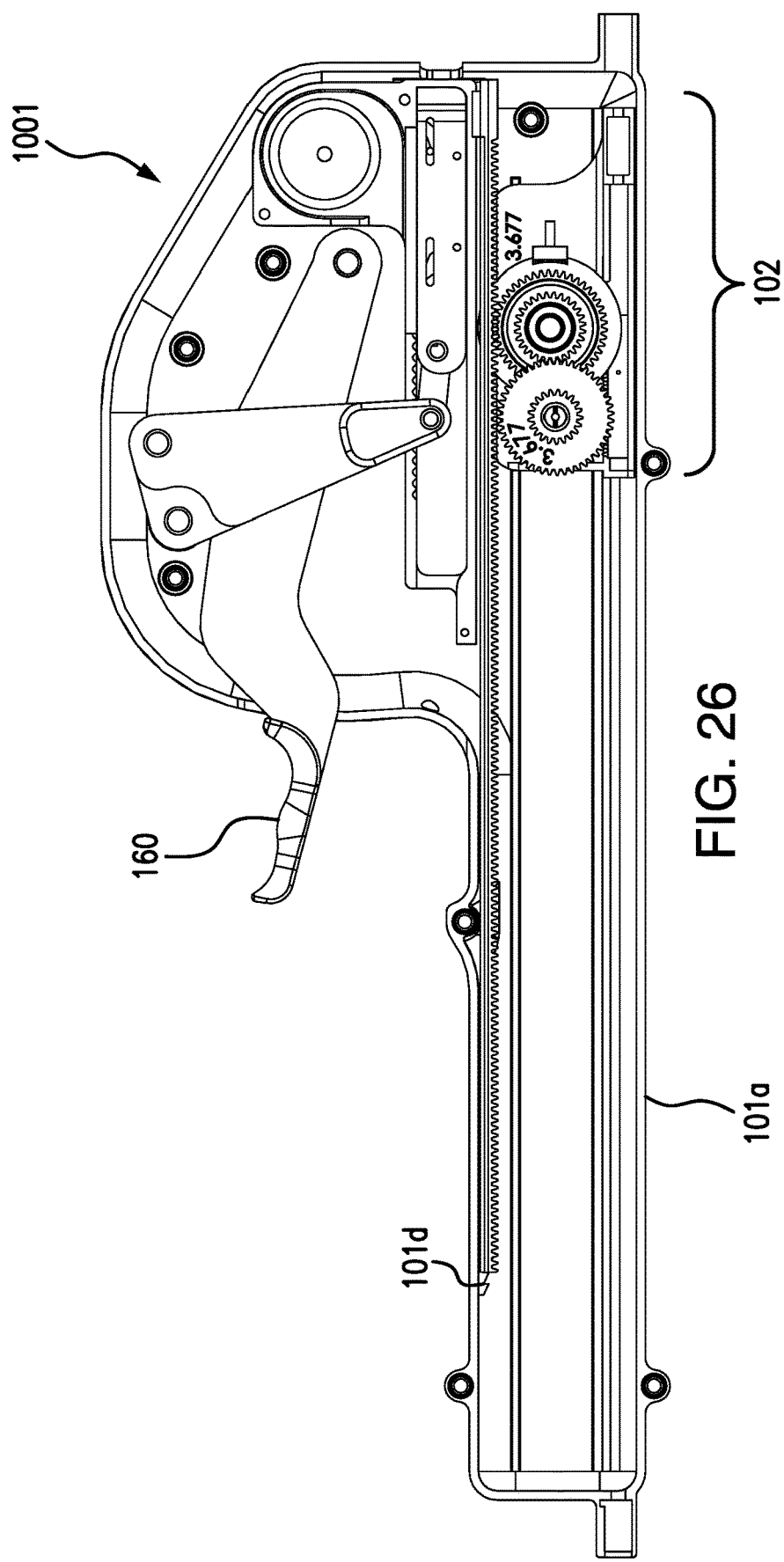
FIG. 26 is a left side view, with a portion of the handle housing removed, of the delivery system of FIG. 24.
Figure 28A:
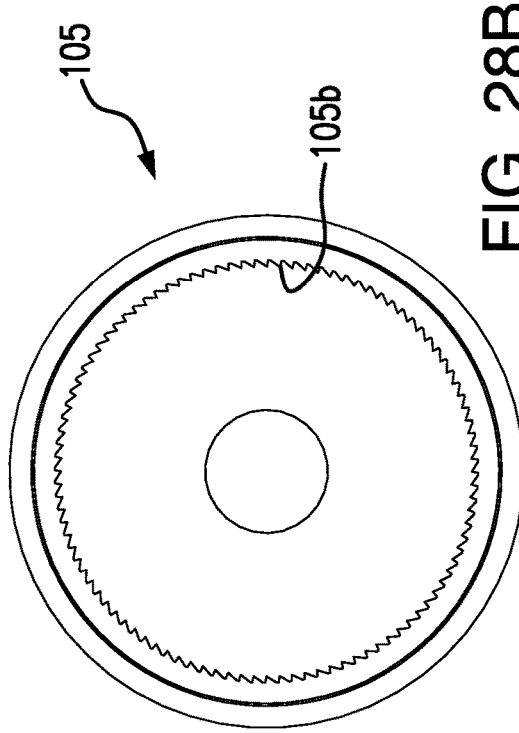
FIGS. 28A-28D provide perspective FIG. 28A, right FIG. 28B, left FIG. 28C, and front FIG. 28D views of the planet carrier of the delivery system of FIG. 24.
Figure 28B:
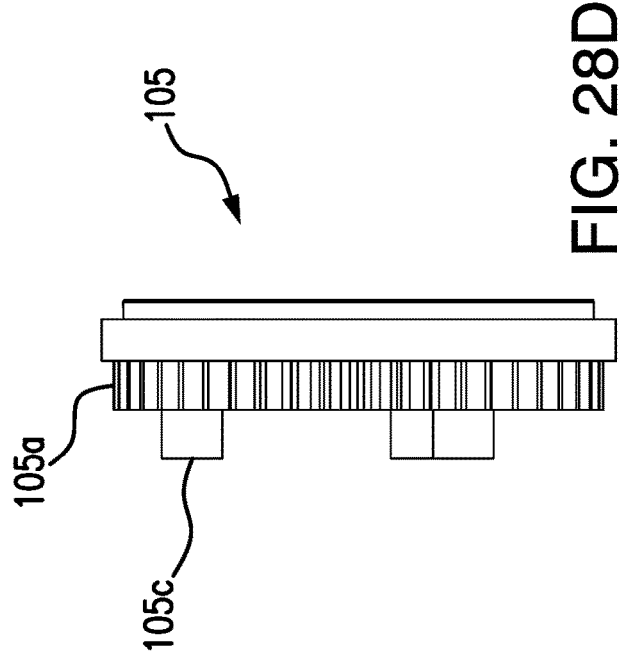
Figure 28C:
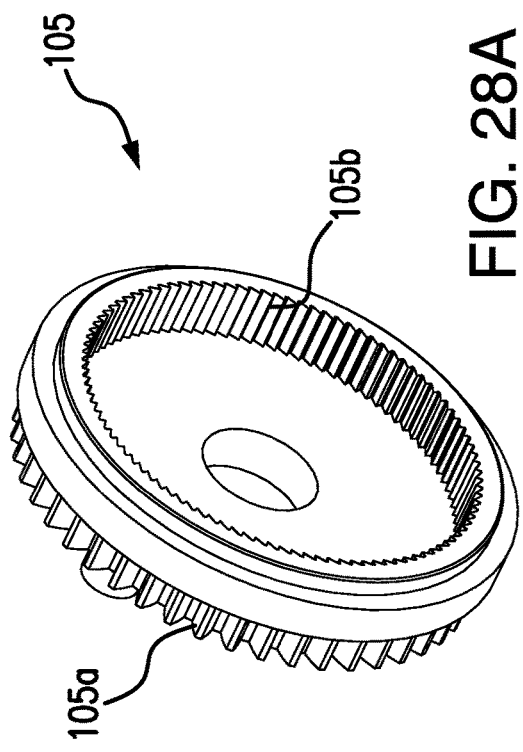
Figure 28D:
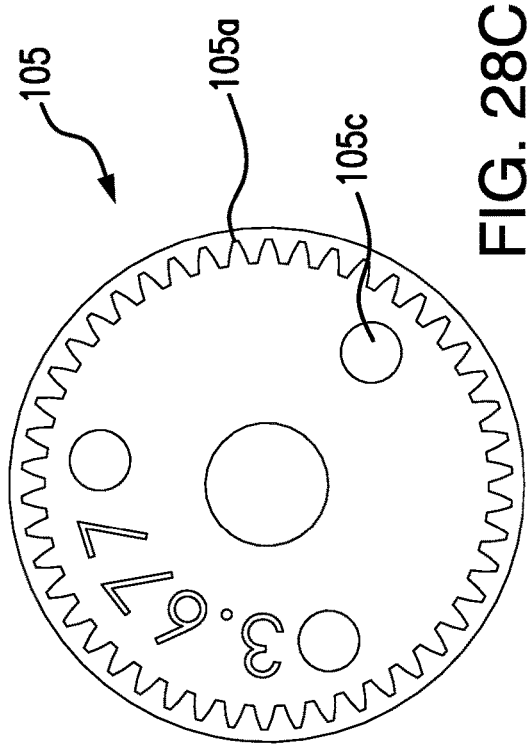
Figure 30B:
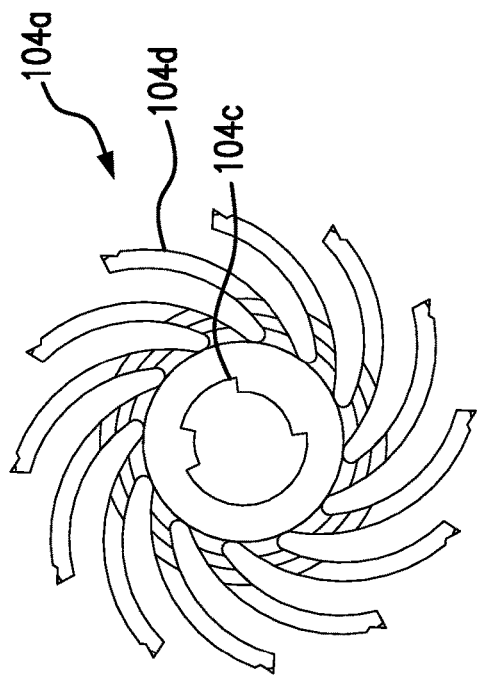
FIGS. 30A-30D provide perspective FIG. 30A, right FIG. 30B, left FIG. 30C, and front FIG. 30D views of the first clutch driver of the delivery system of FIG. 24.
Figure 30D:
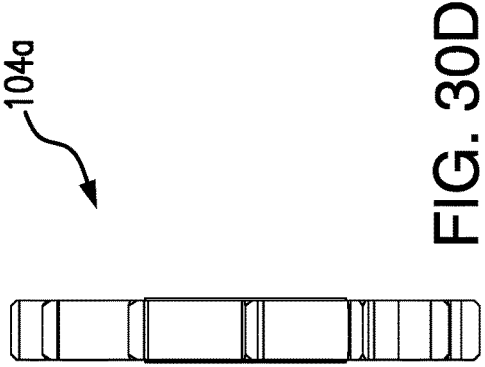
Figure 30A:
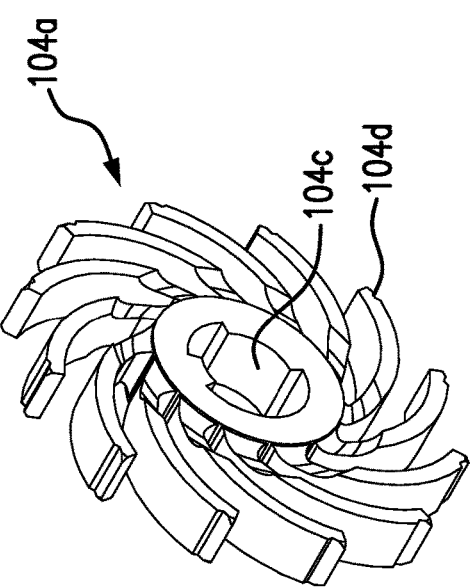
Figure 30C:
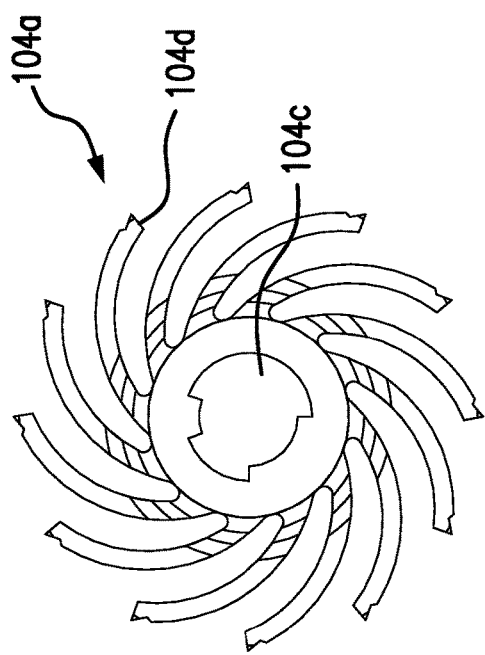
Figure 31B:
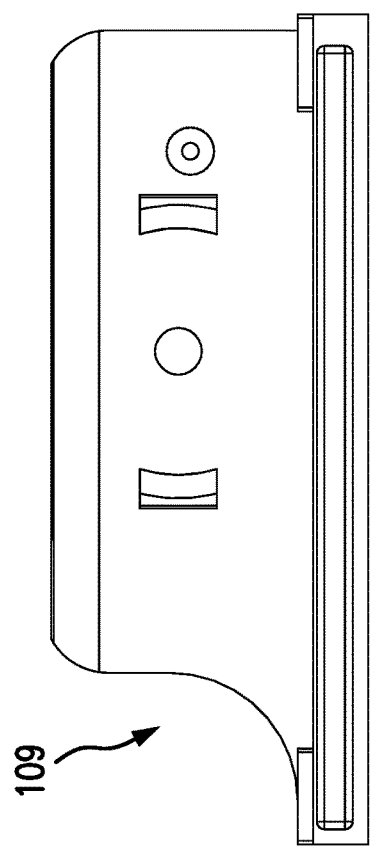
FIGS. 31A-31D provide perspective FIG. 31A, right FIG. 31B, left FIG. 31C, and front FIG. 31D views of the shuttle frame of the delivery system of FIG. 24.
Figure 31D:
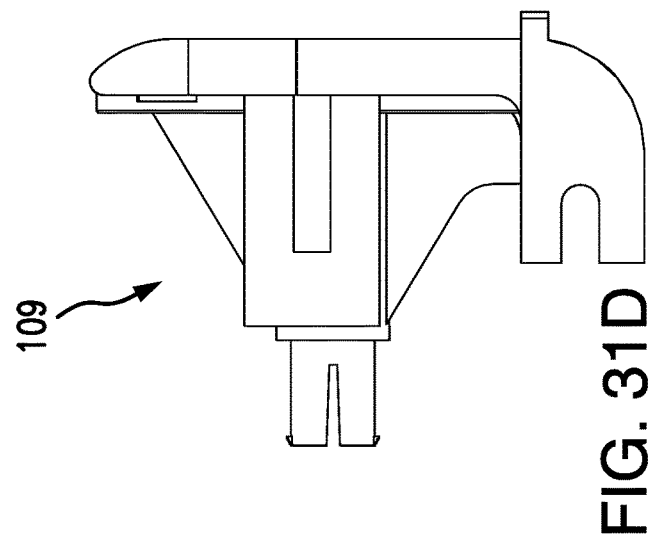
Figure 31A:
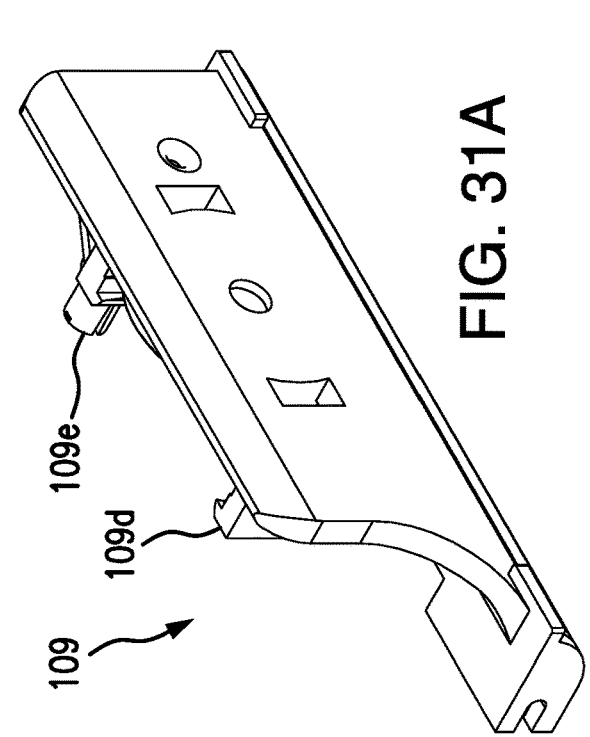
Figure 31C:
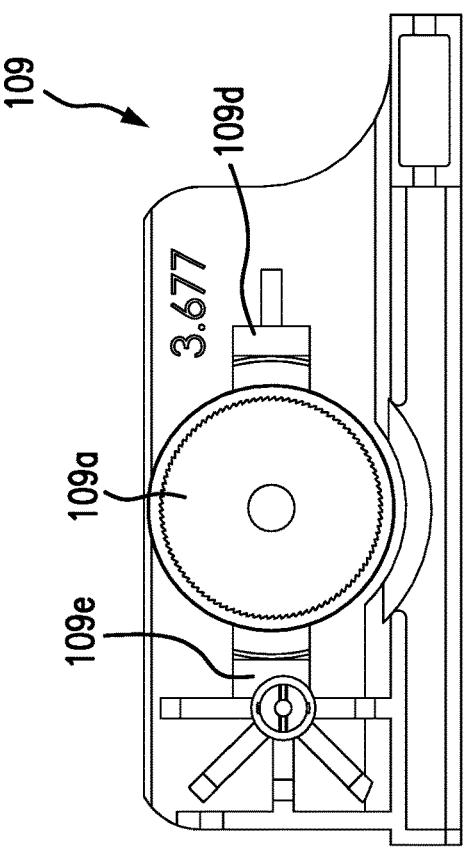
Figure 32A:
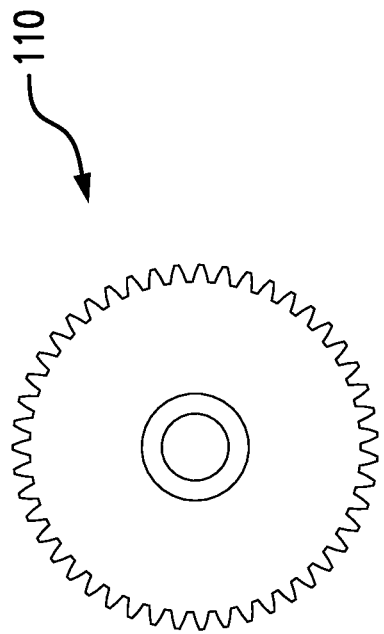
FIGS. 32A-32D provide perspective FIG. 32A, right FIG. 32B, left FIG. 32C, and front FIG. 32D views of the intermediate gear of the delivery system of FIG. 24.
Figure 32C:
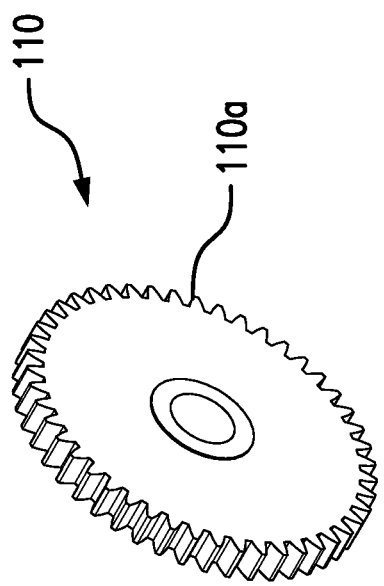
Figure 32B:
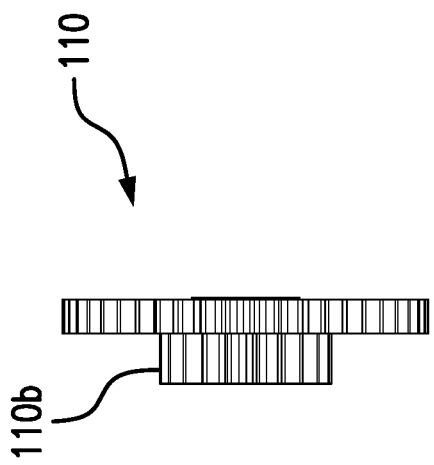
Figure 32D:
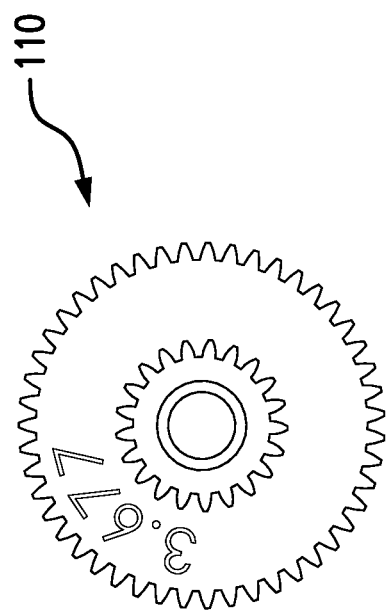
Figure 33A:
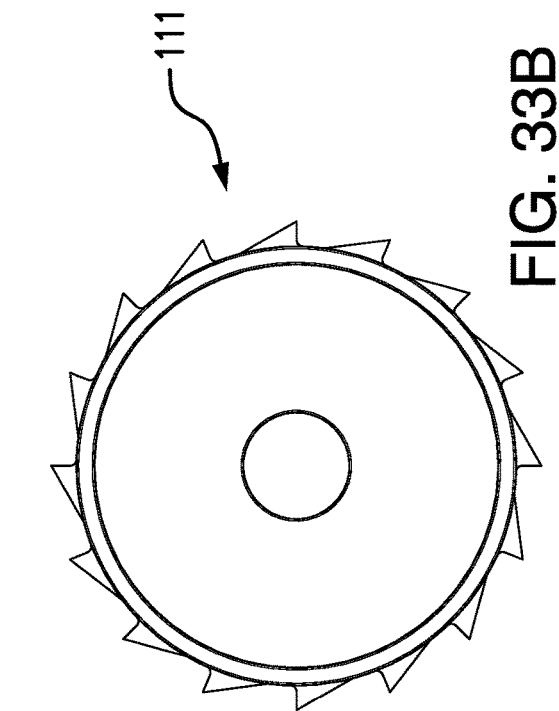
FIGS. 33A-33D provide perspective FIG. 33A, right FIG. 33B, left FIG. 33C, and front FIG. 33D views of the clutch release of the delivery system of FIG. 24.
Figure 33B:
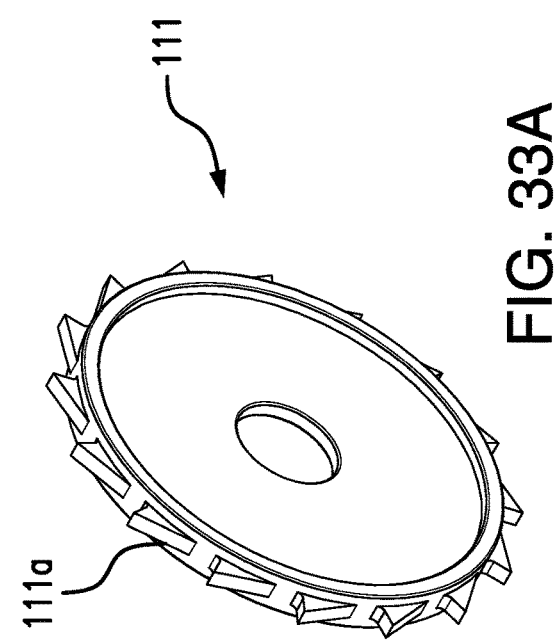
Figure 33D:
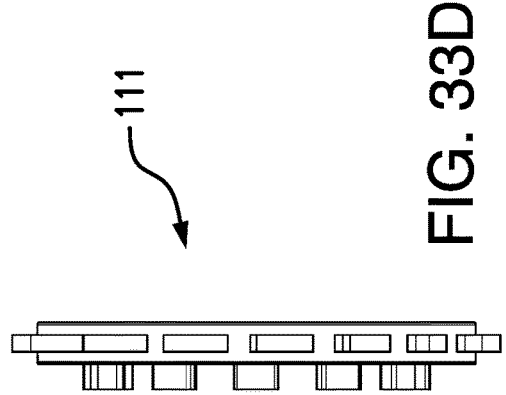
Figure 33C:
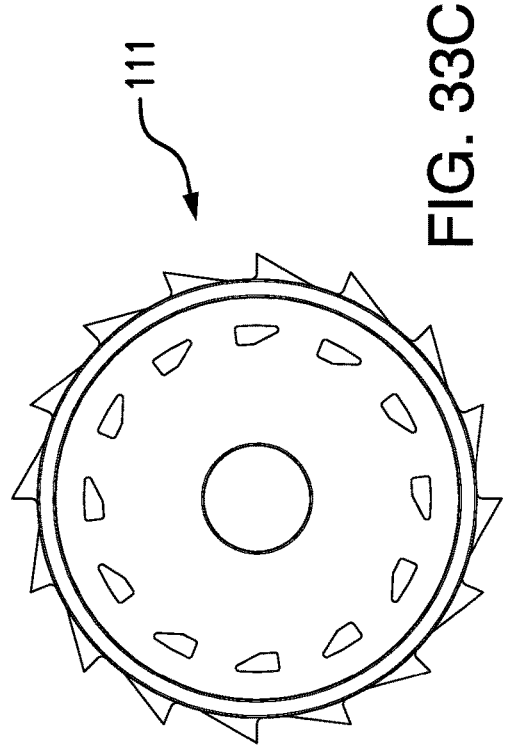

Referring now to FIG. 24 for the purpose of illustration and not limitation, another exemplary embodiment of a system for delivering an implant is provided and designated generally by reference character 1001. Portions of this exemplary embodiment are depicted in FIGS. 25-35. Elements that are similar to the previously described embodiment have been given like numbers. The delivery system 1001 can be configured to deliver an implant in a similar manner as described herein above.

The delivery system 1001 can include a handle 101, an outer tubular member 122, an inner shaft member 121, and an implant 123, for example, a braided implant. The handle 101 can include a trigger 160 and an actuation assembly 102, which can be configured to move the inner shaft member 121 and the outer tubular member 122 relative to the handle 101 as described above upon deployment of the trigger 160 from the first position to the second position and return from the second position to the first position. The trigger 160 can include a lock as described herein above.

Referring now to FIGS. 25-35 for the purpose of illustration and not limitation, the actuation assembly 102 can include a planetary gear system. For purpose of illustration and not limitation, the actuation assembly 102 can be suitably similar to that of the previous embodiment. However, as an alternative to the actuation assembly of the previous embodiment, certain modifications can be incorporated. For example, the ratchet rack 108 can be operatively meshed with the planet carrier 105, and the driving rack 112 can be operatively meshed with the ring gear 107.

The actuation assembly 102 can include a sun gear shaft 103 (which can include a sun gear portion 103*a*, a sheath pinion 103*b*, and a clutch engagement portion 103*c*; FIG. 27), a planet carrier 105 (which can include a circumferential pinion 105*a*, a clutch component 105*b*, and at least one pin 105*c*; FIG. 28), at least one planet gear 106, a ring gear 107 (which can include a circumferential pinion 107*a* and a ring gear portion 107*b*; FIG. 29), a first clutch driver 104*a* and a second clutch driver 104*b*, both identical in shape (each can include a sun gear shaft engagement portion 104*c* and a clutch portion 104*d*; FIG. 30). The actuation assembly 102 can include a shuttle frame 109. The shuttle frame 109 can have the planet carrier 105, planet gears 106, sun gear shaft 103, ring gear 107, and first and second clutch drivers (104*a* and 104*b*) disposed thereon. The shuttle frame 109 can be disposed within the handle 101 and can be moveable relative to the handle 101 along the length of the handle 101. The shuttle frame 109 can include a clutch engagement portion 109*a*, a cavity 109*b* which can receive a ferrule coupled to the proximal end of the outer tubular member 122, and clips 109*d* and 109*e*, which can hold the planetary gear system in place on the shuttle frame 109. The planet carrier 105, planet gears 106, sun gear shaft 103 and ring gear 107 can perform as the respective elements of the planetary gear system as described above. The actuation assembly can also include a ratchet rack 108. The actuation assembly can be functionally coupled to the trigger 160 by a driving rack 112, which can be supported by the handle 101. The actuation assembly can include a clutch release 111 which can engage a stop 101d disposed on the handle, as described herein above with regard to system 1000.

During operation, the user can deploy the trigger 160 from the first position to the second position (referred to herein as the "first action"). The trigger 160 can cause the driving rack 112 to move in a proximal direction. The driving rack 112, functionally meshed with the circumferential pinion 107a of the ring gear 107, can impart rotational motion on the ring gear 107 (FIG. 34). The ring gear portion 107b of the ring gear 107 can be operatively meshed with the planet gears 106, and can impart rotational motion on the planet gears 106. The planet gears 106 are operatively meshed with the sun gear portion 103a of the sun gear shaft 103 and thus can be constrained from rotating freely because they. The movement of the planet gears 106, which are disposed on the pins 105c of the planet carrier 105, can impart rotational motion on the planet carrier 105. The planet carrier 105 and the sun gear shaft 103 can be rotationally coupled by the second clutch driver 104b when rotating in the first action; thus, rotation can be transmitted to the sun gear shaft 103 in a 1:1 ratio. The first clutch driver 104a can allow the sun gear shaft 103 to rotate freely relative to the shuttle frame 109 during the first action. The sheath pinion 103b of the sun gear shaft 103 can be meshed with the large spur gear 110a of an intermediate gear 110, and can impart rotational motion on the intermediate gear 110. The small spur gear 110b of the intermediate gear 110 can be operatively meshed with a rack 101c disposed on the second handle housing portion 101b; thus, the rotational motion of the intermediate gear 110 can impart linear motion on the shuttle frame 109 in the proximal direction. The outer tubular member 122, which can be fixedly coupled to the shuttle frame 109, can move proximally relative to the handle 101. The circumferential pinion 105a of the planet carrier 105 can be operatively meshed with a ratchet rack 108, and rotation of the planet carrier 105 can move the ratchet rack 108 distally (FIG. 35). The inner shaft member 121, which can be fixedly coupled to the ratchet rack 108, moves distally. Thus, during the first action, the inner shaft member 121 can move distally relative to the handle 101 and the outer tubular member 122 can move proximally relative to the handle 101.

Upon return of the trigger 160 from the second position to the first position (herein referred to as the "second action"), the driving rack 112 can move distally relative to the handle 101. The driving rack 112 can impart rotational motion on the ring gear 107. The ring gear 107 can impart rotational motion on the three planet gears 106. The planet gears 106 can rotate about the sun gear shaft 103, which can be held stationary relative the shuttle frame 109 via the first clutch driver 104a. The planet gears 106 can impart rotational motion on the planet carrier 105. Linear motion in the proximal direction can be transmitted to the ratchet rack 108 by the planet carrier 105. The inner shaft member 121, fixedly coupled to the ratchet rack 108, can move proximally relative to the handle 101. Thus, during the second action, the inner shaft member 121 can move proximally relative to the handle 101 and the outer tubular member 122 can be stationary relative to the handle 101.

Figure 36:
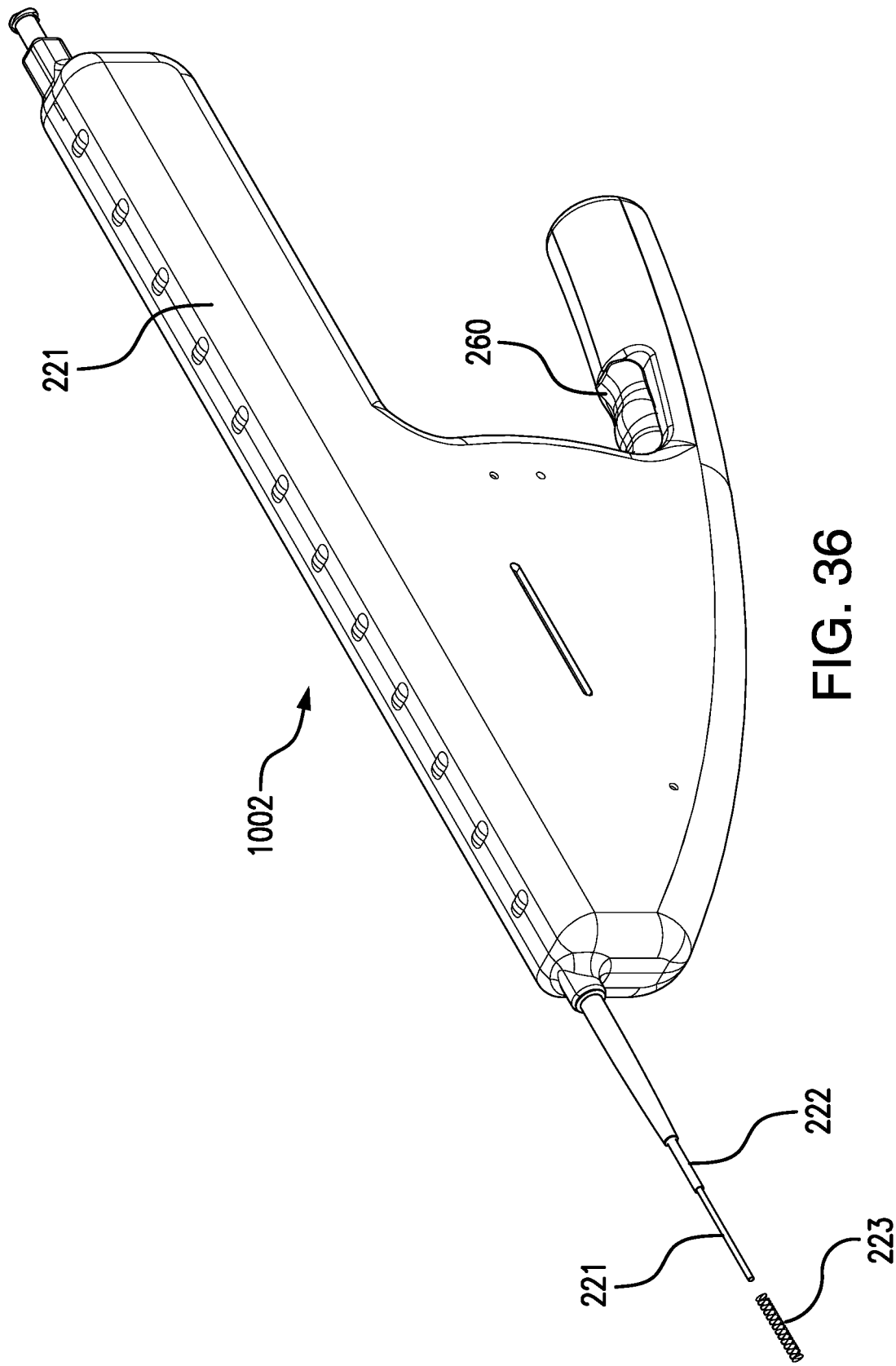
FIG. 36 is a perspective view of a yet another exemplary embodiment of delivery system in accordance with the disclosed subject matter.
Figure 37:
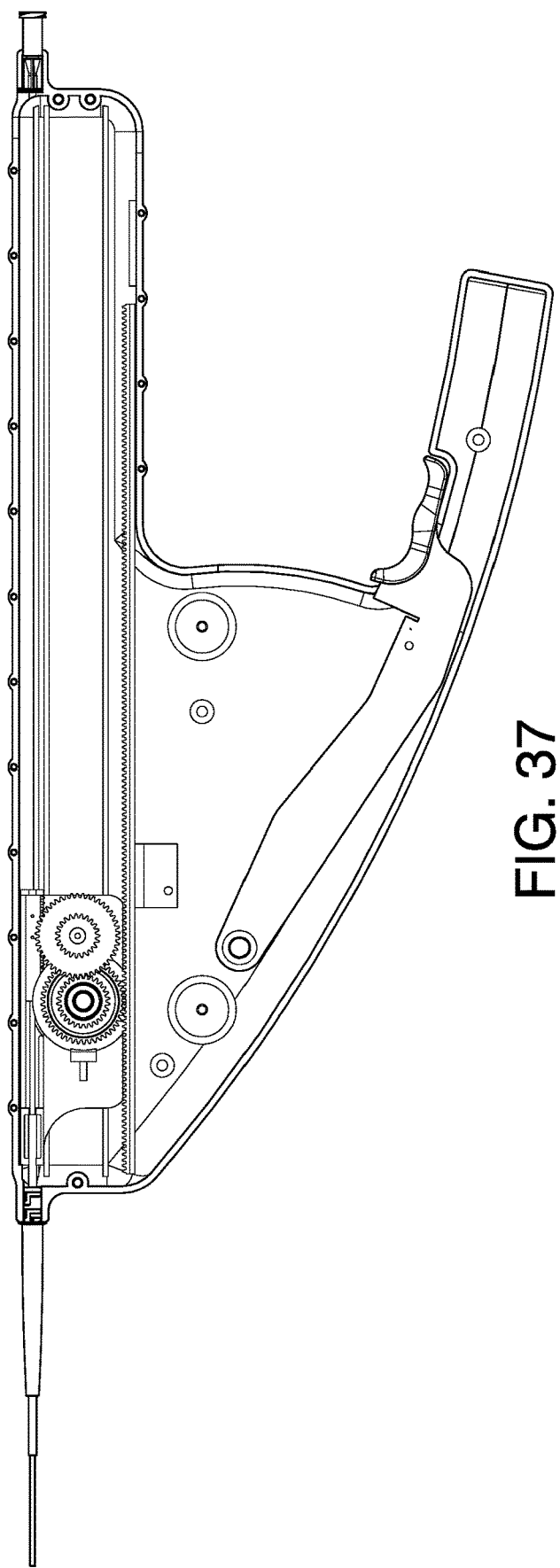
FIG. 37 is a right side view, with a portion of the handle housing removed, of the delivery system of FIG. 36.
Figure 38:
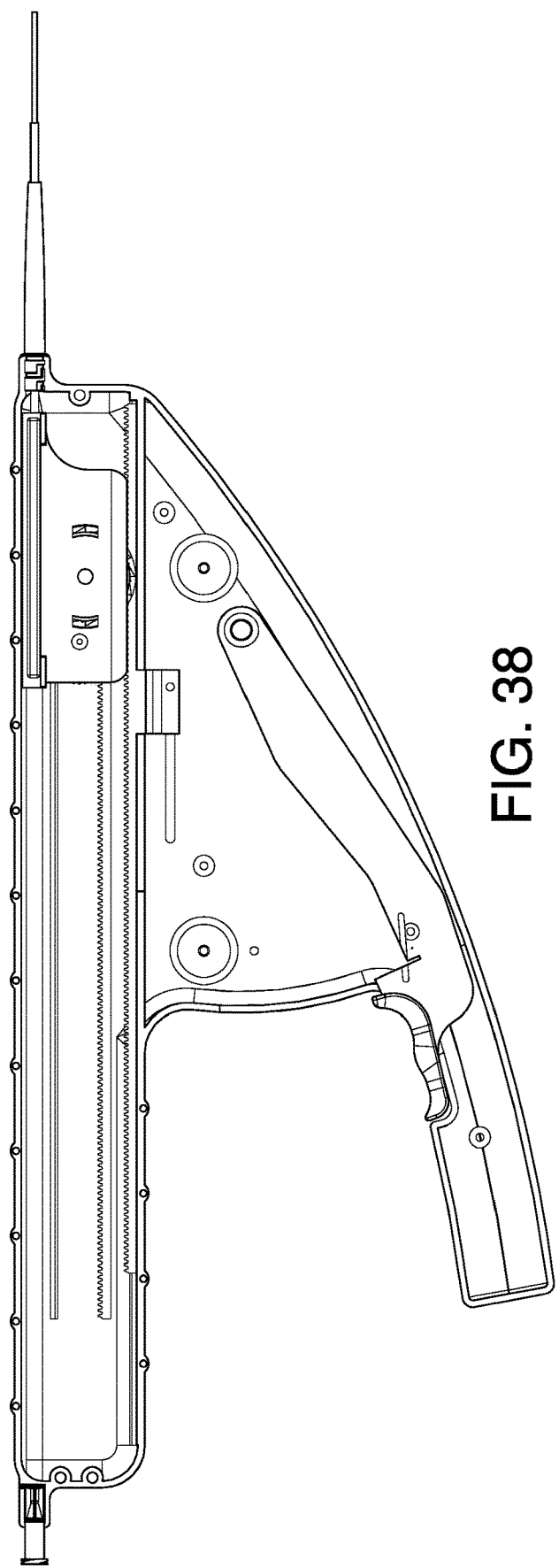
FIG. 38 is a left side view, with a portion of the handle housing removed, of the delivery system of FIG. 36.
Figure 39B:
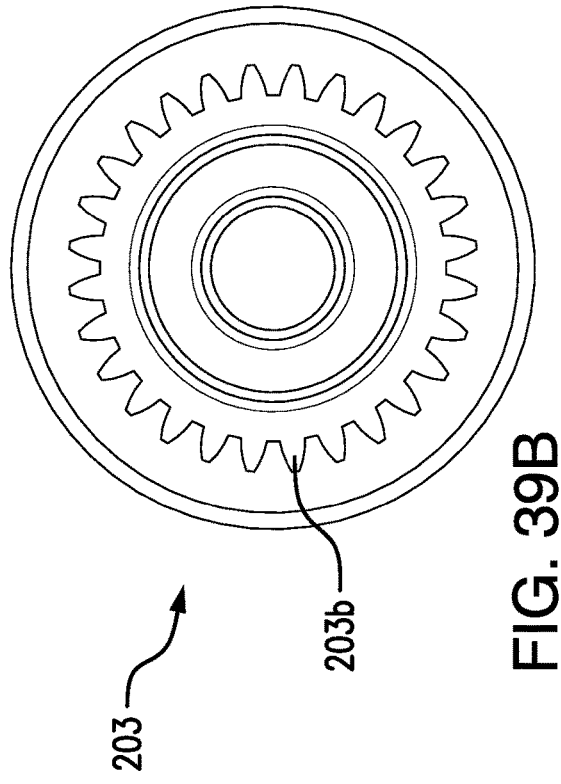
FIGS. 39A-39D provide perspective FIG. 39A, right FIG. 39B, left FIG. 39C, and front FIG. 39D views of the sun gear shaft of the delivery system of FIG. 36.
Figure 39D:
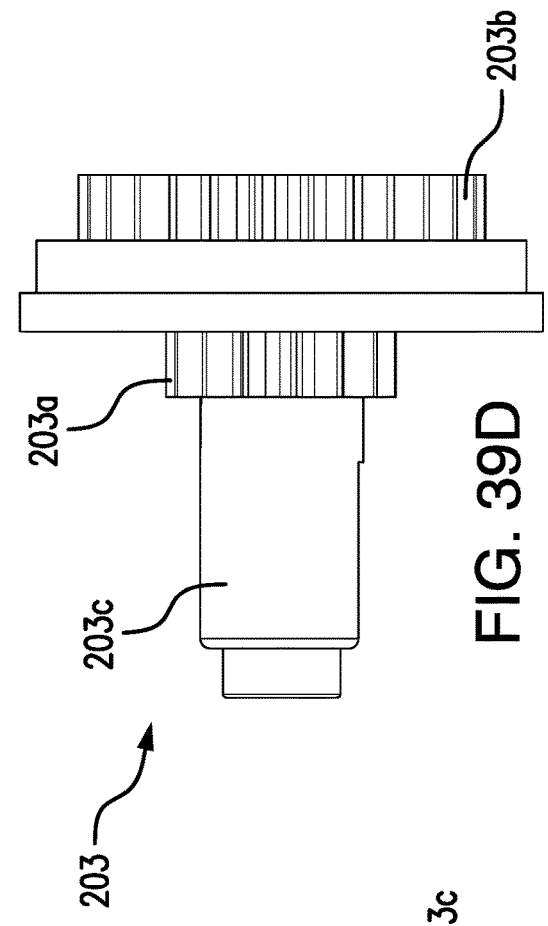
Figure 39A:
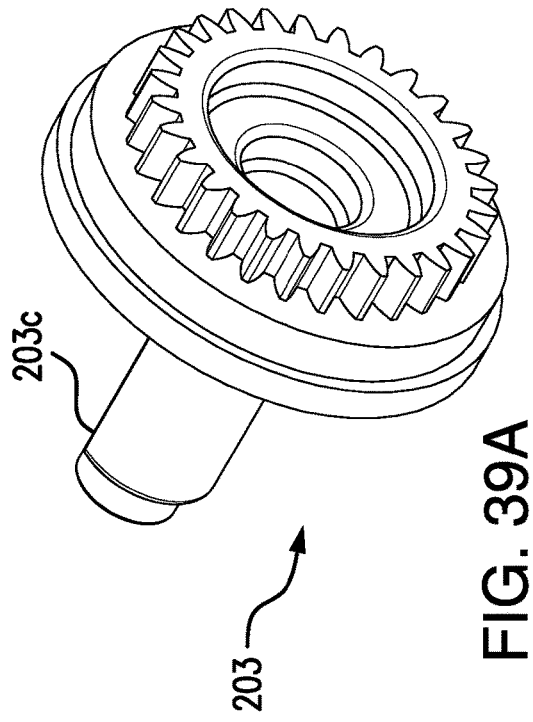
Figure 39C:
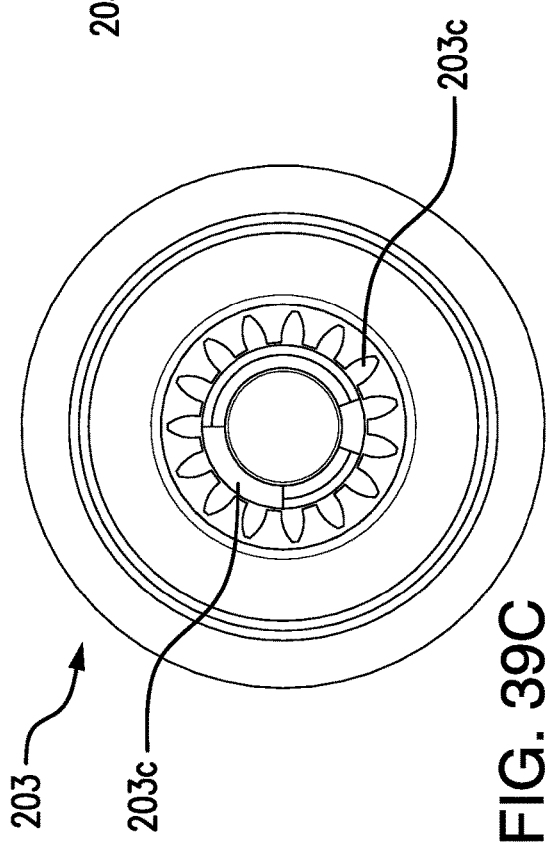
Figure 40A:
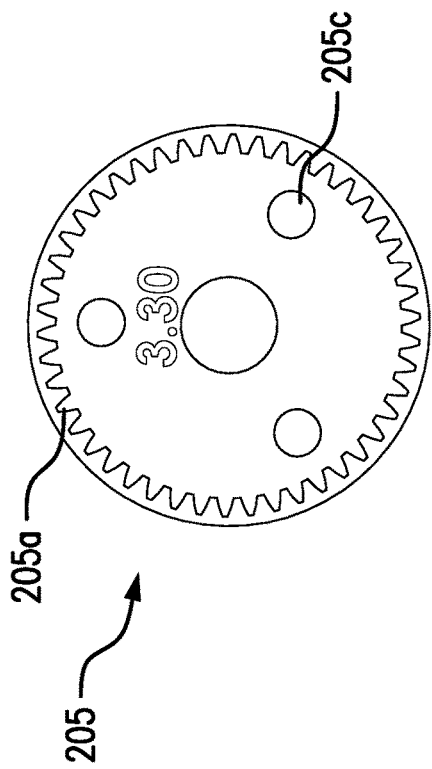
FIGS. 40A-40D provide perspective FIG. 40A, right FIG. 40B, left FIG. 40C, and front FIG. 40D views of the planet carrier of the delivery system of FIG. 36.
Figure 40C:
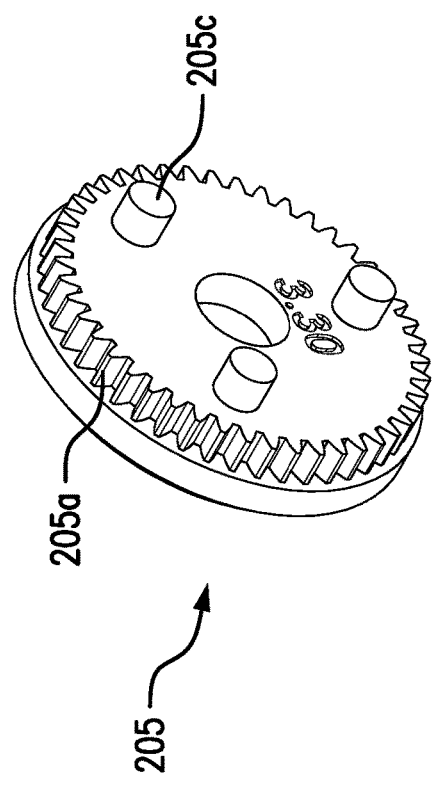
Figure 40B:
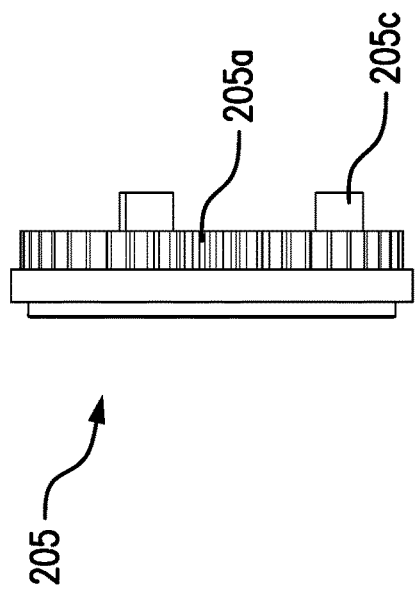
Figure 40D:
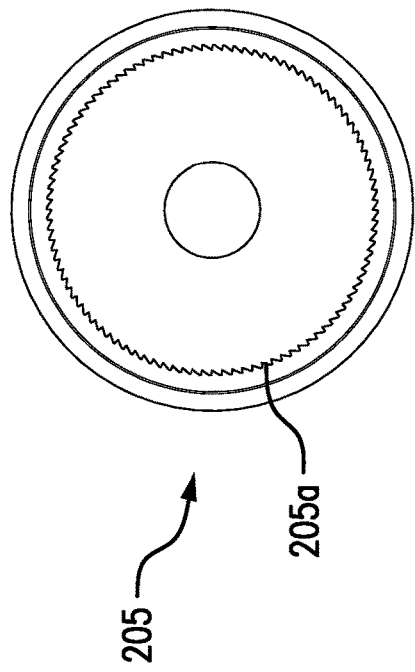
Figure 41B:
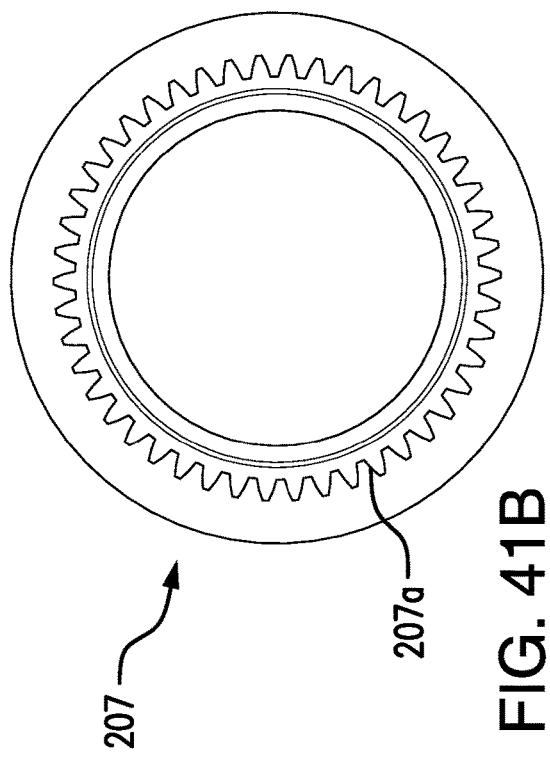
FIGS. 41A-41D provide perspective FIG. 41A, right FIG. 41B, left FIG. 41C, and front FIG. 41D views of the ring gear of the delivery system of FIG. 36.
Figure 41D:
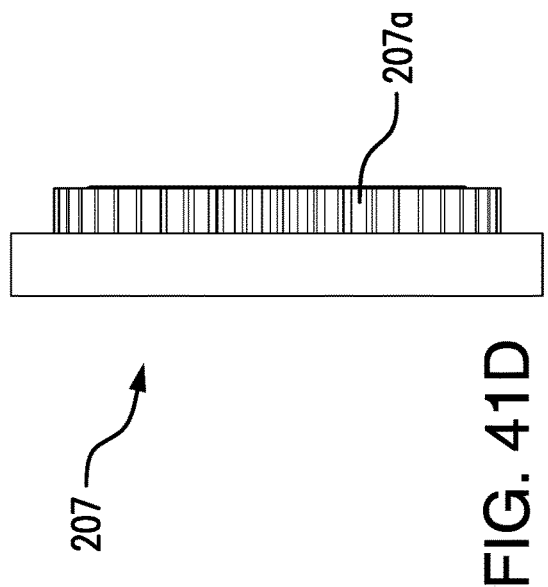
Figure 41A:
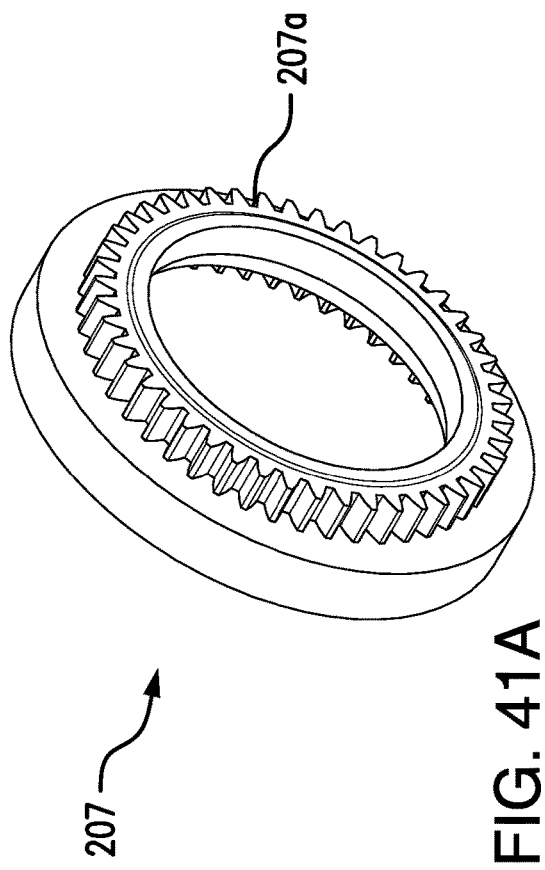
Figure 41C:
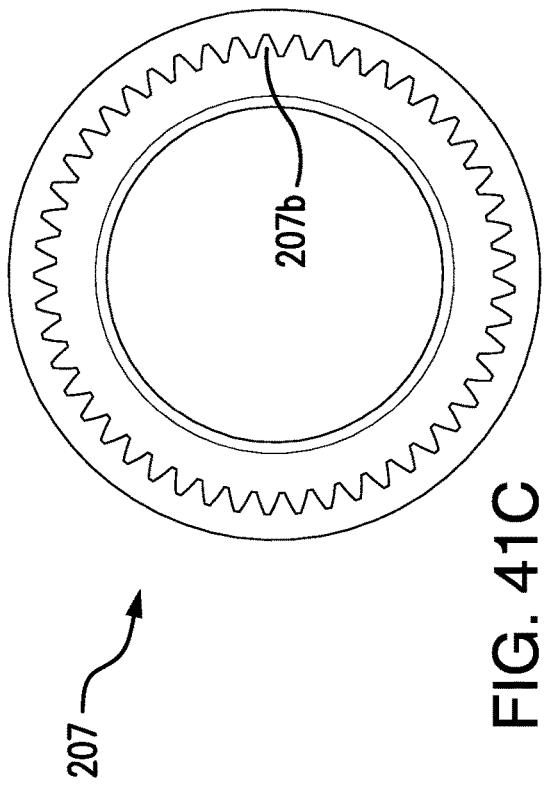
Figure 42A:
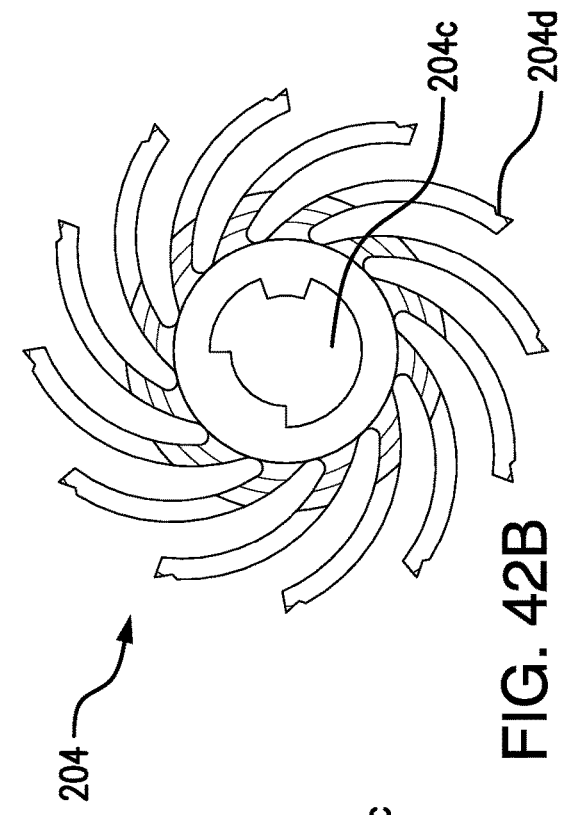
FIGS. 42A-42D provide perspective FIG. 42A, right FIG. 42B, left FIG. 42C, and front FIG. 42D views of the first clutch driver of the delivery system of FIG. 36.
Figure 42B:
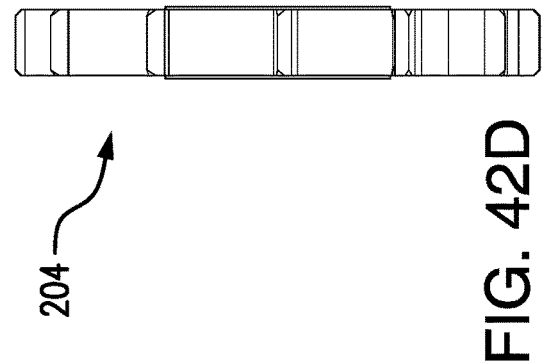
Figure 42C:
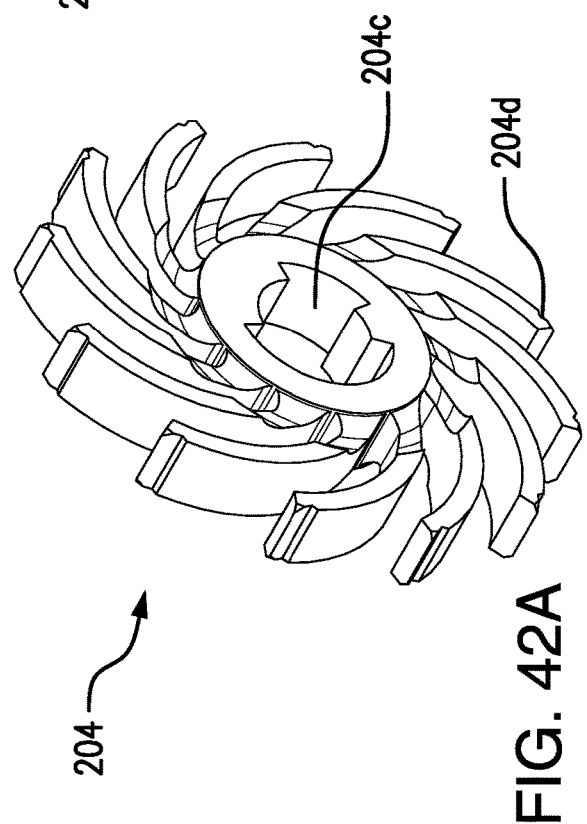
Figure 42D:
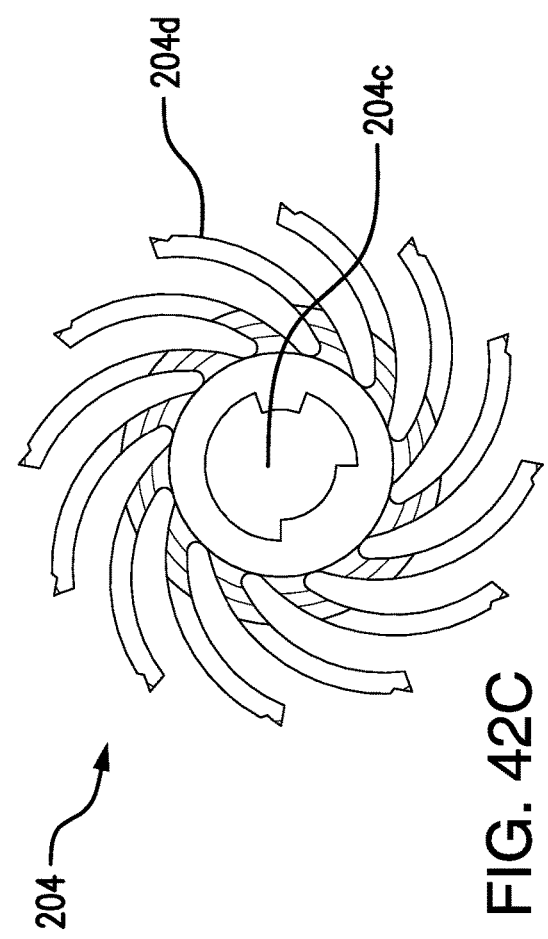
Figure 43B:
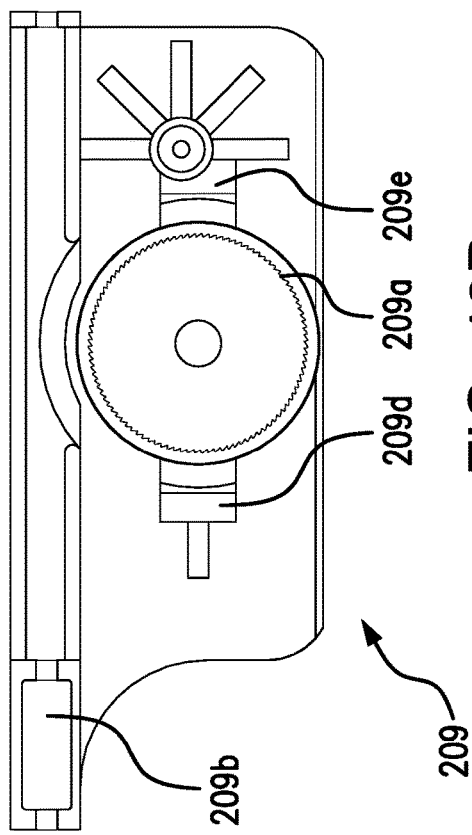
FIGS. 43A-43D provide perspective FIG. 43A, right FIG. 43B, left FIG. 43C, and front FIG. 44D views of the shuttle frame of the delivery system of FIG. 36.
Figure 43D:
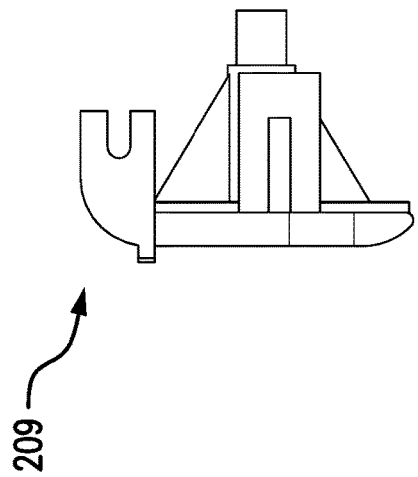
Figure 43A:
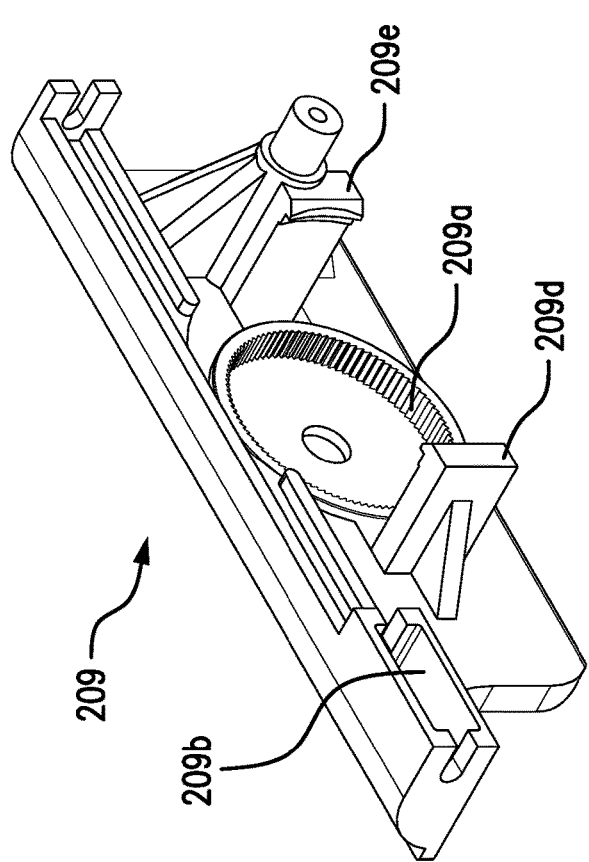
Figure 43C:
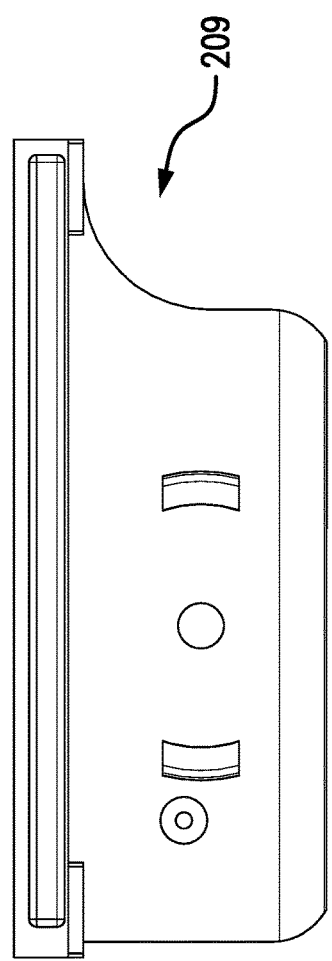
Figure 44B:
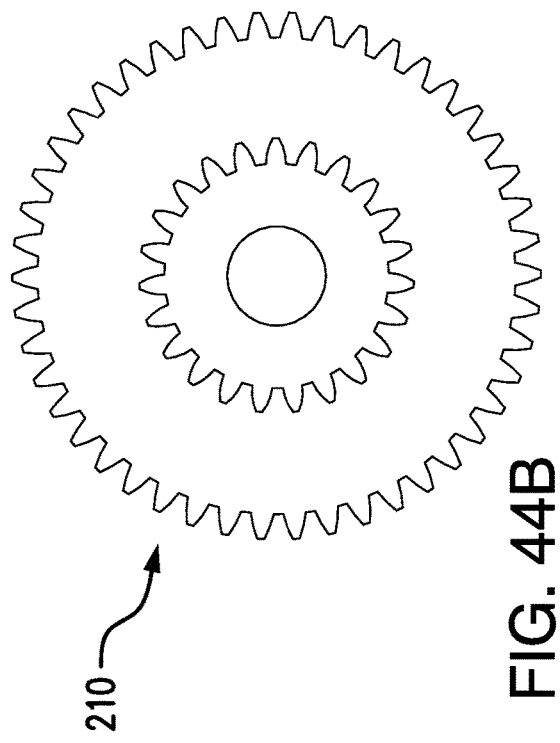
FIGS. 44A-44D provide perspective FIG. 44A, right FIG. 44B, left FIG. 44C, and front FIG. 44D views of the intermediate gear of the delivery system of FIG. 36.
Figure 44D:
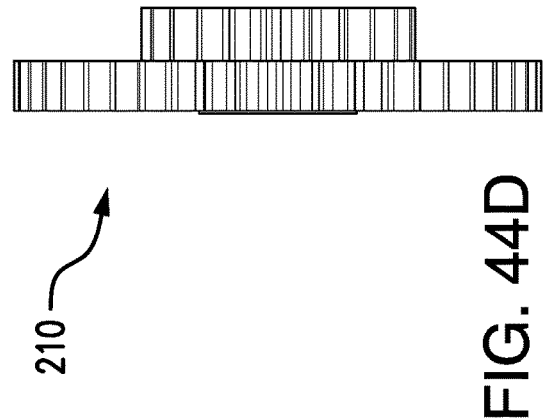
Figure 44A:
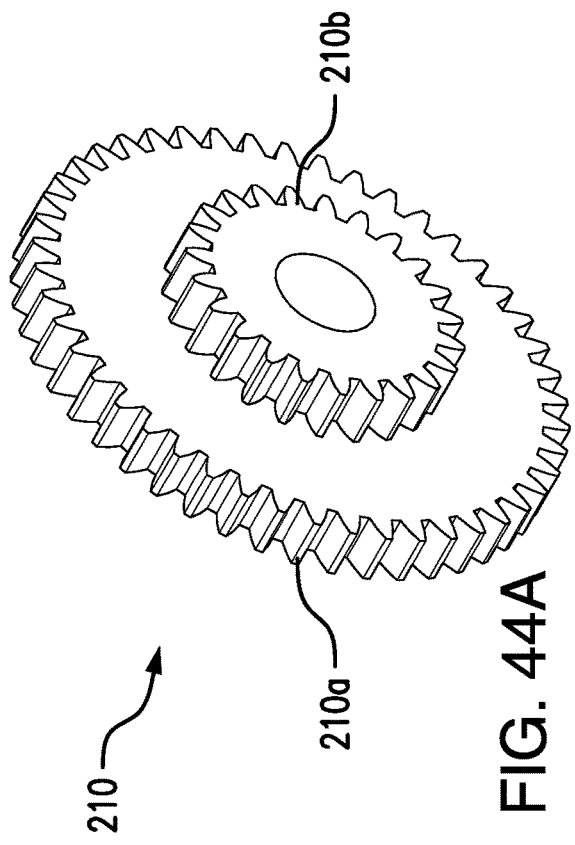
Figure 44C:
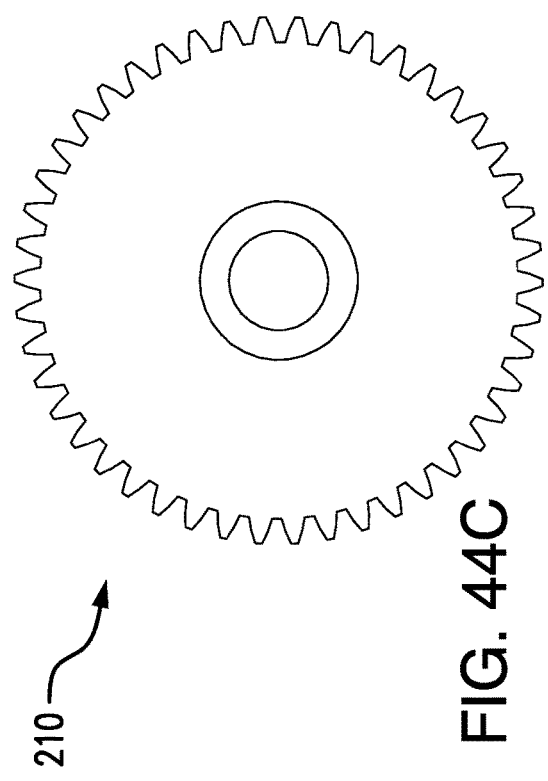
Figure 45B:
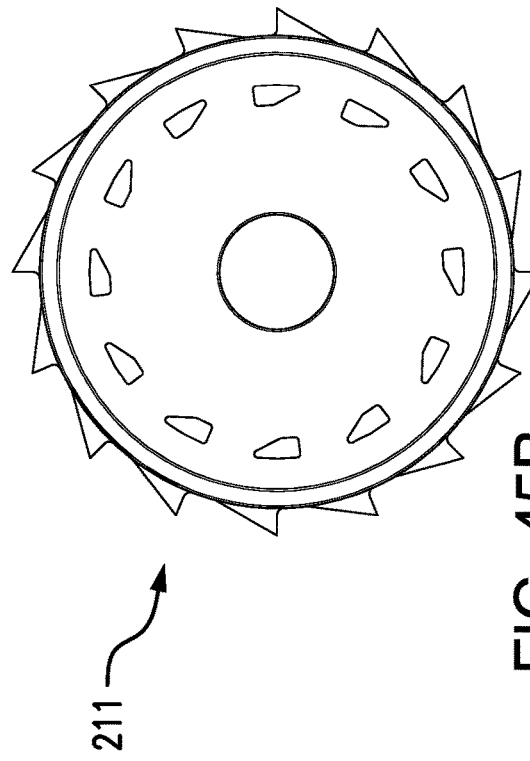
FIGS. 45A-45D provide perspective FIG. 45A, right FIG. 45B, left FIG. 45C, and front FIG. 45D views of the clutch release of the delivery system of FIG. 36.
Figure 45D:
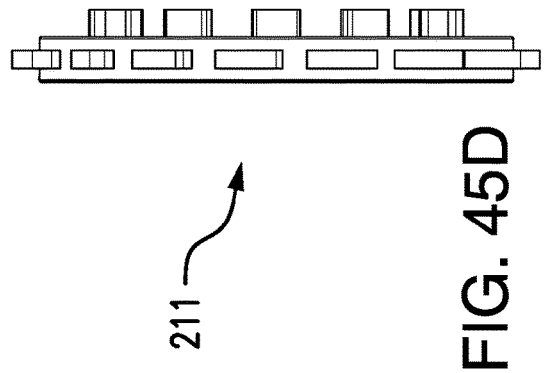
Figure 45A:
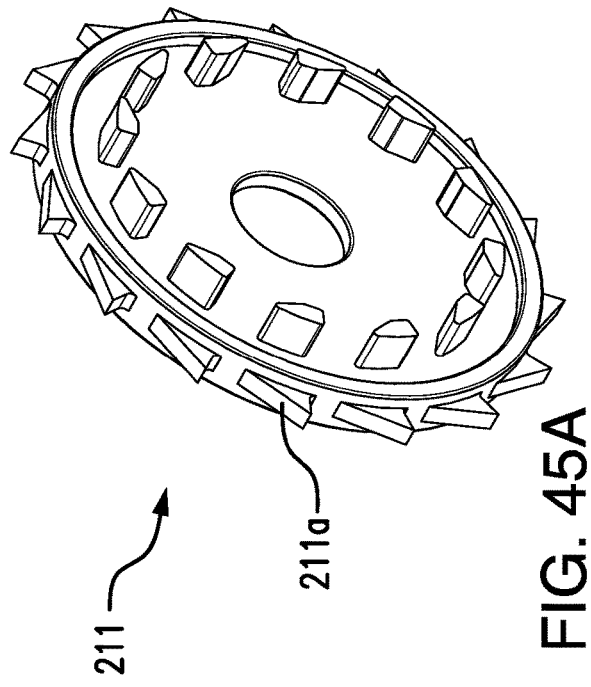
Figure 45C:
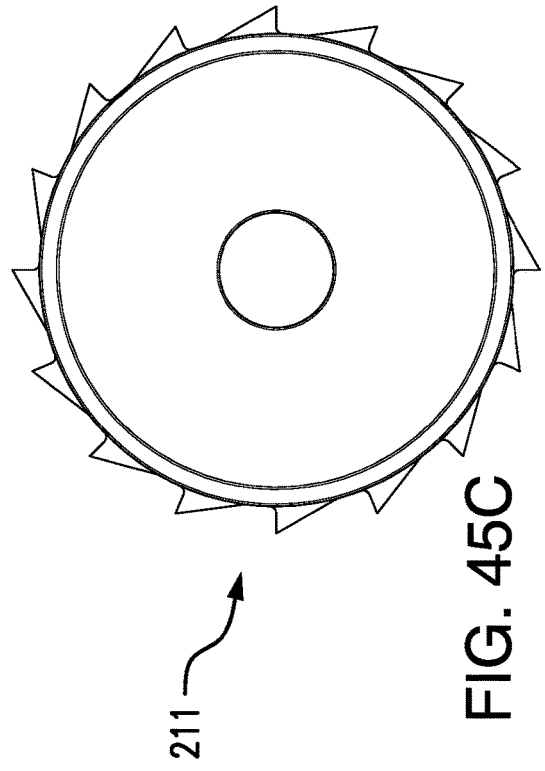

Referring to FIG. 36 for the purpose of illustration and not limitation, an exemplary embodiment of a system for delivering an implant is provided and designated generally by reference character 1002. Portions of this exemplary embodiment are depicted in FIGS. 37-45. Elements that are similar to the previously described embodiments have been given like numbers, and unless described otherwise, the element can include the same features as described above. The delivery system 1002 can be configured to deliver an implant in a similar manner as described hereinabove.

The delivery system 1002 can include a handle 201, an outer tubular member 222, an inner shaft member 221, and an implant 223, for example, a braided implant. The handle 201 can include a trigger 260 and an actuation assembly 202, which can be configured to move the inner shaft member 221 and the outer tubular member 222 relative to the handle 201 as described above upon deployment of the trigger 260 from the first position to the second position and return from the second position to the first position. The trigger 260 can include a lock as described herein above.

Referring now to FIGS. 37-45 for the purpose of illustration and not limitation, the actuation assembly 202 can include a planetary gear system as embodied in delivery system 1001. For example, the actuation assembly 202 can include a sun gear shaft 203 (which can include a sun gear portion 203a, a sheath pinion 203b, and a clutch engagement portion 203c; FIG. 39), a planet carrier 205 (which can include a circumferential pinion 205a, a clutch component 205b, and at least one pin 205c; FIG. 40), at least one planet gear 206, a ring gear 207 (which can include a circumferential pinion 207a and a ring gear portion 207b; FIG. 41), a first clutch driver 204a and a second clutch driver 204b, both identical in shape (each can include sun gear shaft engagement portion 204c and a clutch portion 204d; FIG. 42). The actuation assembly 202 can include a shuttle frame 209. The shuttle frame 209 can have the planet carrier 205, planet gears 206, sun gear shaft 203, ring gear 207, and first and second clutch drivers (204a and 204b) disposed thereon. The shuttle frame 209 can be disposed within the handle 201 and can be moveable relative to the handle 201 along the length of the handle 201. The shuttle frame 209 can include a clutch engagement portion 209a, a cavity 209b which can receive a ferrule coupled to the proximal end of the outer tubular member 222, and clips 209d and 209e, which can hold the planetary gear system in place on the shuttle frame 209. The planet carrier 205, planet gears 206, sun gear shaft 203 and ring gear 207 can perform as the respective elements of the planetary gear system as described above. The actuation assembly can also include a ratchet rack 208. The actuation assembly can be functionally coupled to the trigger 260 by a driving rack 212, which can be supported by the handle 201. The actuation assembly can include a clutch release 211 which can engage a stop 201d disposed on the handle, as described herein above with regard to system 1000.

During operation, the user can deploy the trigger 260 from the first position to the second position (referred to herein as the "first action"). The trigger 260 can cause the driving rack 212 to move in a proximal direction. The driving rack 212, functionally meshed with the circumferential pinion 207a of the ring gear 207, can impart rotational motion on the ring gear 207. The ring gear portion 207b of the ring gear 207 can be operatively meshed with the planet gears 106, and can impart rotational motion on the planet gears 206. The planet gears 206 can be constrained from rotating freely because they are operatively meshed with the sun gear portion 203a of the sun gear shaft 203. The movement of the planet gears 206, which are disposed on the pins 205c of the planet carrier 205, can impart rotational motion on the planet carrier 205. The planet carrier 205 and the sun gear shaft 203 can be rotationally coupled by the second clutch driver 204b when rotating in the first action; thus, rotation can be transmitted to the sun gear shaft 203 in a 1:1 ratio. The first clutch driver 204a can allow the sun gear shaft 203 to rotate freely relative to the shuttle frame 209 during the first action. The sheath pinion 203b of the sun gear shaft 203 can be meshed with the large spur gear 210a of an intermediate gear 210, and can impart rotational motion on the intermediate gear 210. The small spur gear 210b of the intermediate gear 210 can be operatively meshed with a rack 201c disposed on the second handle housing portion 201b; thus, the rotational motion of the intermediate gear 210 can impart linear motion on the shuttle frame 209 in the proximal direction. The outer tubular member 222, which can be fixedly coupled to the shuttle frame 209 can move proximally relative to the handle 201. The circumferential pinion 205a of the planet carrier 205 can be operatively meshed with a ratchet rack 208, and rotation of the planet carrier 205 can move the ratchet rack 208 distally. The inner shaft member 221, which can be fixedly coupled to the ratchet rack 208, moves distally. Thus, during the first action, the inner shaft member 221 can move distally relative to the handle 201 and the outer tubular member 222 can move proximally relative to the handle 101.

Upon return of the trigger 260 from the second position to the first position (herein referred to as the "second action"), the driving rack 212 can move distally relative to the handle 201. The driving rack 212 can impart rotational motion on the ring gear 207. The ring gear 207 can impart rotational motion on the three planet gears 206. The planet gears 206 can rotate about the sun gear shaft 203, which can be held stationary relative the shuttle frame 209 via the first clutch driver 204a. The planet gears 106 can impart rotational motion on the planet carrier 205. Linear motion in the proximal direction can be transmitted to the ratchet rack 208 by the planet carrier 205. The inner shaft member 221, fixedly coupled to the ratchet rack 208, can move proximally relative to the handle 201. Thus, during the second action, the inner shaft member 221 can move proximally relative to the handle 201 and the outer tubular member 222 can be stationary relative to the handle 201.

Figure 46:
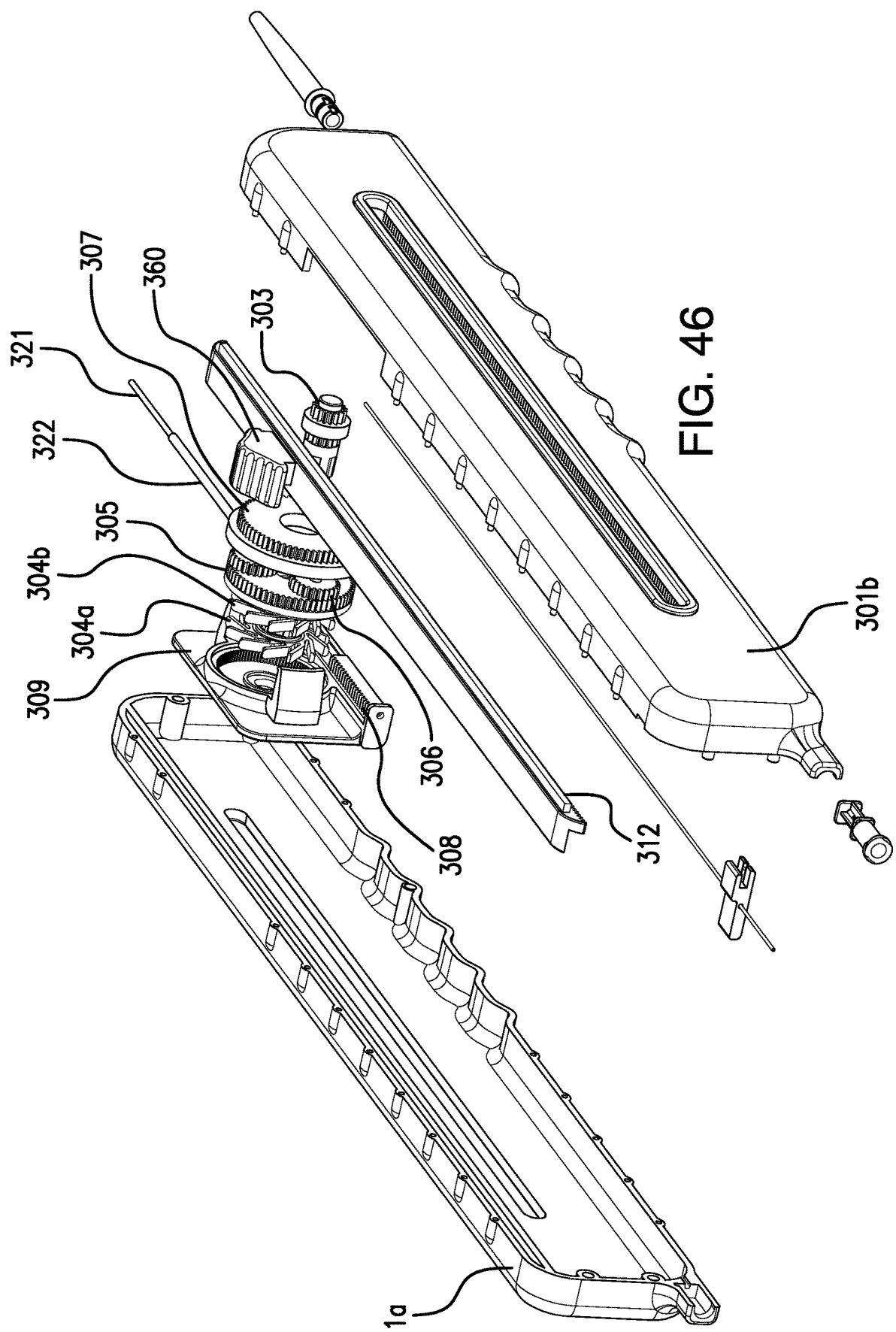
FIG. 46 is an exploded view of a further exemplary embodiment of a delivery system in accordance with the disclosed subject matter.
Figure 47B:
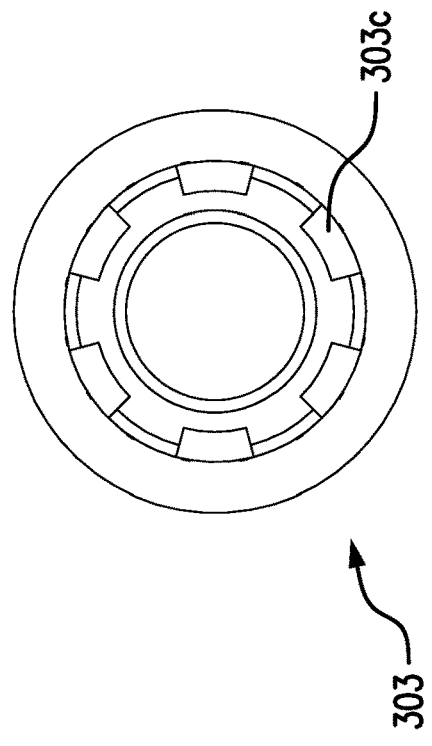
FIGS. 47A-47D provide perspective FIG. 47A, right FIG. 47B, left FIG. 47C, and front FIG. 47D views of the sun gear shaft of the delivery system of FIG. 46.
Figure 47D:
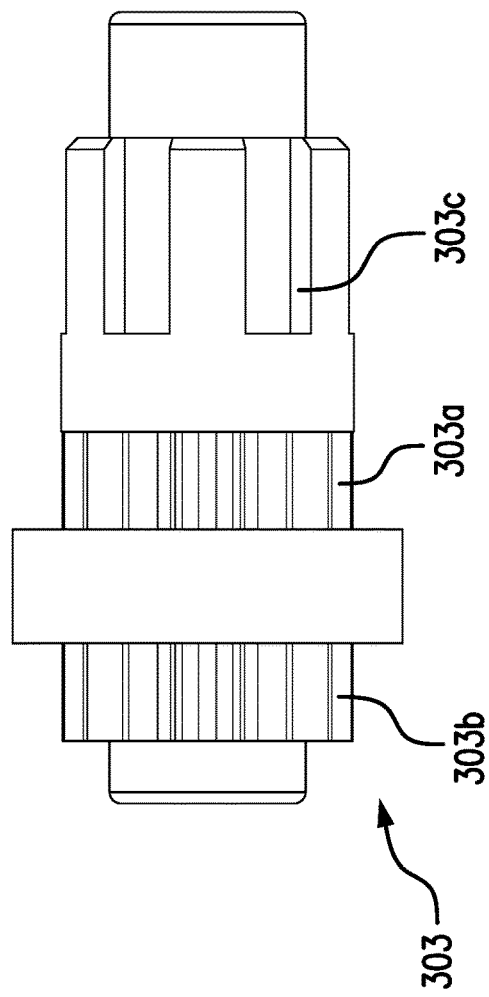
Figure 47A:
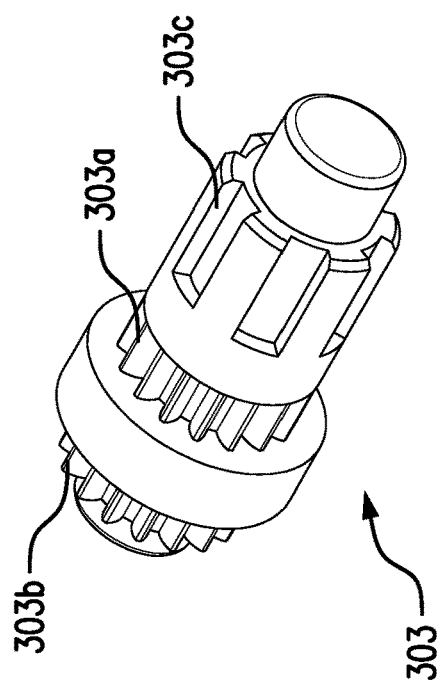
Figure 47C:
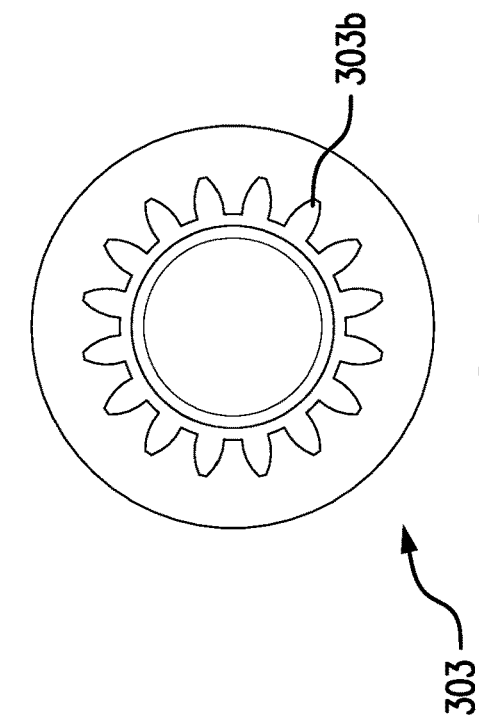
Figure 48B:
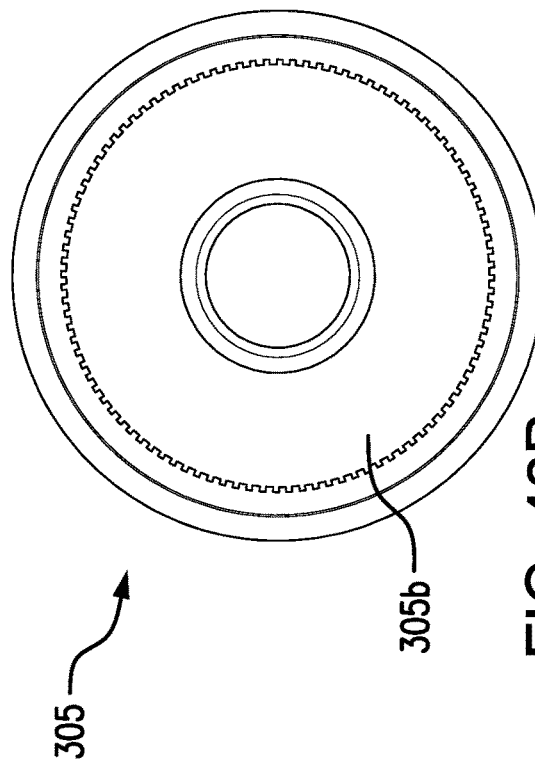
FIGS. 48A-48D provide perspective FIG. 48A, right FIG. 48B, left FIG. 48C, and front FIG. 48D views of the planet carrier of the delivery system of FIG. 46.
Figure 48D:
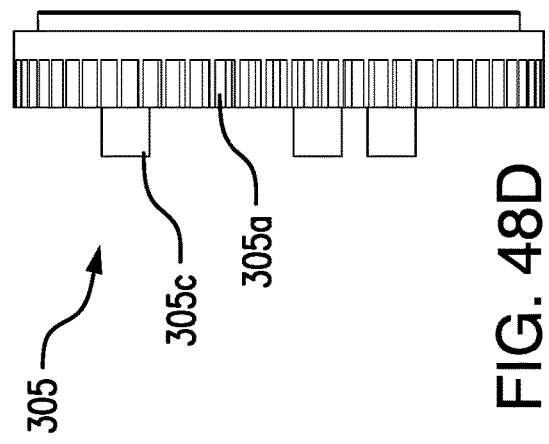
Figure 48A:
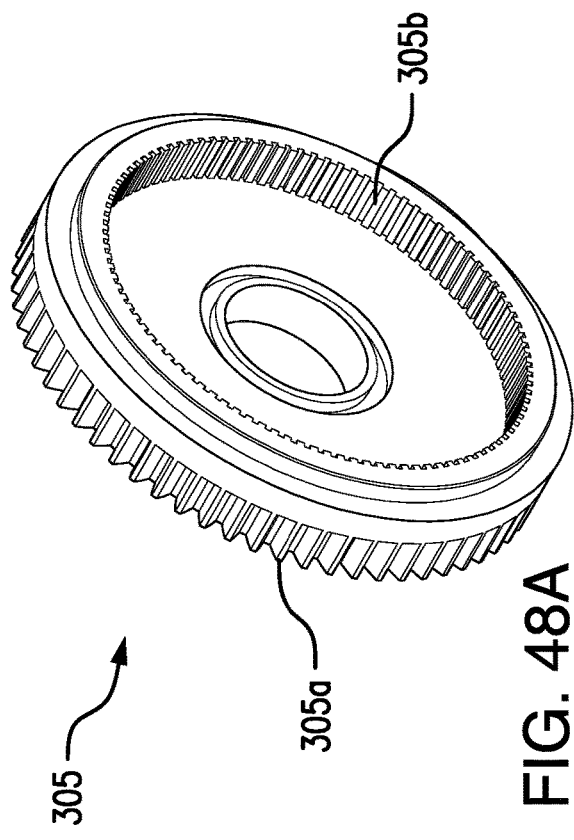
Figure 48C:
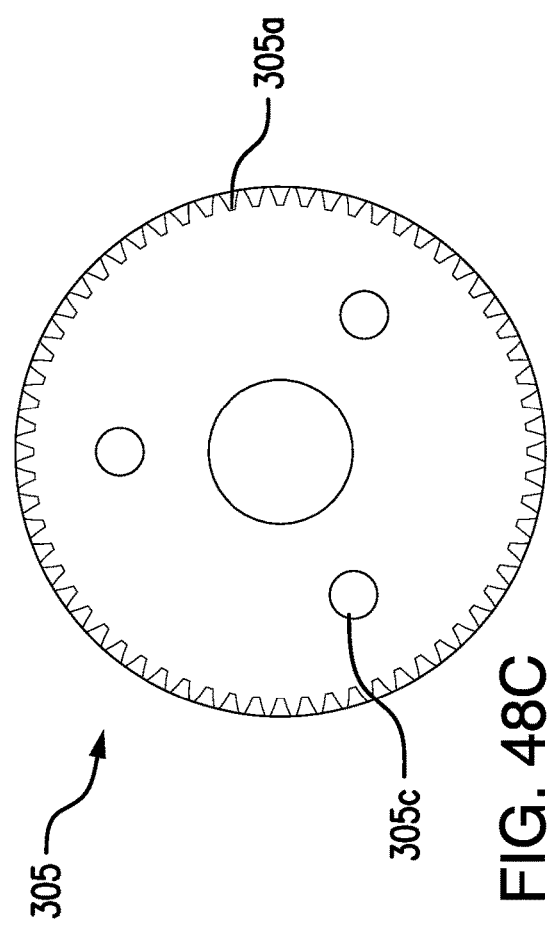
Figure 49A:
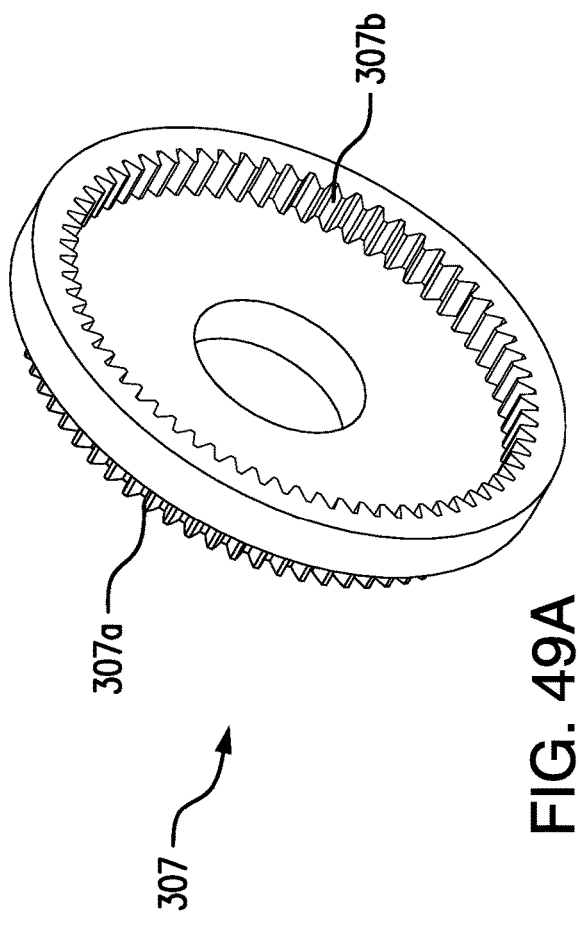
FIGS. 49A-49D provide perspective FIG. 49A, right FIG. 49B, left FIG. 49C, and front FIG. 49D views of the ring gear of the delivery system of FIG. 46.
Figure 49B:
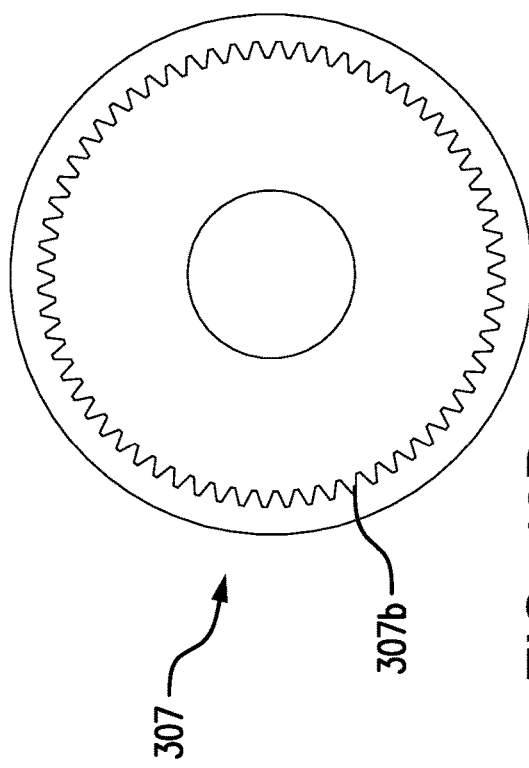
Figure 49C:
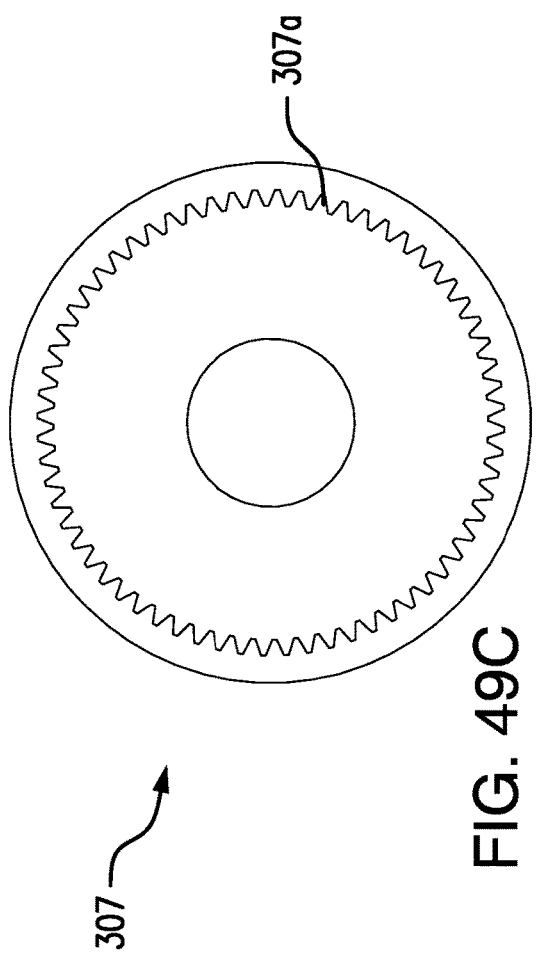
Figure 49D:
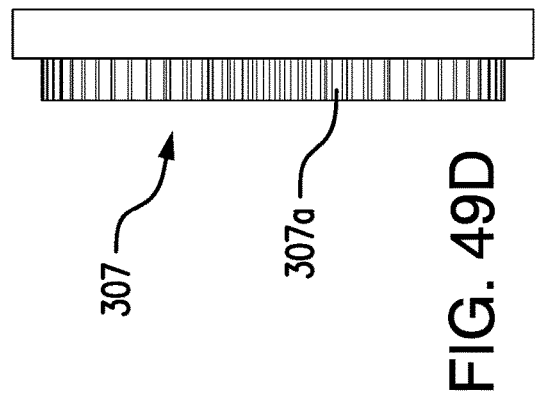
Figure 50A:
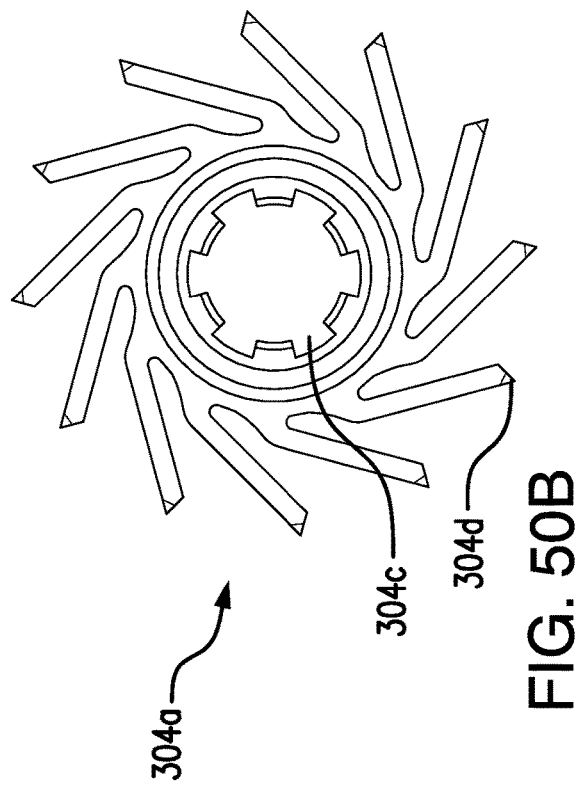
FIGS. 50A-50D provide perspective FIG. 50A, right FIG. 50B, left FIG. 50C, and front FIG. 50D views of the first clutch driver of the delivery system of FIG. 46.
Figure 50B:
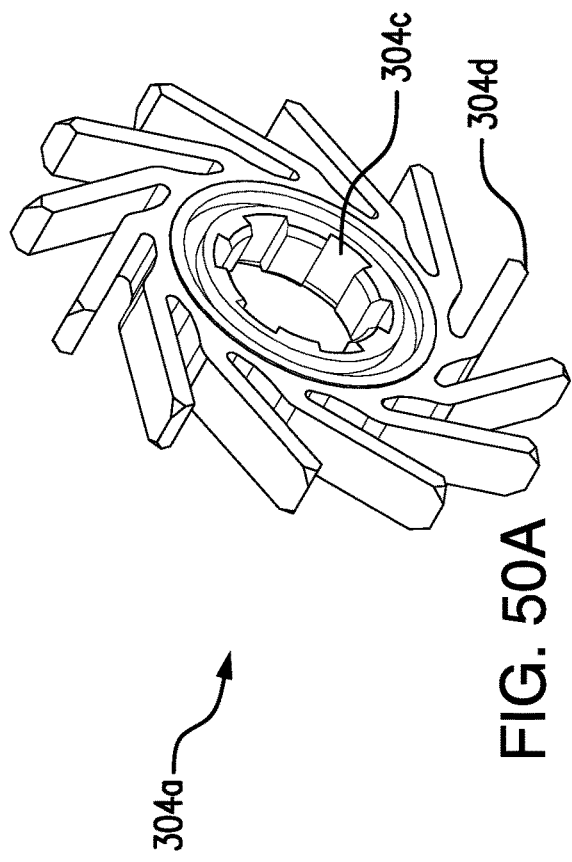
Figure 50C:
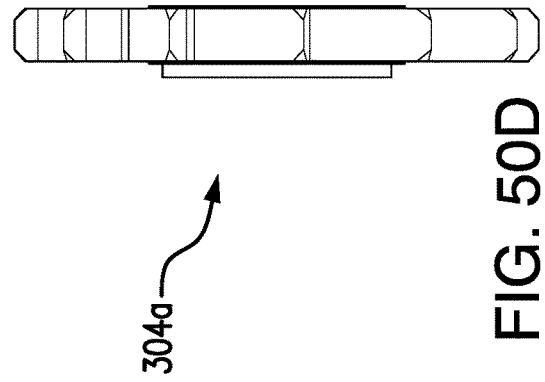
Figure 50D:
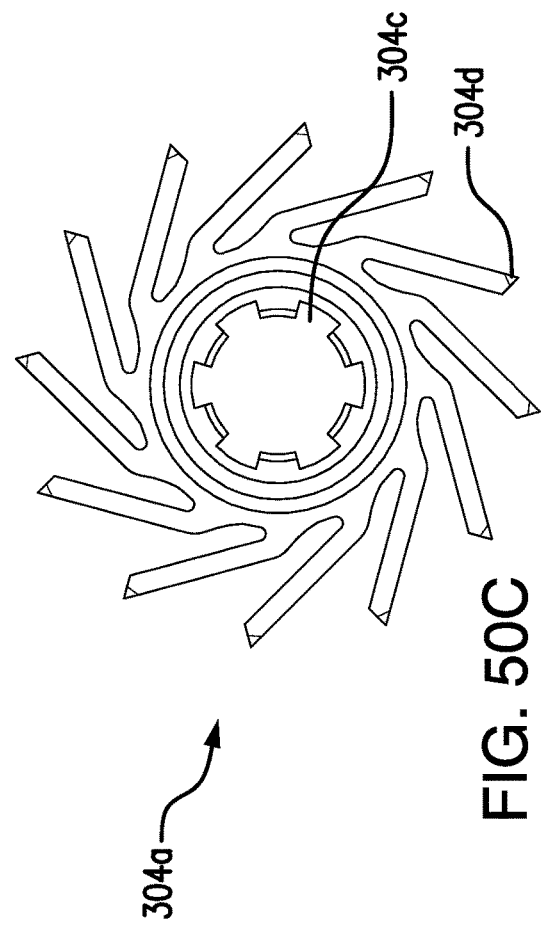
Figure 51B:
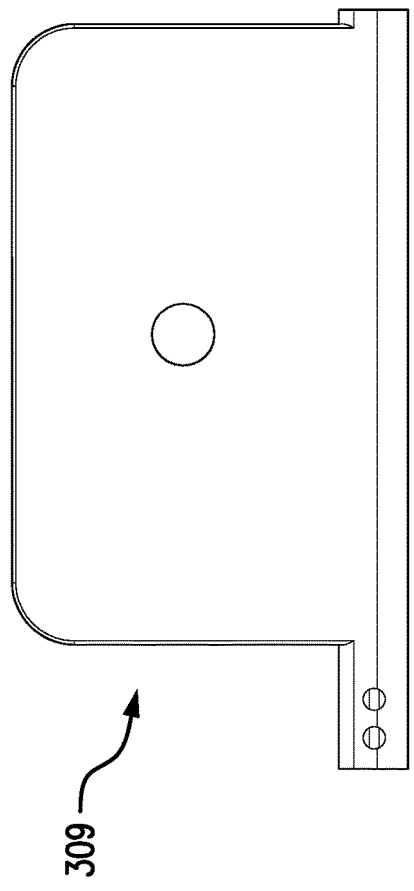
FIGS. 51A-51D provide perspective FIG. 51A, right FIG. 51B, left FIG. 51C, and front FIG. 51D views of the shuttle frame of the delivery system of FIG. 46.
Figure 51D:
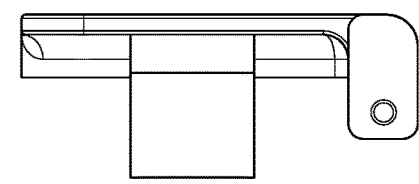
Figure 51A:
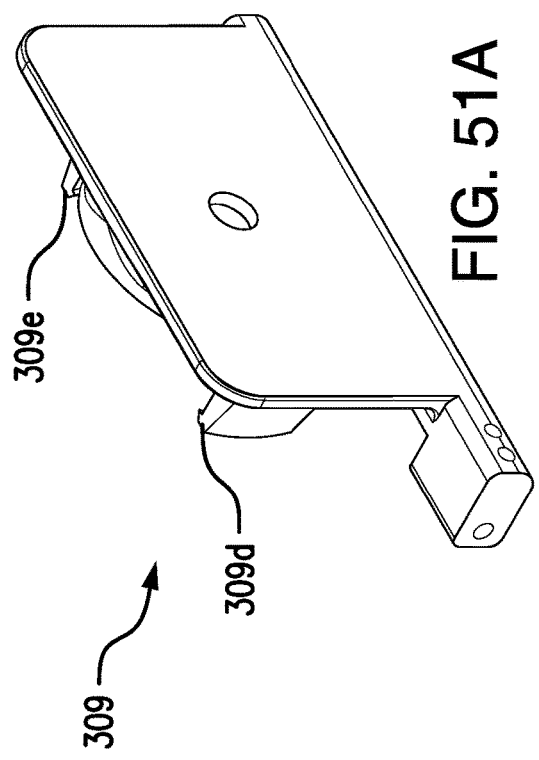
Figure 51C:
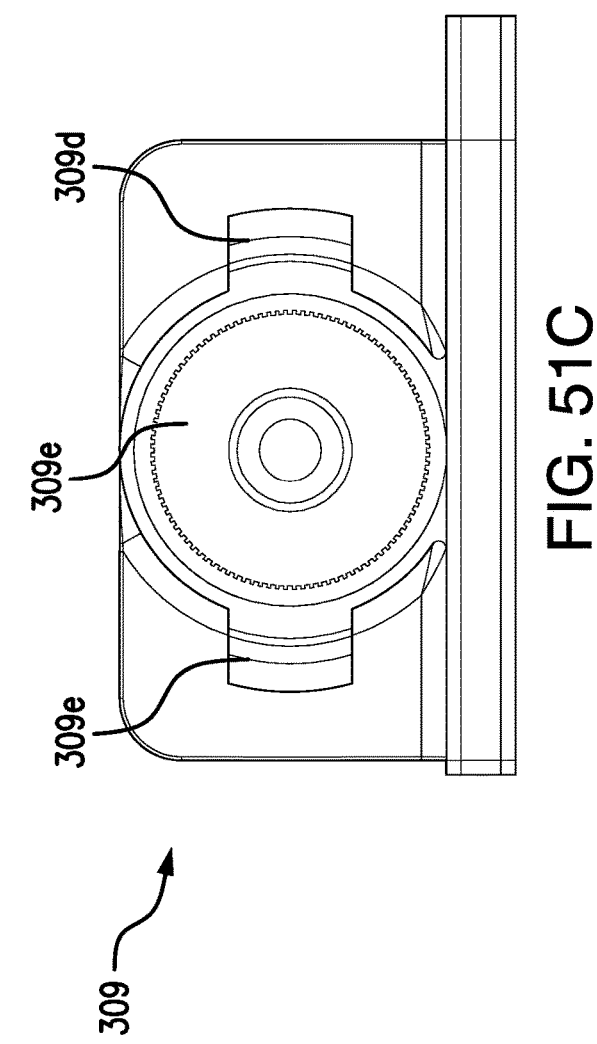

Referring to FIG. 46 for the purpose of illustration and not limitation, an exemplary embodiment of a system for delivering an implant is provided and designated generally by reference character 1003. Portion of this exemplary embodiment are depicted in FIGS. 47-51. Elements that are similar to the previously described embodiments have been given like number, and unless described otherwise, the elements can include the same features as described above.

The delivery system 1003 can include a handle 301, an outer tubular member 322, an inner shaft member 321, and an implant 323, for example, a braided implant. The handle 301 can include a trigger 360 and an actuation assembly 302, which can be configured to move the inner shaft member 321 and the outer tubular member 322 relative to the handle 301 as described above upon deployment of the trigger 360 from the first position to the second position and return from the second position to the first position. The trigger 360 can include a lock as described herein above.

Referring now to FIGS. 47-51 for the purpose of illustration and not limitation, the actuation assembly 302 can include a planetary gear system as embodied in delivery system 1001. For example, the actuation assembly 302 can include a sun gear shaft 303 (which can include a sun gear portion 303a, a sheath pinion 303b, and a clutch engagement portion 303c; FIG. 47), a planet carrier 305 (which can include a circumferential pinion 305a, a clutch component 305b, and a least one pin 305c; FIG. 48), at least one planet gear 306, a ring gear 307 (which can include a circumferential pinion 307a and a ring gear portion 307b; FIG. 49), a first clutch driver 304a and a second clutch driver 304b, both identical in shape (each can include including a sun gear shaft engagement portion 304c and a clutch portion 304d; FIG. 50). The actuation assembly 302 can include a shuttle frame 309. The shuttle frame 309 can have the planet carrier 305, planet gears 306, sun gear shaft 303, ring gear 307, and first and second clutch drivers 304a, 304b disposed thereon. The shuttle frame 309 can be disposed within the handle 301 and can be moveable relative to the handle 301 along the length of the handle 301. The shuttle frame 309 can include clips 309d and 309e, which can hold the planetary gear system in place on the shuttle frame 309. The planet carrier 305, planet gears 306, sun gear shaft 303, and ring gear 307 can perform as the respective elements of the planetary gear system as described above. The actuation assembly can also include a ratchet rack 308. The actuation assembly can be functionally coupled to the trigger 360 by a driving rack 312, which can be supported by the handle 301.

During operation, the user can deploy the trigger 360 from the first position to the second position (referred to herein as the "first action"). The trigger 360 can cause the driving rack 312 to move in a proximal direction. The driving rack 312, functionally meshed with the circumferential pinion 307a of the ring gear 307, can impart rotational motion on the ring gear 307. The ring gear portion 307b of the ring gear 307 can be operatively meshed with the planet gears 306, and can impart rotational motion on the planet gears 306. The planet gears 306 can be constrained from rotating freely because they are operatively meshed with the sun gear portion 303a of the sun gear shaft 303. The movement of the planet gears 306, which are disposed on the pins 305c of the planet carrier 305, can impart rotational motion on the planet carrier 305. The planet carrier 305 and the sun gear shaft 303 are rotationally coupled by the second clutch driver 304b when rotating in the first action; thus, rotation can be transmitted to the sun gear shaft 303 in a 1:1 ratio. The first clutch driver 304a allows the sun gear shaft 303 to rotate freely relative to the shuttle frame 309 during the first action. The sheath pinion 303b of the sun gear shaft 303 can be meshed a rack 301c disposed on the second handle housing portion 301b; thus, the rotational motion of the sun gear shaft 303 can impart linear motion on the shuttle frame 309 in the proximal direction. The outer tubular member 322, which can be fixedly coupled to the shuttle frame 309 can move proximally relative to the handle 301. The circumferential pinion 305a of the planet carrier 305 can be operatively meshed with a ratchet rack 308, and rotation of the planet carrier 305 can move the ratchet rack 308 distally. The inner shaft member 321, which can be fixedly coupled to the ratchet rack 308, moves distally. Thus, during the first action, the inner shaft member 321 can move distally relative to the handle 301 and the outer tubular member 322 can move proximally relative to the handle 301.

Upon return of the trigger 360 from the second position to the first position (herein referred to as the "second action"), the driving rack 312 can move distally relative to the handle 301. The driving rack 312 can impart rotational motion on the ring gear 307. The ring gear 307 can impart rotational motion on the three planet gears 306. The planet gears 306 can rotate about the sun gear shaft 303, which can be held stationary relative the shuttle frame 309 via the first clutch driver 304a. The planet gears 306 can impart rotational motion on the planet carrier 305. Linear motion can be transmitted to the ratchet rack 308 by the planet carrier 305. The inner shaft member 321 can move proximally relative to the handle 301. Thus, during the second action, the inner shaft member 321 can move proximally relative to the handle 301 and the outer tubular member 322 can be stationary relative to the handle 301.

Figure 52:
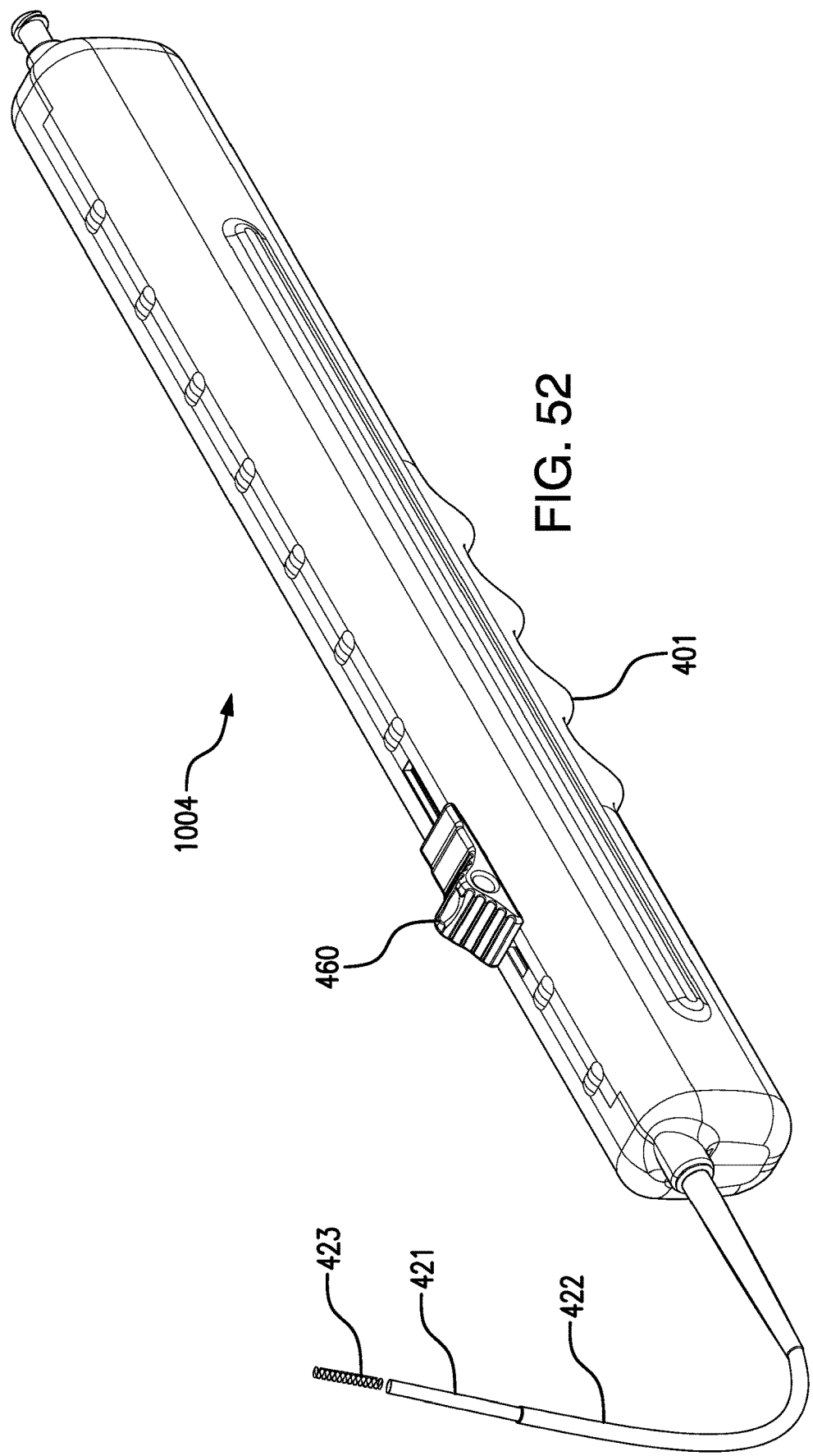
FIG. 52 is a perspective view of another exemplary embodiment of a delivery system in accordance with the disclosed subject matter.
Figure 53:
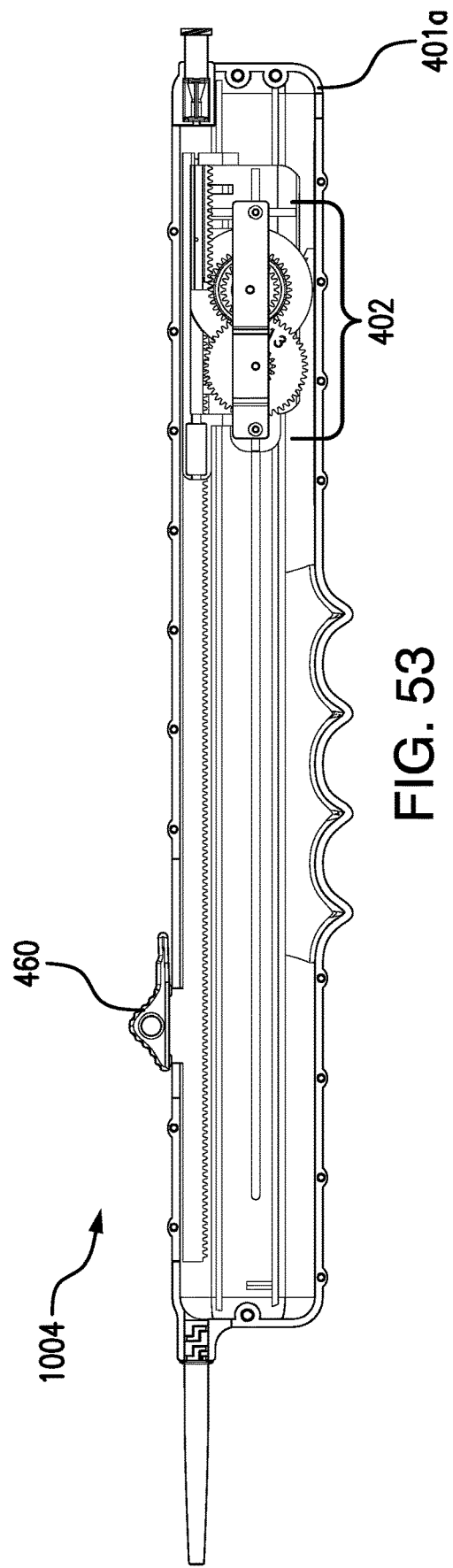
FIG. 53 is a right side view, with a portion of the handle housing removed, of the delivery system of FIG. 52.
Figure 54:
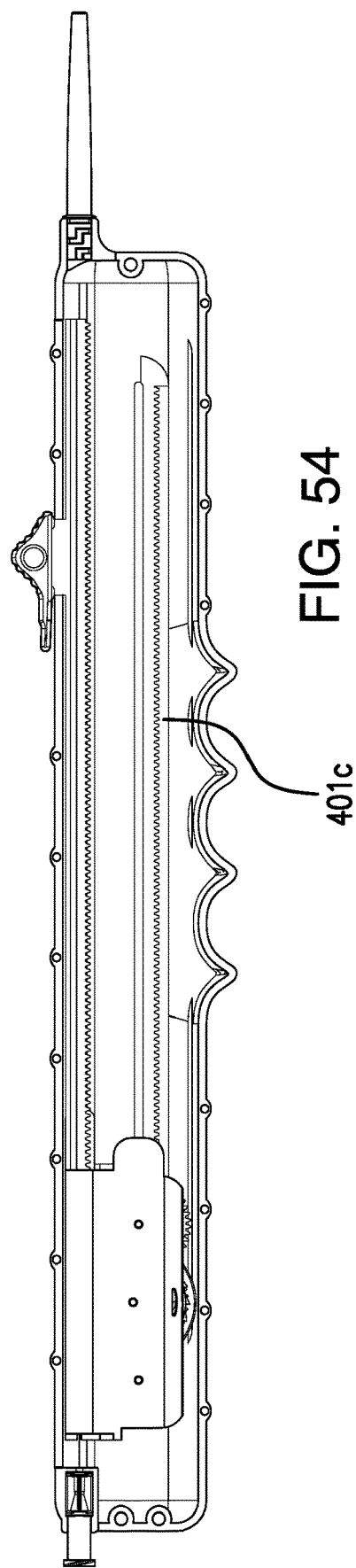
FIG. 54 is a left side view, with a portion of the handle housing removed, of the delivery system of FIG. 52.
Figure 55B:
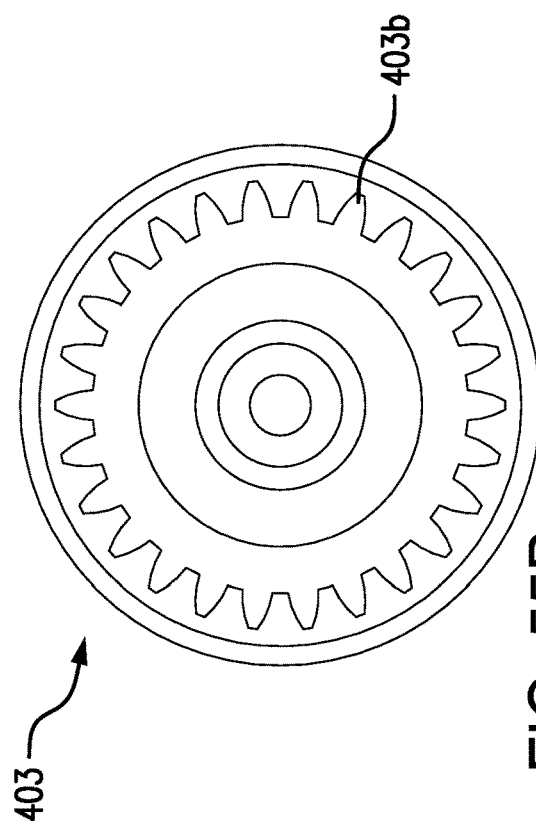
FIGS. 55A-55D provide perspective FIG. 55A, right FIG. 55B, left FIG. 55C, and front FIG. 55D views of the sun gear shaft of the delivery system of FIG. 52.
Figure 55D:
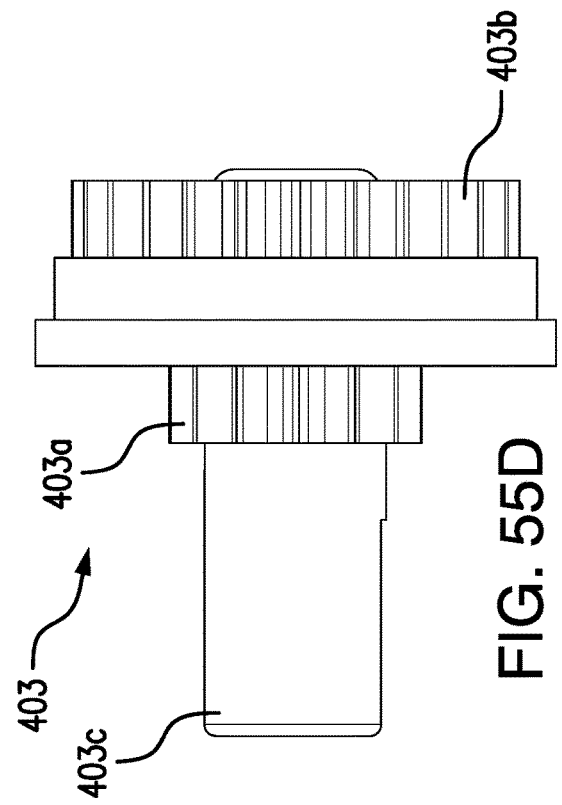
Figure 55A:
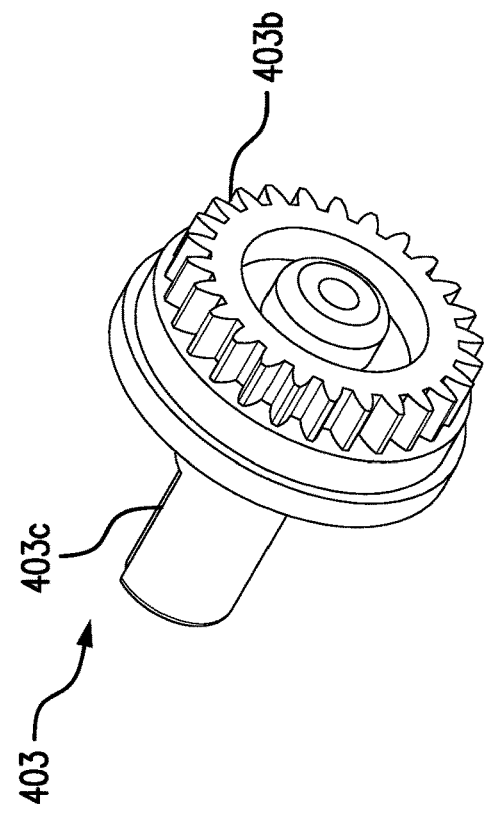
Figure 55C:
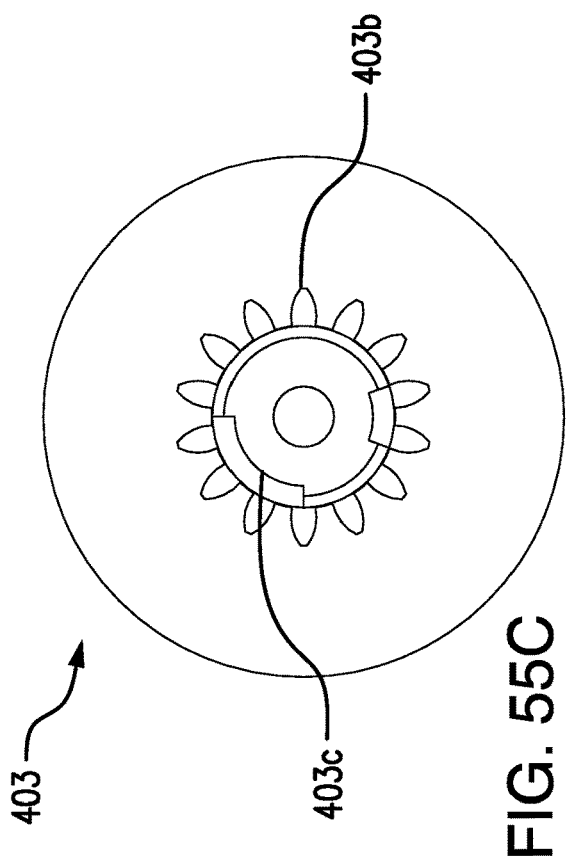
Figure 56B:
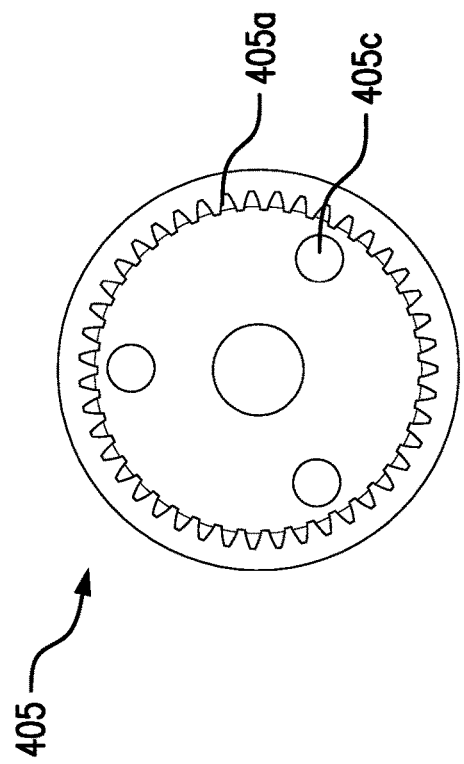
FIGS. 56A-56D provide perspective FIG. 56A, right FIG. 56B, left FIG. 56C, and front 56D views of the planet carrier of the delivery system of FIG. 52.
Figure 56A:
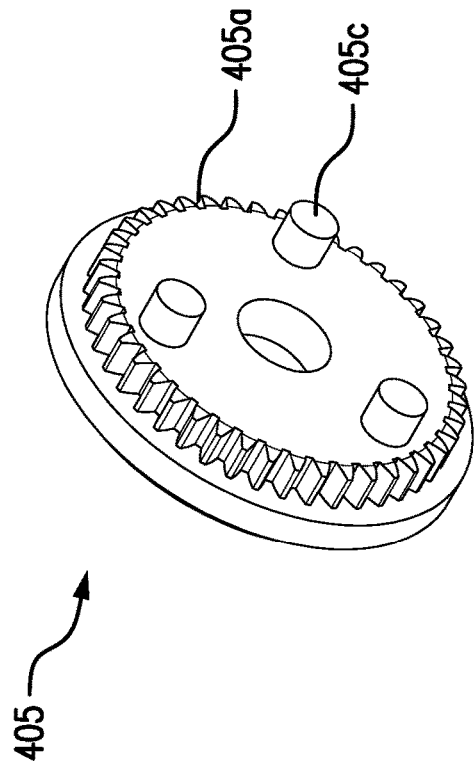
Figure 56D:
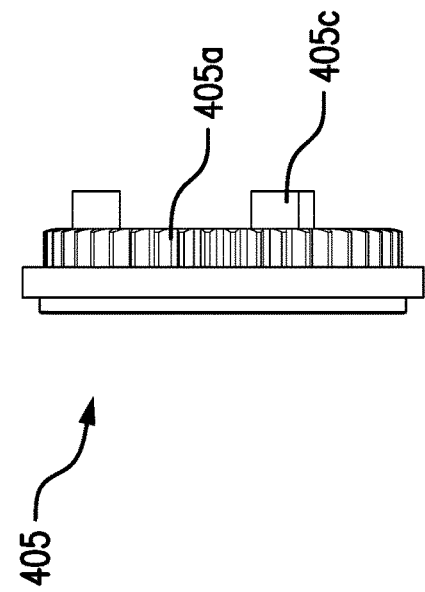
Figure 56C:
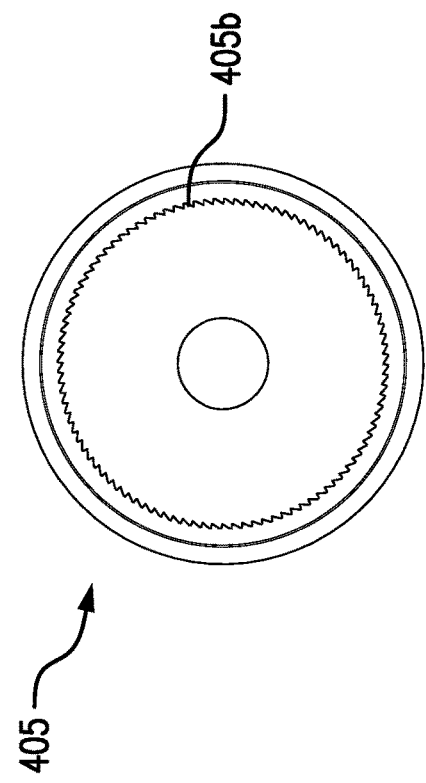
Figure 57A:
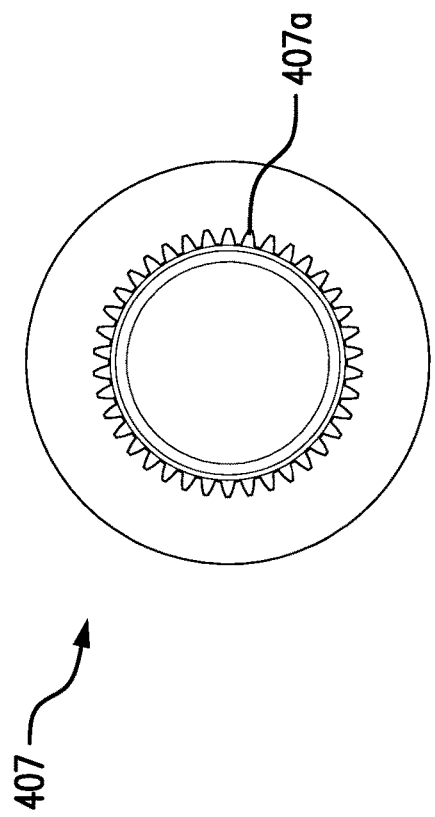
FIGS. 57A-57D provide perspective FIG. 57A, right FIG. 57B, left FIG. 57C, and front FIG. 57D views of the ring gear of the delivery system of FIG. 52.
Figure 57B:
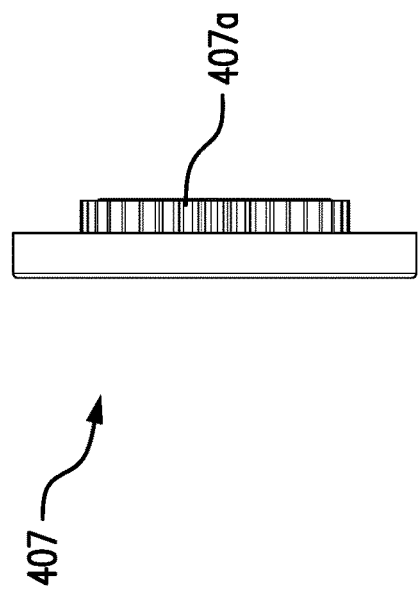
Figure 57C:
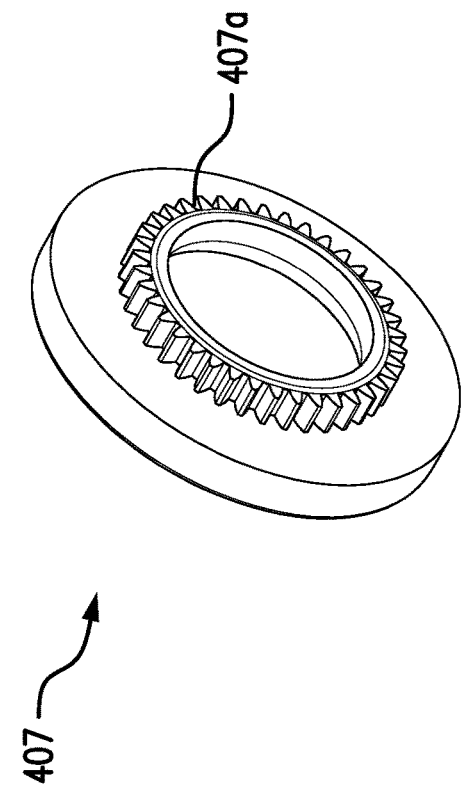
Figure 57D:
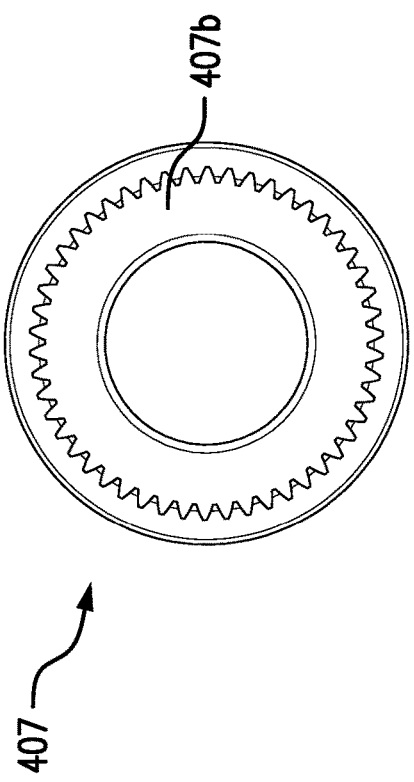
Figure 58B:
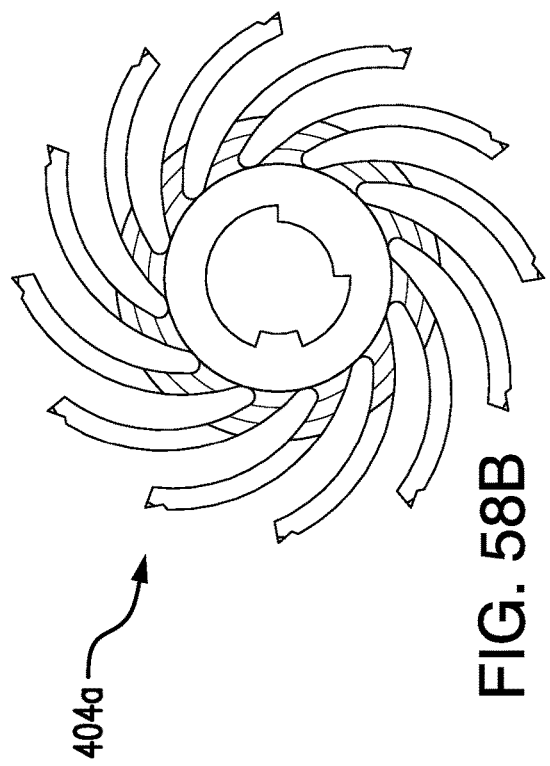
FIGS. 58A-58D provide perspective FIG. 58A, right FIG. 58B, left FIG. 58C, and front FIG. 58D views of the first clutch driver of the delivery system of FIG. 52.
Figure 58D:
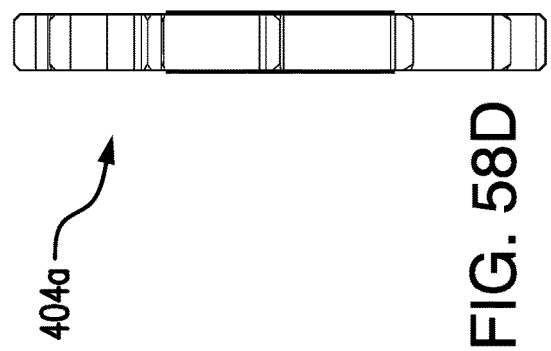
Figure 58A:
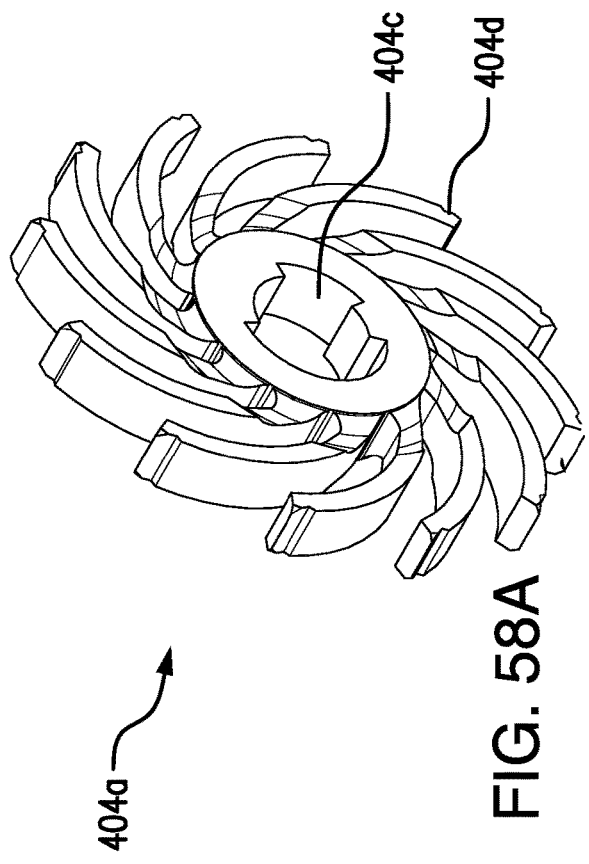
Figure 58C:
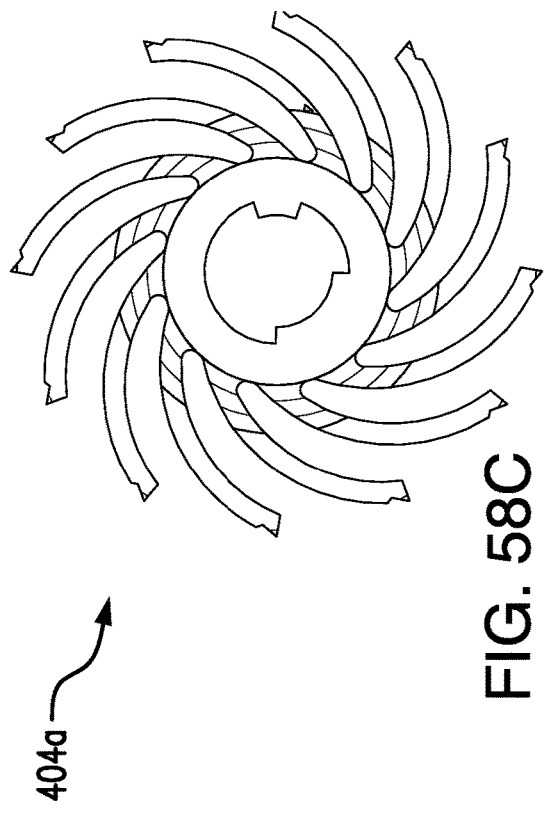
Figure 60A:
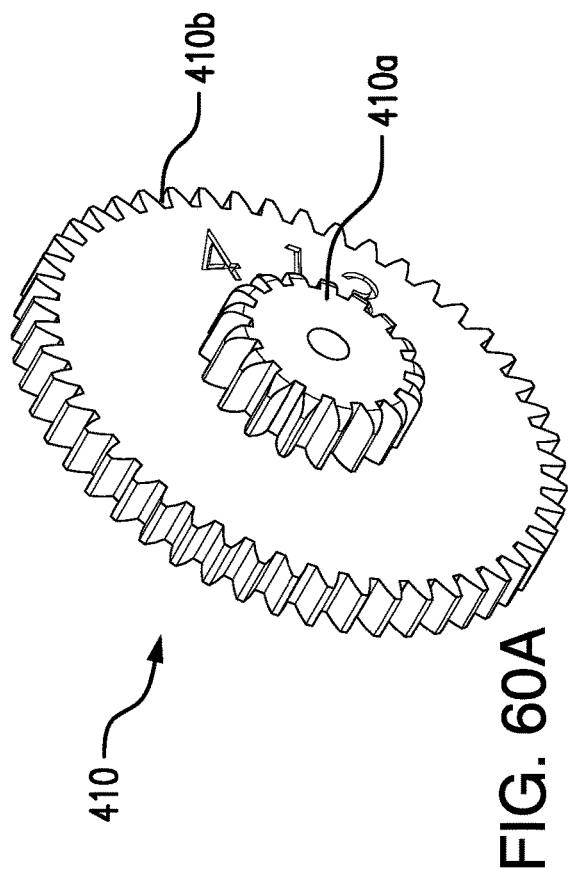
FIGS. 60A-60D provide perspective FIG. 60A, right FIG. 60B, left FIG. 60C, and front FIG. 60D views of the intermediate gear of the delivery system of FIG. 52.
Figure 60B:
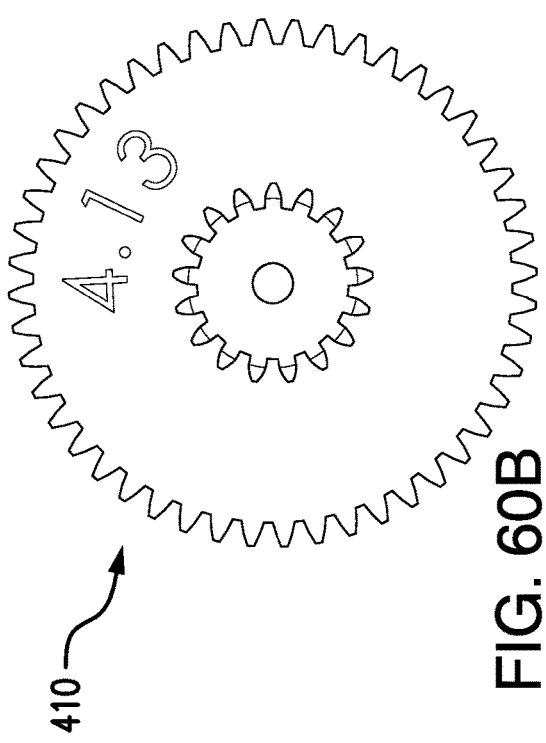
Figure 60D:
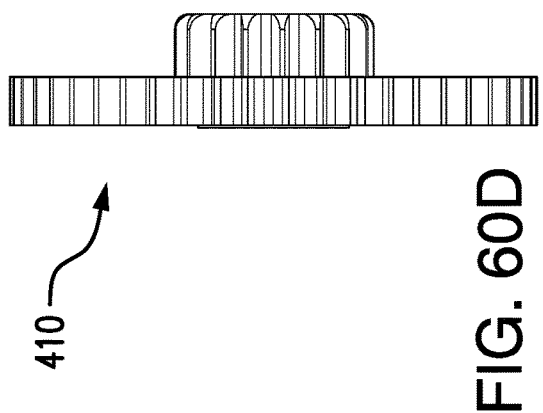
Figure 60C:
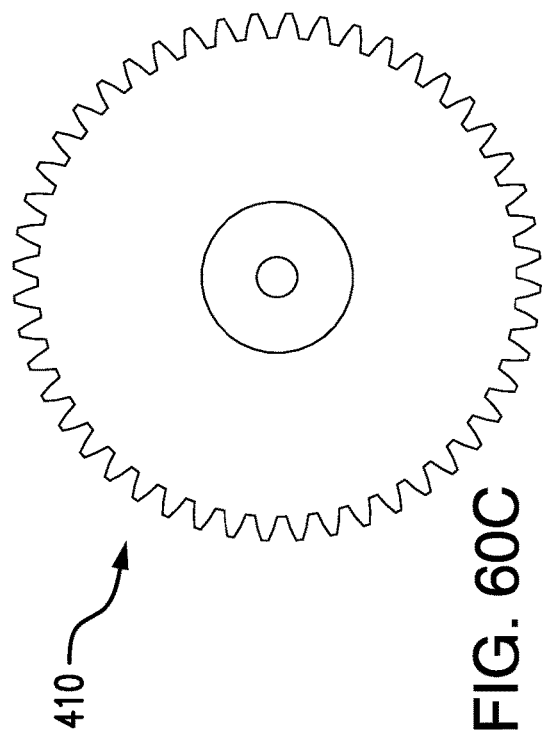
Figure 61B:
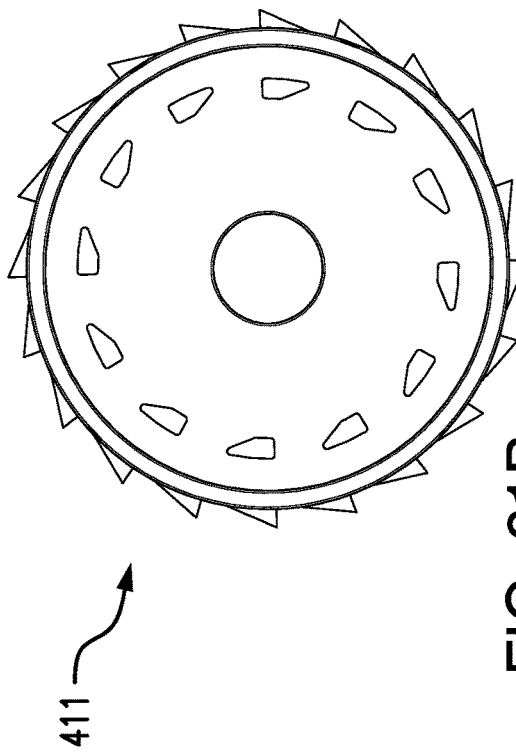
FIGS. 61A-61D provide perspective FIG. 61A, right FIG. 61B, left FIG. 61C, and front FIG. 61D views of the clutch release of the delivery system of FIG. 52.
Figure 61D:
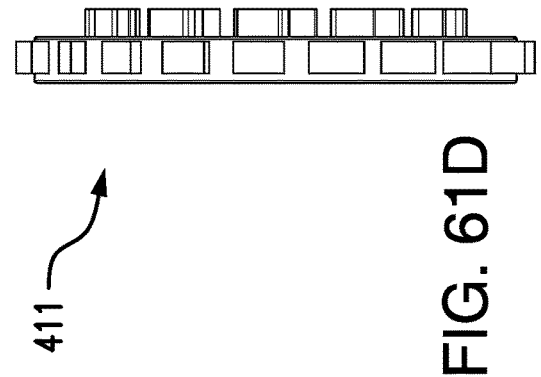
Figure 61A:
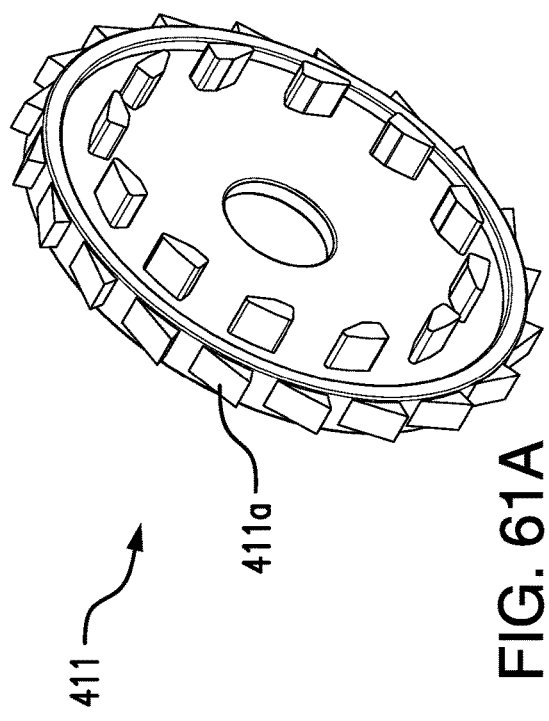
Figure 61C:
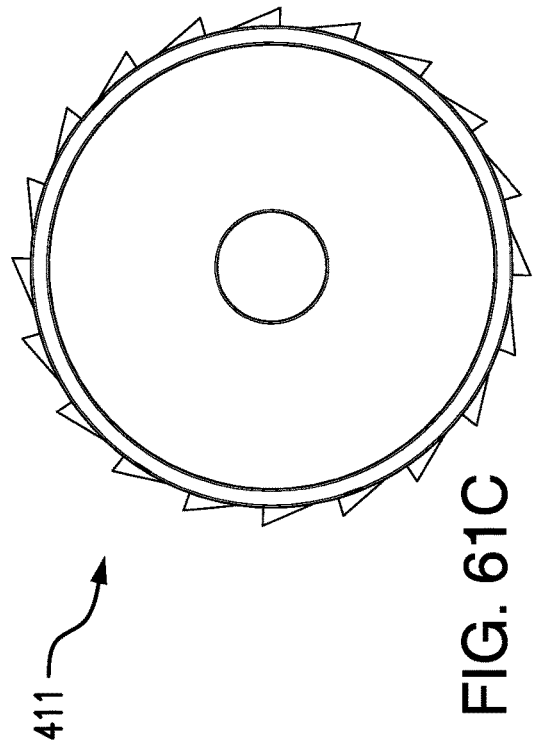

Referring now to FIG. 52 for the purpose of illustration and not limitation, an exemplary embodiment of a system for delivering an implant is provided and designated generally by reference character 1004. Portions of this exemplary embodiment are depicted in FIGS. 53-61. Elements that are similar to the previously described embodiment have been given like numbers. The delivery system 1004 can be configured to deliver an implant in a similar manner as described herein above.

The delivery system 1004 can include a handle 401, an outer tubular member 422, an inner shaft member 421, and an implant 423, for example, a braided implant. The handle 401 can include a trigger 460 and an actuation assembly 402, which can be configured to move the inner shaft member 421 and the outer tubular member 422 relative to the handle 401 as described above upon deployment of the trigger 460 from the first position to the second position and return from the second position to the first position. The trigger 460 can include a lock as described herein above.

Referring now to FIGS. 53-61 for the purpose of illustration and not limitation, the actuation assembly 402 can include a planetary gear system as embodied in delivery system 1000. For example, the actuation assembly 402 can include a sun gear shaft 403 (which can include a sun gear portion 403a, a sheath pinion 403b, and a clutch engagement portion 403c; FIG. 55), a planet carrier 405 (which can include a circumferential pinion 405a, a clutch component 405b, and at least one pin 405c; FIG. 56), at least one planet gear 406, a ring gear 407 (which can include a circumferential pinion 407a and a ring gear portion 407b; FIG. 57), a first clutch driver 404a and a second clutch driver 404b, both identical in shape (each can include including a sun gear shaft engagement portion 404c and a clutch portion 404d; FIG. 58). The actuation assembly 402 can include a shuttle frame 409. The shuttle frame 409 can have the planet carrier 405, planet gears 406, sun gear shaft 403, ring gear 407, and first and second clutch drivers (404a and 404b) disposed thereon. The shuttle frame 409 can be disposed within the handle 401 and can be moveable relative to the handle 401 along the length of the handle 401. The shuttle frame 409 can include a clutch engagement portion 409a, a cavity 409b which can receive a ferrule coupled to the proximal end of the outer tubular member 422, and a guide 409c. The actuation assembly 402, can include a plate 414 disposed on the shuttle assembly 409. The plate 414 can hold portions of the actuation assembly 402 in place and can protect the actuation assembly 402. The actuation assembly 402 can include at least one boss 413 configured to engage at least one boss track disposed within the handle 401 to thereby guide the shuttle frame 409 along the handle. The at least one boss can include a first boss 413a disposed through an axis of the sun gear shaft 403. The actuation assembly can include a second boss 413b and a third boss 413c, each disposed through the plate 414 and the shuttle frame 409. The second boss 413b and third boss 413c can hold the plate 414 in place on the shuttle frame 409. The actuation assembly 402 can include a fourth boss 413d disposed through an axis of the intermediate gear 410. The fourth boss 413d can engage the handle to guide the actuation assembly 402 as it moves relative to the handle 401. The actuation assembly can be functionally coupled to the trigger 460 by a driving rack 412, which can be supported in the guide 409c. The actuation assembly can include a clutch release 411 which can engage a stop 401d disposed on the handle, as described herein above with regard to system 1000.

During operation, the user can deploy the trigger 460 from the first position to the second position (referred to herein as the "first action"). The trigger 460 can cause the driving rack 412 to move in the distal direction. The driving rack 412, functionally meshed with the circumferential pinion 405a of the planet carrier 405, can impart rotational motion on the planet carrier 405. The planet carrier 405 can impart rotational motion on the three planet gears 406. The planet gears 406 can be constrained from rotating freely because they can be meshed with the sun gear portion 403a of the sun gear shaft 403. The three planet gears 406 can be meshed with the ring gear portion 407b of the ring gear 407, and can impart rotational motion on the ring gear 407. The ring gear 407, which can be meshed with the ratchet rack 408, and can drive the ratchet rack 408 distally. The inner shaft member 421, which can be fixedly coupled to the ratchet rack 408, moves distally. The planet carrier 405 can be rotationally coupled to the sun gear shaft 403 by the second clutch driver 404b when rotating in the first action; thus, rotation can be transmitted to the sun gear shaft 403 in a 1:1 ratio. The first clutch driver 404a can allow the sun gear shaft 403 to rotate freely relative to the shuttle frame 409 during the first action. The sheath pinion 403b of the sun gear shaft 403 can be meshed with the large spur gear 410a of the intermediate gear 410, and can impart rotational motion on the intermediate gear 410. The small spur gear 410b of the intermediate gear 410 can be operatively meshed with a rack 401c disposed on the second handle housing portion 401b; thus, the rotational motion of the intermediate gear 410 can impart linear motion on the shuttle frame 409 in the proximal direction. The outer tubular member 422, which can be fixedly coupled to the shuttle frame 409, can move proximally relative to the handle. Thus, during the first action, the inner shaft member 421 can move distally relative to the handle 401 and the outer tubular member 422 can move proximally relative to the handle 401.

Upon return of the trigger 460 from the second position to the first position (herein referred to as the "second action"), the driving rack 412 can move proximally relative to the handle 401. The driving rack 412 can impart rotational motion to the planet carrier 405. The planet carrier 405 can transmit rotational motion to the three planet gears 406. The planet gears 406 can rotate about the sun gear shaft 403, which can be held stationary relative the shuttle frame 409 via the first clutch driver 404a. The planet gears 406 can impart rotary motion to the ring gear 407. Linear motion can be transmitted to the ratchet rack 408 in the proximal direction by the ring gear 407. The inner shaft member 421, which can be fixedly coupled to the ratchet rack 408, can move proximally relative to the handle 401. Thus, during the second action, the inner shaft member moves proximally relative to the handle 401 and the outer tubular member 422 can be stationary relative to the handle.

Figure 62:
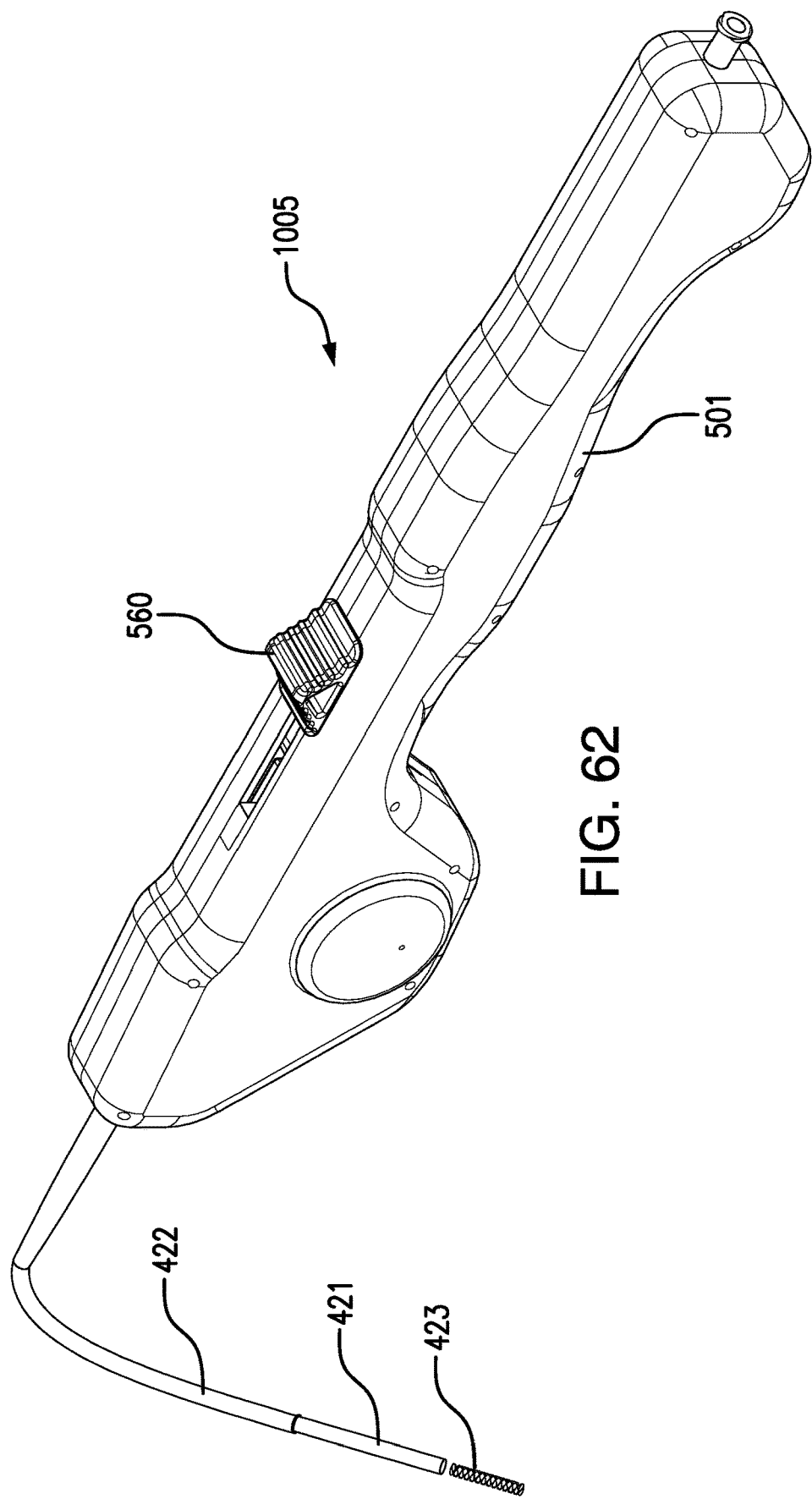
FIG. 62 is a perspective view of a further exemplary embodiment of a delivery system in accordance with the disclosed subject matter.
Figure 63:
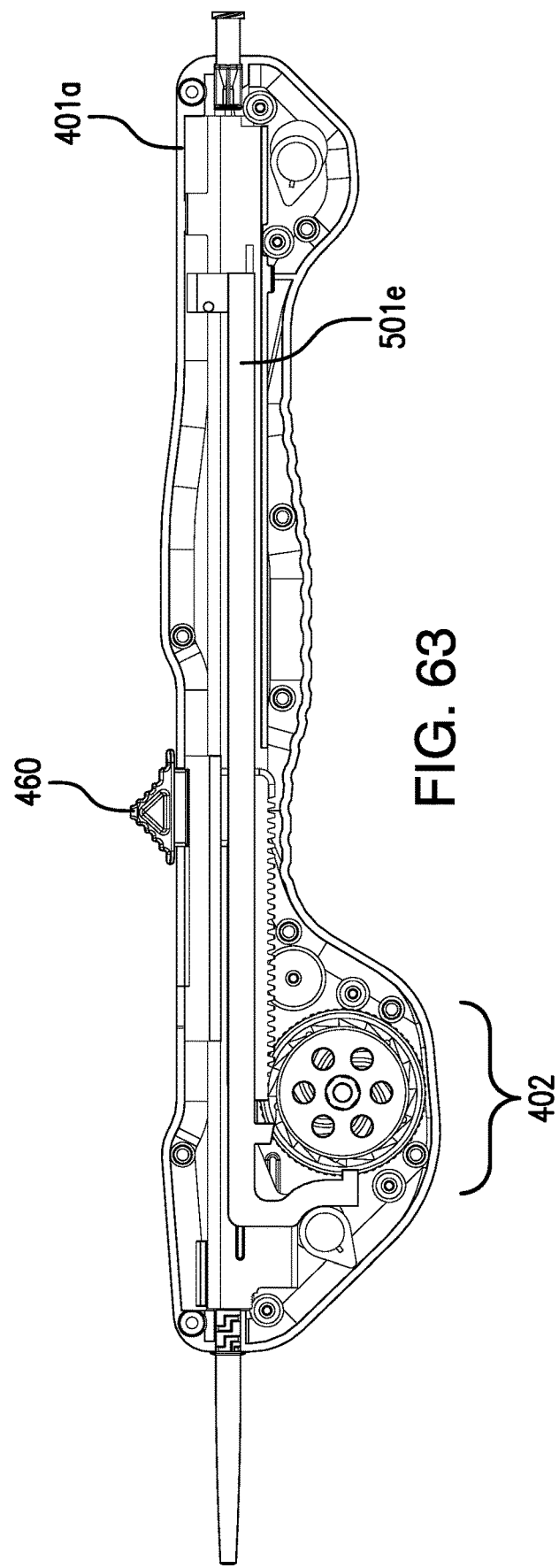
FIG. 63 is a right side view, with a portion of the handle housing removed, of the delivery system of FIG. 62.
Figure 64:
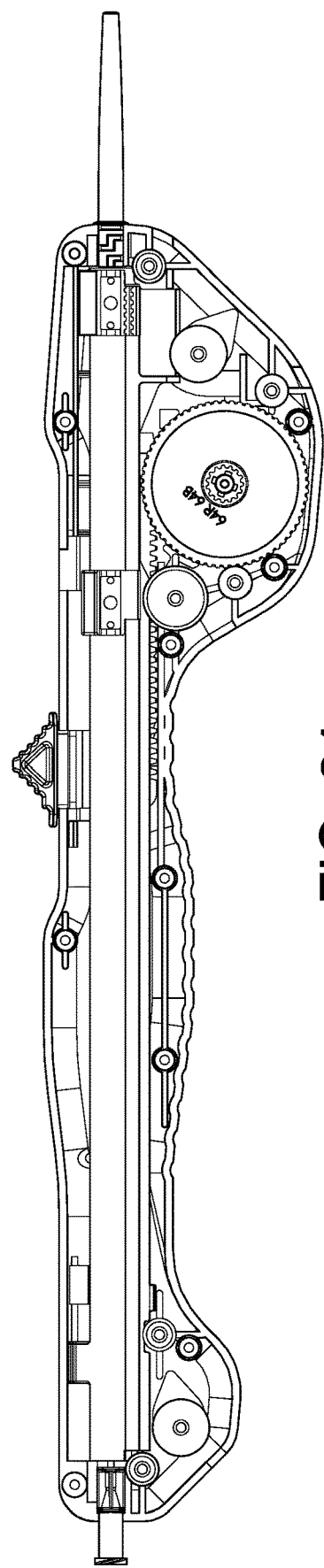
FIG. 64 is a left side view, with a portion of the handle housing removed, of the delivery system of FIG. 62.
Figure 66B:
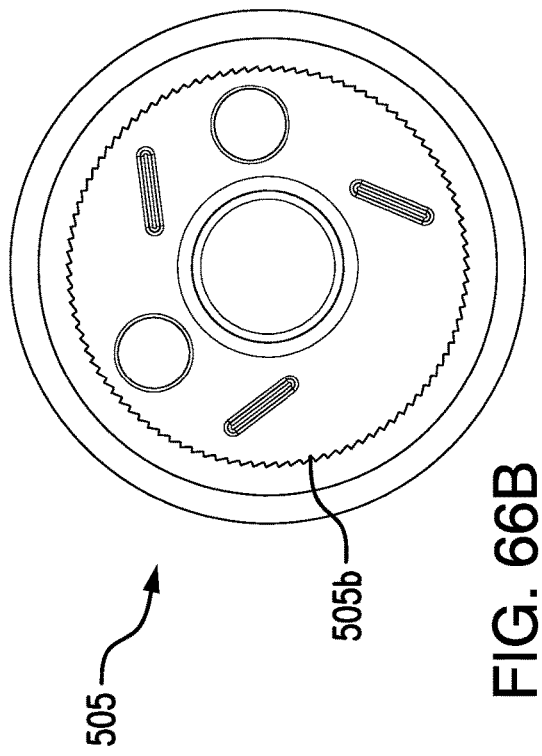
FIGS. 66A-66D provide perspective FIG. 66A, right FIG. 66B, left FIG. 66C, and front FIG. 66D views of the planet carrier of the delivery system of FIG. 62.
Figure 66A:
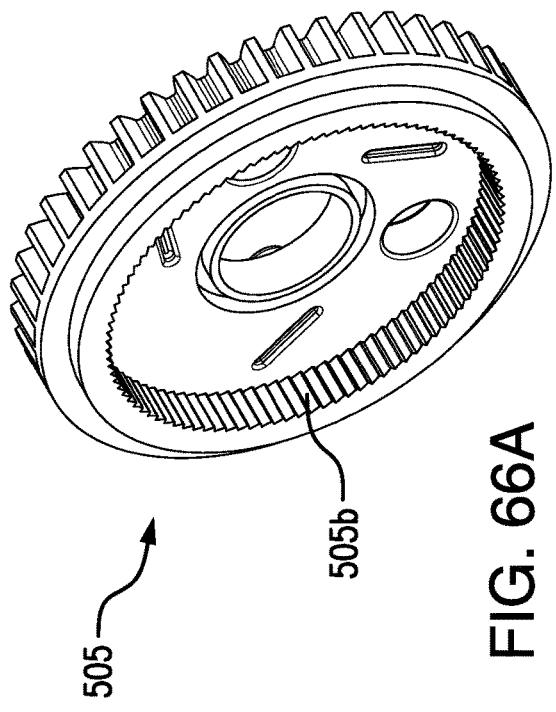
Figure 66D:
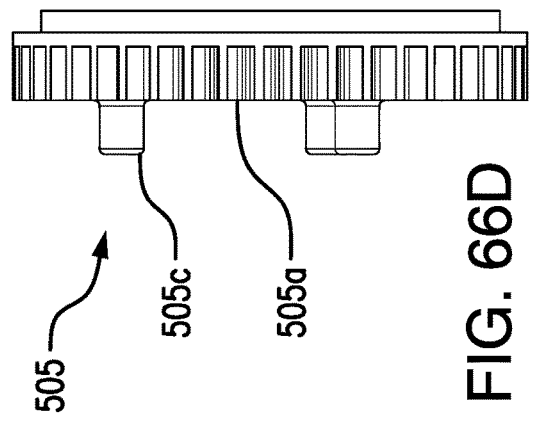
Figure 66C:
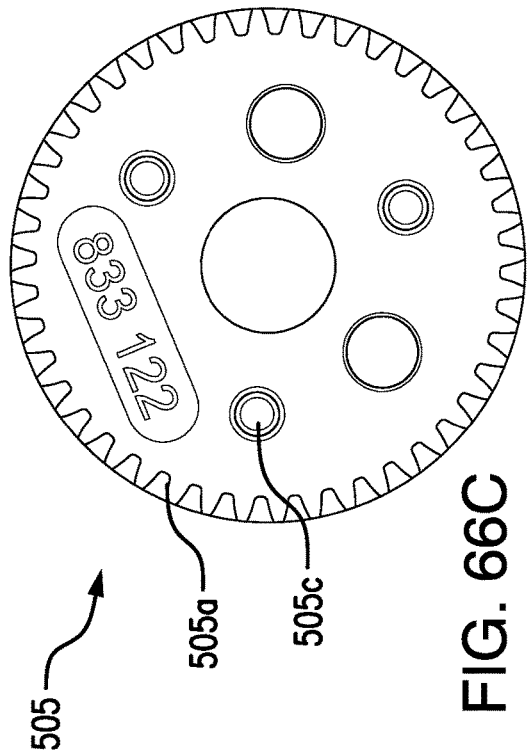
Figure 67A:
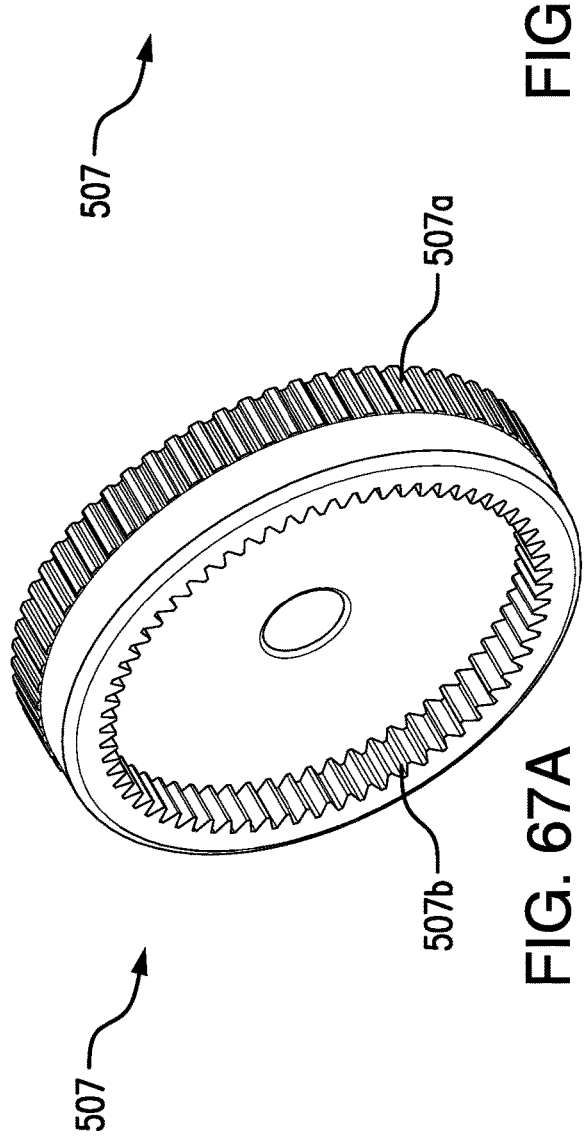
FIGS. 67A-67D provide perspective FIG. 67A, right FIG. 67B, left FIG. 67C, and front FIG. 67D views of the ring gear of the delivery system of FIG. 62.
Figure 67B:
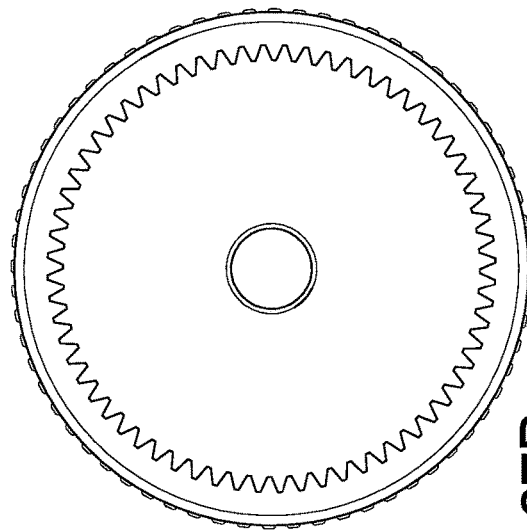
Figure 67C:
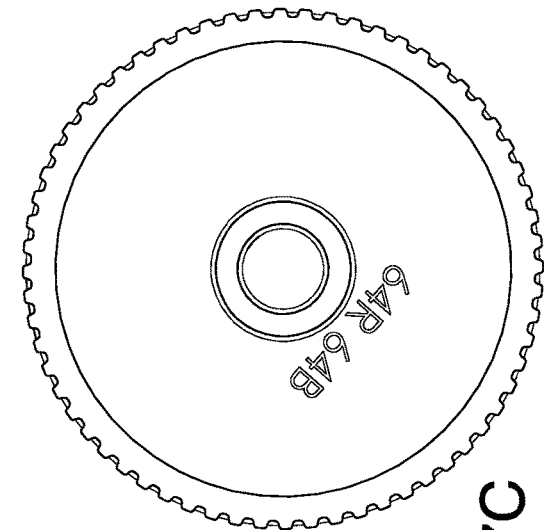
Figure 67D:
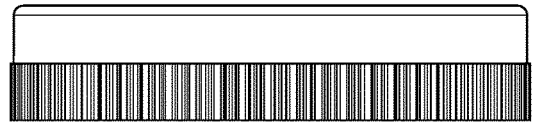
Figure 68A:
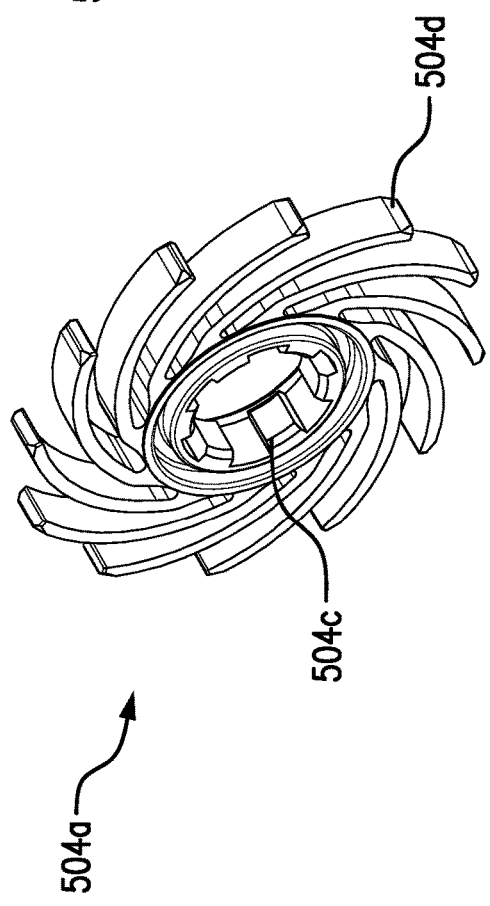
FIGS. 68A-68D provide perspective FIG. 68A, right FIG. 68B, left FIG. 68C, and front FIG. 68D views of the first clutch driver of the delivery system of FIG. 62.
Figure 68B:
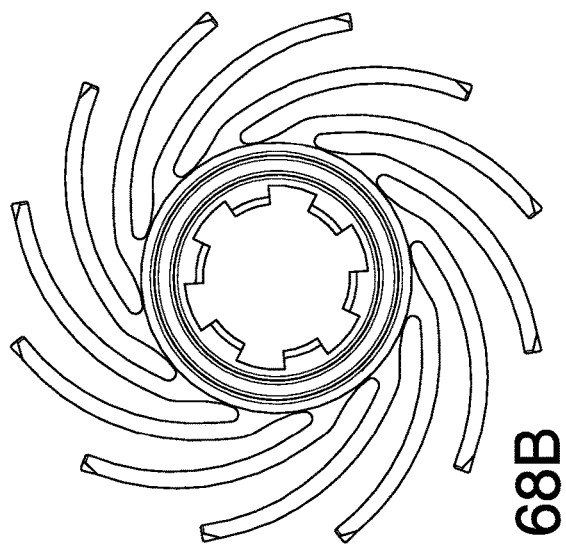
Figure 68C:
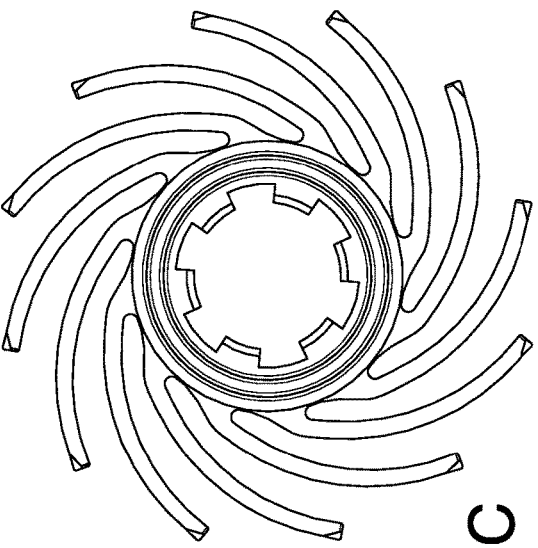
Figure 68D:
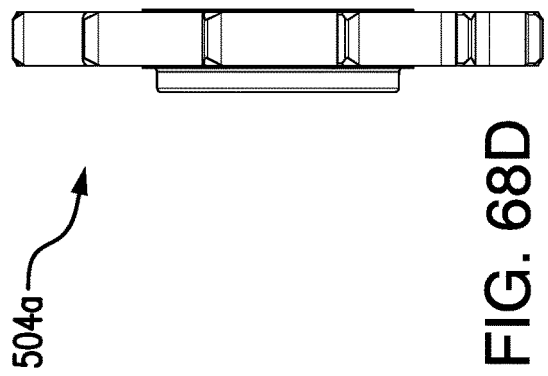
Figure 69B:
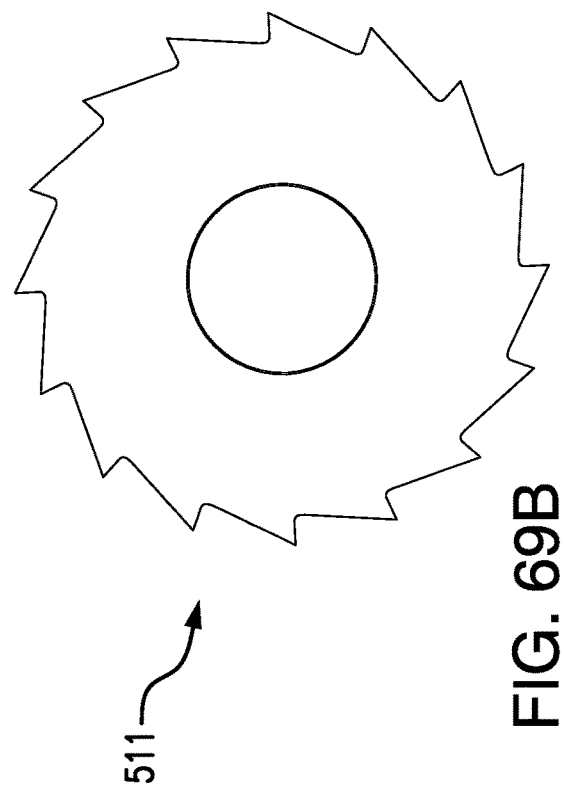
FIGS. 69A-69D provide perspective FIG. 69A, right FIG. 69B, left FIG. 69C, and front FIG. 69D views of the clutch release of the delivery system of FIG. 62.
Figure 69D:
Figure 69A:
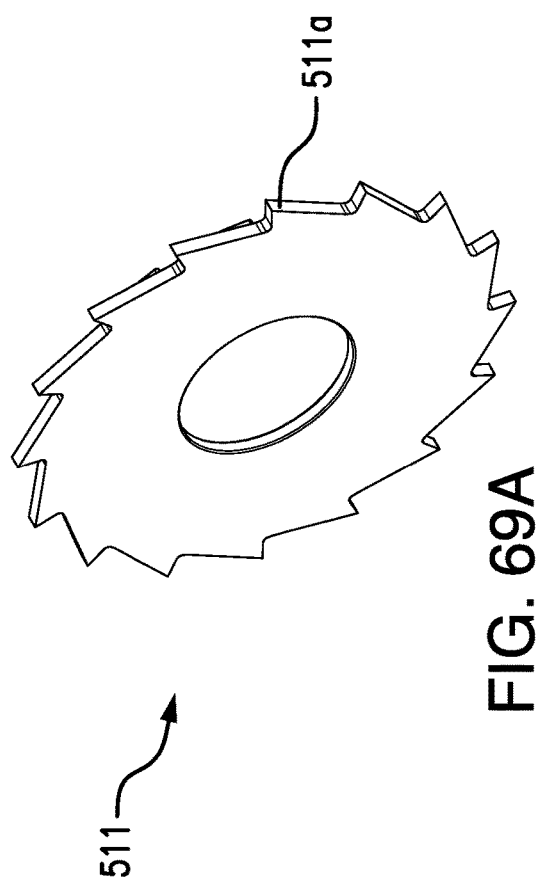
Figure 69C:
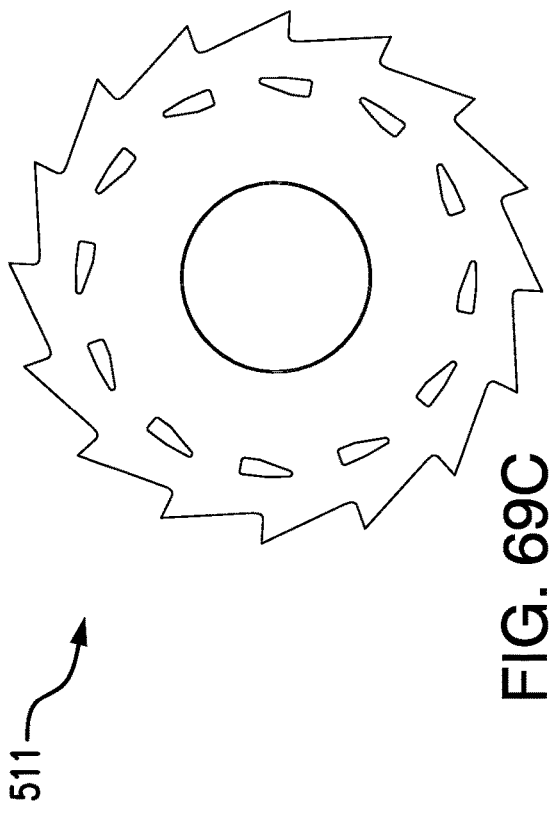
Figure 70A:
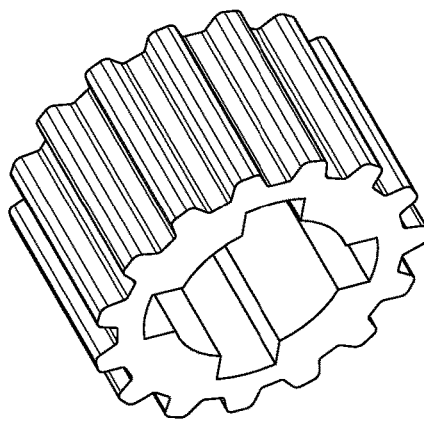
FIGS. 70A-70D provide perspective FIG. 70A, right FIG. 70B, left FIG. 70C, and front FIG. 70D views of the ratchet gear of the delivery system of FIG. 62.
Figure 70B:
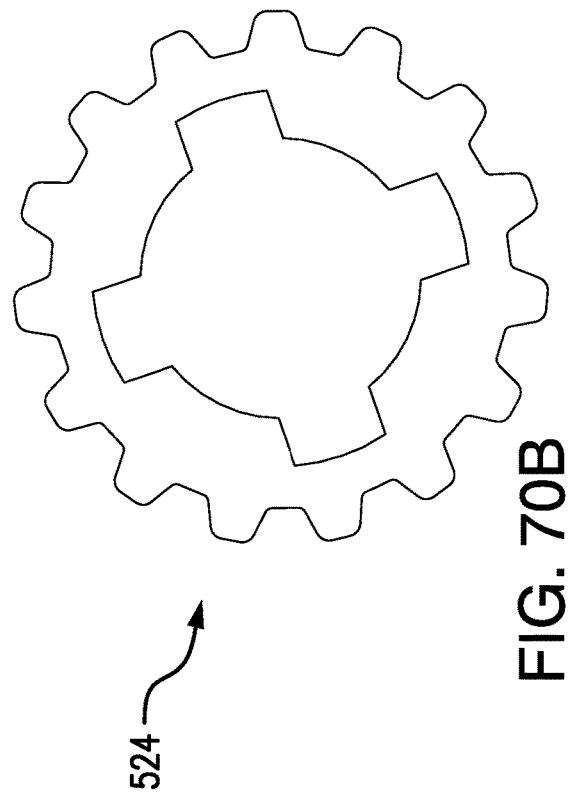
Figure 70C:
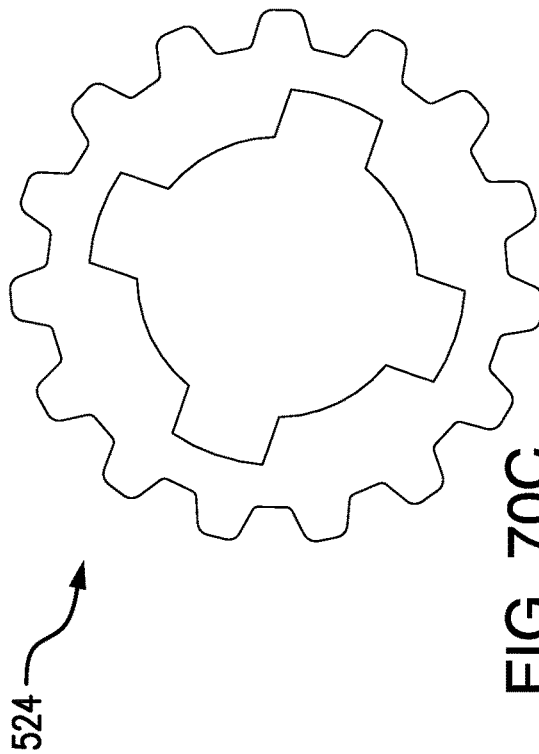
Figure 70D:
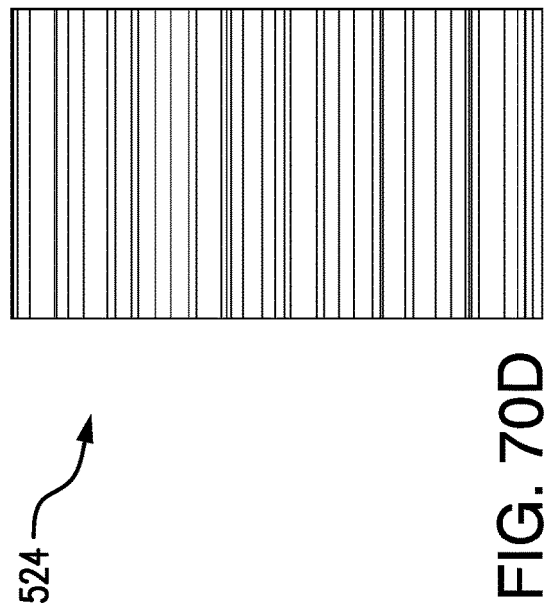
Figure 71B:
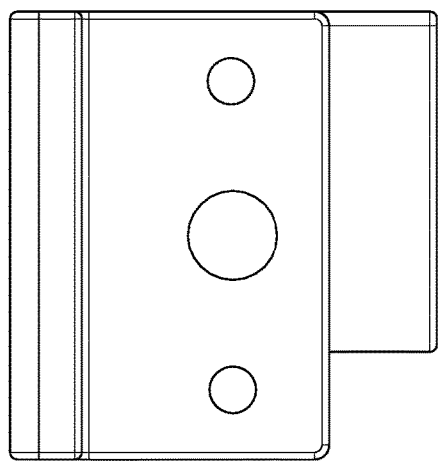
FIGS. 71A-71D provide perspective FIG. 71A, right FIG. 71B, left FIG. 71C, and front FIG. 71D views of the sheath gondola of the delivery system of FIG. 62.
Figure 71D:
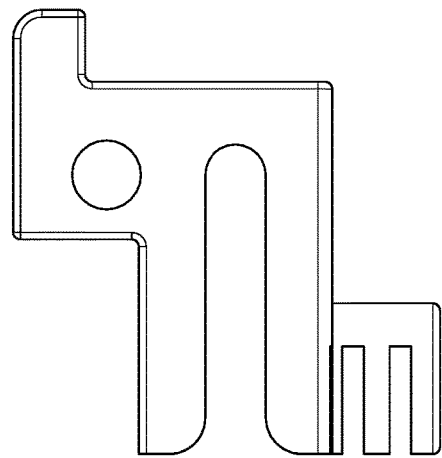
Figure 71A:
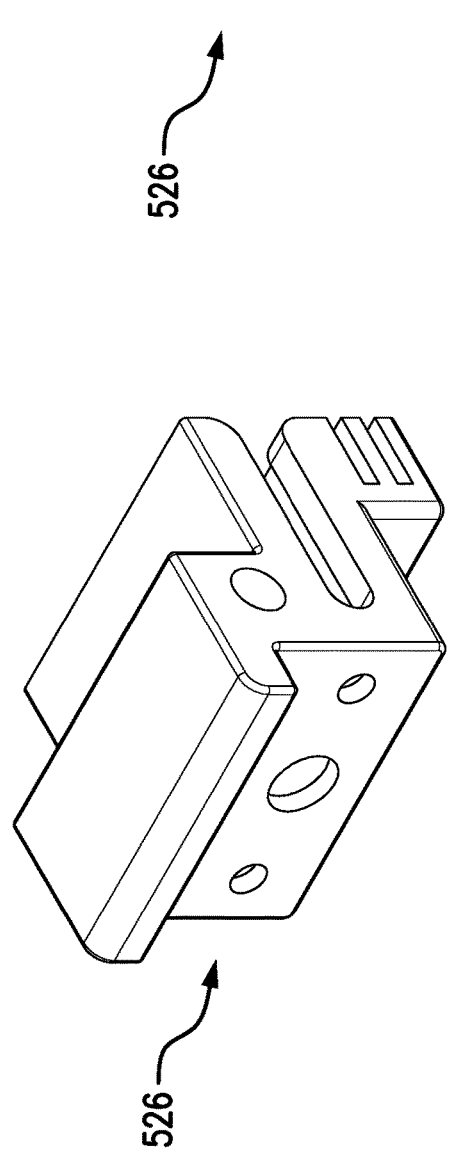
Figure 71C:
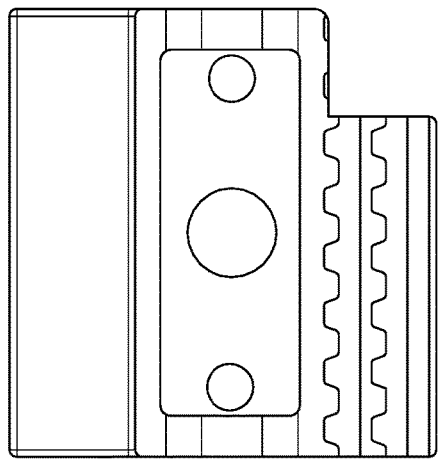
Figure 72B:
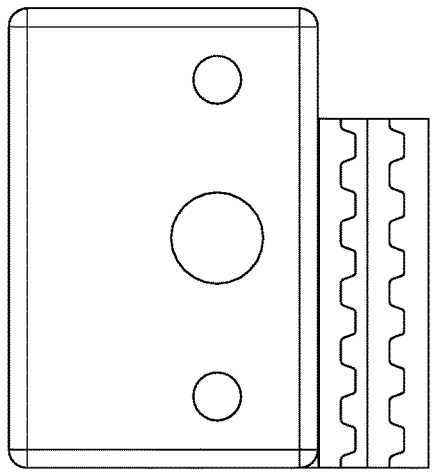
FIGS. 72A-72D provide perspective FIG. 72A, right FIG. 72B, left FIG. 72C, and front FIG. 72D views of the ratchet gondola of the delivery system of FIG. 62.
Figure 72D:
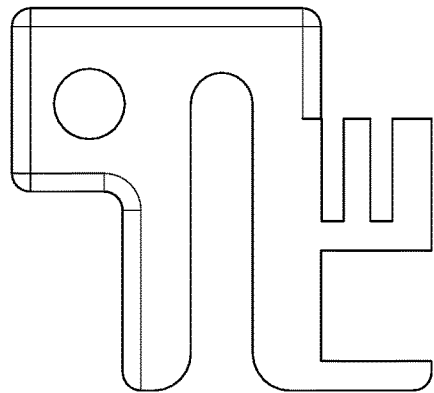
Figure 72A:
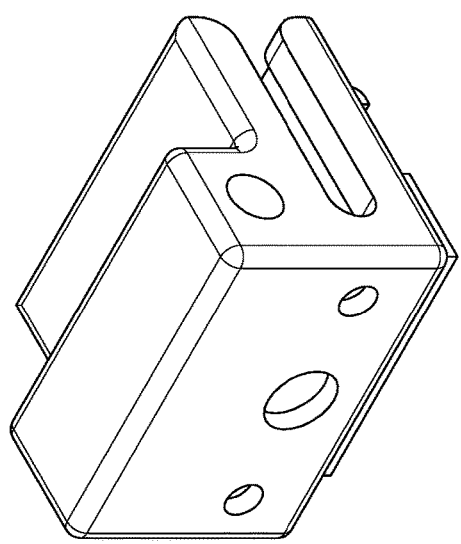
Figure 72C:
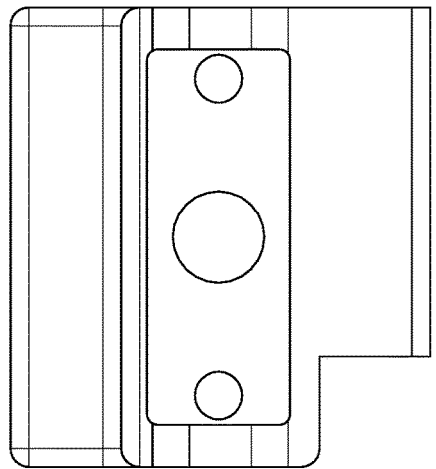
Figure 73B:
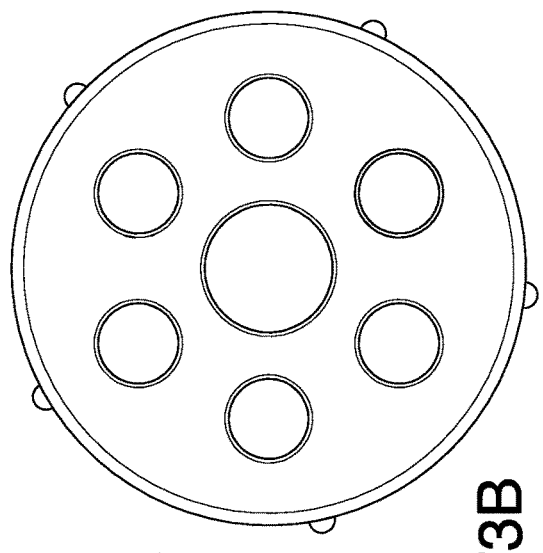
FIGS. 73A-73D provide perspective FIG. 73A, right FIG. 73B, left FIG. 73C, and front FIG. 73D views of the clutch ring of the delivery system of FIG. 62.
Figure 73D:
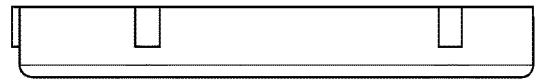
Figure 73A:
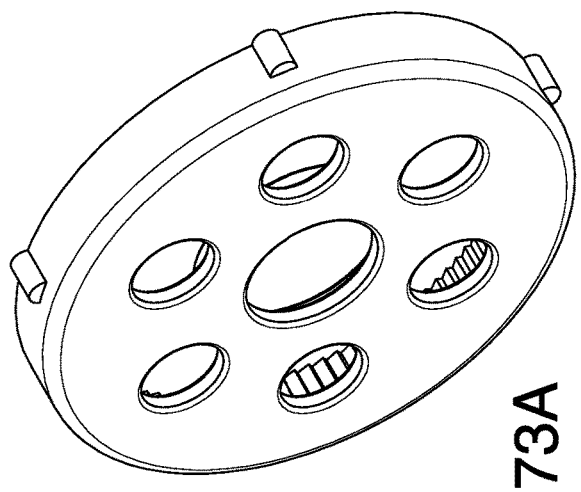
Figure 73C:
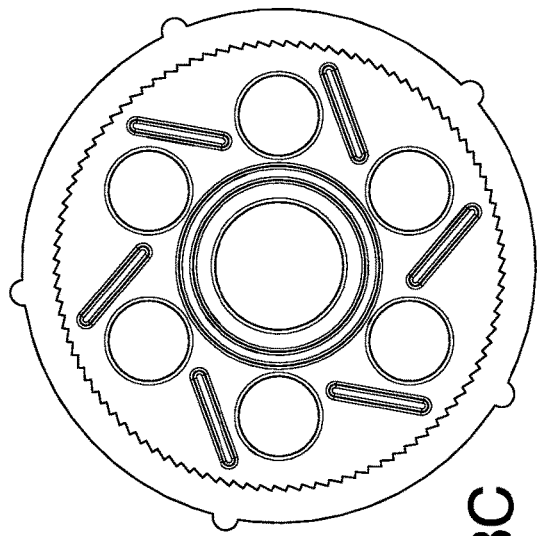
Figure 74:
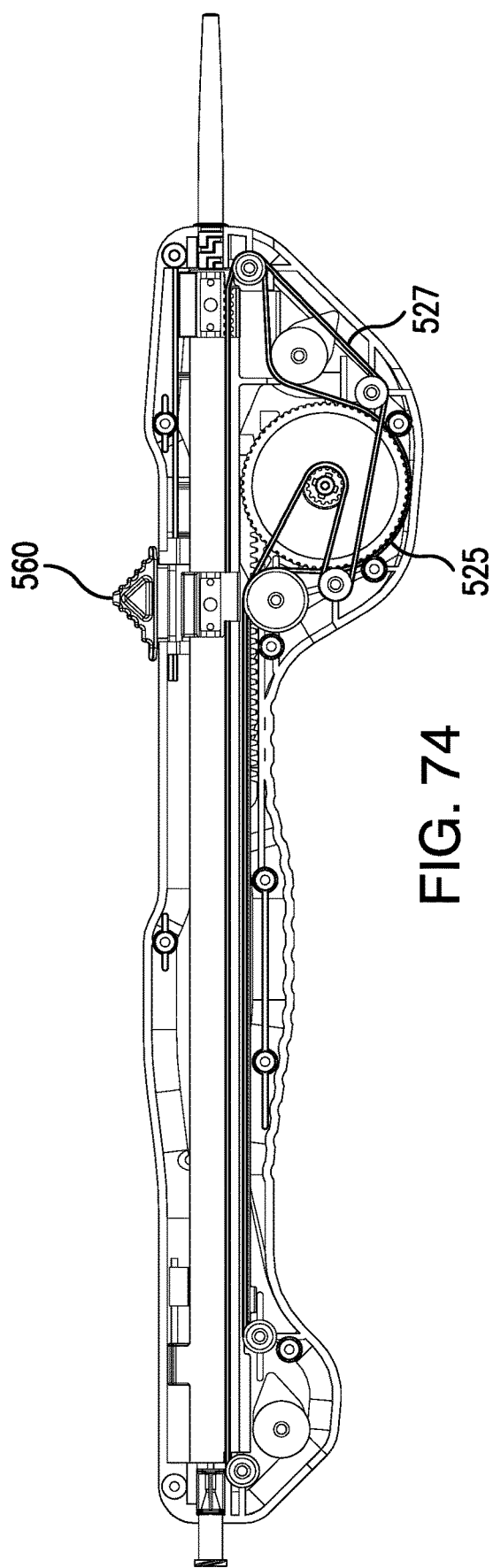
FIG. 74 is a left side view, with a portion of the handle housing removed, of the delivery system of FIG. 62.
Figure 75:
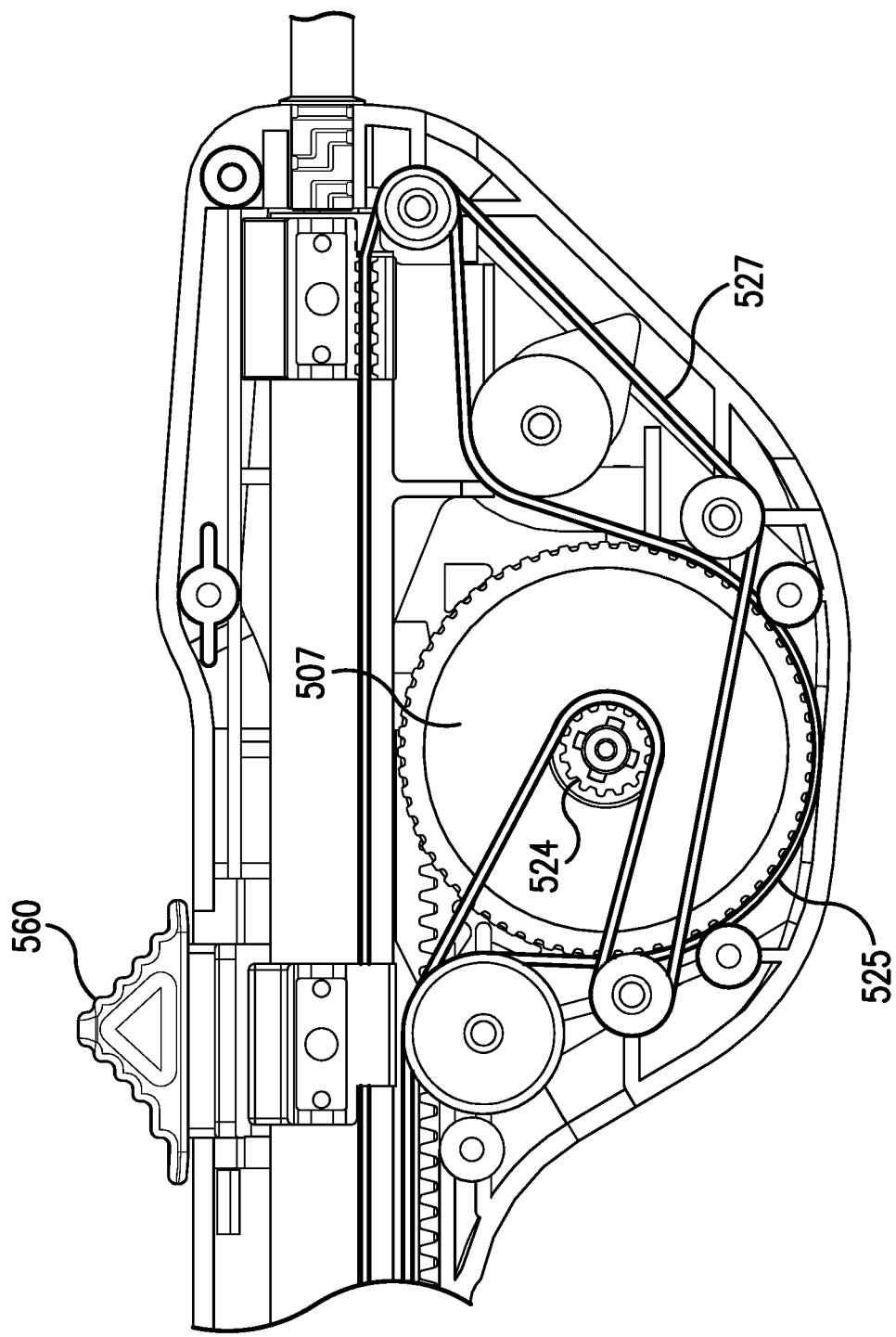
FIG. 75 is an enlarged in view of a portion of the delivery system of FIG. 63.
Figure 76:
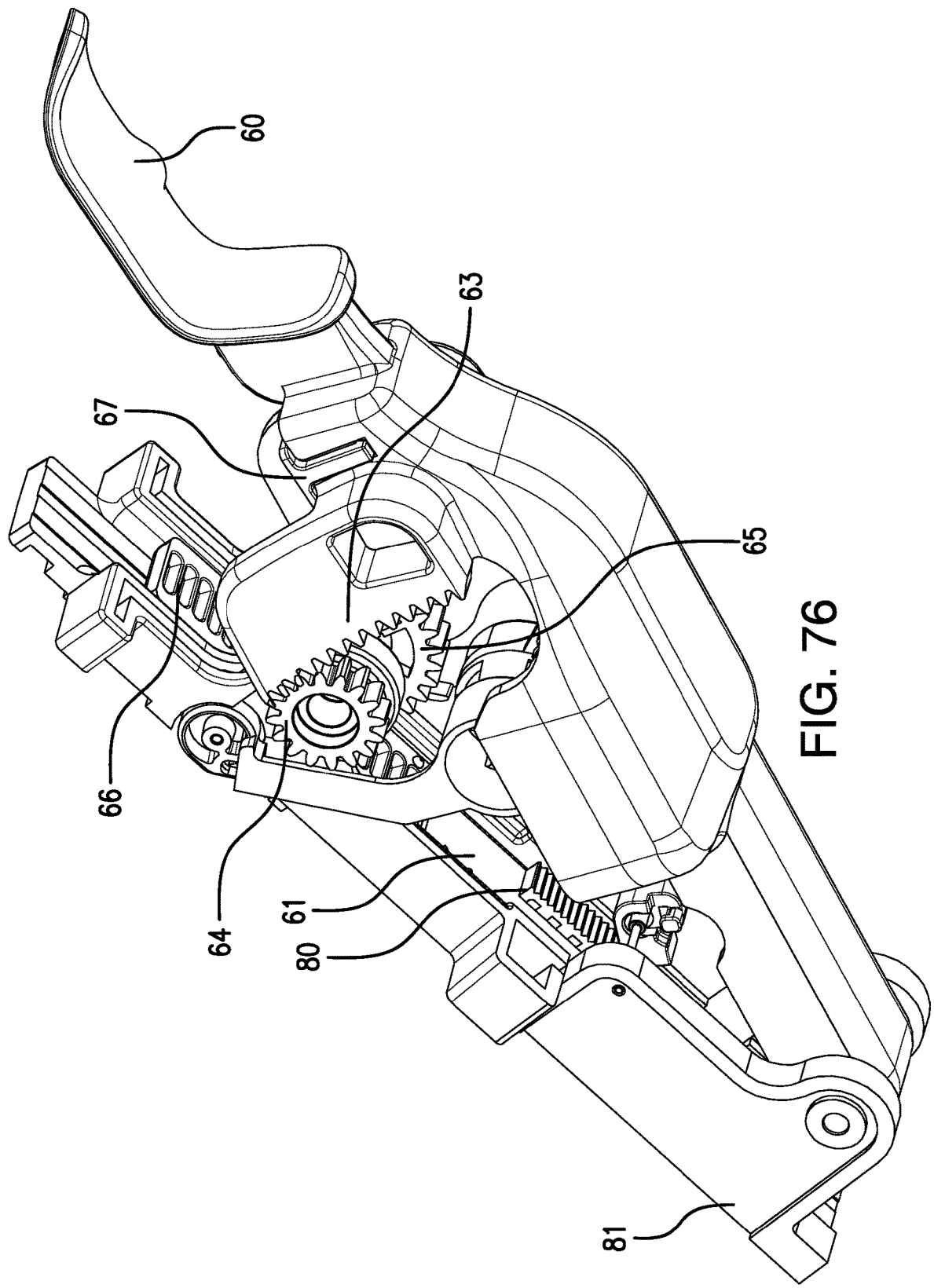
FIG. 76 provides a top perspective view of selected elements of the trigger assembly of the delivery system of FIG. 1A.
Figure 77B:
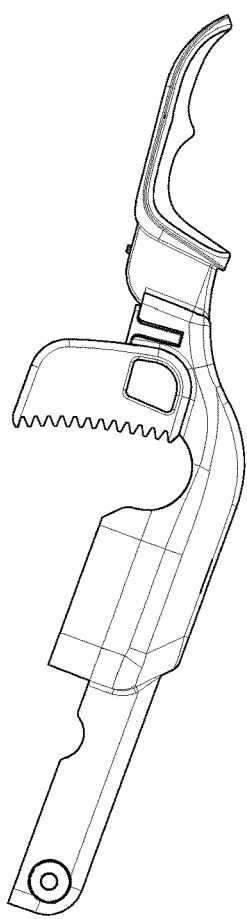
FIGS. 77A-77D provide perspective FIG. 77A, right FIG. 77B, left FIG. 77C, and front FIG. 77D views of the trigger of the delivery system of FIG. 1A.
Figure 77D:
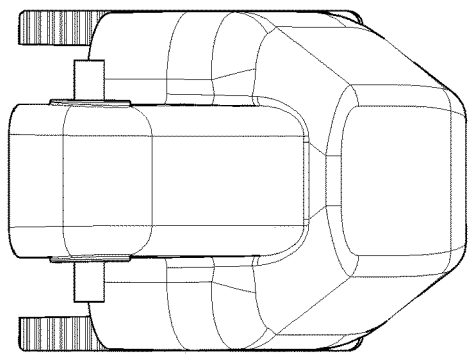
Figure 77A:
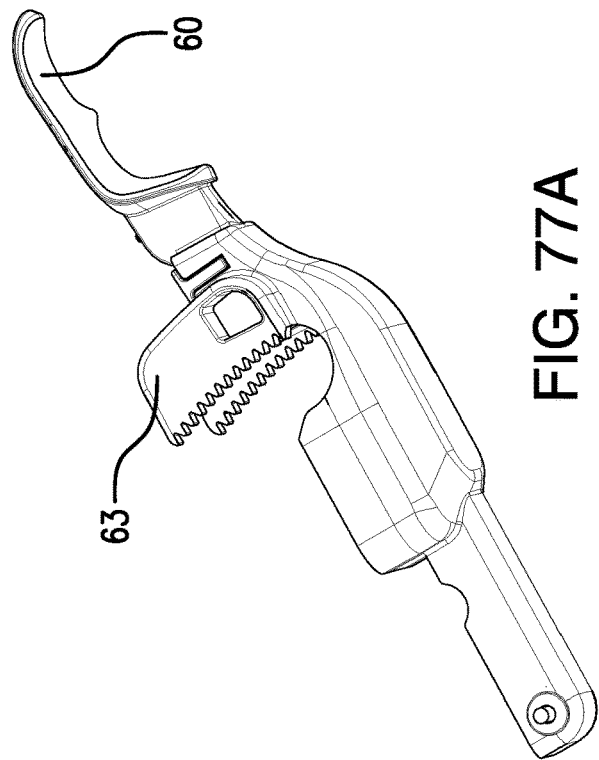
Figure 77C:
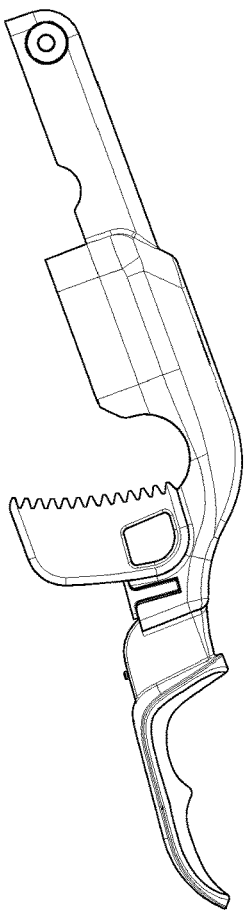
Figure 78B:
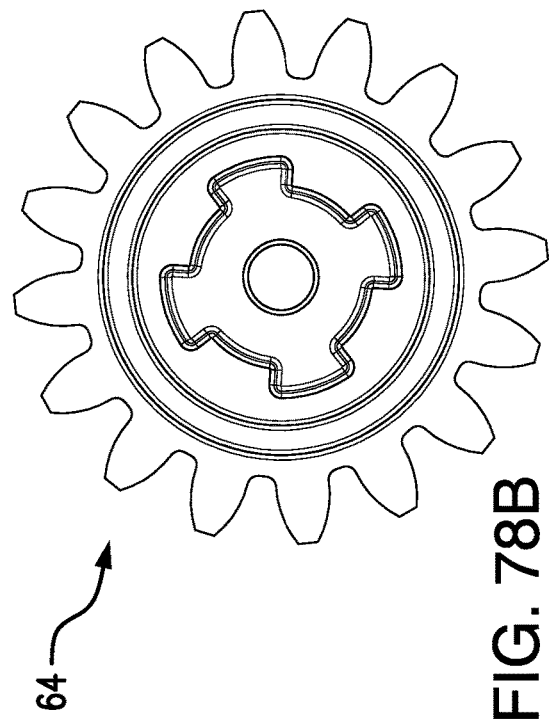
FIGS. 78A-78D provide perspective FIG. 78A, right FIG. 78B, left FIG. 78C, and front FIG. 78D views of the trigger pinion of the delivery system of FIG. 1A.
Figure 78D:
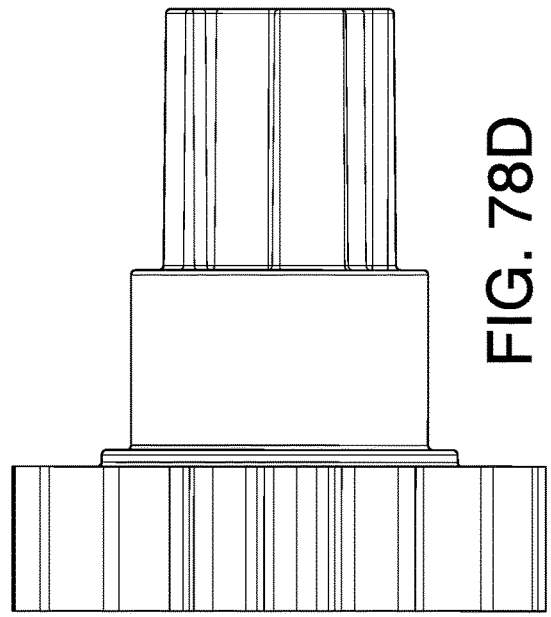
Figure 78A:
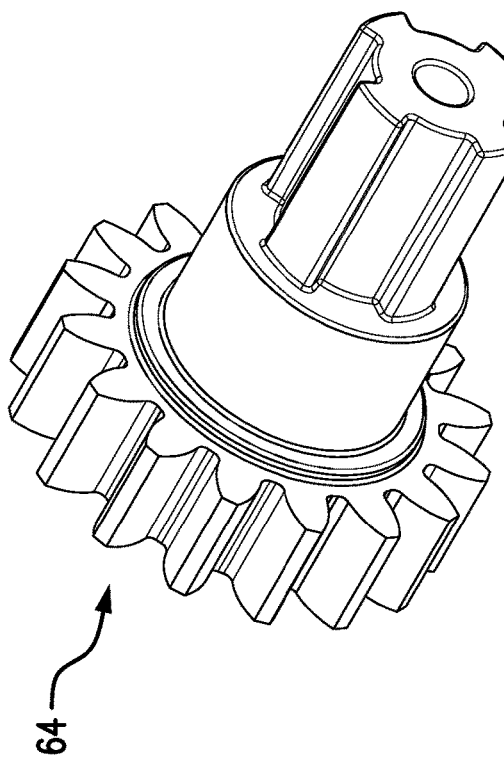
Figure 78C:
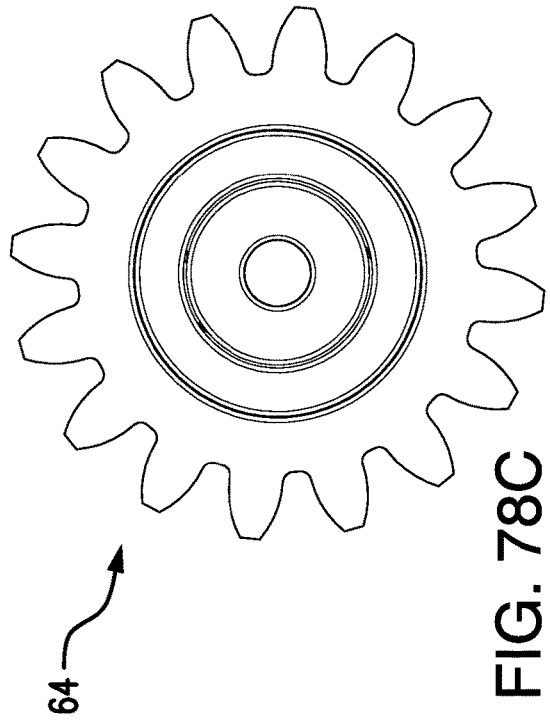
Figure 79B:
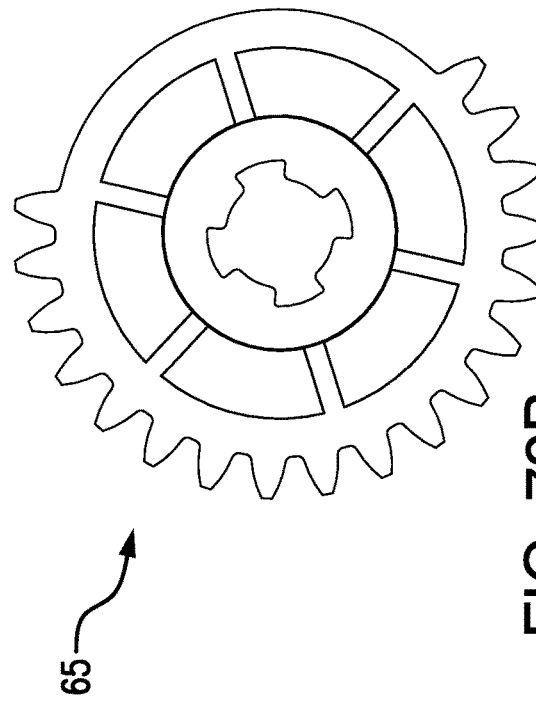
FIGS. 79A-79D provide perspective FIG. 79A, right FIG. 79B, left FIG. 79C, and front FIG. 79D views of the slide pinion of the delivery system of FIG. 1A.
Figure 79D:
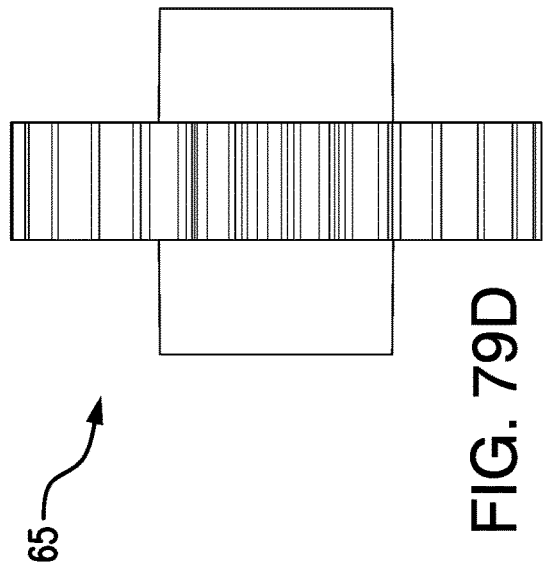
Figure 79A:
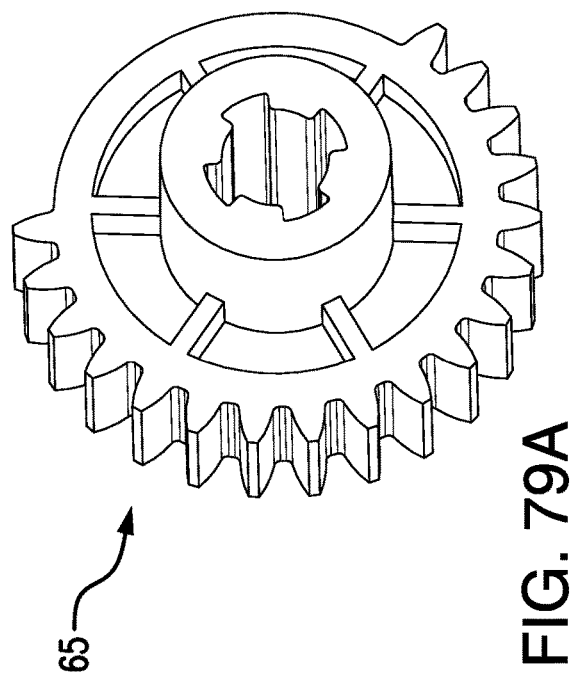
Figure 79C:
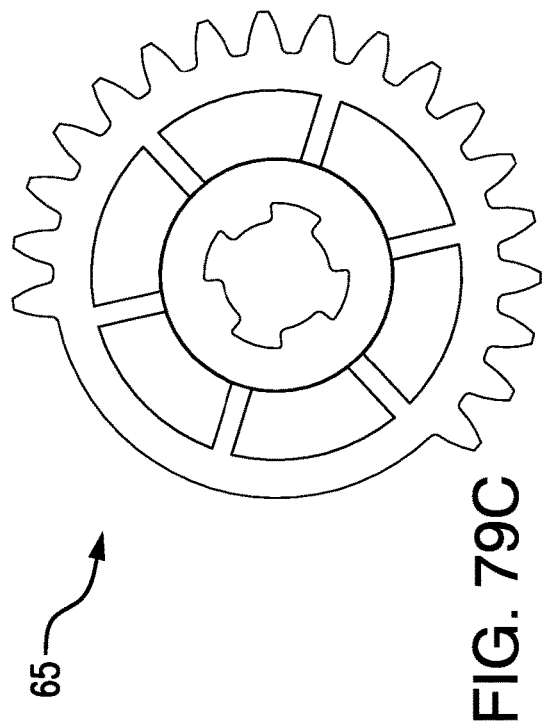
Figure 81B:
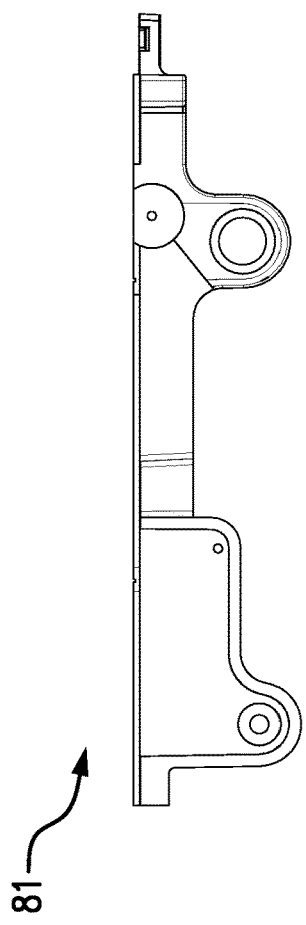
FIGS. 81A-81D provide perspective FIG. 81A, right FIG. 81B, left FIG. 81C, and front FIG. 81D views of the base of the delivery system of FIG. 1A.
Figure 81D:
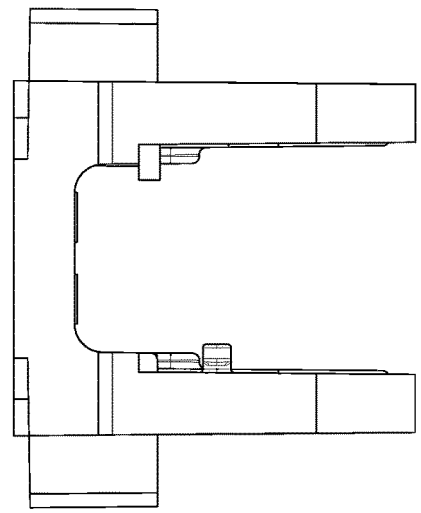
Figure 81A:
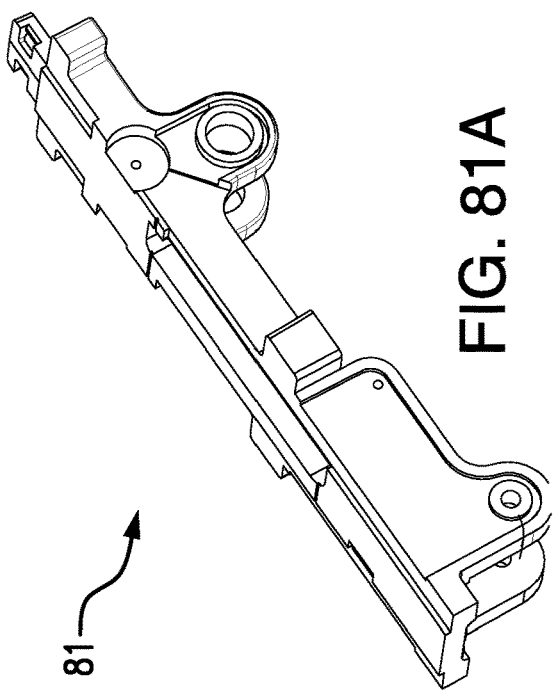
Figure 81C:
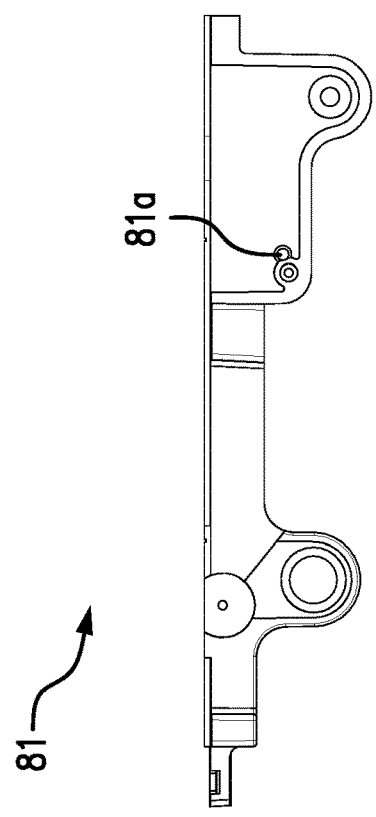
Figure 82:
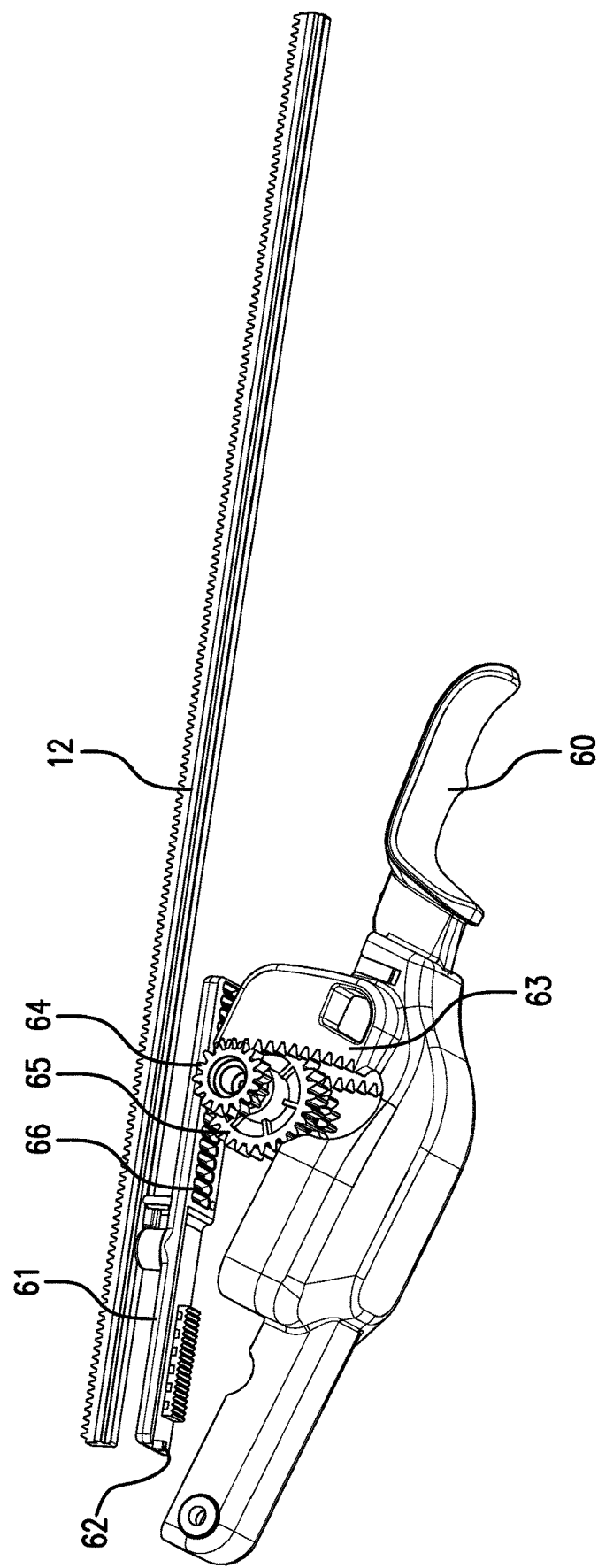
FIG. 82 is a perspective view illustrating the relationship between selected elements of the delivery system of FIG. 1A.

Referring to FIG. 62 for the purpose of illustration and not limitation, an exemplary embodiment of a system for delivering an implant is provided and designated generally by reference character 1005. Portions of this exemplary embodiment are depicted in FIGS. 63-75. Elements that are similar to the previously described embodiment have been given like numbers. The delivery system 1005 can be configured to deliver an implant in a similar manner as described herein above.

The delivery system 1005 can include a handle 501, an outer tubular member 522, an inner shaft member 521, and an implant 523, for example, a braided implant. The handle 501 can include a trigger 560 and an actuation assembly 502, which can be configured to move the inner shaft member 521 and the outer tubular member 522 relative to the handle 501 as described above upon deployment of the trigger 560 from the first position to the second position and return from the second position to the first position. The trigger 560 can include a lock as described herein above.

Referring now to FIGS. 63-75 for the purpose of illustration and not limitation, the actuation assembly 502 can include a planetary gear system similar to the planetary gear system disclosed in system 1000. In lieu of a shuttle frame and a ratchet rack coupled to the outer tubular member and inner shaft member, respectively, the system 1005 can include gondolas disposed on tension elements, as described further below.

For example, the actuation assembly 502 can include a sun gear shaft 503 (which can include a sun gear portion 503a, a clutch engagement portion 503c, and a sheath gear engagement portion 503d; FIG. 65), a planet carrier 505 (which can include a circumferential pinion 505a, a clutch component 505b, and at least one pin 505c; FIG. 66), at least one planet gear 456, a ring gear 507 (which can include a circumferential pinion 507a and a ring gear portion 507b; FIG. 67), a first clutch driver 404a and a second clutch driver 404b, both identical in shape (each can include including a sun gear shaft engagement portion 504c and a clutch portion 504d; FIG. 68). The actuation assembly can include a sheath gear 524, which can engage the sheath gear engagement portion 503d of the sun gear shaft 503. The actuation assembly can include a first tension element 525, and a sheath gondola 526 disposed on the first tension element. The first tension element can be functionally coupled to the sheath gear 524. The sheath gondola 526 can be fixedly coupled to the outer tubular member 522. The actuation assembly can include a second tension element 527, and a ratchet gondola 528 disposed on the second tension element. The second tension element 527 can be functionally coupled to the circumferential pinion 507a of the ring gear 507. The ratchet gondola 528 can be fixedly attached the inner shaft member 521. The actuation assembly can include a clutch ring 531, which can be fixedly placed within the handle 501 and can provide a clutch engagement portion for the first clutch driver 501a. Alternatively, the handle 501 can include a clutch engagement portion to engage the first clutch driver 501a. The system can further include a plurality of pulley elements 529, which can be used to guide the first and second tension elements, and at least two tensioners 530a, 530b, which can be used to achieve the desired tension in the first and second tension elements. The actuation assembly can be functionally coupled to the trigger 560 by a driving rack 512. The actuation assembly can include a clutch release 511 which can engage a stop 501e disposed within the handle, and configured to engage the clutch release 511 when the sheath gondola has moved the stop 501e into place.

During operation, the user can deploy the trigger 560 from the first position to the second position (referred to herein as the "first action"). The trigger 560 can cause the driving rack 512 to move in the distal direction. The driving rack 512, functionally meshed with the circumferential pinion 505a of the planet carrier 505, can impart rotational motion on the planet carrier 505. The planet carrier 505 can impart rotational motion on the three planet gears 506. The planet gears 506 can be constrained from rotating freely because they can be meshed with the sun gear portion 503a of the sun gear shaft 503. The three planet gears 506 can be meshed with the ring gear portion 507b of the ring gear 507, and can impart rotational motion on the ring gear 407. The ring gear 507, which can be functionally coupled to the ratchet gondola 528 by the second tension element 527, can cause the ratchet gondola 528 to move distally. The inner shaft member 521, which can be fixedly coupled to the ratchet gondola 528, can move distally. The planet carrier 505 can be rotationally coupled to the sun gear shaft 503 by the second clutch driver 504b when rotating in the first action; thus, rotation can be transmitted to the sun gear shaft 503 in a 1:1 ratio. The first clutch driver 504a can allow the sun gear shaft 503 to rotate freely relative to the clutch ring 531 during the first action. The sheath gear engagement portion 503d of the sun gear shaft 503 can functionally engage the sheath gear 524, and can impart rotational motion on sheath gear 524. The sheath gear 524, which can be functionally coupled to the sheath gondola 526 by the first tension element 525, can cause the sheath gondola 526 to move proximally. The outer tubular member 522, which can be fixedly coupled to the sheath gondola 526, can move proximally relative to the handle. Thus, during the first action, the inner shaft member 521 can move distally relative to the handle 501 and the outer tubular member 522 can move proximally relative to the handle 501.

Upon return of the trigger 560 from the second position to the first position (herein referred to as the "second action"), the driving rack 512 can move proximally relative to the handle 501. The driving rack 512 can impart rotational motion to the planet carrier 505. The planet carrier 505 can transmit rotational motion to the three planet gears 506. The planet gears 506 can rotate about the sun gear shaft 503, which can be held stationary relative the clutch ring 531 via the first clutch driver 504a. The planet gears 506 can impart rotary motion to the ring gear 507. The ring gear 507 can drive the ratchet gondola 528 proximally via the second tension element 527. The inner shaft member 521, which can be fixedly coupled to the ratchet gondola 528, can move proximally relative to the handle 501. Thus, during the second action, the inner shaft member can move proximally relative to the handle 501 and the outer tubular member 422 can be stationary relative to the handle.

In accordance with the described subject matter, and as noted above, a trigger assembly for a delivery system is also provided. The trigger assembly includes a trigger functionally connected to the actuation assembly by a driving rack, a gear train functionally disposed between the trigger and the driving rack. The gear train includes a trigger gear sector, a trigger pinion operatively meshed with the trigger gear sector, a slide pinion operatively coupled to the trigger pinion, and a slide rack disposed on a slide coupled to the driving rack and operatively meshed with the trigger pinion.

Figure 83:
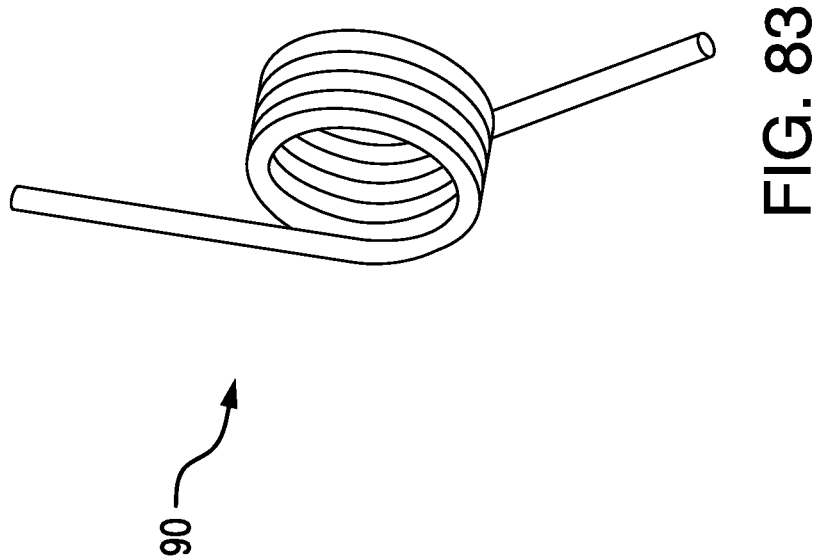
FIG. 83 provides a perspective view of the spring of the delivery system of FIG. 1A.

With regard to the trigger assembly, FIGS. 76-85 depict portions of the delivery system 1000 described herein above. The trigger 60 is operatively coupled to the handle and moveable between a first position and a second position. Furthermore the trigger can be biased towards the first and/or second position, for example, by a spring 91 (FIG. 83). As described in further detail below, the trigger assembly can further include a ratchet mechanism 80 which can prevent moving the trigger between the first and second positions. Particularly, the ratchet can be configured to require a full stroke of the trigger in one direction to allow motion of the trigger in the opposite direction.

As embodied herein, and with reference to FIG. 2, the trigger 60 can be coupled to the actuation assembly 2 by a driving rack 12. For example, the trigger 60 can be functionally coupled to the driving rack by gear train. The gear train can include a trigger gear sector 63 (FIG. 77), a trigger pinion 64 (FIG. 78), a slide pinion 65 (FIG. 79), a slide 61 (FIG. 80; sometimes referred to as an intermediate element) having a slide rack 66, and a base 81 that can support certain elements of the gear train (FIG. 81). The trigger 63 can be pivotally coupled to the base 81. The trigger gear sector 63 can be coupled to the trigger 60, for example, the trigger gear sector 63 can be unitary with the trigger 60, and can be operatively meshed with the trigger pinion 64. The trigger pinion 64 can be operatively coupled to the slide pinion 65. For example, the trigger pinion 64 and the slide pinion 65 can be coupled by splines and grooves, such as, four splines on the trigger pinion 64 configured to be received by four grooves in the slide pinion 65 as depicted in FIGS. 78 and 79. The slide pinion 65 can be operatively meshed with the slide rack 66 disposed on the slide 61. The driving rack 12 can be coupled to the slide 61. The driving rack 12 can be fixedly coupled or releasably coupled to the slide 61. As an example and not by way of limitation, the driving rack 12 can have a bayonet-type engagement with the slide 61. Furthermore, more than one trigger gear sector and/or trigger pinion can be provided, as shown, for example, in FIGS. 1-3, and 76, the gear train can include two trigger gear sectors 63 and two trigger pinions 64. Each of the trigger pinions 64 can be coupled to the slide pinion 65 as described above.

As embodied herein, the slide pinion 65 can be quad symmetrical. For example, the slide pinion 65 can have 28 teeth evenly distributed in sets of 7. The number of grooves can be a factor of the number of teeth, for example, 4 grooves and 28 teeth. Such a configuration can allow for symmetry between the teeth and the grooves of the slide pinion 65, and thus ease of assembly and/or use. Accordingly, when the slide pinion 65 is coupled the trigger pinion 64, the teeth are in proper alignment. Additionally or alternatively, the slide pinion 65 can include teeth around only a portion of the circumference. For example, rather than including teeth about the entire circumference, a number of teeth (e.g., 10 teeth) can be removed or omitted. This arrangement can accommodate other elements, for example, the movement of spring 90 (described in greater detail below) toward the slide pinion 65 during movement of the trigger 60 when space is restricted. Furthermore, at least one spline can be configured to align radially a selected location, e.g., a missing tooth, so as to allow for self-alignment.

With reference to FIGS. 83 and 84, for the purpose of illustration and limitation, a spring 90 can be provided. The spring can be, for example, a torsion spring 90. Additional springs can likewise be provided, e.g., two springs 90, as, depicted in FIG. 76. The spring 90 can be coupled to the trigger such that energy is stored in the spring 90 upon deployment of the trigger 60 from the first position to the second position. The energy stored in the spring 90 thus can be configured to bias the trigger 60 to return from the second position to the first position. The spring 90 can be housed within a spring support 91 (FIG. 84). The spring support can be coupled to the trigger 60 and the base 81. The spring support 91 can house the spring 90 such that energy is stored in the spring 90 when the trigger 60 is in the first position, e.g., the spring support 91 can hold the spring 90 in a pre-loaded position. Such a configuration can cause a force to be felt as the user initially begins to move the trigger 60 from the first position to the second position. Additionally, by providing such a configuration, the spring can provide additional force or bias to assist in returning the trigger 60 from the second position to the first position, and thus ensure that the trigger 60 returns from the second position to the first position.

The spring support 90 can be configured to house and/or strengthen the spring, such as an exoskeleton arrangement. For example, the spring support 90 can have legs configured to engage the legs of the torsion spring 90, as depicted in FIG. 84. The legs of the spring support 91 can be configured to move with the legs of the torsion spring 90. If the spring includes a barrel portion, the spring support 91 can also include a barrel portion to accommodate the barrel portion of the spring 90. The spring support 91 can be a single piece element, or can include several elements coupled together to form the spring support (FIG. 84C). The elements when assembled thus can be configured to allow the spring support to move with the spring 90, but prevent the spring from fully relaxing. The spring support 91 thus can reduce or prevent loads on other elements of the delivery system, for example, the trigger 60 and the base 81, which can be plastic. That is, the spring support 91 can be made from metal or other suitably strong materials, preferably such materials that are not susceptible to creep under stress.

In accordance with another aspect of the disclosed subject matter, the delivery system can include a ratchet mechanism. With reference to FIG. 85, for the purpose of illustration and not limitation, the system can include ratchet mechanism 80. The ratchet mechanism 80 can include a first state and a second state. The first state can be configured to allow the trigger 60 to move toward the second position and prohibit motion toward the first position. The second state can be configured to allow the trigger 60 to move toward the first position and prohibit motion toward the second position. Such a system thus can be configured to require the user to perform a full stroke of the trigger 60 between the first and second position before allowing return movement in the opposite direction.

The ratchet mechanism 80 can include a first pawl 82. The first pawl 82 can be supported by a peg 86 coupled to the base 81. The first pawl 82 can pivot relative the peg, and thus relative the base 81. The first pawl 82 can also be coupled to one end of a ratchet spring 87 (not shown for purpose of clarity), which can be coupled to the base 81 at its opposite end. The ratchet mechanism 80 also can include a trigger ratchet rack 83 and the like. The trigger ratchet rack 83 can be disposed on the slide 61. The trigger ratchet rack 83 can be configured to engage the first pawl 82 to permit unidirectional motion of the slide 61. By limiting the slide 61 to unidirectional motion, the trigger can likewise be limited to unidirectional motion (i.e., toward the first state or toward the second state). The first pawl 82 can have a first state configured to allow the trigger 60 to move toward the second position and prohibit motion toward the first position and a second state configured to allow the trigger 60 to move toward the first position and prohibit motion toward the second position. The ratchet spring 87 can keep the pawl 82 biased toward the first position or the second position, selectively. That is, the pawl 82 can be configured to switch from the first state to the second state as the trigger approaches the second position from the first position. Likewise, the pawl 82 can be configured to switch from the second state to the first state as the trigger approaches the first position from the second position. For example and not by way of limitation, the trigger ratchet rack 83 can be configured to move past the first pawl 83, as the trigger approaches either the first position or the second position, respectively, and thus allow the first pawl 82 to move freely to the alternate state due to the bias of ratchet spring 87. As described herein, the pawl 82 can engage the ratchet rack 83 in both the first position and the second position. Additionally or alternatively, the ratchet mechanism can be configured with more than one rack, for example a dual rack, and the pawl 82 can engage a different rack in each state. The pawl 82 can be moved out of the first or second position to a third position (e.g., a defeated position) in which the pawl 82 does not engage the trigger ratchet rack 83. As an example, the pawl 82 can be moved to the defeated position by moving the pawl 83 perpendicular to the trigger ratchet rack 83 along peg 86. The base 81 can include a defeat hole 81a (FIG. 81C), which can be aligned with the pawl 82 and can be aligned with a similar defeat hole 1k in the handle 1, such that the pawl 82 can be defeated by pushing an instrument through the defeat holes and urging the pawl 82 along the peg 86. Peg 86 can be configured to prevent the pawl 82 from returning to the first or second positions once the pawl has been moved to the defeated position. For example and as shown in FIG. 85D, the peg 86 can have a variable diameter. The pawl 82 can be disposed on the larger diameter in the first or second position, and can be disposed on the smaller diameter in the defeated position. Additionally or alternatively, a rib 62 can be included on the slide 61, as shown in FIGS. 80A, 80C, 82, and 85B and configured to prevent the pawl 82 from unintentionally moving transversely to the defeat position prior to use, for example, during shipment or storage of the delivery system 1000. Furthermore, the rib 62 can be configured to only secure the pawl prior to engagement of the trigger 60. For example, once the trigger is engaged, the rib 62 and pawl 82 are no longer in alignment and the pawl 82 can move toward the defeat position when desired. Furthermore, a damper can be disposed on the pawl 82, for example rubber, for reduced noise. The ratchet spring 87 can also be dampened.

For purpose of illustration, reference is now made to the operation of the system with the actuation assembly disclosed herein. In operation, the user can deploy the trigger 60 from the first position to the second position (referred to herein as the "first action"). The trigger can cause movement of the trigger gear sector 63. The trigger gear sector 63 can be functionally meshed with the trigger pinion 64 and can cause rotation of the trigger pinion 64. The trigger pinion 64 can be operatively coupled to the slide pinion 65, and can cause rotation of the slide pinion 65. The slide pinion 65 can be functionally engaged with the slide rack 66 and can cause the slide rack 66 to move distally. The slide rack 66 can be coupled to the driving rack 12, and the driving rack 12 can also move distally. The driving rack 12 can be functionally coupled to the actuation assembly, and can cause the inner shaft member 21 to move distally relative to the handle, and the outer tubular member to move proximally relative to the handle, as described herein above. Thus and as noted above, during the first action, the inner shaft member 21 can move distally relative to the handle 1 and the outer tubular member 22 can move proximally relative to the handle 1. During the first action, the pawl 82 can be in the first state and can be configured to allow the trigger 60 to move toward the second position and prohibit motion toward the first position. The pawl 82 can be configured to switch from the first state to the second state as the trigger approaches the second position from the first position.

Upon return of the trigger 60 from the second position to the first position (herein referred to as the "second action"), which can be caused, for example, by the energy stored in the spring 90, the trigger can cause movement of the trigger gear sector 63 in the opposition direction as the first action. The trigger gear sector 63 can cause rotation of the trigger pinion 64. The trigger pinion 64 can cause rotation of the slide pinion 65. The slide pinion 65 can cause the slide rack 66 to move proximally. The driving rack 12 can be functionally coupled to the actuation assembly, and can cause the inner shaft member 21 to move proximally relative to the handle, and the outer tubular member 22 remain stationary relative to the handle, as described herein above. Thus and as noted above, during the second action, the inner shaft member 21 moves proximally relative to the handle 1 and the outer tubular member 22 is stationary relative to the handle. During the second action, the pawl 82 can be in the second state and can be configured to allow the trigger 60 to move toward the first position and prohibit motion toward the second position. The pawl 82 can be configured to switch from the second state to the first state as the trigger approaches the first position from the second position.

Figure 87:
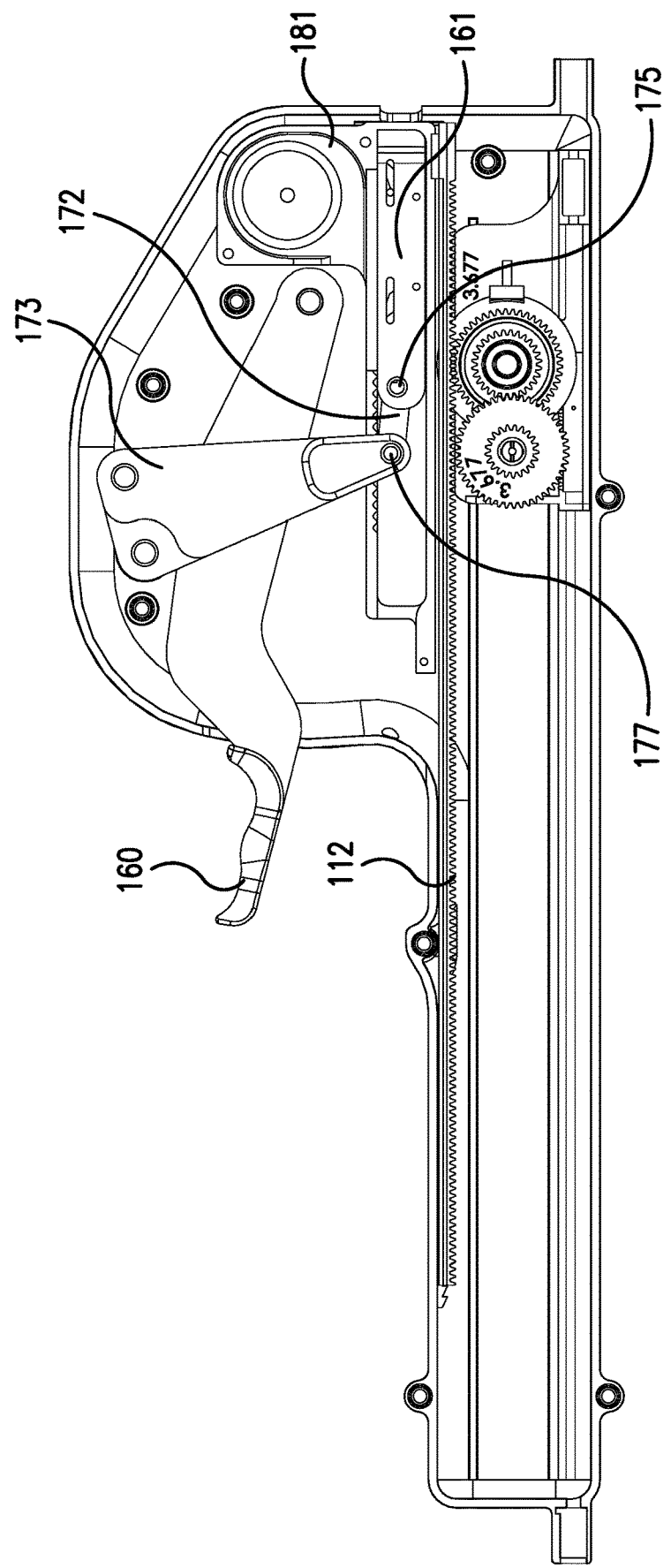
FIG. 87 is a left side view, with a portion of the handle housing removed, of the delivery system of FIG. 24.

In accordance with an alternative embodiment of the disclosed subject matter, a delivery system is provided wherein the trigger is coupled to the driving rack by a plurality of link elements. FIGS. 86-88 depict for the purpose of illustration and not limitation, portions of the delivery system 1001 described herein above. Elements that are similar to the previously described embodiment have been given like numbers. The delivery system 1001 can be configured to deliver an implant in a similar manner as described herein above.

With reference to the exemplary embodiment herein, the trigger 160 can be coupled to the driving rack 112 by a plurality of link elements. The link elements can include a first and second linear links 171 and 172, a triangle link 173, and a slide 161. A base 181 can support the slide 161 and can have a trigger ratchet rack 183 disposed thereon. The first linear link 171 can be coupled to the trigger 160 at a first joint 174. The second linear link can be coupled to the slide 161 at a second joint 175. The triangle link 173 can be coupled to the first linear link 171 at a third joint 176 and the second linear link 172 at a fourth joint 177. The triangle link 173 can be coupled to the handle at a fifth joint 178 and the trigger 160 can be coupled to the handle at a sixth joint 179. Each of the first, second, third, fourth, fifth, and sixth joints (174-179) can be pivot joints. The third joint 176, fourth joint 177, and fifth joint 178 can define a triangle. The slide 161 can be coupled to the driving rack 112. The driving rack 112 can be fixedly coupled or releasably coupled to the slide 161. As an example and not by way of limitation, the driving rack 112 can have a bayonet-type engagement with the slide 161 (sometimes referred to herein as an intermediate element). A spring (not shown), such as a constant force spring or tape measure spring, can be coupled to the slide 161 and configured to bias the trigger 160 toward the first position. The spring can be supported in base 181. In particular embodiments, the spring can be coupled to any suitable link of the plurality of links to bias the trigger 160 toward the first position.

With reference to FIG. 88A-88D, for the purpose of illustration and not limitation, the system can also include a ratchet mechanism 180. The ratchet mechanism 180 can include a first state and a second state. The first state can be configured to allow the trigger 160 to move toward the second position and prohibit motion toward the first position. The second state can be configured to allow the trigger 160 to move toward the first position and prohibit motion toward the second position. Such a system can be configured to require the user to perform a full stroke of the trigger 160 between the first and second position, such as described above.

As embodied herein, for illustration and not limitation, the ratchet mechanism 180 can include a first pawl 182 as well as a second pawl 184. The first and second pawls 182 and 184 can be supported on the slide 161 and can include a ratchet trip 185 disposed between the first and second pawls 182 and 184. The first and second pawls 182 and 184 can each have a first state in which the pawls engage the trigger ratchet rack 183 to permit unidirectional motion of the slide.

The first pawl 182 can allow motion in a first direction and the second pawl 182 can allow motion in a second direction. The first and second pawls 182 and 184 can each have a second state wherein the first and second pawls 182 and 184 do not engage the trigger ratchet rack 183. That is, when the first pawl 182 is in the first state the second pawl 184 can be in the second state, and when the second pawl 184 is in the first state the first pawl 182 can be in the second state. As the trigger 160 approaches the second position from the first position, the ratchet trip 185 can cause the first pawl 182 to switch (or disengage) to from the first state to the second state and the ratchet trip 185 can cause the second pawl 184 to switch (or engage) from the second state to the first state. Likewise, as the trigger 160 approaches the first position from the second position, the ratchet trip 185 can cause the first pawl 182 to switch (or engage) from the second state to the first state and the ratchet trip 185 can cause the second pawl 184 to switch (or disengage) from the first state to the second state. The system can be configured to ensure that the pawls are not simultaneous in the first state. The first pawl 182 and the second pawl 184 can each be in the second position at the same time to defeat the ratchet mechanism 180. Furthermore, the pawls and springs can be damped as described hereinabove.

In operation of this exemplary embodiment, the user can deploy the trigger 160 from the first position to the second position (referred to herein as the "first action"). The trigger 160 can pivot at the sixth joint 179 (clockwise in FIG. 86). The trigger 160 can pull on the first linear link 171, which can cause the triangle link 173 to pivot at fifth joint 178 (counter clockwise in FIG. 86). The triangle link 173 can pull second linear link 172 proximally, which can pull slide 161, and therefore driving rack 112, proximally. The driving rack 112 can be functionally coupled to the actuation assembly, and can cause the inner shaft member 121 to move distally relative to the handle, and the outer tubular member 222 to move proximally relative to the handle, as described above. Thus and as noted above, during the first action, the inner shaft member 121 can move distally relative to the handle 101 and the outer tubular member 122 can move proximally relative to the handle 101. During the first action, the first pawl 182 can be in the first state and can be configured to allow the trigger 160 to move toward the second position and prohibit motion toward the first position. The second pawl 184 can be in the second position, and thus not engaged with the trigger ratchet rack 183. First and second pawls 182 and 184 can be configured to switch from the first state to the second state and from the second state to the first state, respectively, as the trigger approaches the second position from the first position. The transition of each pawl can be timed such that each pawl 182 and 184 is in the second state for a period of time before the second pawl 184 switches to the first state.

Upon return of the trigger 160 from the second position to the first position (herein referred to as the "second action"), which can be caused, for example, by the energy stored in the spring 190, the trigger 160 can pivot at the sixth joint 179 (counter clockwise in FIG. 86). The trigger can push on the first linear link 171, which can cause the triangle link 173 to pivot at fifth joint 178 (clockwise in FIG. 86). The triangle link 173 can push the second linear link 172 distally, which can push slide 161, and therefore driving rack 112, distally. The driving rack 112 can be functionally coupled to the actuation assembly, and can cause the inner shaft member 121 to move proximally relative to the handle, and the outer tubular member 122 remain stationary relative to the handle, as described above. Thus and as noted above, during the second action, the inner shaft member 121 moves proximally relative to the handle 101 and the outer tubular member 122 is stationary relative to the handle. During the second action, the second pawl 184 can be in the first state and can be configured to allow the trigger 160 to move toward the first position and prohibit motion toward the second position. The first pawl 182 can be in the second position and thus not engaged with the trigger ratchet rack 183. First and second pawls 182 and 184 thus can be configured to switch from the second state to the first state and from the first state to the second state, respectively, as the trigger approaches the first position from the second position. Additionally or alternatively, the transition of each pawl can be timed such that each pawl 182 and 184 is in the second state for a desired period of time before the first pawl 182 switches to the first state.

As embodied herein, upon deployment of the trigger 160 from the first position to the second position and return of the trigger 160 from the second position to the first position, the third joint 176 can trace a non-linear path. Such non-linear motion can result in a variable force required to move the trigger 160 between positions along the path of the trigger 160.

Figure 90:
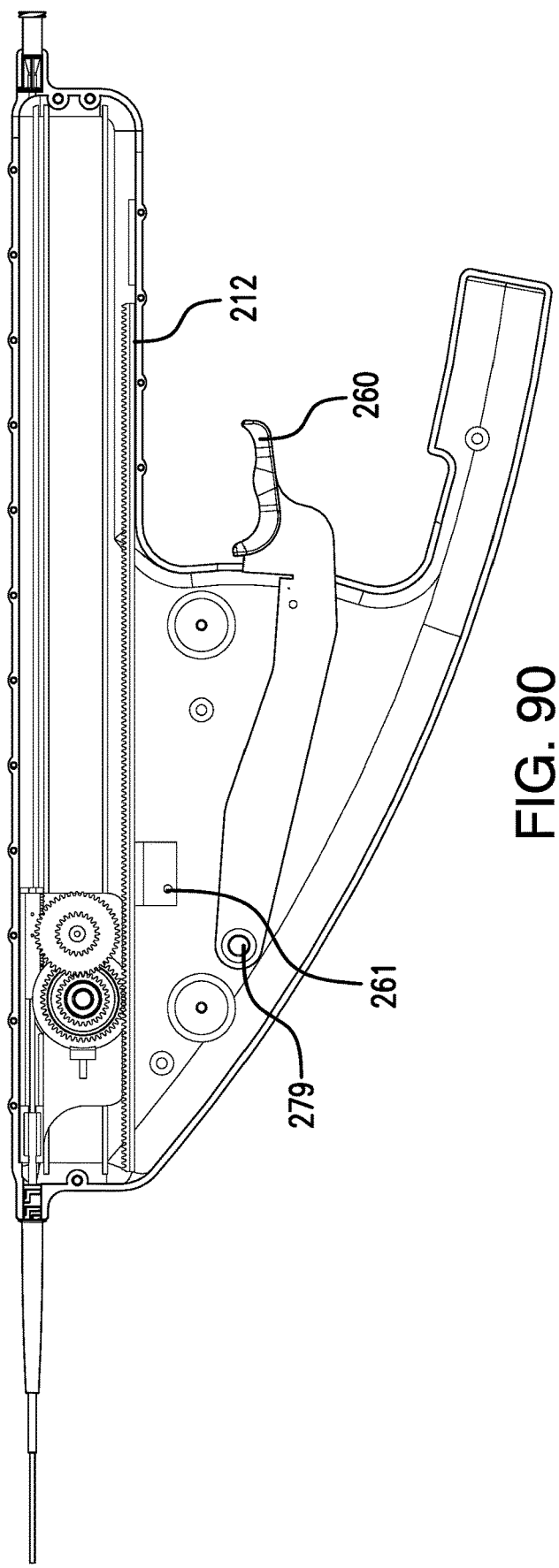
FIG. 90 is a right side view, with a portion of the handle housing removed, of the delivery system of FIG. 36.
Figure 91:
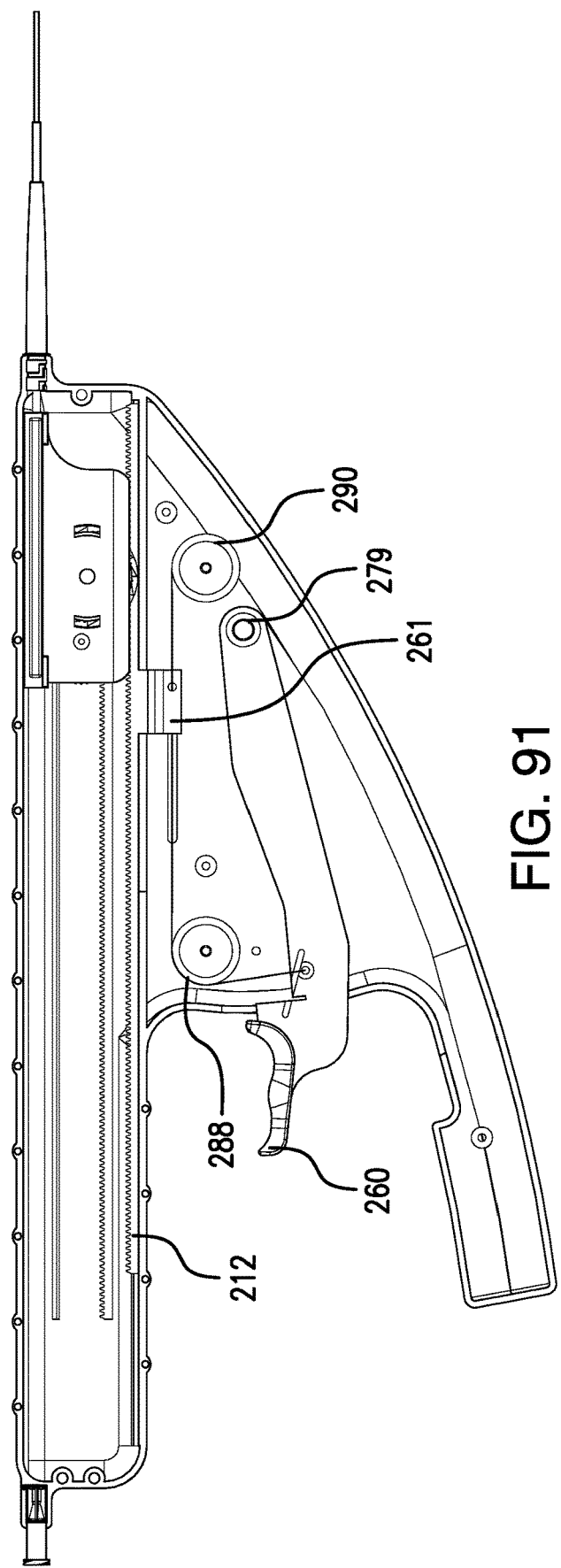
FIG. 91 is a left side view, with a portion of the handle housing removed, of the delivery system of FIG. 36.

In accordance with an alternative embodiment of the disclosed subject matter, a delivery system is provided wherein the trigger is coupled to the driving rack by a trigger pulley system. Referring now to FIG. 88A-88D for the purpose of illustration and not limitation, a perspective view of delivery system 1002 is provided. Portions of this exemplary embodiment are depicted in FIGS. 90 and 91. Elements that are similar to the previously described embodiment have been given like numbers. The delivery system 1002 can be configured to deliver an implant in a similar manner as described herein above.

Figure 89:
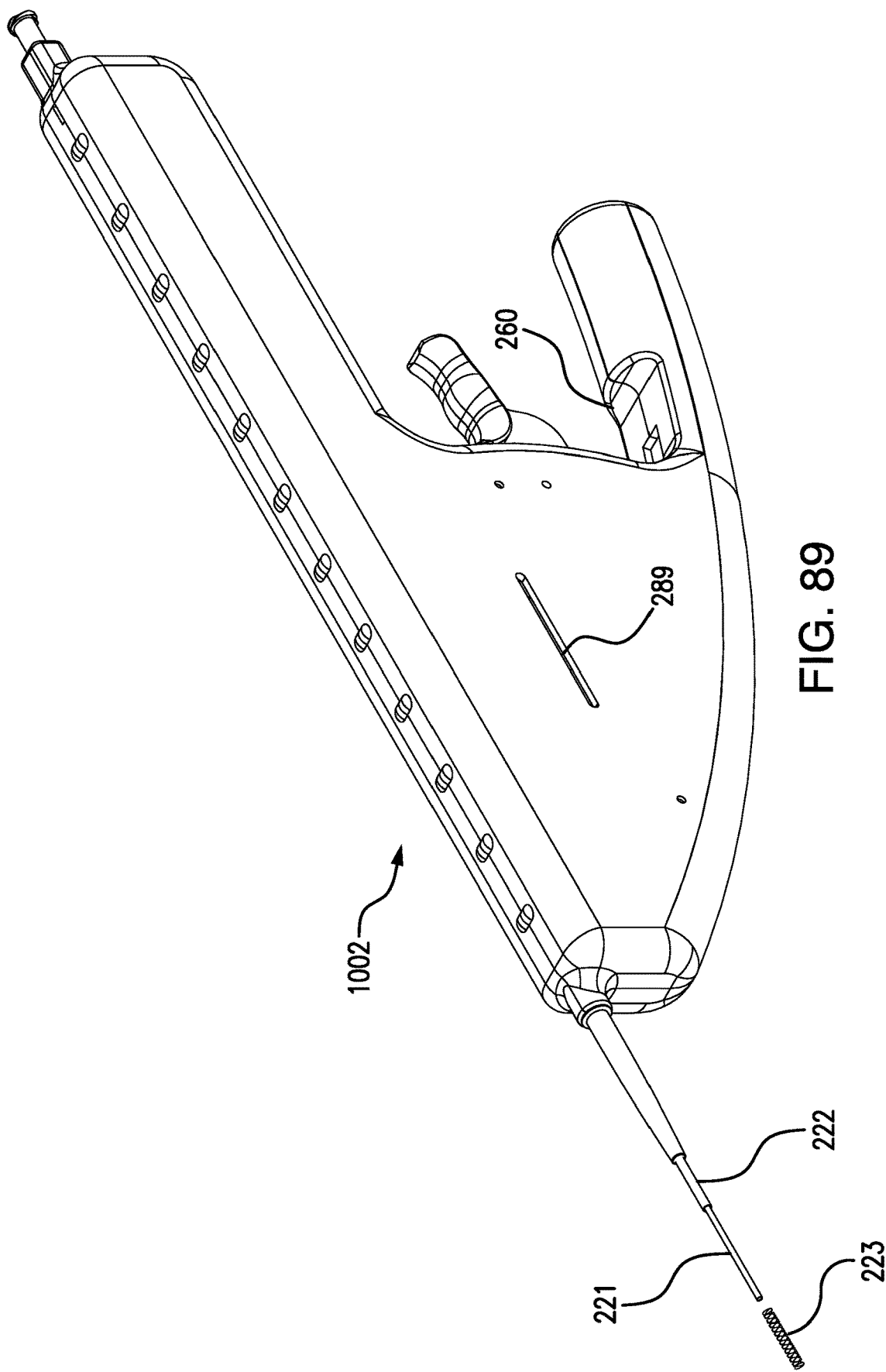
FIG. 89 is a perspective view of the delivery system of FIG. 36.

The trigger 260 can be coupled to the driving rack 212 by a trigger pulley system. For example, the trigger 260 can be coupled to the handle at joint 279, which can be a pivot joint. The trigger 260 can be coupled to the slide 261 by a tether 288. The slide 261 can be coupled to the driving rack 212. The driving rack 212 can be fixedly coupled or releasably coupled to the slide 261. As an example and not by way of limitation, the driving rack 212 can have a bayonet-type engagement with the slide 261 (sometimes referred to herein as an intermediate element). Additionally, the slide can be coupled to a spring 290, for example, a constant force spring. The spring 290 can bias the slide toward a distal position and the trigger 260 in the first position. The spring can be supported in base 281. Additionally, the handle 201 can include a window 289 (FIG. 89), which can be used to manually move the slide.

In operation, the user can deploy the trigger 260 from the first position to the second position (referred to herein as the "first action"). The trigger 260 can pivot at the joint 279 (clockwise in FIG. 90). The tether 288 coupled to the trigger 260 and the slide 261 can pull the slide 261, and therefore the driving rack 212, proximally. The driving rack 212 can be functionally coupled to the actuation assembly, and can cause the inner shaft member 221 to move distally relative to the handle, and the outer tubular member 222 to move proximally relative to the handle, as described hereinabove. Thus and as noted above, during the first action, the inner shaft member 221 can move distally relative to the handle 201 and the outer tubular member 222 can move proximally relative to the handle 201.

Upon return of the trigger 260 from the second position to the first position (herein referred to as the "second action"), which can be caused, for example, by the energy stored in the spring 290 pulling the slide 261 distally, the driving rack 212 can be moved distally. The driving rack 212 can be functionally coupled to the actuation assembly, and can cause the inner shaft member 221 to move proximally relative to the handle, and the outer tubular member 222 remain stationary relative to the handle, as described hereinabove. Thus and as noted above, during the second action, the inner shaft member 221 moves proximally relative to the handle 201 and the outer tubular member 222 is stationary relative to the handle.

Figure 92:
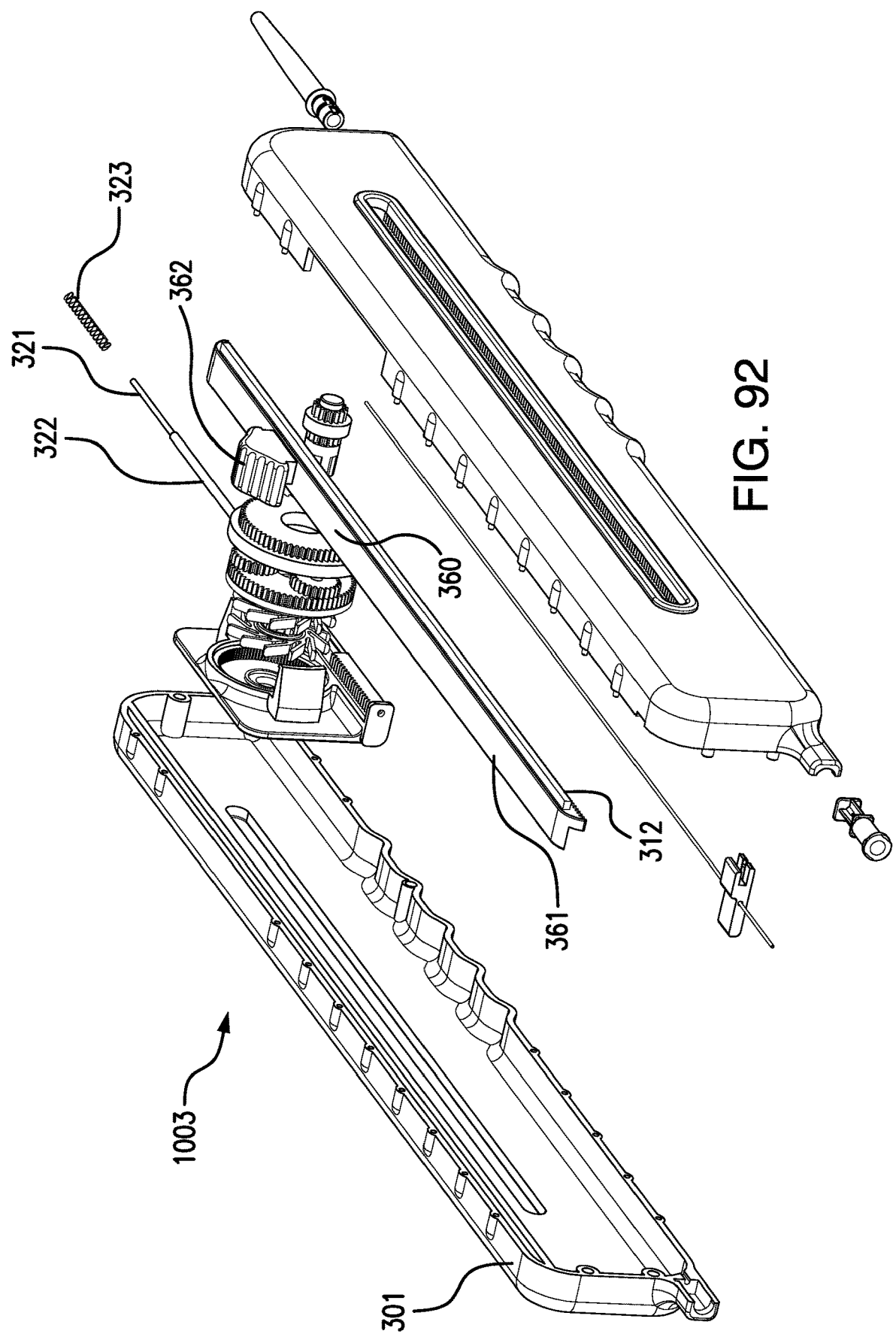
FIG. 92 is an exploded view of the delivery system of FIG. 46.

Referring now to FIG. 92 for the purpose of illustration and not limitation, an exploded view of delivery system 1003 is provided. Elements that are similar to the previously described embodiment have been given like numbers. The delivery system 1003 can be configured to deliver an implant in a similar manner as described herein above.

The trigger 360 can include a slide 361 that can include an engagement surface 362 to be engaged by the user. The driving rack 312 can be fixedly coupled or releasably coupled to the slide 361. As an example and not by way of limitation, the driving rack 312 and the slide 361 can be a unitary member. The trigger 360 can be coupled to a spring, which can bias the trigger 360 toward the first position.

During operation, the user can deploy the trigger 360 from the first position to the second position (referred to herein as the "first action"). The trigger, and therefore the slide 361 and the driving rack 312, can move in a proximal direction. The driving rack 312 can be functionally coupled to the actuation assembly, and can cause the inner shaft member 321 to move distally relative to the handle, and the outer tubular member 322 to move proximally relative to the handle, as described above. Thus and as noted above, during the first action, the inner shaft member 321 can move distally relative to the handle 301 and the outer tubular member 322 can move proximally relative to the handle 301.

Upon return of the trigger 360 from the second position to the first position (hereinafter referred to as the "second action"), the trigger 360, and therefore the slide 361 and the driving rack 312 can move in a distally relative to the handle 301. The driving rack 312 can be functionally coupled to the actuation assembly, and can cause the inner shaft member 321 to move proximally relative to the handle, and the outer tubular member 322 remain stationary relative to the handle, as described above. Thus and as noted above, during the second action, the inner shaft member 321 moves proximally relative to the handle 301 and the outer tubular member 322 is stationary relative to the handle.

Figure 93:
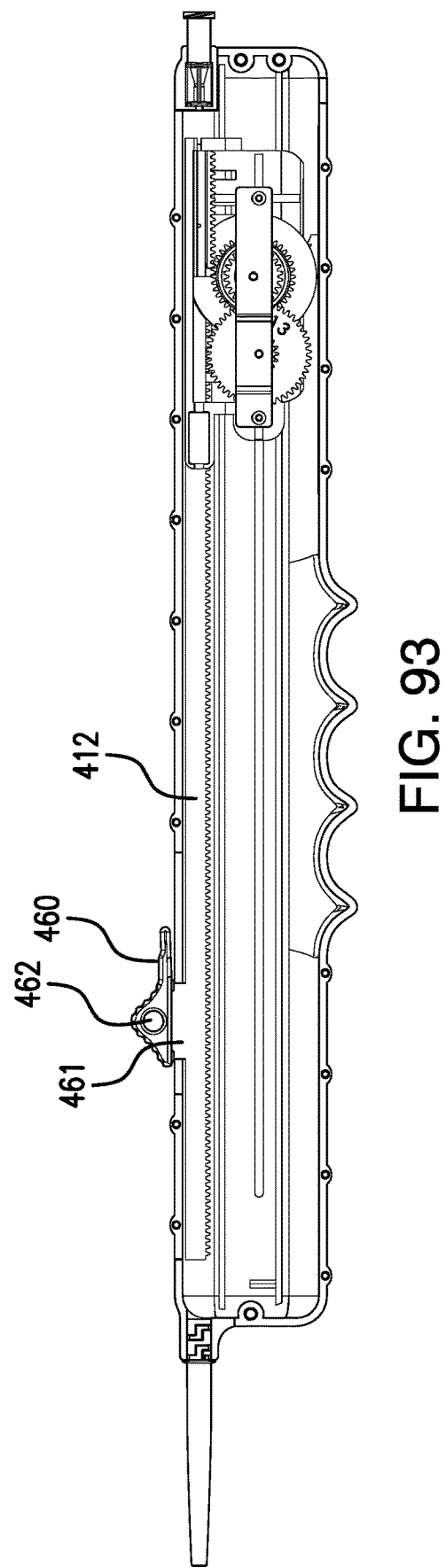
FIG. 93 is a right side view, with a portion of the handle housing removed, of the delivery system of FIG. 52.
Figure 94:
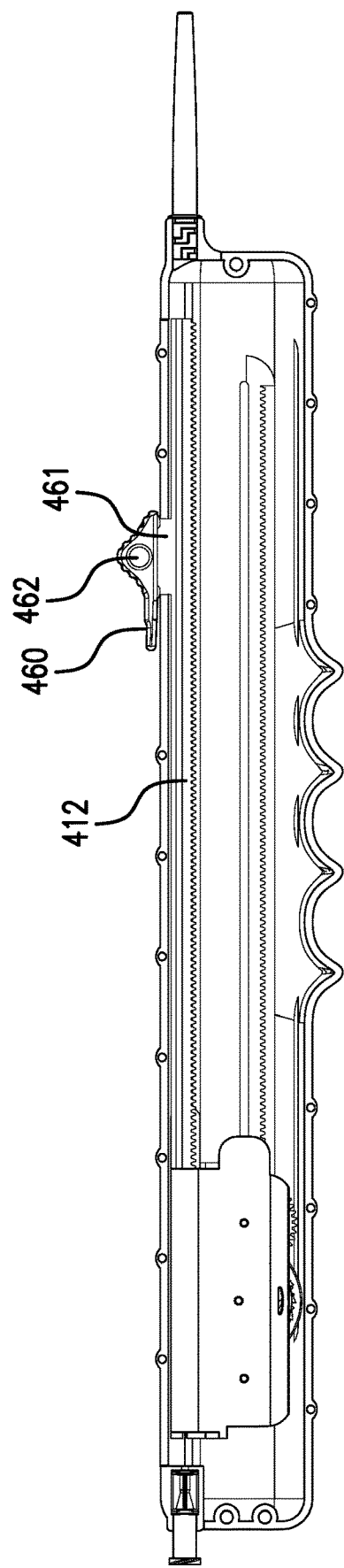
FIG. 94 is a left side view, with a portion of the handle housing removed, of the delivery system of FIG. 52.

FIGS. 93 and 94 provide, for the purpose of illustration and not limitation, portion of delivery system 1004. Elements that are similar to the previously described embodiment have been given like numbers. The delivery system 1004 can be configured to deliver an implant in a similar manner as described herein above.

The trigger 460 can include a slide 461 that can include an engagement surface 462 to be engaged by the user. The driving rack 412 can be fixedly coupled or releasably coupled to the slide 461. As an example and not by way of limitation, the driving rack 412 and the slide 461 can be a unitary member. The trigger 460 can be coupled to a spring, which can bias the trigger 460 toward the first position.

During operation, the user can deploy the trigger 460 from the first position to the second position (referred to herein as the "first action"). The trigger, and therefore the slide 461 and the driving rack 412, can move in a distal direction. The driving rack 412 can be functionally coupled to the actuation assembly, and can cause the inner shaft member 421 to move distally relative to the handle, and the outer tubular member 422 to move proximally relative to the handle, as described above. Thus and as noted above, during the first action, the inner shaft member 421 can move distally relative to the handle 301 and the outer tubular member 422 can move proximally relative to the handle 401.

Upon return of the trigger 460 from the second position to the first position (herein referred to as the "second action"), the trigger 460, and therefore the slide 461 and the driving rack 412 can move in a proximal relative to the handle 401. The driving rack 412 can be functionally coupled to the actuation assembly, and can cause the inner shaft member 421 to move proximally relative to the handle, and the outer tubular member 422 remain stationary relative to the handle, as described above. Thus and as noted above, during the second action, the inner shaft member 421 moves proximally relative to the handle 401 and the outer tubular member 422 is stationary relative to the handle.

Figure 95:
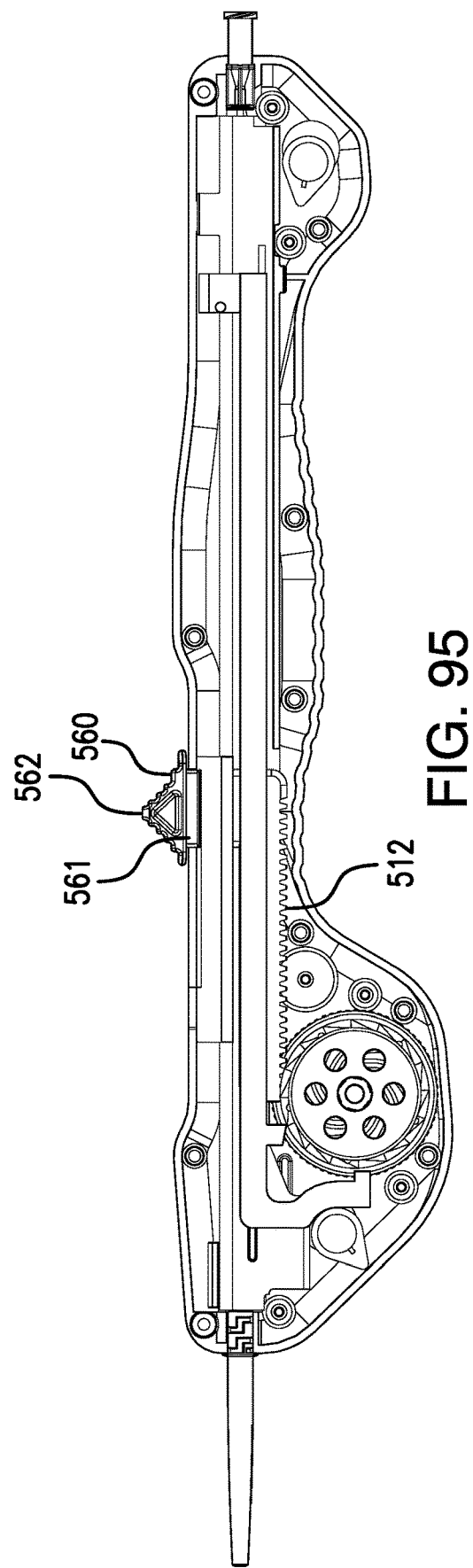
FIG. 95 is a right side view, with a portion of the handle housing removed, of the delivery system of FIG. 62.
Figure 96:
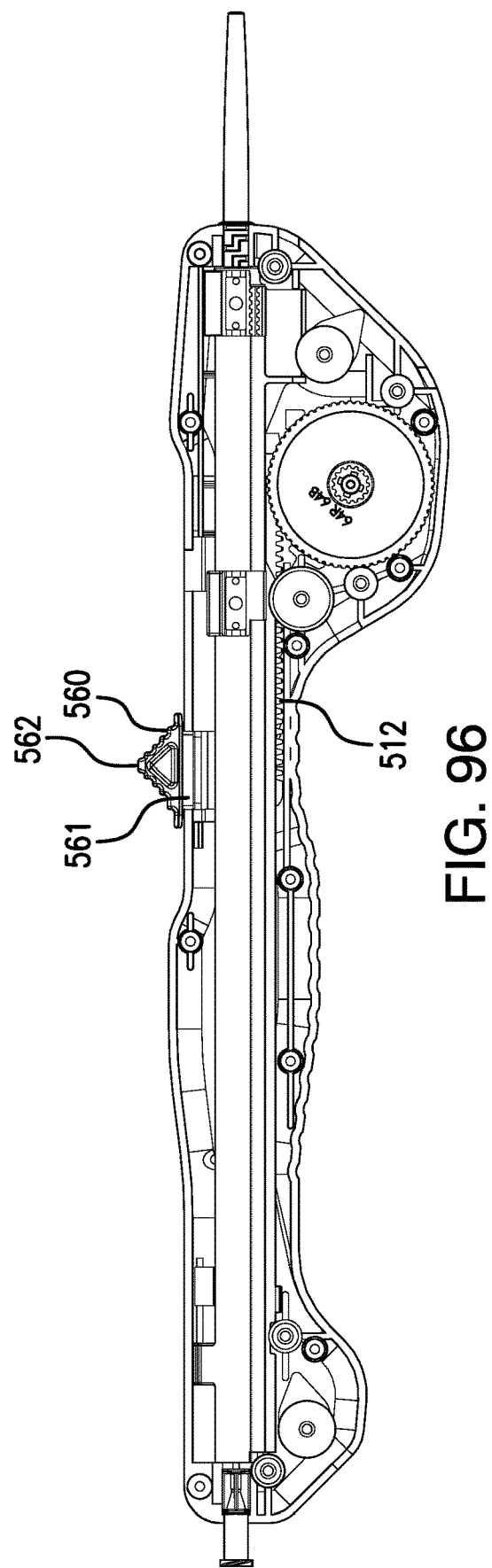
FIG. 96 is a left side view, with a portion of the handle housing removed, of the delivery system of FIG. 62.

FIGS. 95 and 96 provide, for the purpose of illustration and not limitation, portion of delivery system 1005. Elements that are similar to the previously described embodiment have been given like numbers. The delivery system 1005 can be configured to deliver an implant in a similar manner as described herein above.

The trigger 560 can include a slide 561 that can include an engagement surface 562 to be engaged by the user. The driving rack 512 can be fixedly coupled or releasably coupled to the slide 561. As an example and not by way of limitation, the driving rack 512 and the slide 561 can be a unitary member. The trigger 560 can be coupled to a spring, which can bias the trigger 560 toward the first position.

During operation, the user can deploy the trigger 560 from the first position to the second position (referred to herein as the "first action"). The trigger, and therefore the slide 561 and the driving rack 512, can move in a distal direction. The driving rack 512 can be functionally coupled to the actuation assembly, and can cause the inner shaft member 521 to move distally relative to the handle, and the outer tubular member 522 to move proximally relative to the handle, as described above. Thus and as noted above, during the first action, the inner shaft member 521 can move distally relative to the handle 501 and the outer tubular member 522 can move proximally relative to the handle 501.

Upon return of the trigger 560 from the second position to the first position (herein referred to as the "second action"), the trigger 560, and therefore the slide 561 and the driving rack 512 can move in a proximal relative to the handle 501. The driving rack 512 can be functionally coupled to the actuation assembly, and can cause the inner shaft member 521 to move proximally relative to the handle, and the outer tubular member 522 remain stationary relative to the handle, as described above. Thus and as noted above, during the second action, the inner shaft member 521 moves proximally relative to the handle 501 and the outer tubular member 522 is stationary relative to the handle.

The embodiments described above can be formed of any suitable materials, for example, the handle and actuation assembly elements can be made from plastic, composites, or metal. As an example, and not by way of limitation, the gears, (for example, the sun gear shaft, planet carrier, planet gears, intermediate gear and ring gear), clutch drivers, shuttle frame, driving rack, and clutch release can be formed by silicon impregnated poly oxymethylene or acetal (e.g., DelRin® sold by DuPont). The ratchet rack can be made of TOPAS. The various pins and springs can be formed from plastic, metal (e.g., stainless steel or aluminum), or music wire. The plate can be formed from plastic or metal. The handle housing portion can be made from glass filled plastics or other plastic resins, for example ADS, polycarbonate, or an ADS polycarbonate blend. A rubber overmold can be used for grip and aesthetics, for example, on the trigger and the handle body. The strain relief 15 can be a soft plastic, for example, polyethylene. The trigger and related elements can be formed by silicon impregnated poly oxymethylene or acetal (e.g., DelRin® sold by DuPont). The various pins and springs can be formed from plastic, metal (e.g., stainless steel or aluminum), or music wire. Spring dampers can be made of UNA, EPVM, Silicon, Eurothane, or Santoprene.

As disclosed herein, a delivery system can be provided with one or more of the described actuations assemblies, trigger assemblies or ratchet mechanisms. For example, a delivery system can be provided including a handle; a trigger operatively coupled to the handle; an actuation assembly operatively coupled to the trigger, the inner shaft member, and the outer tubular member, the actuation assembly having a planet carrier; at least one planet gear operatively coupled to the planet carrier; a sun gear shaft operatively engaged with the planet gear; a ring gear operatively engaged with the planet gear; a first clutch driver configured to limit the sun gear shaft to uni-directional rotational motion; and a second clutch driver configured to uni-directionally lock the sun gear shaft and the planet carrier; and a gear train functionally disposed between the trigger and the actuation assembly, the trigger having a trigger gear sector, a trigger pinion operatively meshed with the trigger gear sector, a slide pinion operatively coupled to the trigger pinion, and a slid rack disposed on a slide and operatively meshed with the trigger pinion. The actuation assembly is configured to displace the outer tubular member in the proximal direction a distance (d) relative to the handle and to separately move the inner shaft member distally a distance (x) relative to the handle upon deployment of the trigger from a first position to a second position, and further wherein the actuation assembly is configured to move the inner shaft member proximally a distance (y) relative to the handle with no displacement of the outer tubular member relative to the handle upon return of the trigger from the second position to the first position.

Additionally, and in accordance with the disclosed subject matter, a delivery system can be provided including a handle; a trigger operatively coupled to the handle; an actuation assembly including a planetary gear system; and a ratchet mechanism functionally coupled to the trigger. The actuation assembly is configured to displace the outer tubular member in the proximal direction a distance (d) relative to the handle and to separately move the inner shaft member distally a distance (x) relative to the handle upon deployment of the trigger from a first position to a second position, and further wherein the actuation assembly is configured to move the inner shaft member proximally a distance (y) relative to the handle with no displacement of the outer tubular member relative to the handle upon return of the trigger from the second position to the first position Furthermore, and in accordance with the disclosed subject matter, a delivery system can be provided including a handle; a trigger operatively coupled to the handle; an actuation assembly operatively coupled to the trigger, the inner shaft member, and the outer tubular member, the actuation assembly having a planet carrier; at least one planet gear operatively coupled to the planet carrier; a sun gear shaft operatively engaged with the planet gear; a ring gear operatively engaged with the planet gear; a first clutch driver configured to limit the sun gear shaft to uni-directional rotational motion; and a second clutch driver configured to uni-directionally lock the sun gear shaft and the planet carrier; a gear train functionally disposed between the trigger and the actuation assembly, the trigger having a trigger gear sector, a trigger pinion operatively meshed with the trigger gear sector, a slide pinion operatively coupled to the trigger pinion, and a slid rack disposed on a slide and operatively meshed with the trigger pinion. The actuation assembly is configured to displace the outer tubular member in the proximal direction a distance (d) relative to the handle and to separately move the inner shaft member distally a distance (x) relative to the handle upon deployment of the trigger from a first position to a second position, and further wherein the actuation assembly is configured to move the inner shaft member proximally a distance (y) relative to the handle with no displacement of the outer tubular member relative to the handle upon return of the trigger from the second position to the first position.

In accordance with another aspect of the disclosed subject, a catheter assembly is provided including an outer tubular member, an inner tubular member, and a pusher assembly. The catheter assembly disclosed herein can be used for a variety medical devices. For example, but not by limitation, the catheter assembly disclosed herein can be used in combination with any of the embodiments of delivery system disclosed above or features thereof. For example, the catheter assembly can be used in combination with each of the various delivery system embodiments disclosed above, including each of the actuation assembly embodiments and each of the trigger assembly embodiments disclosed above. As an example, and not by way of limitation, the catheter assembly can be operatively coupled with the actuation assembly of the delivery system embodiment shown in FIG. 1A.

Figure 97:
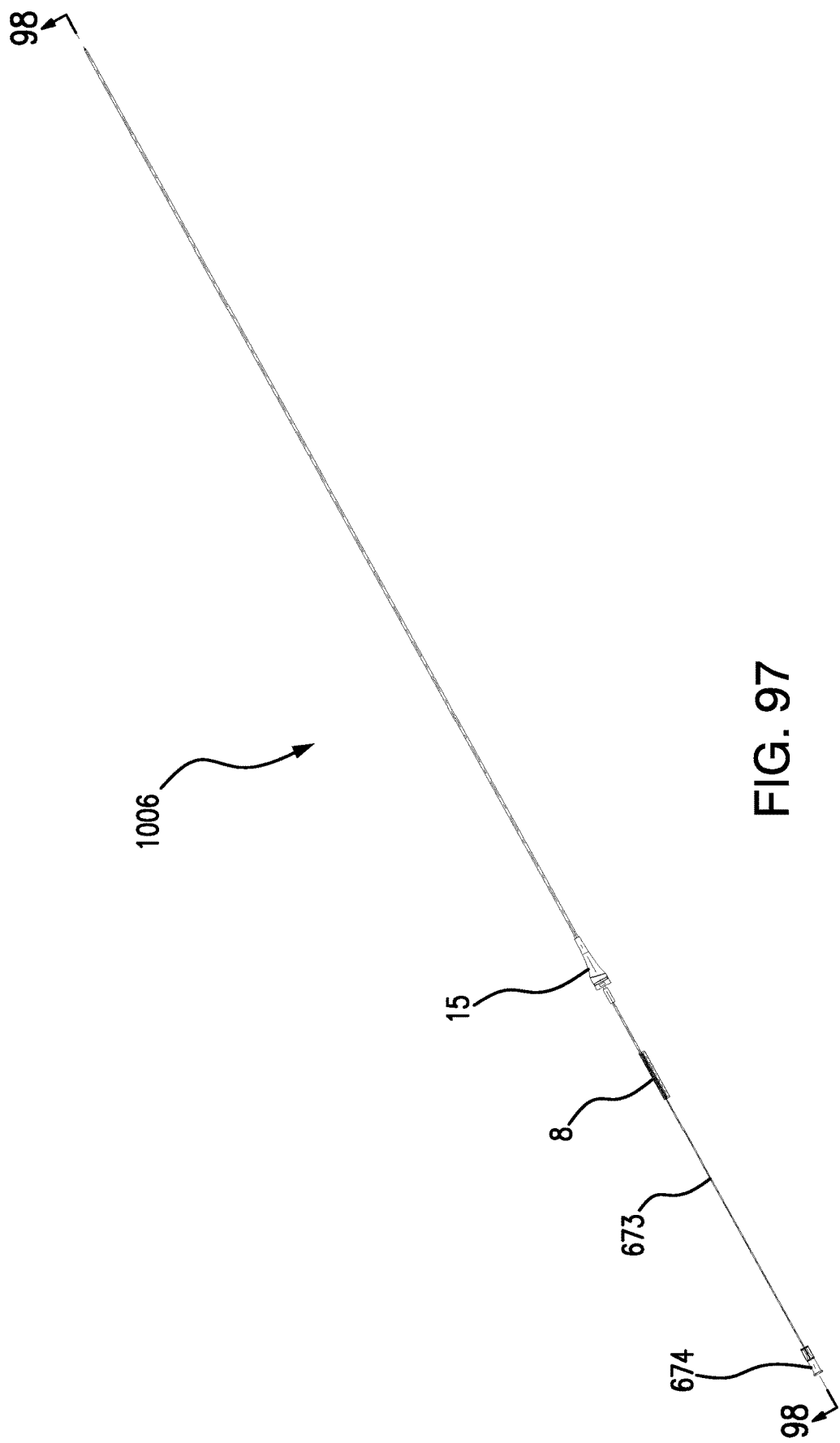
FIG. 97 is a perspective view of an exemplary embodiment of a catheter assembly in accordance with the disclosed subject matter.
Figure 98:
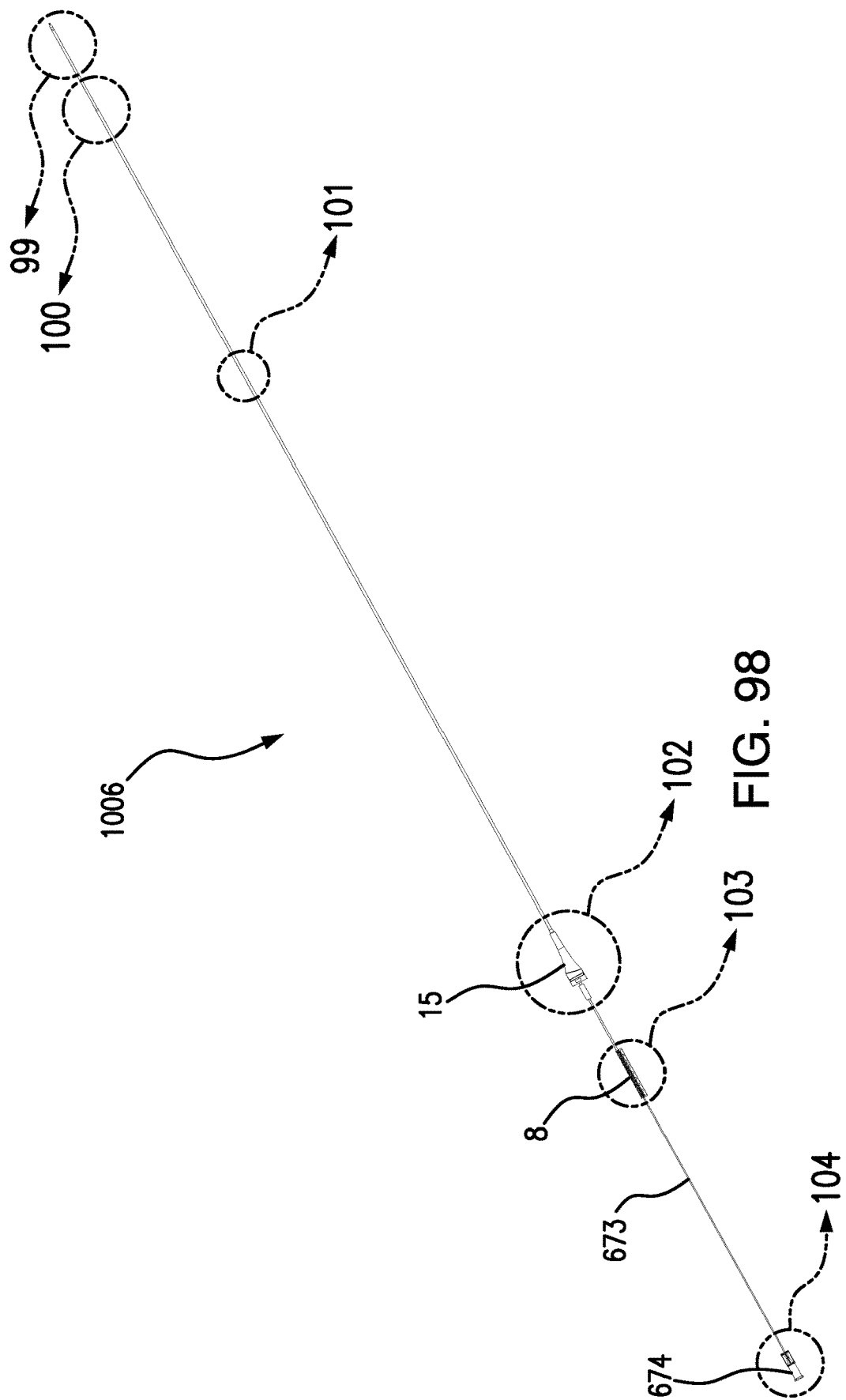
FIG. 98 is a partial cross-sectional view of the catheter assembly of FIG. 97.
Figure 99:
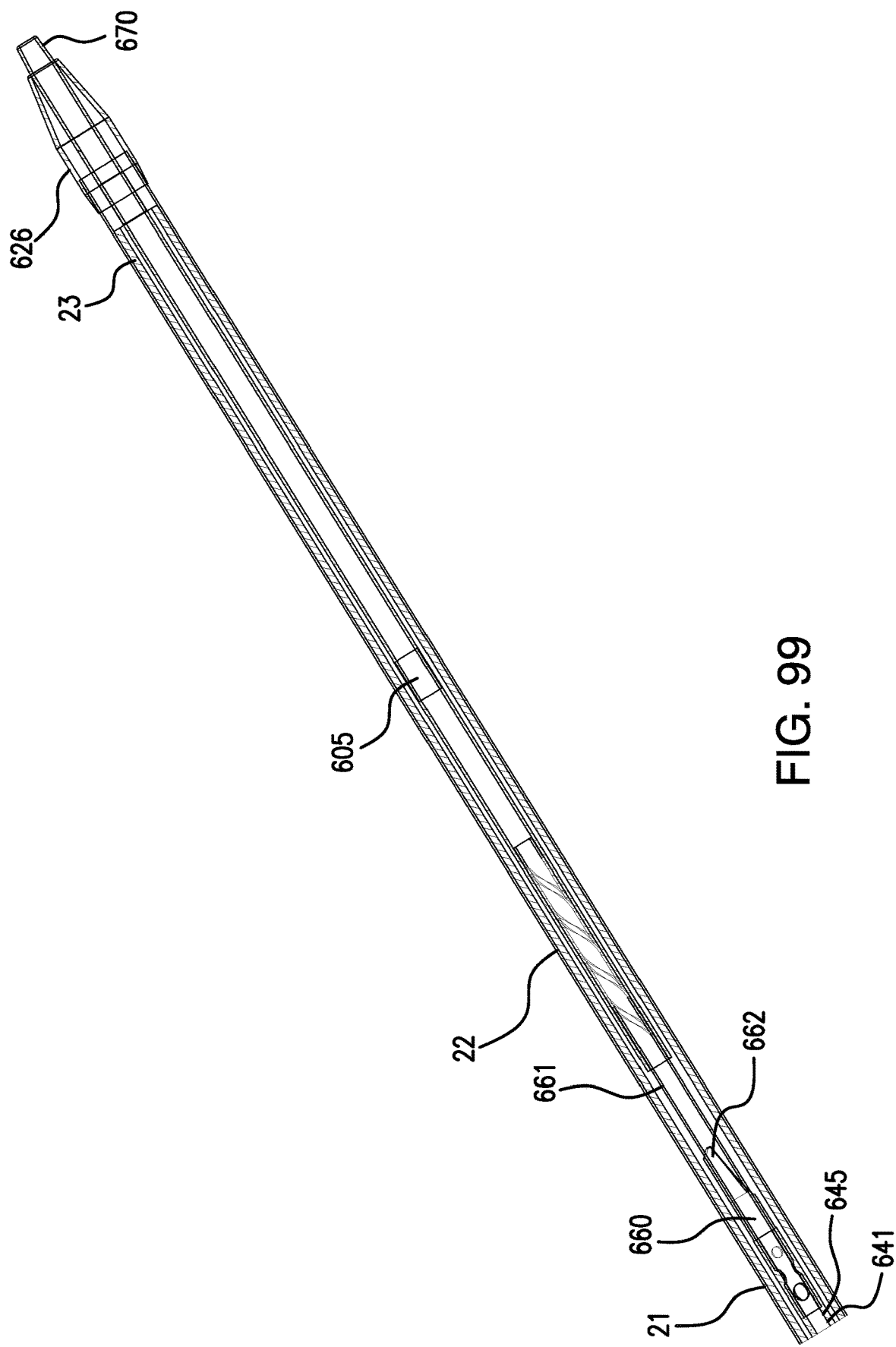
FIG. 99 is an enlarged detail view of section 99.
Figure 100:
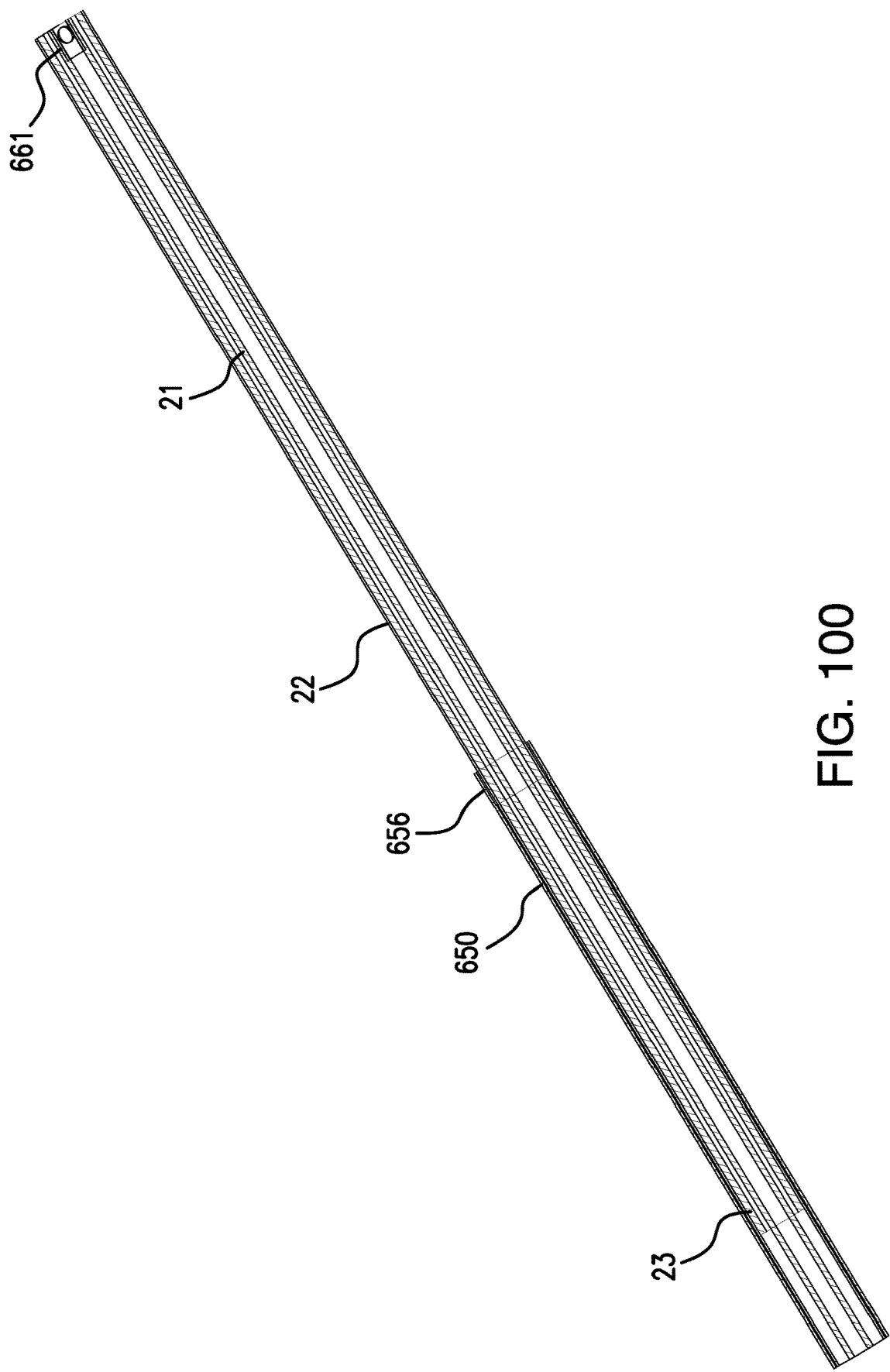
FIG. 100 is an enlarged detail view of section 100.
Figure 101:
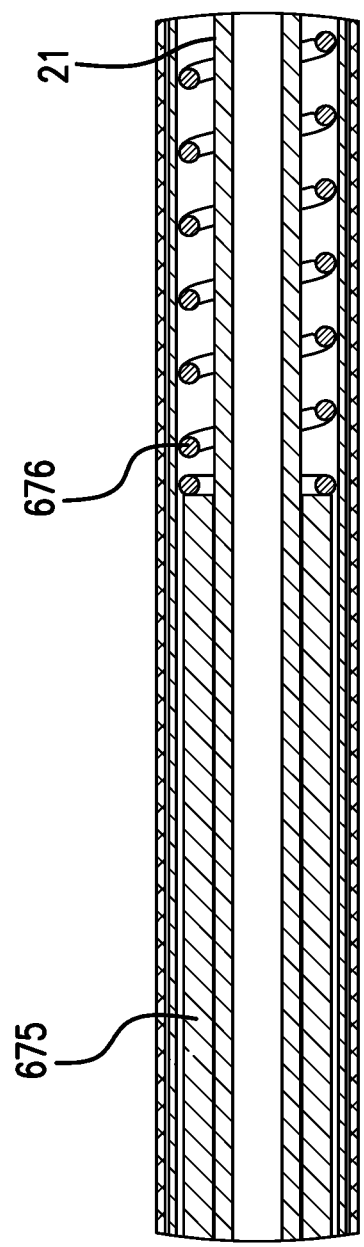
FIG. 101 is an enlarged detail view of section 101.
Figure 102:
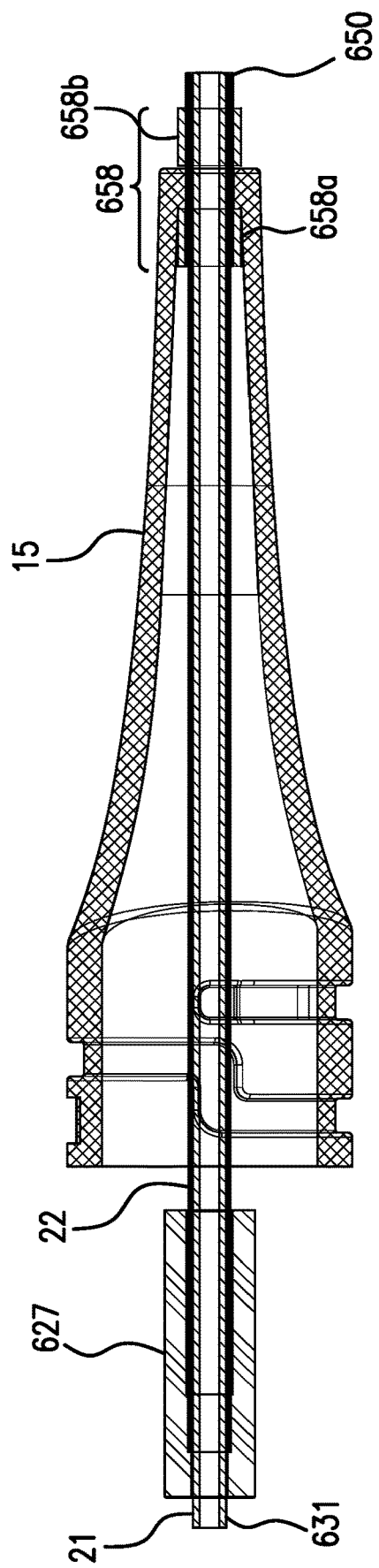
FIG. 102 is an enlarged detail view of section 102.

For the purpose of illustration, and not limitation, an exemplary embodiment of a catheter assembly for delivering a medical device is shown in FIG. 97 and is designated generally by reference character 1006. Enlarged details of this exemplary embodiment are depicted in FIGS. 97-106. As embodied herein, the catheter assembly includes an outer tubular member 22, an inner shaft member 21, and a pusher assembly 660. Additionally, as described further below, the catheter assembly can further include a stabilizer member 650, defining a stabilizer member lumen 651.

For purpose of illustration and not limitation, the outer tubular member 22 of the disclosed subject matter is a multi-layer tubular member defining an outer tubular member lumen 621. The outer tubular member 22 embodied herein has an inner layer 622, a reinforcement layer 623, a middle layer 624, and an outer layer 625. The inner layer 622 can be fluorinated ethylene propylene. The middle layer 624 can be a polymer, for example, polyimide. The outer layer 625 can be a plastic, for example Nylon 12, such as Grilamid. The reinforcement layer 623 is configured to provide additional strength by providing fibers or wires, such as in the form of a braid around the inner layer 622 or as longitudinally extending fibers. For example, the reinforcement layer 623 can be a braid of stainless steel (SST), for example, 0.001×0.005 inch, 304V SST. The braid can include 16 wires having high tensile strength. Although only eight wires are shown in 105A-105D, any number of wires can be provided as needed or desired. As another example, the reinforcement layer 623 can include Kevlar fibers extending longitudinally along the length of the outer tubular member.

Such a four-layer configuration thus provides improved hoop strength and flexibility for the outer tubular member while allowing a thinner wall than traditional catheter configurations. For example, with an inner diameter of about 0.0660 inches and a wall thickness of about 0.0078 inches, an outer diameter of about 0.0738 inches can be achieved, such as by a coating process as noted below. By providing a thinner wall than traditional catheters, an additional tubular member (e.g., the stabilizer member 650, as described further below) can be provided with the catheter assembly 1006 without increasing the overall outer diameter of the catheter assembly 1006 or reducing the hoop strength and flexibility of the catheter assembly 1006. For example, a 6 French or less catheter can be achieved, either with or without an additional tubular member (e.g., stabilizer). In particular embodiments, the catheter can be less than 6 French, for example, the outer profile can be 5 French, 4 French, 3 French, or any suitable increment therebetween. Alternatively, in other particular embodiments, the outer profile can be greater than 6 French. For example, the outer tubular member can be 7 French, 10 French, 15 French, or any suitable increment therebetween.

A proximal end portion of the outer tubular member 22 can be coupled directly to the handle 1 in a fixed relation, if desired, or to the actuation assembly 2 if relative movement of the outer tubular member 22 is desired, such as previously described. As embodied herein, the proximal end portion of the outer tubular member 22 can be coupled to the actuation assembly 2 by a cap seal 627 (see FIG. 102). For example, the cap seal 627 can be cylindrical and received within a cavity of the actuation assembly to allow the outer tubular member 22 to rotate about a central longitudinal axis relative the actuation assembly 2. Such a coupling thus can allow the outer tubular member 22 to rotate about a central longitudinal axis, for example, during insertion of the catheter assembly 1006 and during delivery of the implant. Alternatively, the cap seal 627 can be shaped to mate or engage the actuation assembly to prevent the outer tubular member 22 from rotating relative the actuation assembly 2.

The outer tubular member 22 can have an atraumatic distal tip 626. The atraumatic distal tip 626 can reduce or prevent damage to vessel walls during delivery of the catheter. Additionally, the atraumatic distal tip 626 can be configured to be flexible to allow deployment of the implant 23 through the atraumatic distal tip 626 without splitting thereof. For example, the atraumatic distal tip 626 can be made of Pebax and can be configured with a tapered distal end. The atraumatic distal tip 626 can be a separate member heat bonded to a distal end portion of the outer tubular member 22, for example, the atraumatic distal tip 626 can be heat bonded to an outer diameter of the distal end portion of the outer tubular member 22. Additionally, the atraumatic distal tip 626 can be configured to receive a guidewire therethrough. For example, a guidewire lumen 670 can be disposed at least partially within the outer tubular member lumen 621. The guidewire lumen 670 can be coupled to a distal end of the pusher assembly, as described below, and extend distally of the atraumatic distal tip 626 and out of the outer tubular member 22. The atraumatic distal tip 626 can be flexible enough to collapse onto the guidewire lumen 670. The guidewire lumen 670 can have at least one radiopaque marker 605, such as a band or printed indicia, disposed thereon.

As previously noted, it can be desirable for the catheter assembly of the disclosed subject matter to include a stabilizer 650. For example, and as embodied herein, the delivery system and methods embodied herein can be configured for movement of the outer tubular member 22 relative the handle. The stabilizer provides a location in which to secure position of the delivery system, such as by a hemostatic valve and/or guide catheter, while allowing relative movement of the outer tubular member. The stabilizer member 650 can be a multi-layer tubular member. For example, the stabilizer can have an inner layer 652, a reinforcement layer 653, a middle layer 654, and an outer layer 655. The inner layer 652 can be a synthetic fluoropolymer, for example, polytetrafluoroethylene (PTFE). The middle layer 654 can be a strike layer over the reinforcement layer 653 and can include a polymer, for example, polyimide. The outer layer 655 can be a plastic, for example, Grilimid. The reinforcement layer 653, like the reinforcement layers of the outer tubular member 22 and the inner shaft member 21 can provide additional strength by providing fibers or wires that can be formed as a braid around the inner layer 652 or longitudinally extending fibers. For example, the reinforcement layer 653 can be a braid of stainless steel (SST), for example, 0.0007×0.003 inch, 304V SST. The braid can include 16 wires having high tensile strength. As another example, the reinforcement layer 653 can include Teflon fibers extending longitudinally along the length of the stabilizer member. As with the outer tubular member, such a four-layer configuration can allow for have improved hoop strength and flexibility while having a thinner wall than traditional catheters. Furthermore, and as noted above, by providing tubular members with a thinner wall than traditional catheters, the catheter assembly 1006 can include a combination of an outer tubular member and a stabilizer member without increasing the outer diameter of the catheter assembly 1006 or reducing the hoop strength and flexibility of the catheter assembly 1006. The stabilizer member 650 can be, for example, between 10 and 60 inches long, for example about 25 or 50 inches long, and be less than or equal to 6 French in diameter.

As embodied herein, the stabilizer member 650 can include an atraumatic tip 656 at a distal end of the stabilizer member 650. The atraumatic tip 656 can be formed as a single layer of material extending from the distal end of the stabilizer member 650. For example, the atraumatic tip 656 can be an extension of the outer layer 655 of the stabilizer member 650 beyond the other layers of the stabilizer member 650. For example, the outer layer 655 can extend about 3 mm beyond the other layers. As embodied herein, the atraumatic tip 656 can be a separate element coupled to the stabilizer member, for example, by heat bonding. The atraumatic tip 656 can reduce or prevent damage to vessel walls during delivery of the catheter 1006. The atraumatic tip can also provide a distal covering for the reinforcement layer 653. The outer tubular member 22 can extend distally from the atraumatic tip 656.

As embodied herein, the stabilizer member 650 can be coupled to a strain relief 15 at a proximal end of the stabilizer member 650. The stabilizer member 650 and strain relief 15 can be coupled by stoppers 658a, 658b. The stoppers 658a, 658b can be shaped to allow the stabilizer member 650 to rotate about a central longitudinal axis relative the strain relief 15. For example, the stoppers 658a, 658b can be cylindrical in shape. Such a coupling can allow the stabilizer member 650 to rotate, for example, during insertion of the catheter assembly 1006 and during delivery of the implant, while the handle 1 remains rotationally stationary. Alternatively, the stoppers 658a, 658b, can be shaped to prevent the stabilizer member 650 from rotating relative the strain relief 15. The strain relief 15 can be coupled to the handle 1, for example by a "maze" coupling or integrated key configurations. For example, and as embodied herein, the integrated key configuration can have a maze pattern to receive a protrusion on the housing. A detent can be provided at the end of the maze to engage the protrusion to indicate that the strain relief 15 and the handle 1 are locked together.

During operation, the strain relief 15 can keep the stabilizer member 650 axially stationary relative the handle 1. Accordingly, while the actuation assembly 2 moves the inner shaft member 21, as well as the outer tubular member 22, if so configured, relative to the handle, the stabilizer member 650 remains stationary relative to the handle. This can allow the handle to remain stationary relative the patient while the inner shaft member 21 and the outer tubular member 22 are actuated and the implant is delivered. This configuration can simplify delivery, because a physician solely needs to actuate the trigger while delivering the implant. Furthermore, the stationary stabilizer member 650 can reduce the amount of friction along the inside wall of the vessel between the entry point and the implant delivery location during operation. Such a reduction in friction can reduce the amount of force required to operate the actuation assembly 2 and move the outer tubular member 22. Additionally, the reduction in friction can reduce damage to vessel walls during operation. Alternatively, if the outer tubular member is coupled directly to the handle in a fixed relation, then the strain relief can keep the outer tubular member axially stationary relative to the handle.

As previously noted, the catheter assembly herein further includes an inner shaft member 21. The inner shaft member 21 as embodied herein defines an inner shaft member lumen 672. The inner shaft member 21 includes a proximal inner shaft portion 631 and a distal inner shaft portion 641 which can be formed as a single piece. Alternatively, and as embodied herein, the proximal inner shaft portion 631 can be a proximal inner shaft member (also referred to as element 631) and the distal inner shaft portion 641 can be a distal inner shaft member (also referred to as element 641). That is, the inner shaft member 21 can be composed of two separate members. As noted above, the inner shaft member 21 can be between 25 and 65 inches long, for example, the inner shaft member 21 can be about 34 or 56 inches long. As embodied herein, for illustration, the proximal inner shaft member 631 can thus be between 4 and 19 inches long, for example, about 12 inches long. The distal inner shaft member 641 can be between 14 and 51 inches long, for example, about 22 or 44 inches long. Each of the proximal inner shaft member 631 and the distal inner shaft member 641 can have an inner diameter and an outer diameter. The outer diameter 642 of the distal inner shaft member 641, or at least the proximal end thereof, can be configured to be received within the inner diameter of the proximal inner shaft member. For example, the outer diameter 642 of the distal inner shaft member 641 can be less than the inner diameter 633 of the proximal inner shaft member 631. In this manner, the outer diameter 642 of the distal inner shaft member 641 likewise will be less than the outer diameter 632 of the proximal inner shaft member 631. As embodied herein, a radiopaque marker can be disposed on the inner shaft member 21.

A proximal end portion 644 of the distal inner shaft member 641 can be coupled to a distal end portion 35 of the proximal inner shaft member 631. For example, the proximal inner shaft member 631 can be heat bonded to the distal inner shaft member 641. The proximal inner shaft member 631 and the distal inner shaft member 641 thus can together define the inner shaft member lumen 672. If the proximal end portion of the distal inner shaft member 641 is received within the inner diameter of the proximal inner shaft member 631, the inner diameter at the proximal end portion 644 of the distal inner shaft member 641 can further include a chamfer, funnel or the like 649. In this matter the chamfer 649 can facilitate delivery of a guidewire 671 through the inner shaft member lumen 672 from the proximal inner shaft member 631 to the distal inner shaft member 641.

The proximal inner shaft portion 631 and the distal inner shaft portion 641 can each be a multi-layer tube. For example, each of the proximal inner shaft portion 631 and the distal inner shaft portion 641 can include an inner layer, a reinforcement layer, and an outer layer, which can be any suitable material. For example, the inner layer 636 of the proximal inner shaft portion 631 can be a nylon, for example, rilsan aesno. The reinforcement layer 637 of the proximal inner shaft portion 631 can be a braid layer, such as a braid of SST, for example, 0.001×0.007 inch, 304V SST. Alternatively, the reinforcement layer 637 of the proximal inner shaft portion 631 can include Teflon fibers extending longitudinally along the length of the proximal inner shaft portion. The outer layer 638 of the proximal inner shaft portion 631 can be plastic, for example, grilamid. The inner layer 646 of the distal inner shaft portion 641 can be a nylon, for example a rislan aesno and nylon 612 mixture. The reinforcement layer 647 of the distal inner shaft portion 641 can be a braid layer, such as a braid of SST, for example, 0.001×0.007 inch, 304V SST. Alternatively, the reinforcement layer 647 of the distal inner shaft portion 641 can include Teflon fibers extending longitudinally along the length of the proximal inner shaft portion. The outer layer 648 of the distal inner shaft portion 641 can be plastic, for example, a grilamid and nylon 12 mixture. This three-layer design can provide improved hoop strength and flexibility, and can allow the inner tubular member to have a reduced outer diameter. Additionally, increasing the "PIC count" of the braid (i.e., providing a tighter braid) can improve pushability.

Each of the multi-layer tubular members described herein (i.e., outer tubular member, stabilizer, and inner tubular member portions, as applicable) can be made using a conventional process, such as extrusion, or be formed by a coating process if a lower profile with higher strength is needed. That is, forming each multi-layer tubular member by a coating process yields surprising performance results while providing a thin wall and suitable tolerance (i.e., outer diameter), for example, for a 6 French catheter assembly having a plurality of coaxially aligned tubular members. For example, using a coating process can provide improved flexibility, deliverability, and pushability. Alternatively, each of the multi-layer tubular members described herein can be formed by other known means, for example, a film cast process, a reflow process, and coextrusion. The materials and/or surface of exposed layers of the multi-tubular members can be selected to reduce friction as particular tubular members move relative one another. For example, the outer layers 638, 648 of the proximal inner member 631 and distal inner member 641 (which can both be a plastic) can move with relatively low friction relative to the inner layer 622 of the outer tubular member 22 (which can be fluorinated ethylene propylene). Likewise, the outer layer 635 of the outer tubular member 22 (which can be a plastic) can move with relatively low friction relative the inner layer 652 of the stabilizer member (which can be polytetrafluoroethylene).

Figure 103A:
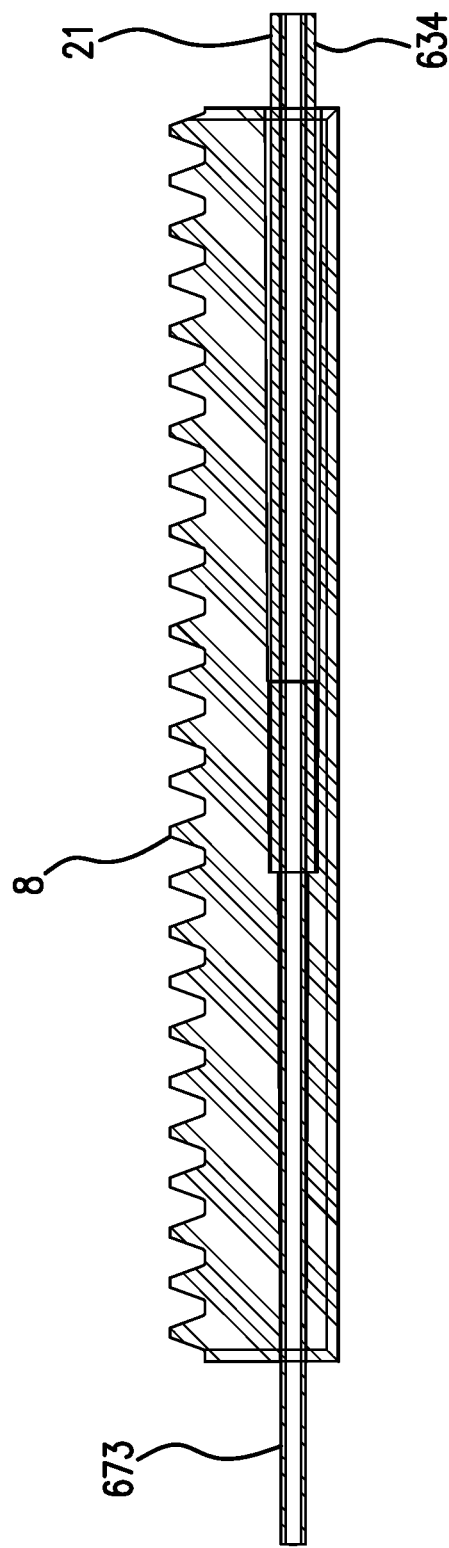
FIG. 103A is an enlarged detail view of section 103 and FIG. 103B is an enlarged perspective detail view of an alternative embodiment of section 103.
Figure 103B:
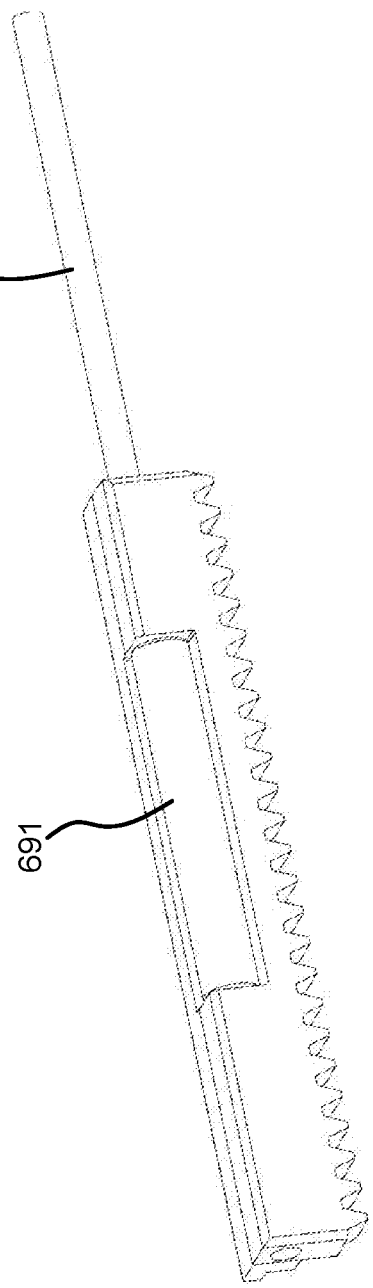
Figure 105B:
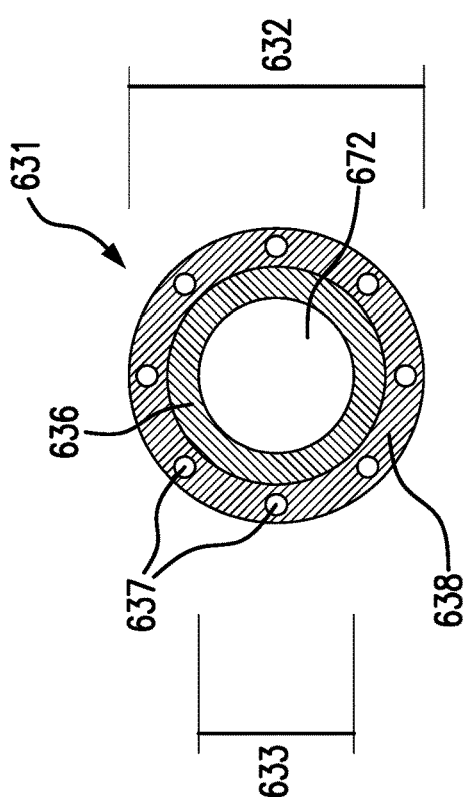
FIGS. 105A-105D provide cross-sectional view of the outer tubular member FIG. 105A proximal inner shaft member FIG. 105B, distal inner shaft member FIG. 105C, and stabilizer member FIG. 105D.
Figure 105D:
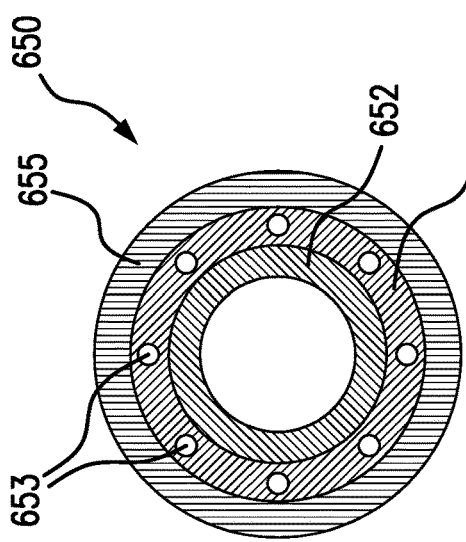
Figure 105A:
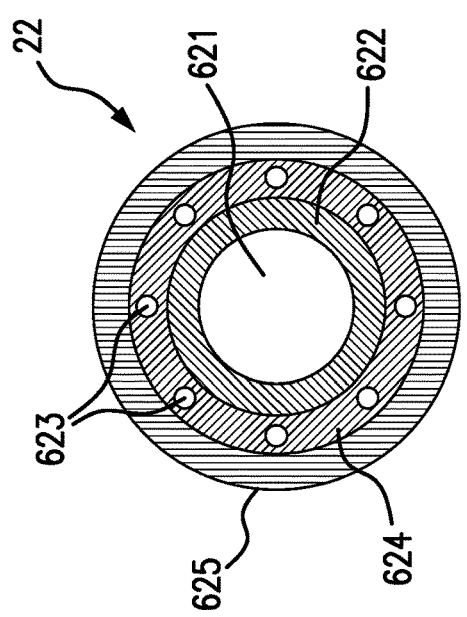
Figure 105C:
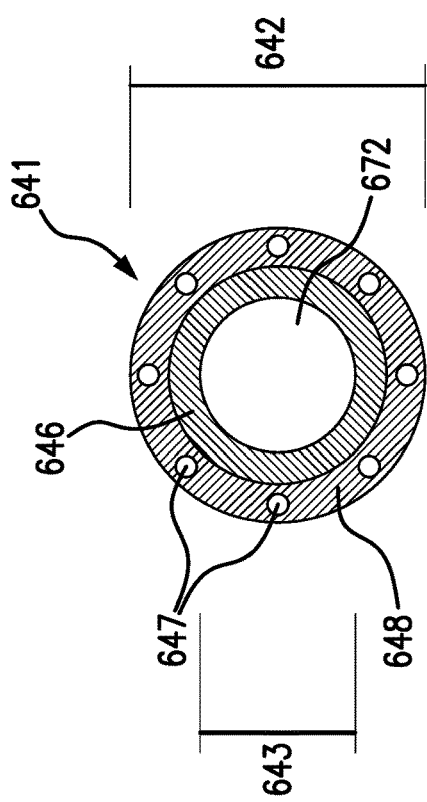
Figure 106:
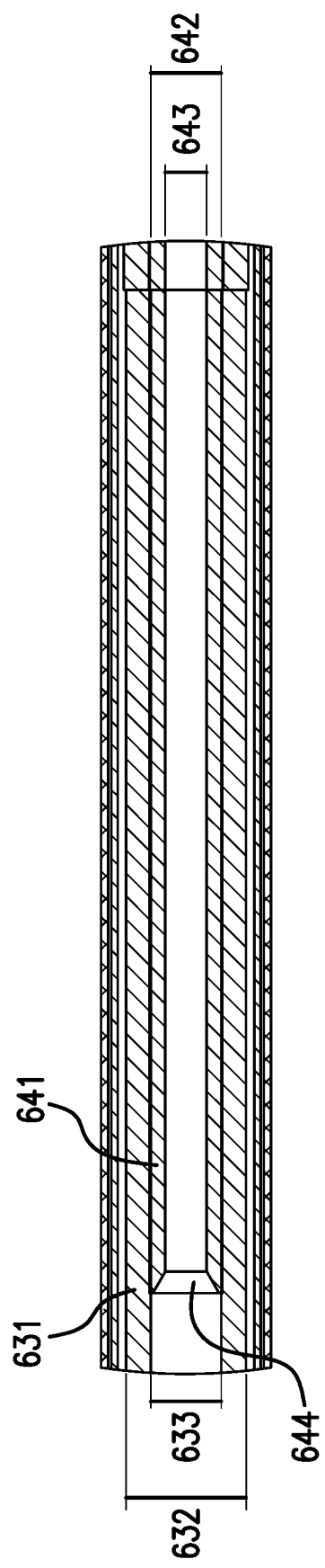
FIG. 106 illustrates the connection between the proximal inner shaft member and the distal inner shaft member prior to bonding.

As embodied herein, a ratchet rack 8 can be coupled to the proximal end portion 634 of the proximal inner shaft portion 631. The ratchet rack 8 can be functionally coupled with the actuation assembly 2 to facilitate movement of the inner shaft member 21 proximally and distally, as described above. As with the outer tubular member, the proximal inner shaft portion 631 and ratchet rack 8 can be coupled such that the inner shaft member 21 can rotate about a longitudinal axis relative the ratchet rack 8. For example, the proximal inner shaft portion 631 and the ratchet rack can be coupled by a cylindrical coupling. Such a coupling can allow the inner shaft member 21 to rotate about a longitudinal axis, for example, during insertion of the catheter assembly 1006 and during delivery of the implant 23, while the actuation assembly 2 remains rotationally stationary. In an alternative embodiment, the inner shaft member 21 and the ratchet rack can be coupled by a rotational sleeve 691, as shown in FIG. 103B. As a further alternative, the proximal inner shaft portion 631 can be coupled to the ratchet rack 8 such that rotation between the two members is prevented.

A hypotube 673 can be disposed at least partially within the inner shaft member lumen 672 defined by the inner shaft member 21. The hypotube 673 can extend proximally of the proximal end portion 634 of the proximal inner shaft member 631. Accordingly, the inner diameter of the proximal inner shaft member 631 can be sized to receive the hypotube 673. During operation, the hypotube 673 can act as a guiding rail for the inner shaft member 21 as the inner shaft member 21 moves proximally and distally relative to the handle 1. The inner shaft member 21 can have a sliding relationship with the hypotube 673. The hypotube 673 can be any suitable length, for example, between 15 and 25 inches, for example, 18 inches. For example, the hypotube length can be selected based on the length of the handle 1. An initial distance between a distal end of the hypotube 673, disposed within the proximal inner shaft member 631, and the proximal end portion of the distal inner shaft member 641 can be the sum of an initial length of the implant 23 and an activation length of the implant 23 (i.e., the length the implant 23 expands upon implantation). A luer 674 can be coupled to a proximal end portion of the hypotube 673.

Figure 107:
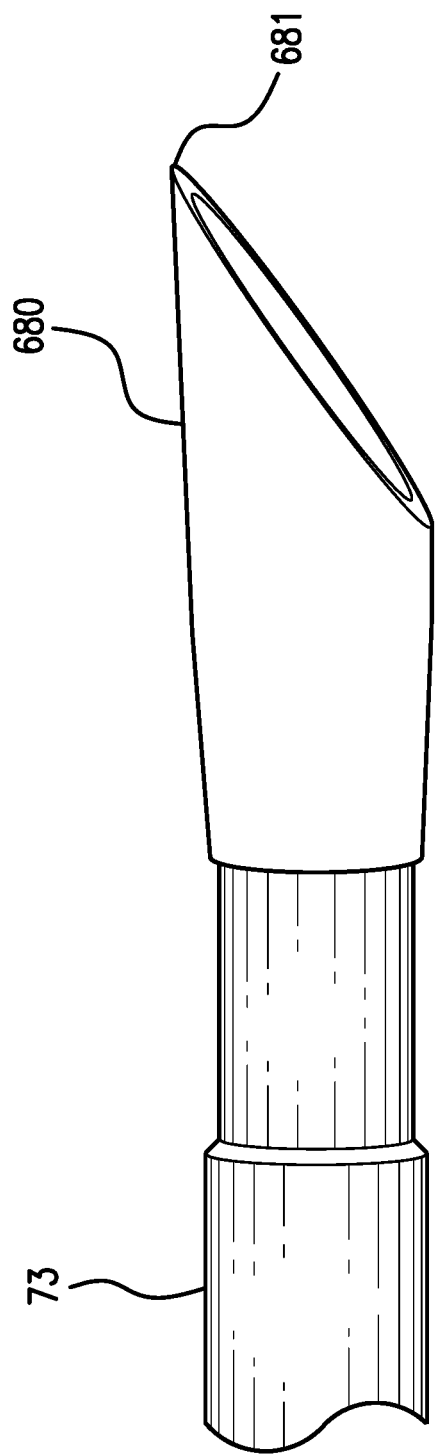
FIG. 107 illustrates an enlarged side view of a distal end of a hypotube of the delivery system of FIG. 1A.
Figure 108:
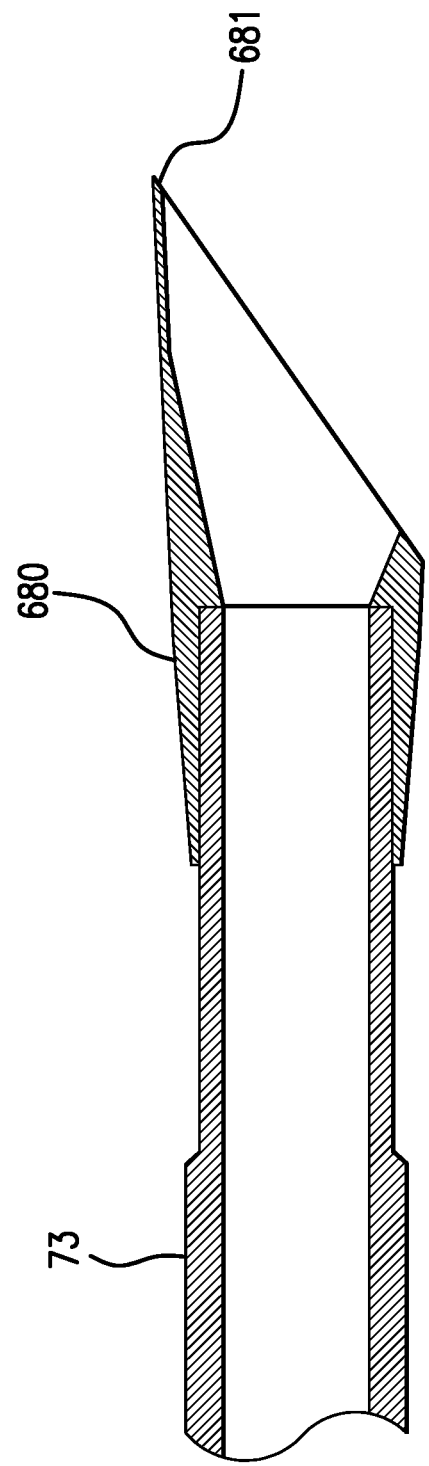
FIG. 108 illustrates a cross-sectional side view of the distal end of the hypotube of FIG. 107.

As shown in FIGS. 107-108, a sleeve 680 can be secured to a distal end of the hypotube 673 to facilitate insertion of a guidewire member through the hypotube 673 from the inner shaft member. As embodied herein, the distal end of the hypotube 673 can include a reduced diameter to receive the sleeve 680, if desired. For example, the reduced diameter can define a groove having a depth generally equal to or greater than the wall thickness of the of the sleeve. Furthermore, the sleeve 680 can have a distal end defining an angle (e.g., 30 degree angle) relative to an axis of the hypotube 673 to form a tapered distal tip 681. Additionally, the sleeve can be cylindrical with constant diameter, or generally conical in shape as shown. The sleeve 680 can be formed of any suitable material and can be selected to be relatively soft and flexible as compared to the material of the hypotube 673. As an example, and not by way of limitation, the sleeve can be a polymer material such as a composite formed of polyamide, polytetrafluoroethylene, and polyether ether ketone.

As previously noted, and as embodied herein, a pusher assembly 660 is disposed within the outer tubular member lumen 621. For purpose of illustration and not limitation, the pusher assembly 660 can have a stem 661 coupled to a distal end portion 645 of the distal inner shaft member 641, and an implant-engaging member 662 extending from the stem 661. The implant-engaging member 662 thus can be configured with a portion that extends radially outwardly and distally. The implant-engaging member 662 can be configured to engage an implant 23, for example, a stent, when distally advanced, and can be configured so as not to engage the implant 23 when proximally retracted. For example, the radially outwardly extending portion of the implant-engaging member 662 can be configured to engage one or more intersections between filaments of a woven or braided stent (e.g., a first intersection between filaments on a first side and second intersection between filaments on a second opposite side). As another example, the radially outwardly extending portion of the implant-engaging member 662 can be configured to engage one or more engageable features of other implants (for example, one or more cutouts in a laser cut stent). Additional details and examples of pusher assemblies can be found in U.S. application Ser. No. 13/118,325, filed on May 27, 2011, which is incorporated herein in its entirety. The implant 23 can be disposed within the outer tubular member lumen 621 and proximate the pusher assembly 660. The implant-engaging member 662 can have an initial position in which the implant-engaging member 662 is disposed within the outer tubular member 22, and a deployed position in which the implant-engaging member 662 extends, at least partially, distally of the outer tubular member 22. As embodied herein, a radiopaque marker can be disposed on the stem 661.

As further embodied herein, the catheter assembly can include a hollow support tube 675 disposed within the outer tubular member lumen 621 and around a least a portion of the inner shaft member 21, for example, the distal inner shaft portion 641. The support tube can be a nylon tube and can be any suitable length, for example, up to 45 inches long. Additionally or alternatively, the catheter assembly can include a support coil 676 (e.g., a support spring) or similar flexible spacing member disposed within the second lumen 621 and around at least a portion of the inner shaft member 21, for example, the distal inner shaft member 641. The support coil 676 can be any suitable length, for example about 4.5 inches long. The support tube 675 and the support coil 676 are provided and configured to reduce kinking of the catheter during delivery through a tortuous path. For example, the support tube 675 and support coil 676 can provide additional support distal of the connection between the proximal inner shaft member 631 and the distal inner shaft member 641. The support coil 676 can provide support to the outer tubular member 22 between a distal end of the support tube 675 and a proximal end of the implant 23.

Further, in accordance with the disclosed subject matter, a delivery system and method is provided incorporating the catheter assembly disclosed herein. As previously noted, the delivery system includes a handle, a trigger and an actuation assembly, as well as the catheter assembly described in detail above.

In accordance with the disclosed subject matter, the outer tubular member 22 can be fixedly coupled to a handle, and can be retracted in a proximal direction by moving the handle in a proximal direction. The trigger can advance the inner shaft member 21 distally. For example, U.S. application Ser. No. 11/876,764, filed on Oct. 22, 2007, which is incorporated by reference in its entirety herein, discloses suitable handles for the delivery system.

U.S. application Ser. No. 14/932,848, filed Nov. 4, 2015, U.S. application Ser. No. 14/932,795, filed Nov. 4, 2015, U.S. application Ser. No. 14/932,875, filed Nov. 4, 2015, U.S. application Ser. No. 14/932,862, filed Nov. 4, 2015, U.S. application Ser. No. 14/932,884, filed Nov. 4, 2015, U.S. application Ser. No. 14/932,805, filed Nov. 4, 2015, U.S. application Ser. No. 14/932,830, filed Nov. 4, 2015, and U.S. application Ser. No. 14/932,900, filed Nov. 4, 2015, each provide additional information regarding delivering an implant using an actuation assembly and a trigger assembly, and are each incorporated herein by reference in their entirety. The catheter system as disclosed herein can also be used with delivery systems including a user-actuatable element that allows a user to move the inner shaft member distally or proximally. Additional information on delivery systems with user-actuatable elements is provided in U.S. application Ser. No. 11/876,764, filed on Oct. 22, 2007, which is incorporated herein by reference in its entirety.

Exemplary materials of certain elements of the embodiments described herein are provided above. However, elements of the embodiments described above can be formed of any suitable materials, for example, plastics, composites, or metals. As an example, the strain relief 15 can be polyethylene. The cap seal 627 can be polycarbonate resin. The luer 674 and ratchet rack 8 and be can be polycarbonate resin. The hypotube 673 and support spring can be SST.

While the disclosed subject matter is described herein in terms of certain preferred embodiments for purpose of illustration and not limitation, those skilled in the art will recognize that various modifications and improvements can be made to the disclosed subject matter without departing from the scope thereof. Moreover, although individual features of one embodiment of the disclosed subject matter can be discussed herein or shown in the drawings of one embodiment and not in other embodiments, it should be readily apparent that individual features of one embodiment can be combined with one or more features of another embodiment or features from a plurality of embodiments.

In addition to the specific embodiments claimed below, the disclosed subject matter is also directed to other embodiments having any other possible combination of the dependent features claimed below and those disclosed above. As such, the particular features presented in the dependent claims and disclosed above can be combined with each other in other possible combinations. Thus, the foregoing description of specific embodiments of the disclosed subject matter has been presented for purposes of illustration and description. It is not intended to be exhaustive or to limit the disclosed subject matter to those embodiments disclosed.

Furthermore, it is recognized that the actuation assembly and delivery system as disclosed herein can be used in a method of delivering an implant. That is, for purpose of illustration, such method would include providing a delivery system as disclosed herein, positioning the distal end portion of the outer tubular member proximate a desired site, and deploying the delivery system to push the implant from the outer tubular member to the desired site.

It will be apparent to those skilled in the art that various modifications and variations can be made in the method and system of the disclosed subject matter without departing from the spirit or scope of the disclosed subject matter. Thus, it is intended that the disclosed subject matter include modifications and variations that are within the scope of the appended claims and their equivalents.

The invention claimed is:

1. A system for delivering an implant, comprising: a catheter assembly, the catheter assembly having an outer tubular member defining an outer tubular member lumen, an inner shaft member disposed at least partially within the outer tubular member lumen, and a pusher assembly coupled to a distal end portion of a distal inner shaft portion; a handle; a trigger operatively coupled to the handle; and an actuation assembly operatively coupled to the trigger and the catheter assembly, the actuation assembly comprising a planet carrier, at least one planet gear operatively coupled to the planet carrier, a sun gear shaft operatively engaged with the at least one planet gear, a ring gear operatively engaged with the at least one planet gear, a first clutch driver configured to limit the sun gear shaft to uni-directional rotational motion, and a second clutch driver configured to uni-directionally lock the sun gear shaft and the planet carrier; wherein the actuation assembly further comprises a shuttle frame having the planet carrier, the at least one planet gear, the sun gear shaft, the ring gear, the first clutch driver and the second clutch driver disposed thereon, and wherein the actuation assembly is configured to displace the outer tubular member in a proximal direction a distance (d) relative to the handle and to separately move the inner shaft member distally a distance (x) relative to the handle upon deployment of the trigger from a first position to a second position, and further wherein the actuation assembly is configured to move the inner shaft member proximally a distance (y) relative to the handle with no displacement of the outer tubular member relative to the handle upon return of the trigger from the second position to the first position.

2. The system of claim 1, wherein the second clutch driver is configured to uni-directionally lock the sun gear shaft and the planet carrier such that the sun gear shaft, planet carrier and the ring gear have a 1:1 ratio of rotation during deployment of the trigger from the first position to the second position.

3. The system of claim 1, wherein the actuation assembly further comprises a clutch release operatively coupled to the second clutch driver and configured to prevent the second clutch driver from uni-directionally locking the sun gear shaft and the planet carrier when the clutch release is engaged by a stop.

4. The system of claim 3, wherein the stop is disposed on the handle, and the stop engages the clutch release when the actuation assembly has moved proximally a distance (z) along the handle.

5. The system of claim 3, wherein the clutch release comprises a saw-tooth portion and wherein the stop comprises a resilient abutment portion, and wherein the resilient abutment portion of the stop engages the saw-tooth portion of the clutch release when the actuation assembly has moved proximally a distance (z) along the handle.

6. The system of claim 1, wherein the first clutch driver is configured to limit the sun gear shaft to uni-directional motion such that the sun gear shaft does not rotate during return of the trigger from the second position to the first position and the at least one planetary gear rotates about the sun gear shaft.

7. The system of claim 1, wherein the sun gear shaft is functionally coupled to the outer tubular member such that upon deployment of the trigger from the first position to the second position the sun gear shaft rotates and thereby causes the outer tubular member to move proximally.

8. The system of claim 1, wherein the shuttle frame is fixedly coupled to the outer tubular member.

9. The system of claim 1, wherein the sun gear shaft is functionally coupled to the handle such that upon deployment of the trigger from the first position to the second position the sun gear shaft rotates and the shuttle frame moves proximally a distance relative to the handle.

10. The system of claim 1, wherein the actuation assembly further comprises an intermediate gear functionally disposed on the shuttle frame between the sun gear shaft and the handle, and operatively engaged with the sun gear shaft.

11. The system of claim 1, wherein the actuation assembly further comprises a ratchet rack fixedly coupled to the inner shaft member and disposed on the shuttle frame.

12. The system of claim 11, wherein the ratchet rack is operatively meshed with the ring gear.

13. The system of claim 1, wherein the actuation assembly further comprises at least one boss configured to engage at least one boss track disposed within the handle to thereby guide the shuttle frame along the handle.

14. The system of claim 13, wherein the at least one boss comprises a first boss disposed through an axis of an intermediate gear functionally disposed on the shuttle frame between the sun gear shaft and the handle, and operatively engaged with the sun gear shaft.

15. The system of claim 14, wherein the at least one boss further comprises a second and third boss, each of the second and third boss disposed through the shuttle frame.

16. The system of claim 15, wherein the at least one boss further comprises a fourth boss disposed through an axis of the sun gear shaft.

17. The system of claim 1, wherein the actuation assembly further comprises a plate disposed on the shuttle frame.

18. The system of claim 1, wherein the sun gear shaft comprises a sun gear portion, a sheath pinion, and a clutch engagement portion.

19. The system of claim 1, wherein the planet carrier comprises a circumferential pinion, a clutch component, and at least one pin.

20. The system of claim 1, wherein the ring gear comprises a circumferential pinion and a ring gear portion.

21. The system of claim 1, wherein the first clutch driver and the second clutch driver each comprises a sun gear shaft engagement portion and a clutch portion.

22. The system of claim 1, further comprising: a gear train functionally disposed between the trigger and the actuation assembly, the gear train having a trigger gear sector, a trigger pinion operatively meshed with the trigger gear sector, a slide pinion operatively coupled to the trigger pinion, and a slide rack disposed on a slide and operatively meshed with the trigger pinion.

23. The system of claim 22, where the slide is coupled to a driving rack.

24. The system of claim 23, wherein the driving rack is operatively engaged with the planet carrier and the driving rack is supported by the shuttle frame.

25. The system of claim 23, wherein the driving rack is fixedly coupled to the slide.

26. The system of claim 23, wherein the driving rack is detachably coupled to the slide.

27. The system of claim 1, the outer tubular member comprising an inner layer, a reinforcement layer, a middle layer, and an outer layer.

28. The system of claim 27, wherein the inner layer of the outer tubular member comprises fluorinated ethylene propylene.

29. The system of claim 27, wherein the reinforcement layer of the outer tubular member comprises a stainless steel braid.

30. The system of claim 27, wherein the reinforcement layer of the outer tubular member comprises Teflon fibers.

31. The system of claim 27, wherein the middle layer of the outer tubular member comprise polyimide.

32. The system of claim 27, wherein the outer layer of the outer tubular member comprises Grilamid.

33. The system of claim 27, wherein the outer tubular member further comprises an atraumatic distal tip having a distally tapered end.

34. The system of claim 33, wherein the atraumatic distal tip is heat bonded to the outer tubular member.

35. The system of claim 33, wherein the atraumatic distal tip is mounted to an outer diameter of the outer tubular member.

36. The system of claim 33, wherein the atraumatic distal tip comprises polyether block amide.

37. The system of claim 1, the inner shaft member comprising a proximal inner shaft portion and a distal inner shaft portion, the distal inner shaft portion having a distal end portion.

38. The system of claim 37, wherein at least one of the proximal inner shaft portion and the distal inner shaft portion comprise an inner layer, a reinforcement layer, and an outer layer.

39. The system of claim 37, wherein the distal inner shaft portion comprises a distal inner shaft member and the proximal inner shaft portion comprises a proximal inner shaft member coupled to the distal inner shaft member.

40. The system of claim 39, wherein a proximal end portion of the distal inner shaft member is heat bonded to a distal end portion of the proximal inner shaft member.

41. The system of claim 39, wherein a proximal end portion of the distal inner shaft portion comprises an inner taper.

42. The system of claim 39, wherein an outer diameter at a proximal end portion of the distal inner shaft member is sized to be received within an inner diameter at a distal end portion of the proximal inner shaft member.

43. The system of claim 37, further comprising a ratchet rack coupled to a proximal end portion of the proximal inner shaft portion.

44. The system of any of claim 1, further comprising a stabilizer member having a stabilizer lumen defined therethrough, the stabilizer lumen having an inner diameter sized to receive the outer tubular member therein.

45. The system of claim 44, wherein the outer tubular member is configured to rotate about a central longitudinal axis relative to the stabilizer member.

46. The system of claim 44, wherein the stabilizer member comprises an inner layer, a reinforcement layer, a middle layer, and an outer layer.

47. The system of claim 44, wherein the stabilizer member comprises a distal end having an atraumatic tip.

48. The system of claim 44, further comprising a strain relief coupled to a proximal end portion of the stabilizer member.

49. The system of claim 48, wherein the stabilizer member is configured to rotate about a central longitudinal axis relative the strain relief.

50. The system of claim 1, wherein the catheter assembly has an outer profile less than or equal to 6 French.

51. The system of claim 1, wherein an implant is disposed within the outer tubular member lumen proximate the pusher assembly.

52. The system of claim 1, further comprising a support tube disposed within the outer tubular member lumen.

53. The system of claim 52, further comprising a support coil disposed within the outer tubular member lumen distal of the support tube.

54. The system of claim 1, wherein the pusher assembly comprises a stem coupled to the inner shaft member and an implant-engaging member extending from the stem.

55. The system of claim 54, further comprising a guidewire lumen coupled to a distal end portion of the stem and extending distally of the outer tubular member.

56. The system of claim 55, wherein the guidewire lumen comprises at least one radiopaque marker.

57. The system of claim 1, further comprising a hypotube disposed at least partially within an inner shaft member lumen defined by the inner shaft member.

58. The system of claim 57, further comprising a polymer sleeve secured to a distal end portion of the hypotube.

59. The system of claim 57, further comprising a luer coupled to a proximal end portion of the hypotube.

60. The system of claim 1, wherein the inner shaft member is configured to rotate about a central axis relative to the actuation assembly.

61. A system for delivering an implant, comprising: a catheter assembly, the catheter assembly having an outer tubular member defining an outer tubular member lumen, an inner shaft member disposed at least partially within the outer tubular member lumen, and a pusher assembly coupled to the distal end portion of the distal inner shaft portion; a handle; a trigger operatively coupled to the handle; and an actuation assembly operatively coupled to the trigger and the catheter assembly, the actuation assembly comprising a planet carrier, at least one planet gear operatively coupled to the planet carrier, a sun gear shaft operatively engaged with the at least one planet gear, a ring gear operatively engaged with the at least one planet gear, a first clutch driver configured to limit the sun gear shaft to unidirectional rotational motion, and a second clutch driver configured to uni-directionally lock the sun gear shaft and the planet carrier; wherein the actuation assembly further comprises a clutch release operatively coupled to the second clutch driver and configured to prevent the second clutch driver from uni-directionally locking the sun gear shaft and the planet carrier when the clutch release is engaged by a stop, and wherein the actuation assembly is configured to displace the outer tubular member in a proximal direction a distance (d) relative to the handle and to separately move the inner shaft member distally a distance (x) relative to the handle upon deployment of the trigger from a first position to a second position, and further wherein the actuation assembly is configured to move the inner shaft member proximally a distance (y) relative to the handle with no displacement of the outer tubular member relative to the handle upon return of the trigger from the second position to the first position.

62. The system of claim 61, wherein the stop is disposed on the handle, and the stop engages the clutch release when the actuation assembly has moved proximally a distance (z) along the handle.

* * * * *